US012325742B2

(12) United States Patent
Munoz-Olaya et al.

(10) Patent No.: US 12,325,742 B2
(45) Date of Patent: *Jun. 10, 2025

(54) ANTI-MESOTHELIN ANTIBODIES

(71) Applicant: INVOX PHARMA LIMITED, London (GB)

(72) Inventors: Jose Munoz-Olaya, Cambridge (GB); Remi Fertin, Cambridge (GB); Francisca Wollerton, Cambridge (GB); Mihriban Tuna, Cambridge (GB); Neil Brewis, Cambridge (GB)

(73) Assignee: INVOX PHARMA LIMITED, London (GB)

( * ) Notice: Subject to any disclaimer, the term of this patent is extended or adjusted under 35 U.S.C. 154(b) by 677 days.

This patent is subject to a terminal disclaimer.

(21) Appl. No.: 17/259,677

(22) PCT Filed: Jul. 12, 2019

(86) PCT No.: PCT/EP2019/068800
§ 371 (c)(1),
(2) Date: Jan. 12, 2021

(87) PCT Pub. No.: WO2020/011970
PCT Pub. Date: Jan. 16, 2020

(65) Prior Publication Data
US 2022/0267421 A1 Aug. 25, 2022

(30) Foreign Application Priority Data
Jul. 12, 2018 (GB) .................... 1811415

(51) Int. Cl.
*C07K 16/18* (2006.01)
*A61K 39/00* (2006.01)
*A61P 35/00* (2006.01)
*C07K 16/28* (2006.01)
*G01N 33/574* (2006.01)

(52) U.S. Cl.
CPC ............. *C07K 16/18* (2013.01); *A61P 35/00* (2018.01); *C07K 16/2878* (2013.01); *G01N 33/57496* (2013.01); *A61K 2039/505* (2013.01); *C07K 2317/31* (2013.01); *C07K 2317/33* (2013.01); *C07K 2317/524* (2013.01); *C07K 2317/526* (2013.01); *C07K 2317/55* (2013.01); *C07K 2317/565* (2013.01); *C07K 2317/732* (2013.01); *C07K 2317/76* (2013.01); *C07K 2317/92* (2013.01)

(58) Field of Classification Search
CPC ............. C07K 16/18; C07K 16/2878; C07K 2317/31; C07K 2317/33; C07K 2317/524; C07K 2317/526; C07K 2317/55; C07K 2317/565; C07K 2317/732; C07K 2317/76; C07K 2317/92; C07K 2317/71; C07K 2317/72; C07K 2317/94; C07K 16/30; A61P 35/00; G01N 33/57496; G01N 33/574; A61K 2039/505; A61K 2039/545

See application file for complete search history.

(56) References Cited

U.S. PATENT DOCUMENTS

| | | | |
|---|---|---|---|
| 3,909,459 A | 9/1975 | Friese et al. | |
| 3,967,230 A | 6/1976 | Kamigaito et al. | |
| 4,004,183 A | 1/1977 | Oki et al. | |
| 5,595,756 A | 1/1997 | Bally et al. | |
| 6,380,664 B1 | 4/2002 | Pollner | |
| 7,288,638 B2 | 10/2007 | Jure-Kunkel et al. | |
| 7,592,426 B2 | 9/2009 | Ebel et al. | |
| 8,217,149 B2 | 7/2012 | Irving et al. | |
| 8,383,796 B2 | 2/2013 | Korman et al. | |
| 8,911,732 B2 | 12/2014 | Dennis et al. | |
| 9,567,399 B1 | 2/2017 | Campbell et al. | |
| 9,617,338 B1 | 4/2017 | Campbell et al. | |
| 10,090,646 B2 | 10/2018 | Takaoka et al. | |
| 10,205,305 B2 | 2/2019 | Uegaki et al. | |
| 10,233,258 B2 | 3/2019 | Akamatsu et al. | |
| 10,604,576 B2 | 3/2020 | Campbell et al. | |
| 11,214,618 B2 | 1/2022 | Tuna et al. | |
| 11,214,620 B2 | 1/2022 | Campbell et al. | |
| 11,548,948 B2 | 1/2023 | Tuna et al. | |
| 11,629,193 B2 | 4/2023 | Tuna et al. | |
| 12,103,976 B2 | 10/2024 | Lakins et al. | |
| 2003/0030355 A1 | 2/2003 | Honda | |
| 2007/0071675 A1 | 3/2007 | Wu et al. | |
| 2009/0055944 A1 | 2/2009 | Korman et al. | |
| 2012/0237498 A1 | 9/2012 | Ahrens et al. | |
| 2012/0276104 A1 | 11/2012 | Woisetschlager | |

(Continued)

FOREIGN PATENT DOCUMENTS

CN 101802006 A 8/2010
CN 104955845 A 9/2015

(Continued)

OTHER PUBLICATIONS

Lamberts et. al. (Clin. Cancer Res. 22(7) 1642-1652. (2016)) (Year: 2016).*

(Continued)

Primary Examiner — Meera Natarajan
Assistant Examiner — Francesca Edgingtongiordan
(74) Attorney, Agent, or Firm — Wolf, Greenfield & Sacks, P.C.

(57) ABSTRACT

The present application relates to antibody molecules that bind mesothelin (MSLN). The antibody molecules find application in the treatment and diagnosis of diseases and disorders, such as cancer.

20 Claims, 5 Drawing Sheets
Specification includes a Sequence Listing.

(56) References Cited

U.S. PATENT DOCUMENTS

| | | |
|---|---|---|
| 2013/0034559 A1 | 2/2013 | Queva et al. |
| 2014/0004121 A1 | 1/2014 | Fanslow, III et al. |
| 2014/0341917 A1 | 11/2014 | Nastri et al. |
| 2015/0214697 A1 | 7/2015 | Yoshida et al. |
| 2015/0259420 A1 | 9/2015 | Triebel et al. |
| 2015/0307620 A1 | 10/2015 | Vella et al. |
| 2016/0043531 A1 | 2/2016 | Firstenberg et al. |
| 2016/0137740 A1 | 5/2016 | Hammond et al. |
| 2016/0244528 A1 | 8/2016 | Gray et al. |
| 2017/0198050 A1 | 7/2017 | Eckelman et al. |
| 2017/0355756 A1 | 12/2017 | Julien et al. |
| 2017/0362321 A1 | 12/2017 | Campbell et al. |
| 2018/0118841 A1 | 5/2018 | Ellmark et al. |
| 2018/0175592 A1 | 6/2018 | Uegaki et al. |
| 2018/0194862 A1 | 7/2018 | Akamatsu et al. |
| 2018/0339031 A1 | 11/2018 | Masternak et al. |
| 2019/0106494 A1 | 4/2019 | Wang et al. |
| 2019/0202920 A1 | 7/2019 | Tuna et al. |
| 2019/0256602 A1 | 8/2019 | Campbell et al. |
| 2019/0330344 A1 | 10/2019 | Tuna et al. |
| 2019/0330351 A1 | 10/2019 | Campbell et al. |
| 2019/0338032 A1 | 11/2019 | Campbell et al. |
| 2019/0338049 A1 | 11/2019 | Tuna et al. |
| 2020/0407446 A1 | 12/2020 | McCourt et al. |
| 2021/0139590 A1 | 5/2021 | Tuna et al. |
| 2021/0237498 A1 | 8/2021 | Yoda et al. |
| 2021/0238299 A1 | 8/2021 | Pechouckova et al. |
| 2021/0277134 A1 | 9/2021 | Lakins et al. |
| 2021/0301022 A1 | 9/2021 | Wollerton et al. |
| 2021/0309753 A1 | 10/2021 | Tuna et al. |
| 2021/0355228 A1 | 11/2021 | Lakins et al. |
| 2022/0048996 A1 | 2/2022 | Tuna et al. |
| 2022/0049007 A1 | 2/2022 | Lakins et al. |
| 2022/0185890 A1 | 6/2022 | Tuna et al. |
| 2022/0185894 A1 | 6/2022 | Campbell et al. |
| 2022/0275092 A1 | 9/2022 | Morrow et al. |
| 2023/0357413 A1 | 11/2023 | Tuna et al. |
| 2023/0406935 A1 | 12/2023 | Tuna et al. |

FOREIGN PATENT DOCUMENTS

| | | | |
|---|---|---|---|
| CN | 104968364 A | | 10/2015 |
| CN | 107523546 A | | 12/2017 |
| CN | 109563171 A | | 4/2019 |
| EP | 1025230 B1 | | 2/2006 |
| EP | 1180123 B1 | | 7/2008 |
| EP | 2407487 A1 | | 1/2012 |
| EP | 2546268 A1 | | 1/2013 |
| EP | 2242771 B1 | | 7/2013 |
| EP | 2905030 A1 | | 8/2015 |
| EP | 2215121 B1 | | 2/2016 |
| EP | 3354661 A1 | | 8/2018 |
| EP | 3470426 A1 | | 4/2019 |
| JP | S51-046628 A | | 4/1976 |
| JP | 2003-022886 A | | 1/2003 |
| JP | 22011-521905 A | | 7/2011 |
| JP | 2012-500006 A | | 1/2012 |
| JP | 2016-513467 A | | 5/2016 |
| JP | 2016-533395 A | | 10/2016 |
| JP | 2017-010741 A | | 1/2017 |
| JP | 2018-508475 A | | 3/2018 |
| RU | 2017112379 A | | 10/2018 |
| TW | 201642897 A | | 12/2016 |
| WO | WO 2001/077342 A1 | | 10/2001 |
| WO | WO 2005/035584 A1 | | 4/2005 |
| WO | WO 2006/072620 A1 | | 7/2006 |
| WO | WO 2006/088447 A1 | | 8/2006 |
| WO | WO 2006/099141 A1 | | 9/2006 |
| WO | WO 2008/003103 A2 | | 1/2008 |
| WO | WO 2008/068048 A2 | | 6/2008 |
| WO | WO 2009/000006 A1 | | 12/2008 |
| WO | WO 2009/068204 A1 | | 6/2009 |
| WO | WO 2009/126944 A1 | | 10/2009 |
| WO | WO 2009/132876 A1 | | 11/2009 |
| WO | WO 2010/019570 A2 | | 2/2010 |
| WO | WO 2010/057047 A1 | | 5/2010 |
| WO | WO 2010/111282 A1 | | 9/2010 |
| WO | WO 2010/124797 A1 | | 11/2010 |
| WO | WO 2012/130831 A1 | | 10/2012 |
| WO | WO 2013/181634 A2 | | 12/2013 |
| WO | WO 2014/004549 A2 | | 1/2014 |
| WO | WO 2014/008218 A1 | | 1/2014 |
| WO | WO 2014/052064 A1 | | 4/2014 |
| WO | WO 2014/089113 A1 | | 6/2014 |
| WO | WO 2014/140180 A1 | | 9/2014 |
| WO | WO 2014/151910 A1 | | 9/2014 |
| WO | WO 2015/048312 A1 | | 4/2015 |
| WO | WO 2015/049537 A1 | | 4/2015 |
| WO | WO 2015/119923 A1 | | 8/2015 |
| WO | WO 2015/138920 A1 | | 9/2015 |
| WO | WO 2015/198312 A1 | | 12/2015 |
| WO | WO 2015/200119 A1 | | 12/2015 |
| WO | WO 2016/028672 A1 | | 2/2016 |
| WO | WO 2016/040880 A1 | | 3/2016 |
| WO | WO 2016/110584 A1 | | 7/2016 |
| WO | WO 2016/111645 A1 | | 7/2016 |
| WO | WO 2016/162505 A1 | | 10/2016 |
| WO | WO 2016/177802 A1 | | 11/2016 |
| WO | WO 2016/185016 A1 | | 11/2016 |
| WO | WO 2016/200782 A1 | | 12/2016 |
| WO | WO 2017/009456 A1 | | 1/2017 |
| WO | WO 2017/015560 A2 | | 1/2017 |
| WO | WO 2017/019846 A8 | | 2/2017 |
| WO | WO 2017/025498 A1 | | 2/2017 |
| WO | WO 2017/049452 A1 | | 3/2017 |
| WO | WO 2017/052241 A1 | | 3/2017 |
| WO | WO 2017/055398 A2 | | 4/2017 |
| WO | WO 2017/062888 A1 | | 4/2017 |
| WO | WO 2017/077085 A2 | | 5/2017 |
| WO | WO 2017/087589 A2 | | 5/2017 |
| WO | WO 2017/087901 A2 | | 5/2017 |
| WO | WO 2017/123650 A2 | | 7/2017 |
| WO | WO 2017/182672 A1 | | 10/2017 |
| WO | WO 2017/193032 A2 | | 11/2017 |
| WO | WO 2017/205738 A1 | | 11/2017 |
| WO | WO 2017/220555 A1 | | 12/2017 |
| WO | WO 2017/220569 A1 | | 12/2017 |
| WO | WO 2017/220990 A9 | | 12/2017 |
| WO | WO 2018/017673 A1 | | 1/2018 |
| WO | WO 2018/056821 A1 | | 3/2018 |
| WO | WO 2018/060480 A1 | | 4/2018 |
| WO | WO 2018/091740 A2 | | 5/2018 |
| WO | WO 2018/115859 A1 | | 6/2018 |
| WO | WO 2018/127610 A1 | | 7/2018 |
| WO | WO 2018/222711 A2 | | 12/2018 |
| WO | WO 2019/025545 A1 | | 2/2019 |

OTHER PUBLICATIONS

Brinkmann et. al. MABS. 9(2):182-212. (2017) (Year: 2017).*
U.S. Appl. No. 17/534,315, filed Nov. 23, 2021, Tuna et al.
U.S. Appl. No. 17/533,230, filed Nov. 23, 2021, Campbell et al.
U.S. Appl. No. 18/166,202, filed Feb. 8, 2023, Tuna et al.
U.S. Appl. No. 18/063,521, filed Dec. 8, 2022, Tuna et al.
U.S. Appl. No. 17/610,873, filed Nov. 12, 2021, Morrow et al.
[No Author Listed] Abstract for CHI Immuno-Oncology Summit Europe. Mar. 18-22, 2019. 1 page. PDR303.
[No Author Listed] First-in-Class bispecific antibodies for cancer immunotherapy. Presentation at Takeda. Dec. 13, 2016. 24 pages. PDR160.
[No Author Listed] F-Star Modular Bispecific Antibodies. Summary for ATLAS deck. Presented at JP Morgan. Jan. 2017. 1 page. PDR159.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.

(56) References Cited

OTHER PUBLICATIONS

Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Brewis, Development of an anti-PD-L1 Fcab. Presentation. Human Antibodies and Hybrodomas Conference. Oct. 22, 2018. PDR 312.
Brewis, Identification of a PD-L1 binding Fcab: a potent inhibitor of immunosuppressive signals. Abstract. Huamn Antibodies and Hybridomas 2018. Jun. 11, 2018. 1 page. PDR282.
Brewis, The use of bispecific antibodies to modulate anti-tumour immune responses. Oral Presentation at ELRIG—Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with anti-human PD-1 (REGN2810) shows enhanced anti-tumor activity in PD-1 x LAG-3 dual-humanized mice and favorable pharmacokinetic and safety profiles in cynomolgus monkey. J Immunother Cancer. 2016;4(Suppl 1):P195. 2 pages.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bispecific mAbs. Oral Presentation at 5th Annual Cell Culture and Bioprocessing Congress. Nov. 6, 2016. 16 pages. PDR142.
Davies, Overcoming the Manufacturing Challenges for Bispecific mAbs. Oral Presentation at Biopronet 3rd Annual Scientific Symposium. Oct. 20, 2016. 16 pages. PDR136.
Daxini et al., Vasculitis associated with immune checkpoint inhibitors—a systematic review. Clin Rheumatol. Sep. 2018;37(9):2579-2584. doi: 10.1007/s10067-018-4177-0. Epub Jun. 19, 2018.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: A LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.
Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.
Doody, In vivo Efficacy of bispecific antibodies targeting two immune-modulatory receptors. Oral Presentation at PEGS Europe. Nov. 4, 2016. 16 pages. PDR144.
Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.
Everett et al., Abstract PR06: A LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.
Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.
Fiehler, Development of an anti-PD-L1 Fcab. Presentation. European Antibody Congress. Oct. 29, 2018. 26 pages. PDR312.
Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.
F-Star, First-in-Class Bispecific Antibodies for Cancer Immunotherapy. Jul. 2016. Presentation. 14 pages. PDR119.
Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.
Gliddon, Pushing all the buttons: innovating in immuno-oncology with mAb. Oral Presentation at Phacilitate Immunotherapy World 2017. Jan. 18, 2017. 11 pages. PDR165.
Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.
Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.
Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.
Hid Cadena et al., Checks and Balances in Autoimmune Vasculitis. Front Immunol. Feb. 22, 2018;9:315. doi: 10.3389/fimmu.2018.00315.
Horn et al., CD3xPDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.
Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilities. Oct. 17-20, 2015. Orlando, FL. doi: 10.1158/1557-3265.OVCA15-PR03. Published Jan. 2016. 8 pages.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.

(56) References Cited

OTHER PUBLICATIONS

Jochems et al., Analyses of functions of an anti-PD-L1/TGFBR2 bispecific fusion protein (M7824). Oncotarget. Sep. 8, 2017;8(43):75217-75231. doi: 10.18632/oncotarget.20680.

Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.

Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.

Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.

Kraman et al., A LAG-3/PD-L1 bispecific antibody inhibits tumour growth in two syngeneic colon carcinoma models. Poster Presentation. BSI/NVVI Congress. Dec. 6, 2016. 1 page. PDR153.

Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.

Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.

Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.

Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.

Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.

Kraman et al., A LAG-3/PD-L1 bispecific antibody inhibits tumour growth in two syngeneic colon carcinoma models. Poster Presentation. International Conference on Human & Translational Immunology. Sep. 16, 2016. 1 page. PDR123.

Kraman et al., A LAG-3/PD-L1 bispecific antibody inhibits tumour growth in two syngeneic colon carcinoma models. Poster 3005. Poster Presentation. Keystome Symposium—Biobetters and Next-Generation Biologics. Jan. 22-26, 2017. 1 page. PDR164.

Kraman et al., Abstract 5651: A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.

La Motte-Mohs et al., Abstract 3217: MGD013, a bispecific PD-1 x LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.

La Motte-Mohs et al., MGD013, a bispecific PD-1 x LAG-3 Dual-Affinity Re-Targeting (DART®) protein with T-cell immunomodulatory activity for cancer treatment. Poster Presentation. 2016. http://ir.macrogenics.com/events.cfm. 1 page.

Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.

Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.

McCourt et al., KY1055; a novel ICOS/PD-L1 bispecific antibody, enhance T cell activation and delivers potent monotherapy anti-tumour response in vivo. Abstract. CIMT 2018. Feb. 28, 2018. 1 page. PDR245.

McCourt et al., KY1055; a novel ICOS/PD-L1 bispecific antibody, enhance T cell activation and delivers potent monotherapy anti-tumour response in vivo. Poster Presentation. CIMT Conference. May 9, 2018. 1 page. PDR 264.

McCourt et al., KY1055; a novel ICOS/PD-L1 bispecific antibody, enhance T cell activation and delivers potent monotherapy anti-tumour response in vivo. Presentation. CIMT Conference. May 9, 2018. 13 pages. PDR265.

Munoz-Olaya, Development of an anti-PD-L1 Fcab. Presentation. PEGS Lisbon. Nov. 16, 2018. 24 pages. PDR321.

Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.

Powles et al., MPDL3280A (anti-PD-L1) treatment leads to clinical activity in metastatic bladder cancer. Nature. Nov. 27, 2014;515(7528):558-62. doi: 10.1038/nature13904.

Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.

Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.

Strauss et al., Phase I Trial of M7824 (MSB0011359C), a Bifunctional Fusion Protein Targeting PD-L1 and TGFβ, in Advanced Solid Tumors. Clin Cancer Res. Mar. 15, 2018;24(6):1287-1295. doi: 10.1158/1078-0432.CCR-17-2653. Epub Jan. 3, 2018.

Tuna, Identification of a PD-L1 binding FCAB: a potent inhibitor of immunosuppressive signals. Abstract. European Antibody Congress. May 3, 2018. 1 page. PDR270.

Tuna, The use of bispecific antibodies to modulate anti-tumour immune responses. Oral Presentation at 10th Annual Proteins and Antibodies Congress. Apr. 24, 2017. 26 pages. PDR183.

Weismann, A LAG-3/PD-L1 Bispecific Antibody Inhibits Tumour Growth In Two Syngeneic Colon Carcinoma Models. International Conference on Human and Translational Immunology. Rhodes, Greece. Sep. 16-21, 2016. Presentation. 6 pages. PDR128.

Wherry, T cell exhaustion. Nat Immunol. Jun. 2011;12(6):492-9. doi: 10.1038/ni.2035.

Wilton, KY1055, a bispecific mAb2 targeting ICOS and PD-L1. Presentation. Feb. 21, 2018. 17 pages. PDR238.

Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.

Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.

Workman et al., Negative regulation of T cell homeostasis by lymphocyte activation gene-3 (CD223). J Immunol. Jan. 15, 2005;174(2):688-95. doi: 10.4049/jimmunol.174.2.688.

Workman et al., The CD4-related molecule, LAG-3 (CD223), regulates the expansion of activated T cells. Eur J Immunol. Apr. 2003;33(4):970-9. doi: 10.1002/eji.200323382.

Wydro, Bispecific antibodies: new opportunities for novel therapies. Oral Presentation at 7th Annual Biologics Symposium. Mar. 1, 2017. 24 pages. PDR172.

Wykes et al., Immune checkpoint blockade in infectious diseases. Nat Rev Immunol. Feb. 2018;18(2):91-104. doi: 10.1038/nri.2017.112. Epub Oct. 9, 2017.

Zhang et al., Structural basis of a novel PD-L1 nanobody for immune checkpoint blockade. Cell Discov. Mar. 7, 2017;3:17004. doi: 10.1038/celldisc.2017.4.

[No Author Listed], FS118 First in Human Study in Patients With Advanced Malignancies. Sponsored by F-star Therapeutics Lim-

(56) References Cited

OTHER PUBLICATIONS ited. Clinical Trial. Retreived from https://clinicaltrials.gov/ct2/show/NCT03440437. Feb. 22, 2018. 7 pages.
Asgarov et al., A new anti-mesothelin antibody targets selectively the membrane-associated form. MAbs. Apr. 2017;9(3):Supplementary Data. doi: 10.1080/19420862.2017.1288770. 6 pages.
Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163. MCT-15-0863. Epub May 18, 2016.
Callahan et al., Targeting T Cell Co-receptors for Cancer Therapy. Immunity. May 17, 2016;44(5):1069-78. doi: 10.1016/j.immuni. 2016.04.023.
Chatterjee et al., Noninvasive Imaging of Immune Checkpoint Ligand PD-L1 in Tumors and Metastases for Guiding Immunotherapy. Mol Imaging. Dec.-Jan. 2017; 16:1536012117718459. doi: 10.1177/1536012117718459. 5 pages.
Chu et al., An Update on Anti-CD137 Antibodies in Immunotherapies for Cancer. Int J Mol Sci. Apr. 12, 2019;20(8):1822. doi: 10.3390/ijms20081822. 17 pages.
Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.
El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027. 4 pages.
Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019. 4 pages.
Faroudi et al., Abstract B009: FS118, a LAG-3/PD-L1 bispecific antibody, capable of driving potent anti-tumour immune responses and overcome PD-(L)1-mediated compensatory. Sep. 25-28, 2019. Fifth CRI-CIMT-EATI-AACR International Cancer Immunotherapy Conference (2019): Translating Science into Survival. Paris. 1 page.
Faroudi et al., FS118, a LAG-3/PD-L1 bispecific antibody, capable of driving potent anti-tumour immune responses and overcome PD-(L)1-mediated compensatory. Sep. 25-28, 2019. Poster. Fifth CRI-CIMT-EATI-AACR International Cancer Immunotherapy Conference (2019): Translating Science into Survival. Paris. 1 page.
Frenzel et al., Phage display-derived human antibodies in clinical development and therapy. MAbs. Oct. 2016;8(7):1177-1194. doi: 10.1080/19420862.2016.1212149. Epub Jul. 14, 2016.
F-Star, Next-Generation Bispecifics for Cancer Immunotherapy. Feb. 2020. Presented on Mar. 11, 2020 at Immuno-Oncology Summit Europe 2020. London. 46 pages.
F-Star, Redirecting T Cells. Overcoming Cancer. Improving Lives. Oct. 2019 Presentation in Investor Meeting. 36 pages.
F-Star, Redirecting T Cells. Overcoming Cancer. Improving Lives. Apr. 2020 Presentation in Investor Meeting. 43 pages.
F-Star, Redirecting T Cells. Overcoming Cancer. Improving Lives. Jan. 2020 Presentation in Investor Meeting. 41 pages.
Gaspar et al., FS120 mAb2, a dual agonist bispecific antibody targeting OX40 and CD137, activates T cells in vitro and induces FcγR-independent anti-tumour activity. SITC 2018. Nov. 7, 2018. Poster. 10 pages.
Gaspar, FS120 mAb2, a dual agonist bispecific antibody targeting OX40 and CD137. SITC 2018. Nov. 11, 2018. Presentation. 12 pages.
Geuijen et al., Abstract 541: An unbiased screen identifies a CD137xPD-L1 bispecific IgG1 antibody with unique T cell activation and binding properties. Cancer Res. 2019;79(13_Supplement):541. Poster Presentation AACR Conference 2019. Jul. 1, 2019. doi: 10.1158/1538-7445.AM2019-541. 4 pages.
Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.
Gunde et al., Abstract 1532: A novel, monovalent tri-specific antibody-based molecule that simultaneously modulates PD-L1 and 4-1BB exhibits potent anti-tumoral activity in vivo. Cancer Res. 2019;79(13_Supplement):1532. AACR Conference 2019. Jul. 1, 2019. doi: 10.1158/1538-7445.AM2019-1532. 4 pages.
Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.
Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.
Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.
Ho et al., A novel high-affinity human monoclonal antibody to mesothelin. Int J Cancer. May 1, 2011;128(9):2020-30. doi: 10.1002/ijc.25557.
Kraman et al., Dual blockade of PD-L1 and LAG-3 with FS118, a unique bispecific antibody, induces CD8+ T-cell activation and modulates the tumour microenvironment to promote anti-tumour immune responses. Apr. 14-18, 2018. Poster 2719. Proceedings of the American Association for Cancer Research Annual Meeting 2018. Chicago, IL. 2 pages.
Kraman et al., Dual blockade of PD-L1 and LAG-3 with FS118, a unique bispecific antibody, induces T-cell activation with the potential to drive potent anti-tumour immune responses. Nov. 7, 2017;5 Suppl 2 (87):Abstract P348. 32nd Annual Meeting and Pre-Conference Programs of the Society for Immunotherapy of Cancer (SITC). Part II. Nov. 8-12, 2017. National Harbor, MD. 2 pages.
Kraman et al., Dual blockade of PD-L1 and LAG-3 with FS118, a unique bispecific antibody, induces T-cell activation with the potential to drive potent anti-tumour immune responses. Apr. 14-18, 2018;78(13 Suppl);Abstract 2719. Proceedings of the American Association for Cancer Research Annual Meeting 2018. Chicago, IL. 5 pages.
Kraman et al., Dual blockade of PD-L1 and LAG-3 with FS118, a unique bispecific antibody, induces T-cell activation with the potential to drive potent anti-tumour immune responses. Poster P348. 32nd Annual Meeting and Pre-Conference Programs of the Society for Immunotherapy of Cancer (SITC). Part II. Nov. 8-12, 2017. National Harbor, MD. 1 page.
Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.
Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.
Kvarnhammar et al., The CTLA-4 x OX40 bispecific antibody ATOR-1015 induces anti-tumor effects through tumor-directed immune activation. J Immunother Cancer. Apr. 11, 2019;7(1):103. doi: 10.1186/s40425-019-0570-8.
Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr 3, 2019. Atlanta, GA. Poster No. 1540. 1 page.
Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.
Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.

(56) References Cited

OTHER PUBLICATIONS

Li et al., Discovery and preclinical characterization of the antagonist anti-PD-L1 monoclonal antibody LY3300054. J Immunother Cancer. Apr. 30, 2018;6(1):31. doi: 10.1186/s40425-018-0329-7. Erratum in: J Immunother Cancer. Jun. 4, 2018;6(1):45.

Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.

Mayes et al., Abstract 539: A bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.

McCourt, Development of an ICOS/PD-L1 Bispecific, Mar. 18-22, 2019. Abstract. Cambridge Healthtech Institute's 4th Annual Immuno-Oncology Summit Europe 2019 (London).

Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.

Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.

Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.

Ryan et al., A novel biologic platform elicits profound T cell costimulatory activity and antitumor immunity in mice. Cancer Immunol Immunother. Apr. 2018;67(4):605-613. doi: 10.1007/s00262-018-2116-1. Epub Jan. 11, 2018.

Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.

Tuna, Delivering the next immuno-oncology breakthrough. PEGS Europe 2018. Nov. 11, 2018. Presentation. 24 pages.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. Jun. 1, 2019. Poster TPS2652. 2019 ASCO Annual Meeting Proceedings. 20 pages.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 4 pages.

Yap et al., Abstract TPS2652: A first-in-human phase I study of FS118, an anti-LAG-3/PD-L1 bispecific antibody in patients with solid tumors that have progressed on prior PD-1/PD-L1 therapy. Journal of Clinical Oncology. May 15, 2019;37(15_suppl). 2019 ASCO Annual Meeting Proceedings. 4 pages.

Yonezawa et al., Boosting Cancer Immunotherapy with Anti-CD137 Antibody Therapy. Clin Cancer Res. Jul. 15, 2015;21(14):3113-20. doi: 10.1158/1078-0432.CCR-15-0263. Epub Apr. 23, 2015.

Zhao et al., Novel Antibody Therapeutics Targeting Mesothelin In Solid Tumors. Clin Cancer Drugs. Oct. 2016;3(2):76-86. doi: 10.2174/2212697X03666160218215744.

International Search Report and Written Opinion for Application No. PCT/EP2019/068800, mailed Nov. 5, 2019.

International Preliminary Report on Patentability for Application No. PCT/EP2019/068800, mailed Jan. 21, 2021.

[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.

Asgarov et al., A new anti-mesothelin antibody targets selectively the membrane-associated form. MAbs. Apr. 2017;9(3):567-577. doi: 10.1080/19420862.2017.1288770.

Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.

Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.

Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).

Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.

Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.

Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.

Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.

Lobner et al., Engineered IgG1-Fc—one fragment to bind them all. Immunol Rev. Mar. 2016;270(1):113-31. doi: 10.1111/imr.12385.

Lobner et al., Two-faced Fcab prevents polymerization with VEGF and reveals thermodynamics and the 2.15 Å crystal structure of the complex. MAbs. Oct. 2017;9(7):1088-1104. doi: 10.1080/19420862.2017.1364825. Epub Aug. 17, 2017.

Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract P124).

Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.

Ramelet et al., Beneficial outcome of combination therapy with 4-1BB targeting antibody. Eur J Cancer. Nov. 29, 2016;69(Suppl 1):S96-S97.

Sallin et al., The anti-lymphoma activities of anti-CD137 monoclonal antibodies are enhanced in FcγRIII(−/−) mice. Cancer Immunol Immunother. Sep. 2014;63(9):947-58. doi: 10.1007/s00262-014-1567-2. Epub Jun. 14, 2014.

Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.

(56) References Cited

OTHER PUBLICATIONS

Shindo et al., Combination immunotherapy with 4-1BB activation and PD-1 blockade enhances antitumor efficacy in a mouse model of subcutaneous tumor. Anticancer Res. Jan. 2015;35(1):129-36.
Vilgelm et al., Combinatorial approach to cancer immunotherapy: strength in numbers. Journal of Leukocyte Biology. 2016;100(2):275-90. Epub Jun. 2, 2016.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.
Xu et al., In vitro characterization of five humanized OKT3 effector function variant antibodies. Cell Immunol. Feb. 2, 20005;200(1):16-26.
U.S. Appl. No. 16/955,450, filed Jun. 18, 2020, Tuna et al.
U.S. Appl. No. 17/259,634, filed Jan. 12, 2021, Munoz-Olaya et al.
U.S. Appl. No. 17/259,680, filed Jan. 12, 2021, Pechouckova et al.
U.S. Appl. No. 17/259,754, filed Jan. 12, 2021, Lakins et al.
U.S. Appl. No. 17/259,642, filed Jan. 12, 2021, Wollerton et al.
U.S. Appl. No. 17/259,714, filed Jan. 12, 2021, Tuna et al.
U.S. Appl. No. 17/259,791, filed Jan. 12, 2021, Lakins et al.
U.S. Appl. No. 17/259,796, filed Jan. 12, 2021, Tuna et al.
PCT/EP2019/068800, Nov. 5, 2019, International Search Report and Written Opinion.
PCT/EP2019/068800, Jan. 21, 2021, International Preliminary Report on Patentability.
Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.
Golfier et al., Anetumab ravtansine: a novel mesothelin-targeting antibody-drug conjugate cures tumors with heterogeneous target expression favored by bystander effect. Mol Cancer Ther. Jun. 2014;13(6):1537-48. doi: 10.1158/1535-7163.MCT-13-0926. Epub Apr. 8, 2014.
Schroeder, Chapter 13: Immunoglobulins and Their Genes. From Arthritis and Allied Conditions: A Textbook of Rheumatology. 15th Ed. vol 1. Eds Koopman et al.Lippincot Williams & Wilkins. pp. 289-304. Supplied by the British Library Jul. 31, 2023.
[No Author Listed], mesothelin isoform 1 preproprotein [*Homo sapiens*]. NCBI Reference Sequence: NP_001170826.1. May 2, 2024. Retrieved from https://www.ncbi.nlm.nih.gov/protein/NP_001170826.1/. 4 pages.
[No Author Listed], mesothelin isoform 1 preproprotein [Mus musculus]. NCBI Reference Sequence: NP_001343215.1. Jun. 18, 2024. Retrieved from https://www.ncbi.nlm.nih.gov/protein/NP_001343215.1. 3 pages.
[No Author Listed], Molecular biological basis of immunotherapy. New and Orphan Drugs for Leukemia Therapeutics. Sep. 30, 2016. 387-390. Retrieved on Dec. 18, 2023. 7 pages.
[No Author Listed], Predicted: mesothelin isoform X4 [Macaca fascicularis]. NCBI Reference Sequence: XP_005590874.2. Jan. 25, 2016. Retrieved from https://www.ncbi.nlm.nih.gov/protein/XP_005590874.2. 2 pages.
[No Author Listed], tumor necrosis factor receptor superfamily member 9 precursor [*Homo sapiens*]. NCBI Reference Sequence: NP_001552.2. Jun. 9, 2024. Retrieved from https://www.ncbi.nlm.nih.gov/protein/NP_001552.2. 4 pages.
Badri et al., Optimization of radiation dosing schedules for proneural glioblastoma. J Math Biol. Apr. 2016;72(5):1301-36. doi: 10.1007/s00285-015-0908-x.
Baylot et al., TCTP Has a Crucial Role in the Different Stages of Prostate Cancer Malignant Progression. Results Probl Cell Differ. 2017;64:255-261. doi: 10.1007/978-3-319-67591-6_13.
Chen et al., Enhancement and destruction of antibody function by somatic mutation: unequal occurrence is controlled by V gene combinatorial associations. Embo J. Jun. 15, 1995;14(12):2784-94. doi: 10.1002/j.1460-2075.1995.tb07278.x.
Cooper, The Development and Causes of Cancer. From The Cell: Molecular Approach. 2nd Ed. Sunderland, MA. Sinauer Associates. 2000. 9 pages.
Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
Han et al., Bispecific anti-CD3 x anti-HER2 antibody mediates T cell cytolytic activity to HER2-positive colorectal cancer in vitro and in vivo. Int J Oncol. Dec. 2014;45(6):2446-54. doi: 10.3892/ijo.2014.2663. Epub Sep. 18, 2014.
Heppner et al., Tumor heterogeneity: biological implications and therapeutic consequences. Cancer Metastasis Rev. 1983;2(1):5-23. doi: 10.1007/BF00046903.
Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.
Kussie et al., A single engineered amino acid substitution changes antibody fine specificity. J Immunol. Jan. 1, 1994;152(1):146-52.
Lin et al., Fc-dependent expression of CD137 on human NK cells: insights into "agonistic" effects of anti-CD137 monoclonal antibodies. Blood. Aug. 1, 2008;112(3):699-707. doi: 10.1182/blood-2007-11-122465. Epub Jun. 2, 2008.
Link et al., Abstract 3752: Preclinical pharmacology of MP0310: a 4-1BB/FAP bispecific DARPin drug candidate promoting tumor-restricted T-cell costimulation. Cancer Res. Jul. 1, 2018;78(13_Supplement):3752.
Liu et al., Abstract 3642: Tumor-antigen expression-dependent activation of the CD137 costimulatory pathway by bispecific DART® proteins. Cancer Res. Jul. 1, 2017;77(13_Supplement):3642.
Lo et al., Effector-attenuating Substitutions That Maintain Antibody Stability and Reduce Toxicity in Mice. J Biol Chem. Mar. 3, 2017;292(9):3900-3908. doi: 10.1074/jbc.M116.767749. Epub Jan. 11, 2017.
Muller et al., Spliceosomal peptide P140 for immunotherapy of systemic lupus erythematosus: results of an early phase II clinical trial. Arthritis Rheum. Dec. 2008;58(12):3873-83. doi: 10.1002/art.24027.
Reichen et al., Abstract 3029: FAP-mediated tumor accumulation of a T-cell agonistic FAP/4-1BB DARPin drug candidate analyzed by SPECT/CT and quantitative biodistribution. Cancer Res. Jul. 1, 2018;78(13_Supplement):3029.
Seckinger et al., Development and characterization of NILK-2301, a novel CEACAM5xCD3 κλ bispecific antibody for immunotherapy of CEACAM5-expressing cancers. J Hematol Oncol. Dec. 12, 2023;16(1):117. doi: 10.1186/s13045-023-01516-3.
Segal et al., Results from an Integrated Safety Analysis of Urelumab, an Agonist Anti-CD137 Monoclonal Antibody. Clin Cancer Res. Apr. 15, 2017;23(8):1929-1936. doi: 10.1158/1078-0432.CCR-16-1272. Epub Oct. 18, 2016.
Shen, et al. Single variable domain-IgG fusion. A novel recombinant approach to Fc domain-containing bispecific antibodies. J Biol Chem. Apr. 21, 2006;281(16):10706-14. doi: 10.1074/jbc.M513415200. Epub Feb. 15, 2006.
Torres et al., The immunoglobulin constant region contributes to affinity and specificity. Trends Immunol. Feb. 2008;29(2):91-7. doi: 10.1016/j.it.2007.11.004. Epub Jan. 10, 2008.
Wang et al., Retargeting T cells for HER2-positive tumor killing by a bispecific Fv-Fc antibody. PLoS One. Sep. 23, 2013;8(9):e75589. doi: 10.1371/journal.pone.0075589. eCollection 2013.
Durham et al., Lymphocyte Activation Gene 3 (LAG-3) modulates the ability of CD4 T-cells to be suppressed in vivo. PLoS One. Nov. 5, 2014;9(11):e109080. doi: 10.1371/journal.pone.0109080. 13 pages.
Gide et al., Distinct Immune Cell Populations Define Response to Anti-PD-1 Monotherapy and Anti-PD-1/Anti-CTLA-4 Combined Therapy. Cancer Cell. Feb. 11, 2019;35(2):238-255.e6. doi: 10.1016/j.ccell.2019.01.003.
Gough et al., OX40 agonist therapy enhances CD8 infiltration and decreases immune suppression in the tumor. Cancer Res. Jul. 1, 2008;68(13):5206-15. doi: 10.1158/0008-5472.CAN-07-6484.

(56) References Cited

OTHER PUBLICATIONS

Hong et al., An Agonistic Anti-CD137 Antibody Disrupts Lymphoid Follicle Structure and T-Cell-Dependent Antibody Responses. Cell Rep Med. Jun. 23, 2020;1(3):100035. doi: 10.1016/j.xcrm.2020.100035.

Kaas et al., IG, TR and IgSF, MHC and MhcSF: what do we learn from the IMGT Colliers de Perles? Brief Funct Genomic Proteomic. Dec. 2007;6(4):253-64. doi: 10.1093/bfgp/elm032. Epub Jan. 21, 2008.

Koyama et al., Adaptive resistance to therapeutic PD-1 blockade is associated with upregulation of alternative immune checkpoints. Nat Commun. Feb. 17, 2016;7:10501. doi: 10.1038/ncomms10501. 9 pages.

Matsuzaki et al., Tumor-infiltrating NY-ESO-1-specific CD8+ T cells are negatively regulated by LAG-3 and PD-1 in human ovarian cancer. Proc Natl Acad Sci U S A. Apr. 27, 2010;107(17):7875-80. doi: 10.1073/pnas.1003345107. Epub Apr. 12, 2010.

Otano et al., CD137 (4-1BB) costimulation of CD8+ T cells is more potent when provided in cis than in trans with respect to CD3-TCR stimulation. Nat Commun. Dec. 15, 2021;12(1):7296. doi: 10.1038/s41467-021-27613-w.

Shepherd et al., T Cell Immunity to Bacterial Pathogens: Mechanisms of Immune Control and Bacterial Evasion. Int J Mol Sci. Aug. 26, 2020;21(17):6144. doi: 10.3390/ijms21176144.

Turaj et al., Augmentation of CD134 (OX40)-dependent NK antitumour activity is dependent on antibody cross-linking. Sci Rep. Feb. 2, 2018;8(1):2278. doi: 10.1038/s41598-018-20656-y.

Ye et al., CD137, an attractive candidate for the immunotherapy of lung cancer. Cancer Sci. May 2020;111(5):1461-1467. doi: 10.1111/cas.14354. Epub Apr. 3, 2020.

Yuan et al., Contributions of Costimulatory Molecule CD137 in Endothelial Cells. J Am Heart Assoc. Jun. 2021;10(11):e020721. doi: 10.1161/JAHA.120.020721. Epub May 22, 2021.

* cited by examiner

SEQUENCE LISTING

```
<160> NUMBER OF SEQ ID NOS: 201

<210> SEQ ID NO 1
<211> LENGTH: 448
<212> TYPE: PRT
<213> ORGANISM: Artificial Sequence
<220> FEATURE:
<223> OTHER INFORMATION: FS28-256 heavy chain (without LALA)
<220> FEATURE:
<221> NAME/KEY: MISC_FEATURE
<222> LOCATION: (50)..(50)
```

```
<223> OTHER INFORMATION: Xaa can be any naturally occurring amino acid
<220> FEATURE:
<221> NAME/KEY: MISC_FEATURE
<222> LOCATION: (52)..(52)
<223> OTHER INFORMATION: Xaa can be any naturally occurring amino acid
<220> FEATURE:
<221> NAME/KEY: MISC_FEATURE
<222> LOCATION: (50)..(52)
<223> OTHER INFORMATION: Cannot be a glycosylation site

<400> SEQUENCE: 1

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Glu Thr
             20                  25                  30

Tyr Met Ser Trp Val Arg Gln Ala Pro Gly Lys Gly Leu Glu Trp Val
         35                  40                  45

Ser Xaa Ile Xaa Pro Thr Tyr Ser Thr Thr Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Tyr Asn Ser Tyr Gln Gly Gly Leu Asp Tyr Trp Gly Gln Gly
        100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                355                 360                 365
Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 2
<211> LENGTH: 448
<212> TYPE: PRT
<213> ORGANISM: Artificial Sequence
<220> FEATURE:
<223> OTHER INFORMATION: FS28-256 heavy chain (with LALA)
<220> FEATURE:
<221> NAME/KEY: MISC_FEATURE
<222> LOCATION: (50)..(50)
<223> OTHER INFORMATION: Xaa can be any naturally occurring amino acid
<220> FEATURE:
<221> NAME/KEY: MISC_FEATURE
<222> LOCATION: (52)..(52)
<223> OTHER INFORMATION: Xaa can be any naturally occurring amino acid
<220> FEATURE:
<221> NAME/KEY: MISC_FEATURE
<222> LOCATION: (50)..(52)
<223> OTHER INFORMATION: Cannot be a glycosylation site

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
                20                  25                  30

Tyr Met Ser Trp Val Arg Gln Ala Pro Gly Lys Gly Leu Glu Trp Val
            35                  40                  45

Ser Xaa Ile Xaa Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
```

```
                210                 215                 220
Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 3
<211> LENGTH: 215
<212> TYPE: PRT
<213> ORGANISM: Artificial Sequence
<220> FEATURE:
<223> OTHER INFORMATION: FS28-256-001, FS28-256-021 and FS28-256-023
      light chain
<220> FEATURE:
<221> NAME/KEY: MISC_FEATURE
<222> LOCATION: (97)..(97)
<223> OTHER INFORMATION: Xaa can be any naturally occurring amino acid
<220> FEATURE:
<221> NAME/KEY: MISC_FEATURE
<222> LOCATION: (98)..(98)
<223> OTHER INFORMATION: Xaa can be any naturally occurring amino acid
<220> FEATURE:
<221> NAME/KEY: MISC_FEATURE
<222> LOCATION: (97)..(98)
<223> OTHER INFORMATION: Cannot be a deamidation site

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Asn Gln Tyr Pro
                 85                  90                  95

Xaa Xaa Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 4
<211> LENGTH: 445
<212> TYPE: PRT
<213> ORGANISM: Artificial Sequence
<220> FEATURE:
<223> OTHER INFORMATION: heavy chain of FS28-024 mAb without LALA

<400> SEQUENCE: 4

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Leu Ser Tyr Ser
             20                  25                  30

Ser Met Ser Trp Val Arg Gln Ala Pro Gly Lys Gly Leu Glu Trp Val
         35                  40                  45

Ser Phe Ile Thr Pro Ser Thr Gly Tyr Thr His Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Leu Thr Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205
```

```
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
        260                 265                 270
Lys Phe Asn Trp Tyr Val Asp Gly Val Glu Val His Asn Ala Lys Thr
    275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
        340                 345                 350
Ser Arg Asp Glu Leu Thr Lys Asn Gln Val Ser Leu Thr Cys Leu Val
    355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
        420                 425                 430
Asn His Tyr Thr Gln Lys Ser Leu Ser Leu Ser Pro Gly
    435                 440                 445

<210> SEQ ID NO 5
<211> LENGTH: 445
<212> TYPE: PRT
<213> ORGANISM: Artificial Sequence
<220> FEATURE:
<223> OTHER INFORMATION: heavy chain of FS28-024 mAb with LALA

<400> SEQUENCE: 5

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Leu Ser Tyr Ser
            20                  25                  30
Ser Met Ser Trp Val Arg Gln Ala Pro Gly Lys Gly Leu Glu Trp Val
        35                  40                  45
Ser Phe Ile Thr Pro Ser Thr Gly Tyr Thr His Tyr Ala Asp Ser Val
    50                  55                  60
Lys Gly Arg Phe Thr Ile Ser Arg Asp Asn Lys Asn Thr Leu Tyr
65                  70                  75                  80
Leu Gln Met Asn Ser Leu Arg Ala Glu Asp Thr Ala Val Tyr Tyr Cys
            85                  90                  95
Ala Arg Arg Ala Leu Thr Phe Asp Tyr Trp Gly Gln Gly Thr Leu Val
        100                 105                 110
Thr Val Ser Ser Ala Ser Thr Lys Gly Pro Ser Val Phe Pro Leu Ala
    115                 120                 125
```

| | | | | | | | | | | | |
|---|---|---|---|---|---|---|---|---|---|---|---|
| Pro | Ser | Ser | Lys | Ser | Thr | Ser | Gly | Gly | Thr | Ala | Ala | Leu | Gly | Cys | Leu |
| | 130 | | | | 135 | | | | 140 | | |

(Amino acid sequence continued)

Pro Ser Ser Lys Ser Thr Ser Gly Gly Thr Ala Ala Leu Gly Cys Leu
　　130　　　　　　　135　　　　　　　140

Val Lys Asp Tyr Phe Pro Glu Pro Val Thr Val Ser Trp Asn Ser Gly
145　　　　　　　150　　　　　　　155　　　　　　　160

Ala Leu Thr Ser Gly Val His Thr Phe Pro Ala Val Leu Gln Ser Ser
　　　　　　165　　　　　　　170　　　　　　　175

Gly Leu Tyr Ser Leu Ser Ser Val Val Thr Val Pro Ser Ser Ser Leu
　　　　180　　　　　　　185　　　　　　　190

Gly Thr Gln Thr Tyr Ile Cys Asn Val Asn His Lys Pro Ser Asn Thr
　　195　　　　　　　200　　　　　　　205

Lys Val Asp Lys Lys Val Glu Pro Lys Ser Cys Asp Lys Thr His Thr
210　　　　　　　215　　　　　　　220

Cys Pro Pro Cys Pro Ala Pro Glu Ala Ala Gly Gly Pro Ser Val Phe
225　　　　　　　230　　　　　　　235　　　　　　　240

Leu Phe Pro Pro Lys Pro Lys Asp Thr Leu Met Ile Ser Arg Thr Pro
　　　　　　245　　　　　　　250　　　　　　　255

Glu Val Thr Cys Val Val Val Asp Val Ser His Glu Asp Pro Glu Val
　　　　260　　　　　　　265　　　　　　　270

Lys Phe Asn Trp Tyr Val Asp Gly Val Glu Val His Asn Ala Lys Thr
275　　　　　　　280　　　　　　　285

Lys Pro Arg Glu Glu Gln Tyr Asn Ser Thr Tyr Arg Val Val Ser Val
290　　　　　　　295　　　　　　　300

Leu Thr Val Leu His Gln Asp Trp Leu Asn Gly Lys Glu Tyr Lys Cys
305　　　　　　　310　　　　　　　315　　　　　　　320

Lys Val Ser Asn Lys Ala Leu Pro Ala Pro Ile Glu Lys Thr Ile Ser
　　　　　　325　　　　　　　330　　　　　　　335

Lys Ala Lys Gly Gln Pro Arg Glu Pro Gln Val Tyr Thr Leu Pro Pro
　　　　340　　　　　　　345　　　　　　　350

Ser Arg Asp Glu Leu Thr Lys Asn Gln Val Ser Leu Thr Cys Leu Val
　　　　355　　　　　　　360　　　　　　　365

Lys Gly Phe Tyr Pro Ser Asp Ile Ala Val Glu Trp Glu Ser Asn Gly
370　　　　　　　375　　　　　　　380

Gln Pro Glu Asn Asn Tyr Lys Thr Thr Pro Pro Val Leu Asp Ser Asp
385　　　　　　　390　　　　　　　395　　　　　　　400

Gly Ser Phe Phe Leu Tyr Ser Lys Leu Thr Val Asp Lys Ser Arg Trp
　　　　　　405　　　　　　　410　　　　　　　415

Gln Gln Gly Asn Val Phe Ser Cys Ser Val Met His Glu Ala Leu His
　　　　　　420　　　　　　　425　　　　　　　430

Asn His Tyr Thr Gln Lys Ser Leu Ser Leu Ser Pro Gly
　　　　435　　　　　　　440　　　　　　　445

<210> SEQ ID NO 6
<211> LENGTH: 1335
<212> TYPE: DNA
<213> ORGANISM: Artificial Sequence
<220> FEATURE:
<223> OTHER INFORMATION: heavy chain of FS28-024 mAb without LALA

<400> SEQUENCE: 6

```
gaagtgcaac tgctggagtc cggtggtggt ctggtacagc cgggtggttc tctgcgtctg     60
agttgcgcgg ccagtggctt taccctcagt tattcttcta tgtcatgggt gcgtcaggct    120
ccgggcaaag gtctggaatg ggttagcttt attactccgt ctactggcta tacccactat    180
gcggatagcg tgaaaggccg ttttaccatt tctcgcgaca acagcaagaa cacgctgtac    240
ctgcagatga actcactgcg tgccgaagat acggccgtgt attactgtgc gagacgggcg    300
```

```
ctgacgttcg actactgggg ccagggaacc ttggtcaccg tctcgagtgc tagcactaag    360
ggcccgtcgg tgttcccgct ggccccatcg tccaagagca catcagggg taccgccgcc     420
ctgggctgcc ttgtgaagga ttactttccc gagcccgtca cagtgtcctg aacagcgga    480
gccctgacct ccggagtgca tactttcccg gctgtgcttc agtcctctgg cctgtactca    540
ttgtcctccg tggtcaccgt cccttcgtcc tccctgggca cccagaccta tatctgtaat    600
gtcaaccata agccctcgaa caccaaggtc gacaagaagg tcgagccgaa gtcgtgcgac    660
aagactcaca cttgcccgcc ttgcccagcc ccggaactgc tgggtggtcc ttcggtgttc    720
ctcttcccgc ccaagccgaa ggatacctg atgatctcac ggaccccga agtgacctgt     780
gtggtggtgg acgtgtccca cgaggacccg gaagtgaaat caattggta cgtggatgga    840
gtggaagtgc acaacgccaa gaccaagcca cgggaagaac agtacaactc tacctaccgc    900
gtggtgtccg tgctcactgt gctgcaccaa gactggctga cgggaagga gtacaagtgc    960
aaagtgtcca acaaggcgct gcctgcccca attgagaaaa ctatctcgaa agccaaggga   1020
cagcctcgag agcctcaagt gtacaccctg cctccctctc gggacgagct gaccaagaac   1080
caagtctccc tgacctgtct ggtcaaggga ttctacccat cggatatcgc cgtgaatgg    1140
gaaagcaacg gacagcccga gaacaactac aagacgactc cgcccgtgct ggattccgac   1200
gggagcttct tcttgtactc caagctgacc gtcgacaaga gcagatggca gcagggaaac   1260
gtgttctcct gctccgtgat gcatgaggcg ctgcacaacc actacactca gaagagcttg   1320
tccctgtcgc ccgga                                                     1335

<210> SEQ ID NO 7
<211> LENGTH: 1335
<212> TYPE: DNA
<213> ORGANISM: Artificial Sequence
<220> FEATURE:
<223> OTHER INFORMATION: heavy chain of FS28-024 mAb with LALA

<400> SEQUENCE: 7
gaagtgcaac tgctggagtc cggtggtggt ctggtacagc cgggtggttc tctgcgtctg     60
agttgcgcgg ccagtggctt taccctcagt tattcttcta tgtcatgggt gcgtcaggct    120
ccgggcaaag gtctggaatg ggttagcttt attactccgt ctactggcta tacccactat    180
gcggatagcg tgaaaggccg ttttaccatt tctcgcgaca acagcaagaa cacgctgtac    240
ctgcagatga actcactgcg tgccgaagat acggccgtgt attactgtgc gagacgggcg    300
ctgacgttcg actactgggg ccagggaacc ttggtcaccg tctcgagtgc tagcactaag    360
ggcccgtcgg tgttcccgct ggccccatcg tccaagagca catcagggg taccgccgcc     420
ctgggctgcc ttgtgaagga ttactttccc gagcccgtca cagtgtcctg aacagcgga    480
gccctgacct ccggagtgca tactttcccg gctgtgcttc agtcctctgg cctgtactca    540
ttgtcctccg tggtcaccgt cccttcgtcc tccctgggca cccagaccta tatctgtaat    600
gtcaaccata agccctcgaa caccaaggtc gacaagaagg tcgagccgaa gtcgtgcgac    660
aagactcaca cttgcccgcc ttgcccagcc ccggaagctg ccggtggtcc ttcggtgttc    720
ctcttcccgc ccaagccgaa ggatacctg atgatctcac ggaccccga agtgacctgt     780
gtggtggtgg acgtgtccca cgaggacccg gaagtgaaat caattggta cgtggatgga    840
gtggaagtgc acaacgccaa gaccaagcca cgggaagaac agtacaactc tacctaccgc    900
gtggtgtccg tgctcactgt gctgcaccaa gactggctga cgggaagga gtacaagtgc    960
```

```
aaagtgtcca acaaggcgct gcctgcccca attgagaaaa ctatctcgaa agccaaggga   1020
cagcctcgag agcctcaagt gtacaccctg cctccctctc gggacgagct gaccaagaac   1080
caagtctccc tgacctgtct ggtcaaggga ttctacccat cggatatcgc cgtggaatgg   1140
gaaagcaacg gacagcccga gaacaactac aagacgactc cgcccgtgct ggattccgac   1200
gggagcttct tcttgtactc caagctgacc gtcgacaaga gcagatggca gcagggaaac   1260
gtgttctcct gctccgtgat gcatgaggcg ctgcacaacc actacactca gaagagcttg   1320
tccctgtcgc ccgga                                                    1335
```

<210> SEQ ID NO 8
<211> LENGTH: 116
<212> TYPE: PRT
<213> ORGANISM: Artificial Sequence
<220> FEATURE:
<223> OTHER INFORMATION: FS28-024 mAb variable domain

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Thr Phe Asp Tyr Trp Gly Gln Gly Thr Leu Val
            100                 105                 110

Thr Val Ser Ser
        115
```

<210> SEQ ID NO 9
<211> LENGTH: 348
<212> TYPE: DNA
<213> ORGANISM: Artificial Sequence
<220> FEATURE:
<223> OTHER INFORMATION: FS28-024 mAb variable domain

<400> SEQUENCE: 9

```
gaagtgcaac tgctggagtc cggtggtggt ctggtacagc cgggtggttc tctgcgtctg   60
agttgcgcgg ccagtggctt taccctcagt tattcttcta tgtcatgggt gcgtcaggct   120
ccgggcaaag gtctggaatg ggttagcttt attactccgt ctactggcta taccactat    180 gcggatagcg tgaaaggccg ttttaccatt tctcgcgaca acagcaagaa cacgctgtac   240
ctgcagatga actcactgcg tgccgaagat acggccgtgt attactgtgc gagacgggcg   300
ctgacgttcg actactgggg ccagggaacc ttggtcaccg tctcgagt               348
```

<210> SEQ ID NO 10
<211> LENGTH: 8
<212> TYPE: PRT
<213> ORGANISM: Artificial Sequence
<220> FEATURE:
<223> OTHER INFORMATION: FS28-024 mAb CDR1 (IMGT)

<400> SEQUENCE: 10

```
Gly Phe Thr Leu Ser Tyr Ser Ser
1               5
```

<210> SEQ ID NO 11
<211> LENGTH: 8
<212> TYPE: PRT
<213> ORGANISM: Artificial Sequence
<220> FEATURE:
<223> OTHER INFORMATION: FS28-024 mAb CDR2 (IMGT)

<400> SEQUENCE: 11

```
Ile Thr Pro Ser Thr Gly Tyr Thr
1               5
```

<210> SEQ ID NO 12
<211> LENGTH: 9
<212> TYPE: PRT
<213> ORGANISM: Artificial Sequence
<220> FEATURE:
<223> OTHER INFORMATION: FS28-024 mAb CDR3 (IMGT)

<400> SEQUENCE: 12

```
Ala Arg Arg Ala Leu Thr Phe Asp Tyr
1               5
```

<210> SEQ ID NO 13
<211> LENGTH: 5
<212> TYPE: PRT
<213> ORGANISM: Artificial Sequence
<220> FEATURE:
<223> OTHER INFORMATION: FS28-024 mAb CDR1 (Kabat)

<400> SEQUENCE: 13

```
Tyr Ser Ser Met Ser
1               5
```

<210> SEQ ID NO 14
<211> LENGTH: 17
<212> TYPE: PRT
<213> ORGANISM: Artificial Sequence
<220> FEATURE:
<223> OTHER INFORMATION: FS28-024 mAb CDR2 (Kabat)

<400> SEQUENCE: 14

```
Phe Ile Thr Pro Ser Thr Gly Tyr Thr His Tyr Ala Asp Ser Val Lys
1               5                   10                  15

Gly
```

<210> SEQ ID NO 15
<211> LENGTH: 7
<212> TYPE: PRT
<213> ORGANISM: Artificial Sequence
<220> FEATURE:
<223> OTHER INFORMATION: FS28-024 mAb CDR3 (Kabat)

<400> SEQUENCE: 15

```
Arg Ala Leu Thr Phe Asp Tyr
1               5
```

<210> SEQ ID NO 16
<211> LENGTH: 215
<212> TYPE: PRT
<213> ORGANISM: Artificial Sequence
<220> FEATURE:
<223> OTHER INFORMATION: light chain of FS28-024 mAb

<400> SEQUENCE: 16

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Ala Ser Ser Tyr Pro
                85                  90                  95
Leu Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 17
<211> LENGTH: 645
<212> TYPE: DNA
<213> ORGANISM: Artificial Sequence
<220> FEATURE:
<223> OTHER INFORMATION: light chain of FS28-024 mAb

<400> SEQUENCE: 17

```
gaaattgtgc tgacccagtc tccgggcacg ttatctctga gccctggtga gcgcgccact      60
ctgtcatgcc gggcttctca aagtgttagc agtagctacc tggcgtggta tcagcaaaaa     120
ccgggccagg ccccgcgtct gctgatttac ggtgcatcca gccgtgccac cggcattcca     180
gatcgttttt ccggtagtgg ttctgggacg gacttcactc tgacaatctc acgcctggaa     240
ccggaggatt ttgcggtgta ttactgccag caagcttctt cttatcctct cacgttcggc     300
caagggacca aggtggaaat caaacgtact gtggccgctc ctagcgtgtt cattttccg      360
ccatccgacg agcagctcaa gtccggcacc gcctccgtgg tctgcctgct caacaacttc     420
taccctcgcg aagctaaggt ccagtggaag gtcgacaatg ccctgcagtc cggaaactcg     480
caggaaagcg tgactgaaca ggactccaag gactccacct attcactgtc ctcgactctg     540
accctgagca aggcggatta cgaaaagcac aaagtgtacg catgcgaagt gacccaccag     600
ggtctttcgt cccccgtgac caagagcttc aacagaggag agtgt                     645
```

<210> SEQ ID NO 18
<211> LENGTH: 108

<212> TYPE: PRT
<213> ORGANISM: Artificial Sequence
<220> FEATURE:
<223> OTHER INFORMATION: variable domain of FS28-024 mAb

<400> SEQUENCE: 18

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Ala Ser Ser Tyr Pro
                85                  90                  95
Leu Thr Phe Gly Gln Gly Thr Lys Val Glu Ile Lys
            100                 105
```

<210> SEQ ID NO 19
<211> LENGTH: 324
<212> TYPE: DNA
<213> ORGANISM: Artificial Sequence
<220> FEATURE:
<223> OTHER INFORMATION: variable domain of FS28-024 mAb

<400> SEQUENCE: 19

```
gaaattgtgc tgacccagtc tccgggcacg ttatctctga gccctggtga gcgcgccact    60
ctgtcatgcc gggcttctca aagtgttagc agtagctacc tggcgtggta tcagcaaaaa   120
ccgggccagg ccccgcgtct gctgatttac ggtgcatcca gccgtgccac cggcattcca   180
gatcgttttt ccggtagtgg ttctgggacg gacttcactc tgacaatctc acgcctggaa   240
ccggaggatt ttgcggtgta ttactgccag caagcttctt cttatcctct cacgttcggc   300
caagggacca aggtggaaat caaa                                          324
```

<210> SEQ ID NO 20
<211> LENGTH: 7
<212> TYPE: PRT
<213> ORGANISM: Artificial Sequence
<220> FEATURE:
<223> OTHER INFORMATION: FS28-024 mAb (IMGT) CDR1

<400> SEQUENCE: 20

```
Gln Ser Val Ser Ser Ser Tyr
1               5
```

<210> SEQ ID NO 21
<211> LENGTH: 3
<212> TYPE: PRT
<213> ORGANISM: Artificial Sequence
<220> FEATURE:
<223> OTHER INFORMATION: FS28-024 mAb (IMGT) CDR2

<400> SEQUENCE: 21

```
Gly Ala Ser
1
```

<210> SEQ ID NO 22
<211> LENGTH: 9

```
<212> TYPE: PRT
<213> ORGANISM: Artificial Sequence
<220> FEATURE:
<223> OTHER INFORMATION: FS28-024 mAb (IMGT) CDR3

<400> SEQUENCE: 22

Gln Gln Ala Ser Ser Tyr Pro Leu Thr
1               5

<210> SEQ ID NO 23
<211> LENGTH: 12
<212> TYPE: PRT
<213> ORGANISM: Artificial Sequence
<220> FEATURE:
<223> OTHER INFORMATION: FS28-024 mAb (Kabat) CDR1

<400> SEQUENCE: 23

Arg Ala Ser Gln Ser Val Ser Ser Ser Tyr Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: FS28-024 mAb (Kabat) CDR2

<400> SEQUENCE: 24

Gly Ala Ser Ser Arg Ala Thr
1               5

<210> SEQ ID NO 25
<211> LENGTH: 9
<212> TYPE: PRT
<213> ORGANISM: Artificial Sequence
<220> FEATURE:
<223> OTHER INFORMATION: FS28-256 mAb  CDR3 (IMGT)

<400> SEQUENCE: 25

Gln Gln Ser Tyr Tyr Tyr Pro Ile Thr
1               5

<210> SEQ ID NO 26
<211> LENGTH: 445
<212> TYPE: PRT
<213> ORGANISM: Artificial Sequence
<220> FEATURE:
<223> OTHER INFORMATION: FS28-024-051 mAb heavy chain without LALA

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Ile Phe Asp Tyr Trp Gly Gln Gly Thr Leu Val
            100                 105                 110
```

Thr Val Ser Ser Ala Ser Thr Lys Gly Pro Ser Val Phe Pro Leu Ala
              115                 120                 125

Pro Ser Ser Lys Ser Thr Ser Gly Gly Thr Ala Ala Leu Gly Cys Leu
          130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
              165                 170                 175

Gly Leu Tyr Ser Leu Ser Ser Val Val Thr Val Pro Ser Ser Ser Leu
              180                 185                 190

Gly Thr Gln Thr Tyr Ile Cys Asn Val Asn His Lys Pro Ser Asn Thr
              195                 200                 205

Lys Val Asp Lys Lys Val Glu Pro Lys Ser Cys Asp Lys Thr His Thr
          210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
              245                 250                 255

Glu Val Thr Cys Val Val Val Asp Val Ser His Glu Asp Pro Glu Val
              260                 265                 270

Lys Phe Asn Trp Tyr Val Asp Gly Val Glu Val His Asn Ala Lys Thr
              275                 280                 285

Lys Pro Arg Glu Glu Gln Tyr Asn Ser Thr Tyr Arg Val Val Ser Val
          290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
              325                 330                 335

Lys Ala Lys Gly Gln Pro Arg Glu Pro Gln Val Tyr Thr Leu Pro Pro
              340                 345                 350

Ser Arg Asp Glu Leu Thr Lys Asn Gln Val Ser Leu Thr Cys Leu Val
              355                 360                 365

Lys Gly Phe Tyr Pro Ser Asp Ile Ala Val Glu Trp Glu Ser Asn Gly
          370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
              405                 410                 415

Gln Gln Gly Asn Val Phe Ser Cys Ser Val Met His Glu Ala Leu His
              420                 425                 430

Asn His Tyr Thr Gln Lys Ser Leu Ser Leu Ser Pro Gly
              435                 440                 445

<210> SEQ ID NO 27
<211> LENGTH: 1335
<212> TYPE: DNA
<213> ORGANISM: Artificial Sequence
<220> FEATURE:
<223> OTHER INFORMATION: FS28-024-051 mAb heavy chain without LALA

<400> SEQUENCE: 27
gaagtgcaac tgctggagtc cggtggtggt ctggtacagc cgggtggttc tctgcgtctg      60
agttgcgcgg ccagtggctt taccctcagt tattcttcta tgtcatgggt cgtcaggct     120 ccgggcaaag gtctggaatg ggttagcttt attactccgt ctactggcta taccactat     180

```
gcggatagcg tgaaaggccg ttttaccatt tctcgcgaca acagcaagaa cacgctgtac    240
ctgcagatga actcactgcg tgccgaagat acggccgtgt attactgtgc gagacgggcg    300
ctgattttcg actactgggg ccagggaacc ctggtcaccg tctcgagtgc tagcactaag    360
ggcccgtcgg tgttcccgct ggccccatcg tccaagagca catcaggggg taccgccgcc    420
ctgggctgcc ttgtgaagga ttactttccc gagcccgtca cagtgtcctg aacagcgga    480 gccctgacct ccgagtgca tactttccg gctgtgcttc agtcctctgg cctgtactca    540
ttgtcctccg tggtcaccgt cccttcgtcc tccctgggca cccagaccta tatctgtaat    600
gtcaaccata agccctcgaa caccaaggtc gacaagaagg tcgagccgaa gtcgtgcgac    660
aagactcaca cttgcccgcc ttgcccagcc ccggaactgc tgggtggtcc ttcggtgttc    720
ctcttcccgc caagccgaa ggataccctg atgatctcac ggacccccga agtgacctgt    780
gtggtggtgg acgtgtccca cgaggacccg gaagtgaaat caattggta cgtggatgga    840 gtggaagtgc acaacgccaa gaccaagcca cgggaagaac agtacaactc tacctaccgc    900
gtggtgtccg tgctcactgt gctgcaccaa gactggctga cgggaagga gtacaagtgc    960 aaagtgtcca acaaggcgct gcctgcccca attgagaaaa ctatctcgaa agccaaggga   1020
cagcctcgag agcctcaagt gtacaccctg cctccctctc gggacgagct gaccaagaac   1080
caagtctccc tgacctgtct ggtcaaggga ttctacccat cggatatcgc cgtggaatgg   1140
gaaagcaacg gacagcccga gaacaactac aagacgactc cgcccgtgct ggattccgac   1200
gggagcttct tcttgtactc caagctgacc gtcgacaaga gcagatggca gcagggaaac   1260
gtgttctcct gctccgtgat gcatgaggcg ctgcacaacc actacactca gaagagcttg   1320
tccctgtcgc ccgga                                                    1335
```

<210> SEQ ID NO 28
<211> LENGTH: 445
<212> TYPE: PRT
<213> ORGANISM: Artificial Sequence
<220> FEATURE:
<223> OTHER INFORMATION: FS28-024-051 mAb heavy chain with LALA

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
```

```
            145                 150                 155                 160
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
            435                 440                 445

<210> SEQ ID NO 29
<211> LENGTH: 1335
<212> TYPE: DNA
<213> ORGANISM: Artificial Sequence
<220> FEATURE:
<223> OTHER INFORMATION: FS28-024-051 mAb heavy chain with LALA

<400> SEQUENCE: 29
gaagtgcaac tgctggagtc cggtggtggt ctggtacagc cgggtggttc tctgcgtctg      60
agttgcgcgg ccagtggctt taccctcagt tattcttcta tgtcatgggt gcgtcaggct     120
ccgggcaaag gtctggaatg ggttagcttt attactccgt ctactggcta taccactat     180 gcggatagcg tgaaaggccg ttttaccatt tctcgcgaca acagcaagaa cacgctgtac     240
ctgcagatga actcactgcg tgccgaagat acggccgtgt attactgtgc gagacgggcg     300
ctgattttcg actactgggg ccagggaacc ctggtcaccg tctcgagtgc tagcactaag     360
ggcccgtcgg tgttcccgct ggccccatcg tccaagagca catcaggggg taccgccgcc     420
```

```
ctgggctgcc ttgtgaagga ttactttccc gagcccgtca cagtgtcctg gaacagcgga      480
gccctgacct ccggagtgca tactttcccg gctgtgcttc agtcctctgg cctgtactca      540
ttgtcctccg tggtcaccgt cccttcgtcc tccctgggca cccagaccta tatctgtaat      600
gtcaaccata agccctcgaa caccaaggtc gacaagaagg tcgagccgaa gtcgtgcgac      660
aagactcaca cttgcccgcc ttgcccagcc ccggaagctg ccggtggtcc ttcggtgttc      720
ctcttcccgc caagcccgaa ggataccctg atgatctcac ggaccccga agtgacctgt       780 gtggtggtgg acgtgtccca cgaggacccg gaagtgaaat tcaattggta cgtggatgga      840
gtggaagtgc acaacgccaa gaccaagcca cgggaagaac agtacaactc tacctaccgc      900
gtggtgtccg tgctcactgt gctgcaccaa gactggctga acgggaagga gtacaagtgc      960
aaagtgtcca acaaggcgct gcctgcccca attgagaaaa ctatctcgaa agccaaggga     1020
cagcctcgag agcctcaagt gtacaccctg cctccctctc gggacgagct gaccaagaac     1080
caagtctccc tgacctgtct ggtcaaggga ttctacccat cggatatcgc cgtggaatgg     1140
gaaagcaacg gacagcccga gaacaactac aagacgactc cgcccgtgct ggattccgac     1200
gggagcttct tcttgtactc caagctgacc gtcgacaaga gcagatggca gcagggaaac     1260
gtgttctcct gctccgtgat gcatgaggcg ctgcacaacc actacactca gaagagcttg     1320
tccctgtcgc ccgga                                                      1335

<210> SEQ ID NO 30
<211> LENGTH: 116
<212> TYPE: PRT
<213> ORGANISM: Artificial Sequence
<220> FEATURE:
<223> OTHER INFORMATION: FS28-024-051 mAb variable domain

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Ile Phe Asp Tyr Trp Gly Gln Gly Thr Leu Val
            100                 105                 110

Thr Val Ser Ser
        115

<210> SEQ ID NO 31
<211> LENGTH: 348
<212> TYPE: DNA
<213> ORGANISM: Artificial Sequence
<220> FEATURE:
<223> OTHER INFORMATION: FS28-024-051 mAb variable domain

<400> SEQUENCE: 31
gaagtgcaac tgctggagtc cggtggtggt ctggtacagc cgggtggttc tctgcgtctg       60
```

```
agttgcgcgg ccagtggctt taccctcagt tattcttcta tgtcatgggt gcgtcaggct    120
ccgggcaaag gtctggaatg ggttagcttt attactccgt ctactggcta tacccactat    180
gcggatagcg tgaaaggccg ttttaccatt tctcgcgaca acagcaagaa cacgctgtac    240
ctgcagatga actcactgcg tgccgaagat acggccgtgt attactgtgc gagacgggcg    300
ctgattttcg actactgggg ccagggaacc ctggtcaccg tctcgagt                 348
```

```
<210> SEQ ID NO 32
<211> LENGTH: 9
<212> TYPE: PRT
<213> ORGANISM: Artificial Sequence
<220> FEATURE:
<223> OTHER INFORMATION: FS28-024-051 mAb CDR3 (IMGT)

<400> SEQUENCE: 32

Ala Arg Arg Ala Leu Ile Phe Asp Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: FS28-024-051 mAb CDR3 (Kabat)

<400> SEQUENCE: 33

Arg Ala Leu Ile Phe Asp Tyr
1               5

<210> SEQ ID NO 34
<211> LENGTH: 9
<212> TYPE: PRT
<213> ORGANISM: Artificial Sequence
<220> FEATURE:
<223> OTHER INFORMATION: FS28-256-001 mAb  CDR3 (IMGT) and (Kabat)

<400> SEQUENCE: 34

Gln Gln His Asn Gln Tyr Pro Asn Thr
1               5

<210> SEQ ID NO 35
<211> LENGTH: 445
<212> TYPE: PRT
<213> ORGANISM: Artificial Sequence
<220> FEATURE:
<223> OTHER INFORMATION: FS28-024-052 mAb heavy chain without LALA

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110
```

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 36
<211> LENGTH: 1335
<212> TYPE: DNA
<213> ORGANISM: Artificial Sequence
<220> FEATURE:
<223> OTHER INFORMATION: FS28-024-052 mAb heavy chain without LALA

<400> SEQUENCE: 36
gaagtgcaac tgctggagtc cggtggtggt ctggtacagc cgggtggttc tctgcgtctg      60
agttgcgcgg ccagtggctt taccctcagt tattcttcta tgtcatgggt gcgtcaggct     120
ccgggcaaag gtctggaatg ggttagcttt attactccgt ctactggcta tcccactat     180
```

```
gcggatagcg tgaaaggccg ttttaccatt tctcgcgaca acagcaagaa cacgctgtac    240
ctgcagatga actcactgcg tgccgaagat acggccgtgt attactgtgc gagacgggcg    300
ctgcttttcg actactgggg ccagggaacc ctggtcaccg tctcgtcggc tagcactaag    360
ggcccgtcgg tgttcccgct ggccccatcg tccaagagca catcaggggg taccgccgcc    420
ctgggctgcc ttgtgaagga ttactttccc gagcccgtca cagtgtcctg aacagcgga    480 gccctgacct ccgagtgca tactttccg gctgtgcttc agtcctctgg cctgtactca    540
ttgtcctccg tggtcaccgt cccttcgtcc tccctgggca cccagaccta tatctgtaat    600
gtcaaccata agccctcgaa caccaaggtc gacaagaagg tcgagccgaa gtcgtgcgac    660
aagactcaca cttgcccgcc ttgcccagcc ccggaactgc tgggtggtcc ttcggtgttc    720
ctcttcccgc caagccgaa ggatacccctg atgatctcac ggaccccga agtgacctgt    780 gtggtggtgg acgtgtccca cgaggacccg gaagtgaaat tcaattggta cgtggatgga    840
gtggaagtgc acaacgccaa gaccaagcca cgggaagaac agtacaactc tacctaccgc    900
gtggtgtccg tgctcactgt gctgcaccaa gactggctga acgggaagga gtacaagtgc    960
aaagtgtcca acaaggcgct gcctgcccca attgagaaaa ctatctcgaa gccaagggga   1020
cagcctcgag agcctcaagt gtacaccctg cctccctctc gggacgagct gaccaagaac   1080
caagtctccc tgacctgtct ggtcaaggga ttctacccat cggatatcgc cgtggaatgg   1140
gaaagcaacg gacagcccga gaacaactac aagacgactc cgcccgtgct ggattccgac   1200
gggagcttct tcttgtactc caagctgacc gtcgacaaga gcagatggca gcagggaaac   1260
gtgttctcct gctccgtgat gcatgaggcg ctgcacaacc actacactca gaagagcttg   1320
tccctgtcgc ccgga                                                    1335
```

<210> SEQ ID NO 37
<211> LENGTH: 445
<212> TYPE: PRT
<213> ORGANISM: Artificial Sequence
<220> FEATURE:
<223> OTHER INFORMATION: FS28-024-052 mAb heavy chain with LALA

<400> SEQUENCE: 37

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
```

```
                145                 150                 155                 160
Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
                    180                 185                 190

Gly Thr Gln Thr Tyr Ile Cys Asn Val Asn His Lys Pro Ser Asn Thr
                    195                 200                 205

Lys Val Asp Lys Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                    245                 250                 255

Glu Val Thr Cys Val Val Val Asp Val Ser His Glu Asp Pro Glu Val
                    260                 265                 270

Lys Phe Asn Trp Tyr Val Asp Gly Val Glu Val His Asn Ala Lys Thr
                    275                 280                 285

Lys Pro Arg Glu Glu Gln Tyr Asn Ser Thr Tyr Arg Val Val Ser Val
                    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                    325                 330                 335

Lys Ala Lys Gly Gln Pro Arg Glu Pro Gln Val Tyr Thr Leu Pro Pro
                    340                 345                 350

Ser Arg Asp Glu Leu Thr Lys Asn Gln Val Ser Leu Thr Cys Leu Val
                    355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                    405                 410                 415

Gln Gln Gly Asn Val Phe Ser Cys Ser Val Met His Glu Ala Leu His
                    420                 425                 430

Asn His Tyr Thr Gln Lys Ser Leu Ser Leu Ser Pro Gly
                    435                 440                 445

<210> SEQ ID NO 38
<211> LENGTH: 1335
<212> TYPE: DNA
<213> ORGANISM: Artificial Sequence
<220> FEATURE:
<223> OTHER INFORMATION: FS28-024-052 mAb heavy chain with LALA

<400> SEQUENCE: 38
gaagtgcaac tgctggagtc cggtggtggt ctggtacagc cgggtggttc tctgcgtctg      60
agttgcgcgg ccagtggctt taccctcagt tattcttcta tgtcatgggt gcgtcaggct     120
ccgggcaaag gtctggaatg ggttagcttt attactccgt ctactggcta tcccactat      180 gcggatagcg tgaaaggccg ttttaccatt tctcgcgaca acagcaagaa cacgctgtac     240
ctgcagatga actcactgcg tgccgaagat acggccgtgt attactgtgc gagacgggcg     300
ctgcttttcg actactgggg ccagggaacc ctggtcaccg tctcgtcggc tagcactaag     360
ggcccgtcgg tgttcccgct ggccccatcg tccaagagca catcaggggg taccgccgcc     420
```

```
ctgggctgcc ttgtgaagga ttactttccc gagcccgtca cagtgtcctg gaacagcgga    480
gccctgacct ccggagtgca tactttcccg gctgtgcttc agtcctctgg cctgtactca    540
ttgtcctccg tggtcaccgt cccttcgtcc tccctgggca cccagaccta tatctgtaat    600
gtcaaccata agccctcgaa caccaaggtc gacaagaagg tcgagccgaa gtcgtgcgac    660
aagactcaca cttgcccgcc ttgcccagcc ccggaagctg ccggtggtcc ttcggtgttc    720
ctcttcccgc caagccgaa ggataccctg atgatctcac ggaccccga agtgacctgt    780 gtggtggtgg acgtgtccca cgaggacccg aagtgaaat tcaattggta cgtggatgga    840
gtggaagtgc acaacgccaa gaccaagcca cggaagaac agtacaactc tacctaccgc    900
gtggtgtccg tgctcactgt gctgcaccaa gactggctga acgggaagga gtacaagtgc    960
aaagtgtcca acaaggcgct gcctgcccca attgagaaaa ctatctcgaa agccaaggga    1020
cagcctcgag agcctcaagt gtacaccctg cctccctctc gggacgagct gaccaagaac    1080
caagtctccc tgacctgtct ggtcaaggga ttctacccat cggatatcgc cgtggaatgg    1140
gaaagcaacg gacagcccga gaacaactac aagacgactc cgcccgtgct ggattccgac    1200
gggagcttct tcttgtactc caagctgacc gtcgacaaga gcagatggca gcagggaaac    1260
gtgttctcct gctccgtgat gcatgaggcg ctgcacaacc actacactca gaagagcttg    1320
tccctgtcgc ccgga    1335

<210> SEQ ID NO 39
<211> LENGTH: 116
<212> TYPE: PRT
<213> ORGANISM: Artificial Sequence
<220> FEATURE:
<223> OTHER INFORMATION: FS28-024-052 mAb variable domain

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110

Thr Val Ser Ser
        115

<210> SEQ ID NO 40
<211> LENGTH: 348
<212> TYPE: DNA
<213> ORGANISM: Artificial Sequence
<220> FEATURE:
<223> OTHER INFORMATION: FS28-024-052 mAb variable domain

<400> SEQUENCE: 40
gaagtgcaac tgctggagtc cggtggtggt ctggtacagc cgggtggttc tctgcgtctg    60
```

```
agttgcgcgg ccagtggctt taccctcagt tattcttcta tgtcatgggt gcgtcaggct    120
ccgggcaaag gtctggaatg ggttagcttt attactccgt ctactggcta tacccactat    180
gcggatagcg tgaaaggccg ttttaccatt tctcgcgaca acagcaagaa cacgctgtac    240
ctgcagatga actcactgcg tgccgaagat acggccgtgt attactgtgc gagacgggcg    300
ctgcttttcg actactgggg ccagggaacc ctggtcaccg tctcgtcg               348
```

```
<210> SEQ ID NO 41
<211> LENGTH: 9
<212> TYPE: PRT
<213> ORGANISM: Artificial Sequence
<220> FEATURE:
<223> OTHER INFORMATION: FS28-024-052 mAb CDR3 (IMGT)

<400> SEQUENCE: 41

Ala Arg Arg Ala Leu Leu Phe Asp Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: FS28-024-052 mAb CDR3 (Kabat)

<400> SEQUENCE: 42

Arg Ala Leu Leu Phe Asp Tyr
1               5

<210> SEQ ID NO 43
<211> LENGTH: 9
<212> TYPE: PRT
<213> ORGANISM: Artificial Sequence
<220> FEATURE:
<223> OTHER INFORMATION: FS28-256-005 mAb CDR3 (IMGT) and (Kabat)

<400> SEQUENCE: 43

Gln Gln Ala Leu Gly Tyr Pro His Thr
1               5

<210> SEQ ID NO 44
<211> LENGTH: 9
<212> TYPE: PRT
<213> ORGANISM: Artificial Sequence
<220> FEATURE:
<223> OTHER INFORMATION: FS28-256-027 mAb CDR3 (IMGT) and (Kabat)

<400> SEQUENCE: 44

Gln Gln Thr Val Pro Tyr Pro Tyr Thr
1               5

<210> SEQ ID NO 45
<211> LENGTH: 445
<212> TYPE: PRT
<213> ORGANISM: Artificial Sequence
<220> FEATURE:
<223> OTHER INFORMATION: FS28-024-053 mAb heavy chain without LALA

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
```

```
              35                  40                  45
Ser Phe Ile Thr Pro Ser Thr Gly Tyr Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Leu Val Phe Asp Tyr Trp Gly Gln Gly Thr Leu Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 46
```

<211> LENGTH: 1335
<212> TYPE: DNA
<213> ORGANISM: Artificial Sequence
<220> FEATURE:
<223> OTHER INFORMATION: FS28-024-053 mAb heavy chain without LALA

<400> SEQUENCE: 46

```
gaagtgcaac tgctggagtc cggtggtggt ctggtacagc cgggtggttc tctgcgtctg      60
agttgcgcgg ccagtggctt taccctcagt tattcttcta tgtcatgggt gcgtcaggct     120
ccgggcaaag gtctggaatg ggttagcttt attactccgt ctactggcta tacccactat     180
gcggatagcg tgaaaggccg ttttaccatt tctcgcgaca acagcaagaa cacgctgtac     240
ctgcagatga actcactgcg tgccgaagat acggccgtgt attactgtgc gagacgggcg     300
ctggtgttcg actactgggg ccagggaacc ctggtcaccg tctcgtcggc tagcactaag     360
ggcccgtcgg tgttcccgct ggccccatcg tccaagagca tcagggggta ccgccgcc     420
ctgggctgcc ttgtgaagga ttactttccc gagcccgtca cagtgtcctg aacagcgga     480
gccctgacct ccggagtgca tactttcccg gctgtgcttc agtcctctgg cctgtactca     540
ttgtcctccg tggtcaccgt cccttcgtcc tccctgggca cccagaccta tatctgtaat     600
gtcaaccata gccctcgaa caccaaggtc gacaagaagg tcgagccgaa gtcgtgcgac     660
aagactcaca cttgcccgcc ttgcccagcc ccggaactgc tgggtggtcc ttcggtgttc     720
ctcttcccgc caagccgaa ggatacc ctg atgatctcac ggaccccga agtgacctgt     780
gtggtggtgg acgtgtccca cgaggacccg gaagtgaaat tcaattggta cgtggatgga     840
gtggaagtgc acaacgccaa gaccaagcca cgggaagaac agtacaactc tacctaccgc     900
gtggtgtccg tgctcactgt gctgcaccaa gactggctga acgggaagga gtacaagtgc     960
aaagtgtcca acaaggcgct gcctgcccca attgagaaaa ctatctcgaa agccaaggga    1020
cagcctcgag agcctcaagt gtacaccctg cctccctctc gggacgagct gaccaagaac    1080
caagtctccc tgacctgtct ggtcaaggga ttctacccat cggatatcgc cgtggaatgg    1140
gaaagcaacg gacagcccga gaacaactac aagacgactc cgcccgtgct ggattccgac    1200
gggagcttct tcttgtactc caagctgacc gtcgacaaga gcagatggca gcagggaaac    1260
gtgttctcct gctccgtgat gcatgaggcg ctgcacaacc actacactca gaagagcttg    1320
tccctgtcgc ccgga                                                    1335
```

<210> SEQ ID NO 47
<211> LENGTH: 445
<212> TYPE: PRT
<213> ORGANISM: Artificial Sequence
<220> FEATURE:
<223> OTHER INFORMATION: FS28-024-053 mAb heavy chain with LALA

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
             85                  90                  95

Ala Arg Arg Ala Leu Val Phe Asp Tyr Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 48
<211> LENGTH: 1335
<212> TYPE: DNA
<213> ORGANISM: Artificial Sequence
<220> FEATURE:
<223> OTHER INFORMATION: FS28-024-053 mAb heavy chain with LALA

<400> SEQUENCE: 48
```

```
gaagtgcaac tgctggagtc cggtggtggt ctggtacagc cgggtggttc tctgcgtctg      60
agttgcgcgg ccagtggctt taccctcagt tattcttcta tgtcatgggt gcgtcaggct     120
ccgggcaaag gtctggaatg ggttagcttt attactccgt ctactggcta taccactat      180
gcggatagcg tgaaaggccg ttttaccatt tctcgcgaca acagcaagaa cacgctgtac     240
ctgcagatga actcactgcg tgccgaagat acggccgtgt attactgtgc gagacgggcg     300
ctggtgttcg actactgggg ccagggaacc ctggtcaccg tctcgtcggc tagcactaag     360
ggcccgtcgg tgttcccgct ggccccatcg tccaagagca tcagggggta ccgccgcc      420
ctgggctgcc ttgtgaagga ttactttccc gagcccgtca cagtgtcctg aacagcgga     480
gccctgacct ccggagtgca tacttttccg gctgtgcttc agtcctctgg cctgtactca     540
ttgtcctccg tggtcaccgt cccttcgtcc tccctgggca cccagaccta tatctgtaat     600
gtcaaccata gccctcgaa  caccaaggtc gacaagaagg tcgagccgaa gtcgtgcgac     660
aagactcaca cttgcccgcc ttgcccagcc ccggaagctg ccggtggtcc ttcggtgttc     720
ctcttcccgc ccaagccgaa ggatacctg  atgatctcac ggaccccga  agtgacctgt     780
gtggtggtgg acgtgtccca cgaggacccg gaagtgaaat tcaattggta cgtggatgga     840
gtggaagtgc acaacgccaa gaccaagcca cgggaagaac agtacaactc tacctaccgc     900
gtggtgtccg tgctcactgt gctgcaccaa gactggctga acgggaagga gtacaagtgc     960
aaagtgtcca acaaggcgct gcctgcccca attgagaaaa ctatctcgaa agccaaggga    1020
cagcctcgag agcctcaagt gtacaccctg cctccctctc gggacgagct gaccaagaac    1080
caagtctccc tgacctgtct ggtcaaggga ttctacccat cggatatcgc cgtggaatgg    1140
gaaagcaacg gacagcccga gaacaactac aagacgactc cgcccgtgct ggattccgac    1200
gggagcttct tcttgtactc caagctgacc gtcgacaaga gcagatggca gcagggaaac    1260
gtgttctcct gctccgtgat gcatgaggcg ctgcacaacc actacactca gaagagcttg    1320
tccctgtcgc ccgga                                                     1335
```

<210> SEQ ID NO 49
<211> LENGTH: 116
<212> TYPE: PRT
<213> ORGANISM: Artificial Sequence
<220> FEATURE:
<223> OTHER INFORMATION: FS28-024-053 mAb variable domain

<400> SEQUENCE: 49

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Val Phe Asp Tyr Trp Gly Gln Gly Thr Leu Val
            100                 105                 110

Thr Val Ser Ser
            115
```

-continued

<210> SEQ ID NO 50
<211> LENGTH: 348
<212> TYPE: DNA
<213> ORGANISM: Artificial Sequence
<220> FEATURE:
<223> OTHER INFORMATION: FS28-024-053 mAb variable domain

<400> SEQUENCE: 50

```
gaagtgcaac tgctggagtc cggtggtggt ctggtacagc cgggtggttc tctgcgtctg    60
agttgcgcgg ccagtggctt taccctcagt tattcttcta tgtcatgggt gcgtcaggct   120
ccgggcaaag gtctggaatg ggttagcttt attactccgt ctactggcta tacccactat   180
gcggatagcg tgaaaggccg ttttaccatt tctcgcgaca acagcaagaa cacgctgtac   240
ctgcagatga actcactgcg tgccgaagat acggccgtgt attactgtgc gagacgggcg   300
ctggtgttcg actactgggg ccagggaacc ctggtcaccg tctcgtcg                348
```

<210> SEQ ID NO 51
<211> LENGTH: 9
<212> TYPE: PRT
<213> ORGANISM: Artificial Sequence
<220> FEATURE:
<223> OTHER INFORMATION: FS28-024-053 mAb CDR3 (IMGT)

<400> SEQUENCE: 51

Ala Arg Arg Ala Leu Val Phe Asp Tyr
1               5

<210> SEQ ID NO 52
<211> LENGTH: 7
<212> TYPE: PRT
<213> ORGANISM: Artificial Sequence
<220> FEATURE:
<223> OTHER INFORMATION: FS28-024-053 mAb CDR3 (Kabat)

<400> SEQUENCE: 52

Arg Ala Leu Val Phe Asp Tyr
1               5

<210> SEQ ID NO 53
<211> LENGTH: 108
<212> TYPE: PRT
<213> ORGANISM: Artificial Sequence
<220> FEATURE:
<223> OTHER INFORMATION: FS28-256-005 mAb variable domain

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Leu Gly Tyr Pro
                85                  90                  95

His Thr Phe Gly Gln Gly Thr Lys Val Glu Ile Lys
            100                 105

<210> SEQ ID NO 54
<211> LENGTH: 324
<212> TYPE: DNA
<213> ORGANISM: Artificial Sequence
<220> FEATURE:
<223> OTHER INFORMATION: FS28-256-005 mAb variable domain

<400> SEQUENCE: 54

```
gaaattgtgc tgacccagtc tccgggcacg ttatctctga gccctggtga gcgcgccact    60
ctgtcatgcc gggcttctca aagtgttagc agtagctacc tggcgtggta tcagcaaaaa   120
ccgggccagg ccccgcgtct gctgatttac ggtgcatcca gccgtgccac cggcattcca   180
gatcgttttt ccggtagtgg ttctgggacg gacttcactc tgacaatctc acgcctggaa   240
ccggaggatt ttgcggtgta ttactgccag caagctttgg gttatcctca tacgttcggc   300
caagggacca aggtggaaat caaa                                          324
```

<210> SEQ ID NO 55
<211> LENGTH: 445
<212> TYPE: PRT
<213> ORGANISM: Artificial Sequence
<220> FEATURE:
<223> OTHER INFORMATION: FS28-024-060 mAb heavy chain with LALA

<400> SEQUENCE: 55

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
```

```
                245                 250                 255
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 56
<211> LENGTH: 108
<212> TYPE: PRT
<213> ORGANISM: Artificial Sequence
<220> FEATURE:
<223> OTHER INFORMATION: FS28-256-027 mAb variable domain

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Val Pro Tyr Pro
                85                  90                  95

Tyr Thr Phe Gly Gln Gly Thr Lys Val Glu Ile Lys
                100                 105

<210> SEQ ID NO 57
<211> LENGTH: 324
<212> TYPE: DNA
<213> ORGANISM: Artificial Sequence
<220> FEATURE:
<223> OTHER INFORMATION: FS28-256-027 mAb variable domain

<400> SEQUENCE: 57
```

```
gaaattgtgc tgacccagtc tccgggcacg ttatctctga gccctggtga gcgcgccact    60
ctgtcatgcc gggcttctca aagtgttagc agtagctacc tggcgtggta tcagcaaaaa   120
ccgggccagg ccccgcgtct gctgatttac ggtgcatcca gccgtgccac cggcattcca   180
gatcgttttt ccggtagtgg ttctgggacg gacttcactc tgacaatctc acgcctggaa   240
ccggaggatt ttgcggtgta ttactgccag caaactgtgc cgtatccgta tacgttcggc   300
caagggacca aggtggaaat caaa                                          324
```

<210> SEQ ID NO 58
<211> LENGTH: 445
<212> TYPE: PRT
<213> ORGANISM: Artificial Sequence
<220> FEATURE:
<223> OTHER INFORMATION: FS28-026 mAb (with LALA) heavy chain

<400> SEQUENCE: 58

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ser Ile Thr Pro Tyr Tyr Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Tyr Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 59
<211> LENGTH: 215
<212> TYPE: PRT
<213> ORGANISM: Artificial Sequence
<220> FEATURE:
<223> OTHER INFORMATION: FS28-026 mAb light chain

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Tyr Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

-continued

```
<210> SEQ ID NO 60
<211> LENGTH: 445
<212> TYPE: PRT
<213> ORGANISM: Artificial Sequence
<220> FEATURE:
<223> OTHER INFORMATION: FS28-091 mAb heavy chain with LALA

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Lys Gly Leu Glu Trp Val
        35                  40                  45

Ser Ser Ile Lys Pro Tyr Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Arg Trp Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

-continued

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 61
<211> LENGTH: 215
<212> TYPE: PRT
<213> ORGANISM: Artificial Sequence
<220> FEATURE:
<223> OTHER INFORMATION: FS28-091 mAb light chain

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 62
<211> LENGTH: 452
<212> TYPE: PRT
<213> ORGANISM: Artificial Sequence
<220> FEATURE:
<223> OTHER INFORMATION: FS28-185 mAb heavy chain with LALA

<400> SEQUENCE: 62

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Thr Thr Ser
            20                  25                  30

Ala Met Ser Trp Val Arg Gln Ala Pro Gly Lys Gly Leu Glu Trp Val
        35                  40                  45

Ser Arg Ile Asn Pro Tyr Glu Gly Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Ser Ile Ala Thr Tyr Tyr Lys Ser Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

```
Val Met His Glu Ala Leu His Asn His Tyr Thr Gln Lys Ser Leu Ser
        435                 440                 445

Leu Ser Pro Gly
    450

<210> SEQ ID NO 63
<211> LENGTH: 119
<212> TYPE: PRT
<213> ORGANISM: Artificial Sequence
<220> FEATURE:
<223> OTHER INFORMATION: FS28-256-001 mAb variable domain

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser
        115

<210> SEQ ID NO 64
<211> LENGTH: 357
<212> TYPE: DNA
<213> ORGANISM: Artificial Sequence
<220> FEATURE:
<223> OTHER INFORMATION: FS28-256-001 mAb variable domain

<400> SEQUENCE: 64
gaagtgcaac tgctggagtc cggtggtggt ctggtacagc cgggtggttc tctgcgtctg      60
agttgcgcgg ccagtggctt taccttcact gagacttata tgagctgggt gcgtcaggct     120
ccgggcaaag gtctggaatg ggttagcaat atttctccga cttatagcac taccaactat     180
gcggatagcg tgaaaggccg ttttaccatt tctcgcgaca acagcaagaa cacgctgtac     240
ctgcagatga actcactgcg tgccgaagat acggccgtgt attactgtgc gagatacaac     300
tcttaccagg gtggcttgga ctactggggc caggaacct tggtcaccgt ctcgagt         357

<210> SEQ ID NO 65
<211> LENGTH: 448
<212> TYPE: PRT
<213> ORGANISM: Artificial Sequence
<220> FEATURE:
<223> OTHER INFORMATION: FS28-256 mAb heavy chain without LALA

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Thr
            20                  25                  30

Tyr Met Ser Trp Val Arg Gln Ala Pro Gly Lys Gly Leu Glu Trp Val
```

```
            35                  40                  45
Ser Asn Ile Ser Pro Thr Tyr Ser Thr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Asn Ser Tyr Gln Gly Gly Leu Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 66
```

<211> LENGTH: 1344
<212> TYPE: DNA
<213> ORGANISM: Artificial Sequence
<220> FEATURE:
<223> OTHER INFORMATION: FS28-256 mAb heavy chain without LALA

<400> SEQUENCE: 66

```
gaagtgcaac tgctggagtc cggtggtggt ctggtacagc cgggtggttc tctgcgtctg     60
agttgcgcgg ccagtggctt taccttcact aacacttata tgagctgggt gcgtcaggct    120
ccgggcaaag gtctggaatg ggttagcaat atttctccga cttatagcac taccaactat    180
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
tcttaccagg gtggcttgga ctactggggc cagggaacct tggtcaccgt ctcgagtgct    360
agcactaagg gcccgtcggt gttcccgctg gccccatcgt ccaagagcac atcagggggt    420
accgccgccc tgggctgcct tgtgaaggat tactttcccg agcccgtcac agtgtcctgg    480
aacagcggag ccctgacctc cggagtgcat actttccggg ctgtgcttca gtcctctggc    540
ctgtactcat gtcctccgtg gtcaccgtc ccttcgtcct ccctgggcac ccagacctat    600
atctgtaatg tcaaccataa gccctcgaac accaaggtcg acaagaaggt cgagccgaag    660
tcgtgcgaca agactcacac ttgcccgcct tgcccagccc cggaactgct gggtggtcct    720
tcggtgttcc tcttcccgcc caagccaag gataccctga tgatctcacg gacccccgaa    780
gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa   1020
gccaagggac agcctcgaga gcctcaagtg tacaccctgc ctccctctcg ggacgagctg   1080
accaagaacc aagtctccct gacctgtctg gtcaagggat tctacccatc ggatatcgcc   1140
gtggaatggg aaagcaacgg acagcccgag aacaactaca agacgactcc gcccgtgctg   1200
gattccgacg ggagcttctt cttgtactcc aagctgaccg tcgacaagag cagatggcag   1260
cagggaaacg tgttctcctg ctccgtgatg catgaggcgc tgcacaacca ctacactcag   1320
aagagcttgt ccctgtcgcc cgga                                          1344
```

<210> SEQ ID NO 67
<211> LENGTH: 448
<212> TYPE: PRT
<213> ORGANISM: Artificial Sequence
<220> FEATURE:
<223> OTHER INFORMATION: FS28-256 mAb heavy chain with LALA

<400> SEQUENCE: 67

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
            85                   90                   95

Ala Arg Tyr Asn Ser Tyr Gln Gly Gly Leu Asp Tyr Trp Gly Gln Gly
            100                 105                  110

Thr Leu Val Thr Val Ser Ser Ala Ser Thr Lys Gly Pro Ser Val Phe
            115                 120                  125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 68
<211> LENGTH: 1344
<212> TYPE: DNA
<213> ORGANISM: Artificial Sequence
<220> FEATURE:
<223> OTHER INFORMATION: FS28-256 mAb heavy chain with LALA

<400> SEQUENCE: 68

```
gaagtgcaac tgctggagtc cggtggtggt ctggtacagc cgggtggttc tctgcgtctg      60
agttgcgcgg ccagtggctt taccttcact aacacttata tgagctgggt cgtcaggct     120 ccgggcaaag gtctggaatg ggttagcaat atttctccga cttatagcac taccaactat    180
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
tcttaccagg gtggcttgga ctactggggc cagggaacct tggtcaccgt ctcgagtgct    360
agcactaagg gcccgtcggt gttcccgctg gccccatcgt ccaagagcac atcagggggt    420
accgccgccc tgggctgcct tgtgaaggat tactttcccg agcccgtcac agtgtcctgg    480
aacagcggag ccctgaccct cggagtgcat actttcccgg ctgtgcttca gtcctctggc    540
ctgtactcat tgtcctccgt ggtcaccgtc ccttcgtcct ccctgggcac ccagacctat    600
atctgtaatg tcaaccataa gccctcgaac accaaggtcg acaagaaggt cgagcccaag    660
tcgtgcgaca agactcacac ttgccccgcct tgcccagccc cggaagctgc cggtggtcct    720
tcggtgttcc tcttcccgcc caagccgaag gataccctga tgatctcacg gacccccgaa    780
gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa    1020
gccaagggac agcctcgaga gcctcaagtg tacaccctgc ctcccctctcg ggacgagctg    1080 accaagaacc aagtctccct gacctgtctg gtcaagggat tctacccatc ggatatcgcc    1140
gtggaatggg aaagcaacgg acagcccgag aacaactaca agacgactcc gcccgtgctg    1200
gattccgacg ggagcttctt cttgtactcc aagctgaccg tcgacaagag cagatggcag    1260
cagggaaacg tgttctcctg ctccgtgatg catgaggcgc tgcacaacca ctacactcag    1320
aagagcttgt ccctgtcgcc cgga                                           1344
```

<210> SEQ ID NO 69
<211> LENGTH: 119
<212> TYPE: PRT
<213> ORGANISM: Artificial Sequence
<220> FEATURE:
<223> OTHER INFORMATION: FS28-256 mAb variable domain

<400> SEQUENCE: 69

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser
        115
```

<210> SEQ ID NO 70
<211> LENGTH: 357
<212> TYPE: DNA
<213> ORGANISM: Artificial Sequence
<220> FEATURE:
<223> OTHER INFORMATION: FS28-256 mAb variable domain

<400> SEQUENCE: 70

```
gaagtgcaac tgctggagtc cggtggtggt ctggtacagc cgggtggttc tctgcgtctg      60
agttgcgcgg ccagtggctt taccttcact aacacttata tgagctgggt gcgtcaggct     120
ccgggcaaag gtctggaatg ggttagcaat atttctccga cttatagcac taccaactat     180
gcggatagcg tgaaaggccg tttttaccatt tctcgcgaca acagcaagaa cacgctgtac     240
ctgcagatga actcactgcg tgccgaagat acggccgtgt attactgtgc gagatacaac     300
tcttaccagg gtggcttgga ctactggggc cagggaacct tggtcaccgt ctcgagt        357
```

<210> SEQ ID NO 71
<211> LENGTH: 8
<212> TYPE: PRT
<213> ORGANISM: Artificial Sequence
<220> FEATURE:
<223> OTHER INFORMATION: FS28-256 mAb CDR1 (IMGT)

<400> SEQUENCE: 71

Gly Phe Thr Phe Thr Asn Thr Tyr
1               5

<210> SEQ ID NO 72
<211> LENGTH: 5
<212> TYPE: PRT
<213> ORGANISM: Artificial Sequence
<220> FEATURE:
<223> OTHER INFORMATION: FS28-256 mAb CDR1 (Kabat)

<400> SEQUENCE: 72

Asn Thr Tyr Met Ser
1               5

<210> SEQ ID NO 73
<211> LENGTH: 8
<212> TYPE: PRT
<213> ORGANISM: Artificial Sequence
<220> FEATURE:
<223> OTHER INFORMATION: FS28-256 mAb CDR2 (IMGT)

<400> SEQUENCE: 73

Ile Ser Pro Thr Tyr Ser Thr Thr
1               5

<210> SEQ ID NO 74
<211> LENGTH: 17
<212> TYPE: PRT
<213> ORGANISM: Artificial Sequence
<220> FEATURE:
<223> OTHER INFORMATION: FS28-256 mAb CDR2 (Kabat)

<400> SEQUENCE: 74

Asn Ile Ser Pro Thr Tyr Ser Thr Thr Asn Tyr Ala Asp Ser Val Lys
1               5                   10                  15

Gly

<210> SEQ ID NO 75

```
<211> LENGTH: 12
<212> TYPE: PRT
<213> ORGANISM: Artificial Sequence
<220> FEATURE:
<223> OTHER INFORMATION: FS28-256 mAb CDR3 (IMGT)

<400> SEQUENCE: 75

Ala Arg Tyr Asn Ser Tyr Gln Gly Gly Leu Asp Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: FS28-256 mAb CDR3 (Kabat)

<400> SEQUENCE: 76

Tyr Asn Ser Tyr Gln Gly Gly Leu Asp Tyr
1               5                   10

<210> SEQ ID NO 77
<211> LENGTH: 215
<212> TYPE: PRT
<213> ORGANISM: Artificial Sequence
<220> FEATURE:
<223> OTHER INFORMATION: FS28-256 mAb light chain

<400> SEQUENCE: 77

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Tyr Tyr Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 78
<211> LENGTH: 645
```

<212> TYPE: DNA
<213> ORGANISM: Artificial Sequence
<220> FEATURE:
<223> OTHER INFORMATION: FS28-256 mAb light chain

<400> SEQUENCE: 78

```
gaaattgtgc tgacccagtc tccgggcacg ttatctctga gccctggtga gcgcgccact    60
ctgtcatgcc gggcttctca aagtgttagc agtagctacc tggcgtggta tcagcaaaaa   120
ccgggccagg ccccgcgtct gctgatttac ggtgcatcca gccgtgccac cggcattcca   180
gatcgttttt ccggtagtgg ttctgggacg gacttcactc tgacaatctc acgcctggaa   240
ccggaggatt ttgcggtgta ttactgccag caatcttatt attatcctat cacgttcggc   300
caagggacca aggtggaaat caaacgtact gtggccgctc tagcgtgtt catttttccg    360
ccatccgacg agcagctcaa gtccggcacc gcctccgtgg tctgcctgct caacaacttc   420
taccctcgcg aagctaaggt ccagtggaag gtcgacaatg ccctgcagtc cggaaactcg   480
caggaaagcg tgactgaaca ggactccaag gactccacct attcactgtc ctcgactctg   540
accctgagca aggcggatta cgaaaagcac aaagtgtacg catgcgaagt gacccaccag   600
ggtctttcgt ccccccgtgac caagagcttc aacagaggag agtgt              645
```

<210> SEQ ID NO 79
<211> LENGTH: 108
<212> TYPE: PRT
<213> ORGANISM: Artificial Sequence
<220> FEATURE:
<223> OTHER INFORMATION: FS28-256 mAb variable domain

<400> SEQUENCE: 79

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Ser Tyr Tyr Tyr Pro
                85                  90                  95
Ile Thr Phe Gly Gln Gly Thr Lys Val Glu Ile Lys
            100                 105
```

<210> SEQ ID NO 80
<211> LENGTH: 324
<212> TYPE: DNA
<213> ORGANISM: Artificial Sequence
<220> FEATURE:
<223> OTHER INFORMATION: FS28-256 mAb variable domain

<400> SEQUENCE: 80

```
gaaattgtgc tgacccagtc tccgggcacg ttatctctga gccctggtga gcgcgccact    60
ctgtcatgcc gggcttctca aagtgttagc agtagctacc tggcgtggta tcagcaaaaa   120
ccgggccagg ccccgcgtct gctgatttac ggtgcatcca gccgtgccac cggcattcca   180
gatcgttttt ccggtagtgg ttctgggacg gacttcactc tgacaatctc acgcctggaa   240
ccggaggatt ttgcggtgta ttactgccag caatcttatt attatcctat cacgttcggc   300
```
caagggacca aggtggaaat caaa                                                  324

<210> SEQ ID NO 81
<211> LENGTH: 448
<212> TYPE: PRT
<213> ORGANISM: Artificial Sequence
<220> FEATURE:
<223> OTHER INFORMATION: FS28-256-001 mAb heavy chain without LALA

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 82
<211> LENGTH: 1344
<212> TYPE: DNA
<213> ORGANISM: Artificial Sequence
<220> FEATURE:
<223> OTHER INFORMATION: FS28-256-001 mAb heavy chain without LALA

<400> SEQUENCE: 82

| | | | | | |
|---|---|---|---|---|---|
| gaagtgcaac | tgctggagtc | cggtggtggt | ctggtacagc | cgggtggttc | tctgcgtctg | 60 |
| agttgcgcgg | ccagtggctt | taccttcact | gagacttata | tgagctgggt | gcgtcaggct | 120 |
| ccgggcaaag | gtctggaatg | ggttagcaat | atttctccga | cttatagcac | taccaactat | 180 |
| gcggatagcg | tgaaaggccg | ttttaccatt | tctcgcgaca | acagcaagaa | cacgctgtac | 240 |
| ctgcagatga | actcactgcg | tgccgaagat | acggccgtgt | attactgtgc | gagatacaac | 300 |
| tcttaccagg | gtggcttgga | ctactggggc | cagggaacct | tggtcaccgt | ctcgagtgct | 360 |
| agcactaagg | gcccgtcggt | gttcccgctg | gccccatcgt | ccaagagcac | atcgggggt | 420 |
| accgccgccc | tgggctgcct | tgtgaaggat | tactttcccg | agcccgtcac | agtgtcctgg | 480 |
| aacagcggag | ccctgacctc | cggagtgcat | actttcccgg | ctgtgcttca | gtcctctggc | 540 |
| ctgtactcat | tgtcctccgt | ggtcaccgtc | ccttcgtcct | ccctgggcac | ccagacctat | 600 |
| atctgtaatg | tcaaccataa | gcccctcgaac | accaaggtcg | acaagaaggt | cgagcccaag | 660 |
| tcgtgcgaca | agactcacac | ttgcccgcct | tgcccagccc | cggaactgct | gggtggtcct | 720 |
| tcggtgttcc | tcttcccgcc | caagccgaag | gatacccctga | tgatctcacg | gacccccgaa | 780 |
| gtgacctgtg | tggtggtgga | cgtgtcccac | gaggacccgg | aagtgaaatt | caattggtac | 840 |
| gtggatggag | tggaagtgca | caacgccaag | accaagccac | gggaagaaca | gtacaactct | 900 |
| acctaccgcg | tggtgtccgt | gctcactgtg | ctgcaccaag | actggctgaa | cgggaaggag | 960 |
| tacaagtgca | agtgtccaa | caaggcgctg | cctgccccaa | ttgagaaaac | tatctcgaaa | 1020 |
| gccaagggac | agcctcgaga | gcctcaagtg | tacaccctgc | ctcccctctcg | ggacgagctg | 1080 |
| accaagaacc | aagtctccct | gacctgtctg | gtcaagggat | tctaccatc | ggatatcgcc | 1140 |
| gtggaatggg | aaagcaacgg | acagcccgag | aacaactaca | agacgactcc | gcccgtgctg | 1200 |
| gattccgacg | ggagcttctt | cttgtactcc | aagctgaccg | tcgacaagag | cagatggcag | 1260 |
| cagggaaacg | tgttctcctg | ctccgtgatg | catgaggcgc | tgcacaacca | ctacactcag | 1320 |
| aagagcttgt | ccctgtcgcc | cgga | | | | 1344 |

<210> SEQ ID NO 83
<211> LENGTH: 215
<212> TYPE: PRT
<213> ORGANISM: Artificial Sequence -continued
<220> FEATURE:
<223> OTHER INFORMATION: FS28-256-001 mAb light chain

<400> SEQUENCE: 83

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asn Gln Tyr Pro
                85                  90                  95

Asn Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 84
<211> LENGTH: 1344
<212> TYPE: DNA
<213> ORGANISM: Artificial Sequence
<220> FEATURE:
<223> OTHER INFORMATION: FS28-256-001 mAb heavy chain with LALA

<400> SEQUENCE: 84

```
gaagtgcaac tgctggagtc cggtggtggt ctggtacagc cgggtggttc tctgcgtctg      60
agttgcgcgg ccagtggctt taccttcact gagacttata tgagctgggt gcgtcaggct     120
ccgggcaaag gtctggaatg ggttagcaat atttctccga cttatagcac taccaactat     180
gcggatagcg tgaaaggccg ttttaccatt tctcgcgaca acagcaagaa cacgctgtac     240
ctgcagatga actcactgcg tgccgaagat acggccgtgt attactgtgc gagatacaac     300
tcttaccagg gtggcttgga ctactgggc cagggaacct tggtcaccgt ctcgagtgct     360
agcactaagg gcccgtcggt gttcccgctg gccccatcgt ccaagagcac atcgggggt     420 accgccgccc tgggctgcct tgtgaaggat tactttcccg agcccgtcac agtgtcctgg     480
aacagcggag ccctgaccct cggagtgcat actttcccgg ctgtgcttca gtcctctggc     540
ctgtactcat tgtcctccgt ggtcaccgtc ccttcgtcct ccctgggcac ccagacctat     600
atctgtaatg tcaaccataa gcccctcgaac accaaggtcg acaagaaggt cgagccgaag     660
```

```
tcgtgcgaca agactcacac ttgcccgcct tgcccagccc cggaagctgc cggtggtcct    720
tcggtgttcc tcttcccgcc caagccgaag gataccctga tgatctcacg gacccccgaa    780
gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa    1020
gccaagggac agcctcgaga gcctcaagtg tacaccctgc ctccctctcg ggacgagctg    1080
accaagaacc aagtctccct gacctgtctg gtcaagggat tctacccatc ggatatcgcc    1140
gtggaatggg aaagcaacgg acagcccgag aacaactaca agacgactcc gcccgtgctg    1200
gattccgacg ggagcttctt cttgtactcc aagctgaccg tcgacaagag cagatggcag    1260
cagggaaacg tgttctcctg ctccgtgatg catgaggcgc tgcacaacca ctacactcag    1320
aagagcttgt ccctgtcgcc cgga                                           1344
```

<210> SEQ ID NO 85
<211> LENGTH: 8
<212> TYPE: PRT
<213> ORGANISM: Artificial Sequence
<220> FEATURE:
<223> OTHER INFORMATION: FS28-256-001 mAb CDR1 (IMGT)

<400> SEQUENCE: 85

Gly Phe Thr Phe Thr Glu Thr Tyr
1               5

<210> SEQ ID NO 86
<211> LENGTH: 5
<212> TYPE: PRT
<213> ORGANISM: Artificial Sequence
<220> FEATURE:
<223> OTHER INFORMATION: FS28-256-001 mAb CDR1 (Kabat)

<400> SEQUENCE: 86

Glu Thr Tyr Met Ser
1               5

<210> SEQ ID NO 87
<211> LENGTH: 448
<212> TYPE: PRT
<213> ORGANISM: Artificial Sequence
<220> FEATURE:
<223> OTHER INFORMATION: FS28-256-005 mAb heavy chain without LALA

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly

|  |  |  |  | 100 |  |  |  | 105 |  |  |  | 110 |  |  |
|--|--|--|--|--|--|--|--|--|--|--|--|--|--|--|
| Thr | Leu | Val | Thr | Val | Ser | Ser | Ala | Ser | Thr | Lys | Gly | Pro | Ser | Val | Phe |

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 88
<211> LENGTH: 1344
<212> TYPE: DNA
<213> ORGANISM: Artificial Sequence
<220> FEATURE:
<223> OTHER INFORMATION: FS28-256-005 mAb heavy chain without LALA

<400> SEQUENCE: 88
gaagtgcaac tgctggagtc cggtggtggt ctggtacagc cgggtggttc tctgcgtctg    60
agttgcgcgg ccagtggctt taccttcact gagacttata tgagctgggt cgtcaggct    120

```
ccgggcaaag gtctggaatg ggttagcaat atttctccga cttatagcac taccaactat    180
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
tcttaccagg gtggcttgga ctactggggc cagggaacct tggtcaccgt ctcgagtgct    360
agcactaagg gcccgtcggt gttcccgctg gccccatcgt ccaagagcac atcaggggt    420 accgccgccc tgggctgcct tgtgaaggat tactttcccg agcccgtcac agtgtcctgg    480
aacagcggag ccctgacctc cggagtgcat actttcccgg ctgtgcttca gtcctctggc    540
ctgtactcat tgtcctccgt ggtcaccgtc cttcgtcct ccctgggcac ccagacctat    600
atctgtaatg tcaaccataa gccctcgaac accaaggtcg acaagaaggt cgagcccgaag    660 tcgtgcgaca agactcacac ttgcccgcct tgcccagccc cggaactgct gggtggtcct    720
tcggtgttcc tcttcccgcc caagccgaag gataccctga tgatctcacg gacccccgaa    780
gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa   1020
gccaagggac agcctcgaga gcctcaagtg tacaccctgc ctccctctcg ggacgagctg   1080
accaagaacc aagtctccct gacctgtctg gtcaaggat tctacccatc ggatatcgcc   1140
gtggaatggg aaagcaacgg acagcccgag aacaactaca agacgactcc gcccgtgctg   1200
gattccgacg gagcttctt cttgtactcc aagctgaccg tcgacaagag cagatggcag   1260
cagggaaacg tgttctcctg ctccgtgatg catgaggcgc tgcacaacca ctacactcag   1320
aagagcttgt ccctgtcgcc cgga                                          1344
```

<210> SEQ ID NO 89
<211> LENGTH: 448
<212> TYPE: PRT
<213> ORGANISM: Artificial Sequence
<220> FEATURE:
<223> OTHER INFORMATION: FS28-256-005 mAb heavy chain with LALA

<400> SEQUENCE: 89

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Glu Thr
             20                  25                  30

Tyr Met Ser Trp Val Arg Gln Ala Pro Gly Lys Gly Leu Glu Trp Val
         35                  40                  45

Ser Asn Ile Ser Pro Thr Tyr Ser Thr Thr Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 90
<211> LENGTH: 215
<212> TYPE: PRT
<213> ORGANISM: Artificial Sequence
<220> FEATURE:
<223> OTHER INFORMATION: FS28-256-005 mAb light chain

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Leu Gly Tyr Pro
                85                  90                  95

His Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 91
<211> LENGTH: 645
<212> TYPE: DNA
<213> ORGANISM: Artificial Sequence
<220> FEATURE:
<223> OTHER INFORMATION: FS28-256-005 mAb light chain

<400> SEQUENCE: 91
gaaattgtgc tgacccagtc tccgggcacg ttatctctga gccctggtga gcgcgccact      60
ctgtcatgcc gggcttctca aagtgttagc agtagctacc tggcgtggta tcagcaaaaa     120
ccgggccagg ccccgcgtct gctgatttac ggtgcatcca gccgtgccac cggcattcca     180
gatcgttttt ccggtagtgg ttctgggacg gacttcactc tgacaatctc acgcctggaa     240
ccggaggatt ttgcggtgta ttactgccag caagctttgg gttatcctca tacgttcggc     300
caagggacca aggtggaaat caaacgtact gtagcagctc cttccgtgtt catctttccg     360
cccagtgatg agcagctgaa gtcaggtact gcttccgtgg tttgcctgct caacaacttt     420
taccccagag aagccaaagt ccagtggaaa gtggacaatg cgttgcaaag cgggaactct     480
caggaatccg tcacagagca ggactctaag gactccacct atagcctctc tagtacgctg     540
acactgagca agccgatta cgagaagcac aaggtgtatg cctgtgaggt tacccatcaa     600
ggccttagct caccagtgac caagagcttc aatagggag aatgc                     645

<210> SEQ ID NO 92
<211> LENGTH: 645
<212> TYPE: DNA
<213> ORGANISM: Artificial Sequence
<220> FEATURE:
<223> OTHER INFORMATION: FS28-256-021 mAb light chain

<400> SEQUENCE: 92
gaaattgtgc tgacccagtc tccgggcacg ttatctctga gccctggtga gcgcgccact      60
ctgtcatgcc gggcttctca aagtgttagc agtagctacc tggcgtggta tcagcaaaaa     120
ccgggccagg ccccgcgtct gctgatttac ggtgcatcca gccgtgccac cggcattcca     180
gatcgttttt ccggtagtgg ttctgggacg gacttcactc tgacaatctc acgcctggaa     240

```
ccggaggatt tgcggtgta ttactgccag caacataatc agtatccgaa tacgttcggc    300
caagggacca aggtggaaat caaacgtact gtagcagctc cttccgtgtt catctttccg    360
cccagtgatg agcagctgaa gtcaggtact gcttccgtgg tttgcctgct caacaacttt    420
taccccagag aagccaaagt ccagtggaaa gtggacaatg cgttgcaaag cgggaactct    480
caggaatccg tcacagagca ggactctaag gactccacct atagcctctc tagtacgctg    540
acactgagca agccgatta cgagaagcac aaggtgtatg cctgtgaggt tacccatcaa    600
ggccttagct caccagtgac caagagcttc aatagggag aatgc                    645
```

<210> SEQ ID NO 93
<211> LENGTH: 108
<212> TYPE: PRT
<213> ORGANISM: Artificial Sequence
<220> FEATURE:
<223> OTHER INFORMATION: FS28-256-021 mAb variable domain

<400> SEQUENCE: 93

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln His Asn Gln Tyr Pro
                85                  90                  95
Asn Thr Phe Gly Gln Gly Thr Lys Val Glu Ile Lys
            100                 105

<210> SEQ ID NO 94
<211> LENGTH: 324
<212> TYPE: DNA
<213> ORGANISM: Artificial Sequence
<220> FEATURE:
<223> OTHER INFORMATION: FS28-256-021 mAb variable domain

<400> SEQUENCE: 94

```
gaaattgtgc tgacccagtc tccgggcacg ttatctctga gccctggtga gcgcgccact     60
ctgtcatgcc gggcttctca aagtgttagc agtagctacc tggcgtggta tcagcaaaaa    120
ccgggccagg ccccgcgtct gctgatttac ggtgcatcca gcgtgccac cggcattcca    180 gatcgttttt ccggtagtgg ttctgggacg gacttcactc tgacaatctc acgcctggaa    240
ccggaggatt tgcggtgta ttactgccag caacataatc agtatccgaa tacgttcggc    300
caagggacca aggtggaaat caaa                                          324
```

<210> SEQ ID NO 95
<211> LENGTH: 215
<212> TYPE: PRT
<213> ORGANISM: Artificial Sequence
<220> FEATURE:
<223> OTHER INFORMATION: FS28-256-027 mAb light chain

<400> SEQUENCE: 95

Glu Ile Val Leu Thr Gln Ser Pro Gly Thr Leu Ser Leu Ser Pro Gly

```
              1               5              10              15
            Glu Arg Ala Thr Leu Ser Cys Arg Ala Ser Gln Ser Val Ser Ser
                            20                  25                  30
            Tyr Leu Ala Trp Tyr Gln Gln Lys Pro Gly Gln Ala Pro Arg Leu Leu
                        35                  40                  45
            Ile Tyr Gly Ala Ser Ser Arg Ala Thr Gly Ile Pro Asp Arg Phe Ser
                    50                  55                  60
            Gly Ser Gly Ser Gly Thr Asp Phe Thr Leu Thr Ile Ser Arg Leu Glu
            65                  70                  75                  80
            Pro Glu Asp Phe Ala Val Tyr Tyr Cys Gln Gln Thr Val Pro Tyr Pro
                            85                  90                  95
            Tyr Thr Phe Gly Gln Gly Thr Lys Val Glu Ile Lys Arg Thr Val Ala
                        100                 105                 110
            Ala Pro Ser Val Phe Ile Phe Pro Pro Ser Asp Glu Gln Leu Lys Ser
                    115                 120                 125
            Gly Thr Ala Ser Val Val Cys Leu Leu Asn Asn Phe Tyr Pro Arg Glu
                    130                 135                 140
            Ala Lys Val Gln Trp Lys Val Asp Asn Ala Leu Gln Ser Gly Asn Ser
            145                 150                 155                 160
            Gln Glu Ser Val Thr Glu Gln Asp Ser Lys Asp Ser Thr Tyr Ser Leu
                            165                 170                 175
            Ser Ser Thr Leu Thr Leu Ser Lys Ala Asp Tyr Glu Lys His Lys Val
                        180                 185                 190
            Tyr Ala Cys Glu Val Thr His Gln Gly Leu Ser Ser Pro Val Thr Lys
                    195                 200                 205
            Ser Phe Asn Arg Gly Glu Cys
                    210                 215

<210> SEQ ID NO 96
<211> LENGTH: 645
<212> TYPE: DNA
<213> ORGANISM: Artificial Sequence
<220> FEATURE:
<223> OTHER INFORMATION: FS28-256-027 mAb light chain

<400> SEQUENCE: 96
gaaattgtgc tgacccagtc tccgggcacg ttatctctga gccctggtga gcgcgccact     60
ctgtcatgcc gggcttctca aagtgttagc agtagctacc tggcgtggta tcagcaaaaa    120
ccgggccagg ccccgcgtct gctgatttac ggtgcatcca gccgtgccac cggcattcca    180
gatcgttttt ccggtagtgg ttctgggacg gacttcactc tgacaatctc acgcctggaa    240
ccggaggatt ttgcggtgta ttactgccag caaactgtgc cgtatccgta cgttcggc      300 caagggacca aggtggaaat caaacgtact gtggccgctc ctagcgtgtt cattttccg     360 ccatccgacg agcagctcaa gtccggcacc gcctccgtgg tctgcctgct caacaacttc    420 tacccctcgcg aagctaaggt ccagtggaag gtcgacaatg ccctgcagtc cggaaactcg   480
caggaaagcg tgactgaaca ggactccaag gactccacct attcactgtc ctcgactctg    540
accctgagca aggcggatta cgaaaagcac aaagtgtacg catgcgaagt gacccaccag    600
ggtctttcgt cccccgtgac caagagcttc aacagaggag agtgt                    645

<210> SEQ ID NO 97
<211> LENGTH: 5
<212> TYPE: PRT
<213> ORGANISM: Artificial Sequence
<220> FEATURE:
```

-continued

```
<223> OTHER INFORMATION: FS28-256-271 mAb CDR1 (Kabat)

<400> SEQUENCE: 97

His Thr Tyr Met Ser
1               5

<210> SEQ ID NO 98
<211> LENGTH: 8
<212> TYPE: PRT
<213> ORGANISM: Artificial Sequence
<220> FEATURE:
<223> OTHER INFORMATION: FS28-256-271 mAb CDR1 (IMGT)

<400> SEQUENCE: 98

Gly Phe Thr Phe Thr His Thr Tyr
1               5

<210> SEQ ID NO 99
<211> LENGTH: 12
<212> TYPE: PRT
<213> ORGANISM: Artificial Sequence
<220> FEATURE:
<223> OTHER INFORMATION: FS28-256-271 mAb CDR3 (IMGT)

<400> SEQUENCE: 99

Ala Arg Tyr Asn Ala Tyr His Ala Ala Leu Asp Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: FS28-256-271 mAb CDR3 (Kabat)

<400> SEQUENCE: 100

Tyr Asn Ala Tyr His Ala Ala Leu Asp Tyr
1               5                   10

<210> SEQ ID NO 101
<211> LENGTH: 8
<212> TYPE: PRT
<213> ORGANISM: Artificial Sequence
<220> FEATURE:
<223> OTHER INFORMATION: FS28-256-018 mAb CDR1 (IMGT)

<400> SEQUENCE: 101

Gly Phe Thr Phe Thr Gln Thr Tyr
1               5

<210> SEQ ID NO 102
<211> LENGTH: 5
<212> TYPE: PRT
<213> ORGANISM: Artificial Sequence
<220> FEATURE:
<223> OTHER INFORMATION: FS28-256-018 mAb CDR1 (Kabat)

<400> SEQUENCE: 102

Gln Thr Tyr Met Ser
1               5

<210> SEQ ID NO 103
<211> LENGTH: 12
<212> TYPE: PRT
<213> ORGANISM: Artificial Sequence
<220> FEATURE:
<223> OTHER INFORMATION: FS28-256-018 mAb CDR3 (IMGT)
```

<400> SEQUENCE: 103

Ala Arg Tyr Asn Ala Tyr Gln Ile Gly Leu Asp Tyr
1               5                   10

<210> SEQ ID NO 104
<211> LENGTH: 10
<212> TYPE: PRT
<213> ORGANISM: Artificial Sequence
<220> FEATURE:
<223> OTHER INFORMATION: FS28-256-018 mAb CDR3 (Kabat)

<400> SEQUENCE: 104

Tyr Asn Ala Tyr Gln Ile Gly Leu Asp Tyr
1               5                   10

<210> SEQ ID NO 105
<211> LENGTH: 448
<212> TYPE: PRT
<213> ORGANISM: Artificial Sequence
<220> FEATURE:
<223> OTHER INFORMATION: FS28-256-021 mAb heavy chain without LALA

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 106
<211> LENGTH: 1344
<212> TYPE: DNA
<213> ORGANISM: Artificial Sequence
<220> FEATURE:
<223> OTHER INFORMATION: FS28-256-021 mAb heavy chain without LALA

<400> SEQUENCE: 106
gaagtgcaac tgctggagtc cggtggtggt ctggtacagc cgggtggttc tctgcgtctg     60
agttgcgcgg ccagtggctt taccttcact catacttata tgagctgggt gcgtcaggct    120
ccgggcaaag gtctggaatg ggttagcaat atttctccga cttatagcac taccaactat    180
gcggatagcg tgaaaggccg ttttaccatt tctcgcgaca caacaagaa cacgctgtac     240 ctgcagatga actcactgcg tgccgaagat acggccgtgt attactgtgc gagatacaac    300
gcgtatcatg ctgctctgga ctactggggc cagggaaccc tggtcaccgt ctcgagtgct    360
agcactaagg gcccgtcggt gttcccgctg gccccatcgt ccaagagcac atcgggggt    420 accgccgccc tgggctgcct tgtgaaggat tactttcccg agcccgtcac agtgtcctgg    480
aacagcggag ccctgacctc cggagtgcat acttttccgg ctgtgcttca gtcctctggc    540
ctgtactcat tgtcctccgt ggtcaccgtc ccttcgtcct ccctgggcac ccagacctat    600
atctgtaatg tcaaccataa gcccctcgaac accaaggtcg acaagaaggt cgagcccaag    660
tcgtgcgaca agactcacac ttgcccgcct tgcccagccc cggaactgct gggtggtcct    720
tcggtgttcc tcttcccgcc caagccgaag gatacctga tgatctcacg acccccgaa     780 gtgacctgtg tggtggtgga cgtgtcccac gaggacccgg aagtgaaatt caattggtac    840
gtggatggag tggaagtgca acgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa    1020
gccaagggac agcctcgaga gcctcaagtg tacaccctgc ctccctctcg ggacgagctg    1080

```
accaagaacc aagtctccct gacctgtctg gtcaagggat tctacccatc ggatatcgcc      1140
gtggaatggg aaagcaacgg acagcccgag aacaactaca agacgactcc gcccgtgctg      1200
gattccgacg ggagcttctt cttgtactcc aagctgaccg tcgacaagag cagatggcag      1260
cagggaaacg tgttctcctg ctccgtgatg catgaggcgc tgcacaacca ctacactcag      1320
aagagcttgt ccctgtcgcc cgga                                             1344
```

<210> SEQ ID NO 107
<211> LENGTH: 448
<212> TYPE: PRT
<213> ORGANISM: Artificial Sequence
<220> FEATURE:
<223> OTHER INFORMATION: FS28-256-021 mAb heavy chain with LALA

<400> SEQUENCE: 107

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

305                 310                 315                 320
Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 108
<211> LENGTH: 1344
<212> TYPE: DNA
<213> ORGANISM: Artificial Sequence
<220> FEATURE:
<223> OTHER INFORMATION: FS28-256-021 mAb heavy chain with LALA

<400> SEQUENCE: 108

| | |
|---|---|
| gaagtgcaac tgctggagtc cggtggtggt ctggtacagc cgggtggttc tctgcgtctg | 60 |
| agttgcgcgg ccagtggctt taccttcact catacttata tgagctgggt gcgtcaggct | 120 |
| ccgggcaaag gtctggaatg ggttagcaat atttctccga cttatagcac taccaactat | 180 |
| gcggatagcg tgaaaggccg ttttaccatt tctcgcgaca caacaagaa cacgctgtac | 240 |
| ctgcagatga actcactgcg tgccgaagat acggccgtgt attactgtgc gagatacaac | 300 |
| gcgtatcatg ctgctctgga ctactggggc cagggaaccc tggtcaccgt ctcgagtgct | 360 |
| agcactaagg gcccgtcggt gttcccgctg gccccatcgt ccaagagcac atcgggggt | 420 |
| accgccgccc tgggctgcct tgtgaaggat tactttcccg agcccgtcac agtgtcctgg | 480 |
| aacagcggag ccctgacctc cggagtgcat actttcccgg ctgtgcttca gtcctctggc | 540 |
| ctgtactcat gtcctccgt ggtcaccgtc ccttcgtcct ccctgggcac ccagacctat | 600 |
| atctgtaatg tcaaccataa gcccctcgaac accaaggtcg acaagaaggt cgagcccaag | 660 |
| tcgtgcgaca agactcacac ttgcccgcct tgcccagccc cggaagctgc ggtggtcct | 720 |
| tcggtgttcc tcttcccgcc caagccgaag ataccctga tgatctcacg gaccccgaa | 780 |
| gtgacctgtg tggtggtgga cgtgtcccac gaggacccgg aagtgaaatt caattggtac | 840 |
| gtggatggag tggaagtgca caacgccaag accaagccac gggaagaaca gtacaactct | 900 |
| acctaccgcg tggtgtccgt gctcactgtg ctgcaccaag actggctgaa cgggaaggag | 960 |
| tacaagtgca agtgtccaa caaggcgctg cctgccccaa ttgagaaaac tatctcgaaa | 1020 |
| gccaagggac agcctcgaga gcctcaagtg tacaccctgc ctcccctcg ggacgagctg | 1080 |
| accaagaacc aagtctccct gacctgtctg gtcaagggat ctacccatc ggatatcgcc | 1140 |
| gtggaatggg aaagcaacgg acagcccgag aacaactaca agacgactcc gcccgtgctg | 1200 |
| gattccgacg ggagcttctt cttgtactcc aagctgaccg tcgacaagag cagatggcag | 1260 |
| cagggaaacg tgttctcctg ctccgtgatg catgaggcgc tgcacaacca ctacactcag | 1320 | aagagcttgt ccctgtcgcc cgga                                                  1344

<210> SEQ ID NO 109
<211> LENGTH: 119
<212> TYPE: PRT
<213> ORGANISM: Artificial Sequence
<220> FEATURE:
<223> OTHER INFORMATION: FS28-256-021 mAb variable domain

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser
        115

<210> SEQ ID NO 110
<211> LENGTH: 357
<212> TYPE: DNA
<213> ORGANISM: Artificial Sequence
<220> FEATURE:
<223> OTHER INFORMATION: FS28-256-021 mAb variable domain

<400> SEQUENCE: 110
gaagtgcaac tgctggagtc cggtggtggt ctggtacagc cgggtggttc tctgcgtctg    60
agttgcgcgg ccagtggctt taccttcact catacttata tgagctgggt gcgtcaggct   120
ccgggcaaag gtctggaatg ggttagcaat atttctccga cttatagcac taccaactat   180
gcggatagcg tgaaaggccg ttttaccatt tctcgcgaca acaacaagaa cacgctgtac   240
ctgcagatga actcactgcg tgccgaagat acggccgtgt attactgtgc gagatacaac   300
gcgtatcatg ctgctctgga ctactggggc cagggaaccc tggtcaccgt ctcgagt      357

<210> SEQ ID NO 111
<211> LENGTH: 8
<212> TYPE: PRT
<213> ORGANISM: Artificial Sequence
<220> FEATURE:
<223> OTHER INFORMATION: FS28-256-014 mAb CDR1 (IMGT)

<400> SEQUENCE: 111

Gly Phe Thr Phe Thr Asp Thr Tyr
1               5

<210> SEQ ID NO 112
<211> LENGTH: 5
<212> TYPE: PRT
<213> ORGANISM: Artificial Sequence
<220> FEATURE:
<223> OTHER INFORMATION: FS28-256-014 mAb CDR1 (Kabat)

<400> SEQUENCE: 112

Asp Thr Tyr Met Ser
1               5

<210> SEQ ID NO 113
<211> LENGTH: 12
<212> TYPE: PRT
<213> ORGANISM: Artificial Sequence
<220> FEATURE:
<223> OTHER INFORMATION: FS28-256-014 mAb CDR3 (IMGT)

<400> SEQUENCE: 113

Ala Arg Tyr Asn Ala Tyr Ala Ala Gly Leu Asp Tyr
1               5                   10

<210> SEQ ID NO 114
<211> LENGTH: 10
<212> TYPE: PRT
<213> ORGANISM: Artificial Sequence
<220> FEATURE:
<223> OTHER INFORMATION: FS28-256-014 mAb CDR3 (Kabat)

<400> SEQUENCE: 114

Tyr Asn Ala Tyr Ala Ala Gly Leu Asp Tyr
1               5                   10

<210> SEQ ID NO 115
<211> LENGTH: 119
<212> TYPE: PRT
<213> ORGANISM: Artificial Sequence
<220> FEATURE:
<223> OTHER INFORMATION: FS28-256-014 mAb variable domain

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser
        115

<210> SEQ ID NO 116
<211> LENGTH: 357
<212> TYPE: DNA
<213> ORGANISM: Artificial Sequence
<220> FEATURE:
<223> OTHER INFORMATION: FS28-256-014 mAb variable domain

<400> SEQUENCE: 116
gaagtgcaac tgctggagtc cggtggtggt ctggtacagc cgggtggttc tctgcgtctg     60
agttgcgcgg ccagtggctt taccttcact gatacttata tgagctgggt gcgtcaggct    120

```
ccgggcaaag gtctggaatg ggttagcaat atttctccga cttatagcac taccaactat    180
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
gcgtatgcgg cgggtcttga ctactggggc cagggaaccc tggtcaccgt ctcgagt      357
```

<210> SEQ ID NO 117
<211> LENGTH: 448
<212> TYPE: PRT
<213> ORGANISM: Artificial Sequence
<220> FEATURE:
<223> OTHER INFORMATION: FS28-256-014 mAb heavy chain without LALA

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

| | | | | | | | | | | | |
|---|---|---|---|---|---|---|---|---|---|---|---|
|Tyr|Lys|Cys|Lys|Val|Ser|Asn|Lys|Ala|Leu|Pro|Ala|Pro|Ile|Glu|Lys|
| | | | |325| | | |330| | | |  |335|   |   |

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

```
<210> SEQ ID NO 118
<211> LENGTH: 1344
<212> TYPE: DNA
<213> ORGANISM: Artificial Sequence
<220> FEATURE:
<223> OTHER INFORMATION: FS28-256-014 mAb heavy chain without LALA

<400> SEQUENCE: 118
gaagtgcaac tgctggagtc cggtggtggt ctggtacagc cgggtggttc tctgcgtctg     60
agttgcgcgg ccagtggctt taccttcact gatacttata tgagctgggt gcgtcaggct    120
ccgggcaaag gtctggaatg ggttagcaat atttctccga cttatagcac taccaactat    180
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
gcgtatgcgc gggtcttgga ctactggggc cagggaaccc tggtcaccgt ctcgagtgct    360
agcactaagg gcccgtcggt gttcccgctg gccccatcgt ccaagagcac atcaggggt     420
accgccgccc tgggctgcct tgtgaaggat tactttcccg agcccgtcac agtgtcctgg    480
aacagcggag ccctgacctc cggagtgcat actttcccgg ctgtgcttca gtcctctggc    540
ctgtactcat gtcctccgt ggtcaccgtc ccttcgtcct ccctgggcac ccagacctat    600
atctgtaatg tcaaccataa gccctcgaac accaaggtcg acaagaaggt cgagccgaag    660
tcgtgcgaca agactcacac ttgcccgcct tgcccagccc cggaactgct gggtggtcct    720
tcggtgttcc tcttcccgcc caagccgaag gatacctga tgatctcacg gacccccgaa    780
gtgacctgtg tggtggtgga cgtgtcccac gaggacccgg aagtgaaatt caattggtac    840
gtggatggag tggaagtgca aacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa   1020
gccaagggac agcctcgaga gcctcaagtg tacaccctgc ctccctctcg ggacgagctg   1080
accaagaacc aagtctccct gacctgtctg gtcaagggat tctacccatc ggatatcgcc   1140
gtggaatggg aaagcaacgg acagcccgag aacaactaca gacgactcc gccgtgctg   1200
gattccgacg ggagcttctt cttgtactcc aagctgaccg tcgacaagag cagatggcag   1260
cagggaaacg tgttctcctg ctccgtgatg catgaggcgc tgcacaacca ctacactcag   1320
aagagcttgt ccctgtcgcc cgga                                         1344
```

<210> SEQ ID NO 119
<211> LENGTH: 448
<212> TYPE: PRT
<213> ORGANISM: Artificial Sequence
<220> FEATURE:
<223> OTHER INFORMATION: FS28-256-014 mAb heavy chain with LALA

<400> SEQUENCE: 119

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 120
<211> LENGTH: 1344
<212> TYPE: DNA
<213> ORGANISM: Artificial Sequence
<220> FEATURE:
<223> OTHER INFORMATION: FS28-256-014 mAb heavy chain with LALA

<400> SEQUENCE: 120
gaagtgcaac tgctggagtc cggtggtggt ctggtacagc cgggtggttc tctgcgtctg      60
agttgcgcgg ccagtggctt taccttcact gatacttata tgagctgggt gcgtcaggct     120
ccgggcaaag gtctggaatg ggttagcaat atttctccga cttatagcac taccaactat     180
gcggatagcg tgaaaggccg tttaccatt tctcgcgaca acagcaagaa cacgctgtac      240
ctgcagatga actcactgcg tgccgaagat acggccgtgt attactgtgc gagatacaac     300
gcgtatgcgc gggtcttga ctactggggc agggaaccc tggtcaccgt ctcgagtgct       360
agcactaagg gcccgtcggt gttcccgctg gccccatcgt ccaagagcac atcaggggt      420 accgccgccc tgggctgcct tgtgaaggat tactttccg agcccgtcac agtgtcctgg      480
aacagcggag ccctgacctc cggagtgcat actttcccgg ctgtgcttca gtcctctggc     540
ctgtactcat tgtcctccgt ggtcaccgtc ccttcgtcct ccctgggcac ccagacctat     600
atctgtaatg tcaaccataa gccctcgaac accaaggtcg acaagaaggt cgagccgaag     660
tcgtgcgaca gagactcacac ttgccccgcct tgcccagccc cggaagctgc cggtggtcct   720
tcggtgttcc tcttcccgcc aagccgaag gataccctga tgatctcacg gacccccgaa      780
gtgacctgtg tggtggtgga cgtgtcccac gaggacccgg aagtgaaatt caattggtac     840
gtggatggag tggaagtgca caacgccaag accaagccac gggaagaaca gtacaactct     900
acctaccgcg tggtgtccgt gctcactgtg ctgcaccaag actggctgaa cgggaaggag     960
tacaagtgca agtgtccaa caaggcgctg cctgccccaa ttgagaaaac tatctcgaaa     1020
gccaagggac agcctcgaga gcctcaagtg tacaccctgc ctccctctcg gacgagctg     1080 accaagaacc aagtctccct gacctgtctg gtcaagggat tctacccatc ggatatcgcc    1140
gtggaatggg aaagcaacgg acagcccgag aacaactaca agacgactcc gcccgtgctg    1200
gattccgacg ggagcttctt cttgtactcc aagctgaccg tcgacaagag cagatggcag    1260 caggggaaacg tgttctcctg ctccgtgatg catgaggcgc tgcacaacca ctacactcag    1320
aagagcttgt ccctgtcgcc cgga                                           1344

<210> SEQ ID NO 121
<211> LENGTH: 119
<212> TYPE: PRT
<213> ORGANISM: Artificial Sequence
<220> FEATURE:
<223> OTHER INFORMATION: FS28-256-018 mAb variable domain
```

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

Thr Leu Val Thr Val Ser Ser
        115

<210> SEQ ID NO 122
<211> LENGTH: 357
<212> TYPE: DNA
<213> ORGANISM: Artificial Sequence
<220> FEATURE:
<223> OTHER INFORMATION: FS28-256-018 mAb variable domain

<400> SEQUENCE: 122
gaagtgcaac tgctggagtc cggtggtggt ctggtacagc cgggtggttc tctgcgtctg     60
agttgcgcgg ccagtggctt taccttcact cagacttata tgagctgggt gcgtcagget    120 ccgggcaaag gtctggaatg ggttagcaat atttctccga cttatagcac taccaactat    180
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
gcttatcaga ttgggttgga ctactggggc cagggaaccc tggtcaccgt ctcgagt       357

<210> SEQ ID NO 123
<211> LENGTH: 448
<212> TYPE: PRT
<213> ORGANISM: Artificial Sequence
<220> FEATURE:
<223> OTHER INFORMATION: FS28-256-023 mAb heavy chain without LALA

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

| Thr | Leu | Val | Thr | Val | Ser | Ser | Ala | Ser | Thr | Lys | Gly | Pro | Ser | Val | Phe |
|---|---|---|---|---|---|---|---|---|---|---|---|---|---|---|---|
| | 115 | | | | 120 | | | | | 125 | | | | | |

| Pro | Leu | Ala | Pro | Ser | Ser | Lys | Ser | Thr | Ser | Gly | Gly | Thr | Ala | Ala | Leu |
|---|---|---|---|---|---|---|---|---|---|---|---|---|---|---|---|
| 130 | | | | | 135 | | | | | 140 | | | | | |

| Gly | Cys | Leu | Val | Lys | Asp | Tyr | Phe | Pro | Glu | Pro | Val | Thr | Val | Ser | Trp |
|---|---|---|---|---|---|---|---|---|---|---|---|---|---|---|---|
| 145 | | | | | 150 | | | | | 155 | | | | | 160 |

| Asn | Ser | Gly | Ala | Leu | Thr | Ser | Gly | Val | His | Thr | Phe | Pro | Ala | Val | Leu |
|---|---|---|---|---|---|---|---|---|---|---|---|---|---|---|---|
| | | | | 165 | | | | | 170 | | | | | 175 | |

| Gln | Ser | Ser | Gly | Leu | Tyr | Ser | Leu | Ser | Ser | Val | Val | Thr | Val | Pro | Ser |
|---|---|---|---|---|---|---|---|---|---|---|---|---|---|---|---|
| | | | 180 | | | | | 185 | | | | | 190 | | |

| Ser | Ser | Leu | Gly | Thr | Gln | Thr | Tyr | Ile | Cys | Asn | Val | Asn | His | Lys | Pro |
|---|---|---|---|---|---|---|---|---|---|---|---|---|---|---|---|
| | 195 | | | | | 200 | | | | | 205 | | | | |

| Ser | Asn | Thr | Lys | Val | Asp | Lys | Lys | Val | Glu | Pro | Lys | Ser | Cys | Asp | Lys |
|---|---|---|---|---|---|---|---|---|---|---|---|---|---|---|---|
| 210 | | | | | 215 | | | | | 220 | | | | | |

| Thr | His | Thr | Cys | Pro | Pro | Cys | Pro | Ala | Pro | Glu | Leu | Leu | Gly | Gly | Pro |
|---|---|---|---|---|---|---|---|---|---|---|---|---|---|---|---|
| 225 | | | | | 230 | | | | | 235 | | | | | 240 |

| Ser | Val | Phe | Leu | Phe | Pro | Pro | Lys | Pro | Lys | Asp | Thr | Leu | Met | Ile | Ser |
|---|---|---|---|---|---|---|---|---|---|---|---|---|---|---|---|
| | | | | 245 | | | | | 250 | | | | | 255 | |

| Arg | Thr | Pro | Glu | Val | Thr | Cys | Val | Val | Val | Asp | Val | Ser | His | Glu | Asp |
|---|---|---|---|---|---|---|---|---|---|---|---|---|---|---|---|
| | | | 260 | | | | | 265 | | | | | 270 | | |

| Pro | Glu | Val | Lys | Phe | Asn | Trp | Tyr | Val | Asp | Gly | Val | Glu | Val | His | Asn |
|---|---|---|---|---|---|---|---|---|---|---|---|---|---|---|---|
| | 275 | | | | | 280 | | | | | 285 | | | | |

| Ala | Lys | Thr | Lys | Pro | Arg | Glu | Glu | Gln | Tyr | Asn | Ser | Thr | Tyr | Arg | Val |
|---|---|---|---|---|---|---|---|---|---|---|---|---|---|---|---|
| 290 | | | | | 295 | | | | | 300 | | | | | |

| Val | Ser | Val | Leu | Thr | Val | Leu | His | Gln | Asp | Trp | Leu | Asn | Gly | Lys | Glu |
|---|---|---|---|---|---|---|---|---|---|---|---|---|---|---|---|
| 305 | | | | | 310 | | | | | 315 | | | | | 320 |

| Tyr | Lys | Cys | Lys | Val | Ser | Asn | Lys | Ala | Leu | Pro | Ala | Pro | Ile | Glu | Lys |
|---|---|---|---|---|---|---|---|---|---|---|---|---|---|---|---|
| | | | | 325 | | | | | 330 | | | | | 335 | |

| Thr | Ile | Ser | Lys | Ala | Lys | Gly | Gln | Pro | Arg | Glu | Pro | Gln | Val | Tyr | Thr |
|---|---|---|---|---|---|---|---|---|---|---|---|---|---|---|---|
| | | | 340 | | | | | 345 | | | | | 350 | | |

| Leu | Pro | Pro | Ser | Arg | Asp | Glu | Leu | Thr | Lys | Asn | Gln | Val | Ser | Leu | Thr |
|---|---|---|---|---|---|---|---|---|---|---|---|---|---|---|---|
| | | 355 | | | | | 360 | | | | | 365 | | | |

| Cys | Leu | Val | Lys | Gly | Phe | Tyr | Pro | Ser | Asp | Ile | Ala | Val | Glu | Trp | Glu |
|---|---|---|---|---|---|---|---|---|---|---|---|---|---|---|---|
| | 370 | | | | | 375 | | | | | 380 | | | | |

| Ser | Asn | Gly | Gln | Pro | Glu | Asn | Asn | Tyr | Lys | Thr | Thr | Pro | Pro | Val | Leu |
|---|---|---|---|---|---|---|---|---|---|---|---|---|---|---|---|
| 385 | | | | | 390 | | | | | 395 | | | | | 400 |

| Asp | Ser | Asp | Gly | Ser | Phe | Phe | Leu | Tyr | Ser | Lys | Leu | Thr | Val | Asp | Lys |
|---|---|---|---|---|---|---|---|---|---|---|---|---|---|---|---|
| | | | | 405 | | | | | 410 | | | | | 415 | |

| Ser | Arg | Trp | Gln | Gln | Gly | Asn | Val | Phe | Ser | Cys | Ser | Val | Met | His | Glu |
|---|---|---|---|---|---|---|---|---|---|---|---|---|---|---|---|
| | | | 420 | | | | | 425 | | | | | 430 | | |

| Ala | Leu | His | Asn | His | Tyr | Thr | Gln | Lys | Ser | Leu | Ser | Leu | Ser | Pro | Gly |
|---|---|---|---|---|---|---|---|---|---|---|---|---|---|---|---|
| | | 435 | | | | | 440 | | | | | 445 | | | |

<210> SEQ ID NO 124
<211> LENGTH: 1344
<212> TYPE: DNA
<213> ORGANISM: Artificial Sequence
<220> FEATURE:
<223> OTHER INFORMATION: FS28-256-023 mAb heavy chain without LALA

<400> SEQUENCE: 124

```
gaagtgcaac tgctggagtc cggtggtggt ctggtacagc cgggtggttc tctgcgtctg    60
agttgcgcgg ccagtggctt taccttcact cagacttata tgagctgggt cgtcaggct   120 ccgggcaaag gtctggaatg ggttagcaat atttctccga cttatagcac taccaactat   180
```

```
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
gcttatcaga ttgggttgga ctactggggc cagggaaccc tggtcaccgt ctcgagtgct    360
agcactaagg gcccgtcggt gttcccgctg gccccatcgt ccaagagcac atcggggggt    420
accgccgccc tgggctgcct tgtgaaggat tactttcccg agcccgtcac agtgtcctgg    480
aacagcggag ccctgacctc cggagtgcat acttccccgg ctgtgcttca gtcctctggc    540
ctgtactcat tgtcctccgt ggtcaccgtc ccttcgtcct ccctgggcac ccagacctat    600
atctgtaatg tcaaccataa gccctcgaac accaaggtcg acaagaaggt cgagccgaag    660
tcgtgcgaca agactcacac ttgcccgcct tgcccagccc cggaactgct gggtggtcct    720
tcggtgttcc tcttcccgcc caagccgaag gatacgctga tgatctcacg gacccccgaa    780
gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa    1020
gccaagggac agcctcgaga gcctcaagtg tacaccctgc ctccctctcg ggacgagctg    1080
accaagaacc aagtctccct gacctgtctg gtcaagggat tctacccatc ggatatcgcc    1140
gtggaatggg aaagcaacgg acagcccgag aacaactaca agacgactcc gcccgtgctg    1200
gattccgacg ggagcttctt cttgtactcc aagctgaccg tcgacaagag cagatggcag    1260
cagggaaacg tgttctcctg ctccgtgatg catgaggcgc tgcacaacca ctacactcag    1320
aagagcttgt ccctgtcgcc cgga                                           1344
```

<210> SEQ ID NO 125
<211> LENGTH: 448
<212> TYPE: PRT
<213> ORGANISM: Artificial Sequence
<220> FEATURE:
<223> OTHER INFORMATION: FS28-256-023 mAb heavy chain with LALA

<400> SEQUENCE: 125

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
                    165                 170                 175
Gln Ser Ser Gly Leu Tyr Ser Leu Ser Ser Val Val Thr Val Pro Ser
                    180                 185                 190
Ser Ser Leu Gly Thr Gln Thr Tyr Ile Cys Asn Val Asn His Lys Pro
                    195                 200                 205
Ser Asn Thr Lys Val Asp Lys Lys Val Glu Pro Lys Ser Cys Asp Lys
                    210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                    245                 250                 255
Arg Thr Pro Glu Val Thr Cys Val Val Val Asp Val Ser His Glu Asp
                    260                 265                 270
Pro Glu Val Lys Phe Asn Trp Tyr Val Asp Gly Val Glu Val His Asn
                    275                 280                 285
Ala Lys Thr Lys Pro Arg Glu Glu Gln Tyr Asn Ser Thr Tyr Arg Val
                    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                    325                 330                 335
Thr Ile Ser Lys Ala Lys Gly Gln Pro Arg Glu Pro Gln Val Tyr Thr
                    340                 345                 350
Leu Pro Pro Ser Arg Asp Glu Leu Thr Lys Asn Gln Val Ser Leu Thr
                    355                 360                 365
Cys Leu Val Lys Gly Phe Tyr Pro Ser Asp Ile Ala Val Glu Trp Glu
                    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                    405                 410                 415
Ser Arg Trp Gln Gln Gly Asn Val Phe Ser Cys Ser Val Met His Glu
                    420                 425                 430
Ala Leu His Asn His Tyr Thr Gln Lys Ser Leu Ser Leu Ser Pro Gly
                    435                 440                 445

<210> SEQ ID NO 126
<211> LENGTH: 1344
<212> TYPE: DNA
<213> ORGANISM: Artificial Sequence
<220> FEATURE:
<223> OTHER INFORMATION: FS28-256-023 mAb heavy chain with LALA

<400> SEQUENCE: 126
gaagtgcaac tgctggagtc cggtggtggt ctggtacagc cgggtggttc tctgcgtctg      60
agttgcgcgg ccagtggctt taccttcact cagacttata tgagctgggt gcgtcaggct     120
ccgggcaaag gtctggaatg ggttagcaat atttctccga cttatagcac taccaactat     180
gcggatagcg tgaaaggccg ttttaccatt tctcgcgaca acagcaagaa cacgctgtac     240
ctgcagatga actcactgcg tgccgaagat acggccgtgt attactgtgc gagatacaac     300
gcttatcaga ttgggttgga ctactggggc caggaacccc tggtcaccgt ctcgagtgct     360
agcactaagg gcccgtcggt gttcccgctg gccccatcgt ccaagagcac atcaggggt     420
```

```
accgccgccc tgggctgcct tgtgaaggat tactttcccg agcccgtcac agtgtcctgg    480
aacagcggag ccctgacctc cggagtgcat actttcccgg ctgtgcttca gtcctctggc    540
ctgtactcat tgtcctccgt ggtcaccgtc ccttcgtcct ccctgggcac ccagacctat    600
atctgtaatg tcaaccataa gccctcgaac accaaggtcg acaagaaggt cgagccgaaa    660
tcgtgcgaca agactcacac ttgcccgcct tgcccagccc cggaagctgc cggtggtcct    720
tcggtgttcc tcttcccgcc caagccaagg ataccctga tgatctcacg gaccccgaa     780 gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa    1020
gccaagggac agcctcgaga gcctcaagtg tacaccctgc ctccctctcg ggacgagctg    1080
accaagaacc aagtctccct gacctgtctg gtcaagggat tctacccatc ggatatcgcc    1140
gtggaatggg aaagcaacgg acagcccgag aacaactaca gacgactcc gcccgtgctg     1200 gattccgacg ggagcttctt cttgtactcc aagctgaccg tcgacaagag cagatggcag    1260
cagggaaacg tgttctcctg ctccgtgatg catgaggcgc tgcacaacca ctacactcag    1320
aagagcttgt ccctgtcgcc cgga                                            1344
```

<210> SEQ ID NO 127
<211> LENGTH: 453
<212> TYPE: PRT
<213> ORGANISM: Artificial Sequence
<220> FEATURE:
<223> OTHER INFORMATION: FS22-053-008/FS28-256-012 mAb2 heavy chain without LALA

<400> SEQUENCE: 127

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

```
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
        245                 250                 255
Arg Thr Pro Glu Val Thr Cys Val Val Val Asp Val Ser His Glu Asp
        260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
        325                 330                 335
Thr Ile Ser Lys Ala Lys Gly Gln Pro Arg Glu Pro Gln Val Tyr Thr
        340                 345                 350
Leu Pro Pro Ser Arg Asp Glu Leu Asn Pro Pro Tyr Leu Phe Ser Asn
        355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
        405                 410                 415
Leu Thr Val Asp Tyr Trp Arg Trp Leu Glu Gly Asn Val Phe Ser Cys
        420                 425                 430
Ser Val Met His Glu Ala Leu His Asn His Tyr Thr Gln Lys Ser Leu
        435                 440                 445
Ser Leu Ser Pro Gly
        450

<210> SEQ ID NO 128
<211> LENGTH: 453
<212> TYPE: PRT
<213> ORGANISM: Artificial Sequence
<220> FEATURE:
<223> OTHER INFORMATION: FS22-053-008/FS28-256-012 mAb2 heavy chain with
      LALA

<400> SEQUENCE: 128

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Thr His Thr
            20                  25                  30
Tyr Met Ser Trp Val Arg Gln Ala Pro Gly Lys Gly Leu Glu Trp Val
        35                  40                  45
Ser Asn Ile Ser Pro Thr Tyr Ser Thr Thr Asn Tyr Ala Asp Ser Val
    50                  55                  60
Lys Gly Arg Phe Thr Ile Ser Arg Asp Asn Lys Asn Thr Leu Tyr
65                  70                  75                  80
Leu Gln Met Asn Ser Leu Arg Ala Glu Asp Thr Ala Val Tyr Tyr Cys
```

```
                85                  90                  95
Ala Arg Tyr Asn Ala Tyr His Ala Ala Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 129
<211> LENGTH: 453
<212> TYPE: PRT
<213> ORGANISM: Artificial Sequence
<220> FEATURE:
<223> OTHER INFORMATION: FS22-053-008/FS28-256-014 mAb2 heavy chain
      without LALA
```

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys

```
                        405                 410                 415
Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 130
<211> LENGTH: 453
<212> TYPE: PRT
<213> ORGANISM: Artificial Sequence
<220> FEATURE:
<223> OTHER INFORMATION: FS22-053-008/FS28-256-014 mAb2 heavy chain with
      LALA

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 131
<211> LENGTH: 453
<212> TYPE: PRT
<213> ORGANISM: Artificial Sequence
<220> FEATURE:
<223> OTHER INFORMATION: FS22-053-008/FS28-256-018 mAb2 heavy chain
      without LALA

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 132
<211> LENGTH: 453
<212> TYPE: PRT
<213> ORGANISM: Artificial Sequence
<220> FEATURE:
<223> OTHER INFORMATION: FS22-053-008/FS28-256-018 mAb2 heavy chain with
      LALA

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
```

```
                100             105             110
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135             140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Asn Pro Pro Tyr Leu Phe Ser Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 133
<211> LENGTH: 453
<212> TYPE: PRT
<213> ORGANISM: Artificial Sequence
<220> FEATURE:
<223> OTHER INFORMATION: FS22-053-008/FS28-256-021 mAb2 heavy chain
      without LALA

<400> SEQUENCE: 133
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
50                      55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Tyr Leu Phe Ser Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Tyr Trp Arg Trp Leu Glu Gly Asn Val Phe Ser Cys
```

```
                420             425            430
Ser Val Met His Glu Ala Leu His Asn His Tyr Thr Gln Lys Ser Leu
            435                 440              445

Ser Leu Ser Pro Gly
    450

<210> SEQ ID NO 134
<211> LENGTH: 453
<212> TYPE: PRT
<213> ORGANISM: Artificial Sequence
<220> FEATURE:
<223> OTHER INFORMATION: FS22-053-008/FS28-256-021 mAb2 heavy chain with
      LALA

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Asn Pro Pro Tyr Leu Phe Ser Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly
    450

<210> SEQ ID NO 135
<211> LENGTH: 453
<212> TYPE: PRT
<213> ORGANISM: Artificial Sequence
<220> FEATURE:
<223> OTHER INFORMATION: FS22-053-008/FS28-256-023 mAb2 heavy chain
      without LALA

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 136
<211> LENGTH: 453
<212> TYPE: PRT
<213> ORGANISM: Artificial Sequence
<220> FEATURE:
<223> OTHER INFORMATION: FS22-053-008/FS28-256-023 mAb2 heavy chain with
      LALA

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

Thr Leu Val Thr Val Ser Ser Ala Ser Thr Lys Gly Pro Ser Val Phe
```

-continued

```
            115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Asn Pro Pro Tyr Leu Phe Ser Asn
                355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly
        450

<210> SEQ ID NO 137
<211> LENGTH: 453
<212> TYPE: PRT
<213> ORGANISM: Artificial Sequence
<220> FEATURE:
<223> OTHER INFORMATION: FS22-053-008/FS28-256-024 mAb2 heavy chain
      without LALA

<400> SEQUENCE: 137

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
```

-continued

```
              435                 440                 445
Ser Leu Ser Pro Gly
            450

<210> SEQ ID NO 138
<211> LENGTH: 453
<212> TYPE: PRT
<213> ORGANISM: Artificial Sequence
<220> FEATURE:
<223> OTHER INFORMATION: FS22-053-008/FS28-256-024 mAb2 heavy chain with
      LALA

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
            450

<210> SEQ ID NO 139
<211> LENGTH: 453
<212> TYPE: PRT
<213> ORGANISM: Artificial Sequence
<220> FEATURE:
<223> OTHER INFORMATION: FS22-053-008/FS28-256-026 heavy chain without
      LALA

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
            35                  40                  45

Ser Asn Ile Ser Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Tyr Asn Ala Tyr Gln Ile Gly Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Asn Pro Pro Tyr Leu Phe Ser Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly
                450

<210> SEQ ID NO 140
<211> LENGTH: 453
<212> TYPE: PRT
<213> ORGANISM: Artificial Sequence
<220> FEATURE:
<223> OTHER INFORMATION: FS22-053-008/FS28-256-026 heavy chain without
      LALA

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
                20                  25                  30

Tyr Met Ser Trp Val Arg Gln Ala Pro Gly Lys Gly Leu Glu Trp Val
                35                  40                  45

Ser Asn Ile Ser Pro Thr Tyr Ser Thr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
```

130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 141
<211> LENGTH: 453
<212> TYPE: PRT
<213> ORGANISM: Artificial Sequence
<220> FEATURE:
<223> OTHER INFORMATION: FS22-053-008/FS28-256-027 mAb2 heavy chain
      without LALA

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

-continued

```
Tyr Met Ser Trp Val Arg Gln Ala Pro Gly Lys Gly Leu Glu Trp Val
        35                  40                  45
Ser Asn Ile Ser Pro Thr Tyr Ser Thr Thr Asn Tyr Ala Asp Ser Val
50                  55                  60
Lys Gly Arg Phe Thr Ile Ser Arg Asp Asn Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Tyr Asn Ala Tyr His Ala Ala Leu Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Asn Pro Pro Tyr Leu Phe Ser Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Tyr Trp Arg Trp Leu Glu Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly
```

-continued

450

<210> SEQ ID NO 142
<211> LENGTH: 453
<212> TYPE: PRT
<213> ORGANISM: Artificial Sequence
<220> FEATURE:
<223> OTHER INFORMATION: FS22-053-008/FS28-256-027 mAb2 heavy chain with
      LALA

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
                355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Glu Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly
    450

<210> SEQ ID NO 143
<211> LENGTH: 450
<212> TYPE: PRT
<213> ORGANISM: Artificial Sequence
<220> FEATURE:
<223> OTHER INFORMATION: FS22-053-008/FS28-024 mAb2 heavy chain without
      LALA

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Thr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

```
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 144
<211> LENGTH: 450
<212> TYPE: PRT
<213> ORGANISM: Artificial Sequence
<220> FEATURE:
<223> OTHER INFORMATION: FS22-053-008/FS28-024 mAb2 heavy chain with
      LALA

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Thr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
```

```
            145                 150                 155                 160
Ala Leu Thr Ser Gly Val His Thr Phe Pro Ala Val Leu Gln Ser Ser
                    165                 170                 175
Gly Leu Tyr Ser Leu Ser Ser Val Val Thr Val Pro Ser Ser Ser Leu
                    180                 185                 190
Gly Thr Gln Thr Tyr Ile Cys Asn Val Asn His Lys Pro Ser Asn Thr
                    195                 200                 205
Lys Val Asp Lys Lys Val Glu Pro Lys Ser Cys Asp Lys Thr His Thr
                    210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                    245                 250                 255
Glu Val Thr Cys Val Val Val Asp Val Ser His Glu Asp Pro Glu Val
                    260                 265                 270
Lys Phe Asn Trp Tyr Val Asp Gly Val Glu Val His Asn Ala Lys Thr
                    275                 280                 285
Lys Pro Arg Glu Glu Gln Tyr Asn Ser Thr Tyr Arg Val Val Ser Val
                    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                    325                 330                 335
Lys Ala Lys Gly Gln Pro Arg Glu Pro Gln Val Tyr Thr Leu Pro Pro
                    340                 345                 350
Ser Arg Asp Glu Leu Asn Pro Pro Tyr Leu Phe Ser Asn Gln Val Ser
                    355                 360                 365
Leu Thr Cys Leu Val Lys Gly Phe Tyr Pro Ser Asp Ile Ala Val Glu
                    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                    405                 410                 415
Asp Tyr Trp Arg Trp Leu Glu Gly Asn Val Phe Ser Cys Ser Val Met
                    420                 425                 430
His Glu Ala Leu His Asn His Tyr Thr Gln Lys Ser Leu Ser Leu Ser
                    435                 440                 445
Pro Gly
    450

<210> SEQ ID NO 145
<211> LENGTH: 450
<212> TYPE: PRT
<213> ORGANISM: Artificial Sequence
<220> FEATURE:
<223> OTHER INFORMATION: FS22-053-008/FS28-024-051 mAb2 heavy chain
      without LALA

<400> SEQUENCE: 145

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Leu Ser Tyr Ser
                20                  25                  30
Ser Met Ser Trp Val Arg Gln Ala Pro Gly Lys Gly Leu Glu Trp Val
            35                  40                  45
```

```
Ser Phe Ile Thr Pro Ser Thr Gly Tyr Thr His Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Arg Ala Leu Ile Phe Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Asn Pro Pro Tyr Leu Phe Ser Asn Gln Val Ser
                355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Tyr Trp Arg Trp Leu Glu Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly
450
```

```
<210> SEQ ID NO 146
<211> LENGTH: 450
<212> TYPE: PRT
<213> ORGANISM: Artificial Sequence
<220> FEATURE:
<223> OTHER INFORMATION: FS22-053-008/FS28-024-051 mAb2 heavy chain with
      LALA

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Tyr Leu Phe Ser Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 147
<211> LENGTH: 450
<212> TYPE: PRT
<213> ORGANISM: Artificial Sequence
<220> FEATURE:
<223> OTHER INFORMATION: FS22-053-008/FS28-024-052 mAb2 heavy chain
      (without LALA)

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 148
<211> LENGTH: 450
<212> TYPE: PRT
<213> ORGANISM: Artificial Sequence
<220> FEATURE:
<223> OTHER INFORMATION: FS22-053-008/FS28-024-052 mAb2 heavy chain
      (with LALA)

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser

```
                165                 170                 175
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 149
<211> LENGTH: 450
<212> TYPE: PRT
<213> ORGANISM: Artificial Sequence
<220> FEATURE:
<223> OTHER INFORMATION: FS22-053-008/FS28-024-053 mAb2 heavy chain
      without LALA

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 150
<211> LENGTH: 450
<212> TYPE: PRT

<213> ORGANISM: Artificial Sequence
<220> FEATURE:
<223> OTHER INFORMATION: FS22-053-008/FS28-024-053 mAb2 heavy chain with LALA

<400> SEQUENCE: 150

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Leu | Ser | Tyr | Ser |
| | | | 20 | | | | | 25 | | | | | 30 | | |
| Ser | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Phe | Ile | Thr | Pro | Ser | Thr | Gly | Tyr | Thr | His | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Arg | Ala | Leu | Val | Phe | Asp | Tyr | Trp | Gly | Gln | Gly | Thr | Leu | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| | 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | 195 | | | | | 200 | | | | | 205 | | | |
| Lys | Val | Asp | Lys | Lys | Val | Glu | Pro | Lys | Ser | Cys | Asp | Lys | Thr | His | Thr |
| | 210 | | | | | 215 | | | | | 220 | | | | |
| Cys | Pro | Pro | Cys | Pro | Ala | Pro | Glu | Ala | Ala | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | 275 | | | | | 280 | | | | | 285 | | | |
| Lys | Pro | Arg | Glu | Glu | Gln | Tyr | Asn | Ser | Thr | Tyr | Arg | Val | Val | Ser | Val |
| | 290 | | | | | 295 | | | | | 300 | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Pro | Ala | Pro | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Tyr | Thr | Leu | Pro | Pro |
| | | | 340 | | | | | 345 | | | | | 350 | | |
| Ser | Arg | Asp | Glu | Leu | Asn | Pro | Pro | Tyr | Leu | Phe | Ser | Asn | Gln | Val | Ser |
| | | 355 | | | | | 360 | | | | | 365 | | | |
| Leu | Thr | Cys | Leu | Val | Lys | Gly | Phe | Tyr | Pro | Ser | Asp | Ile | Ala | Val | Glu |
| | 370 | | | | | 375 | | | | | 380 | | | | |

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Tyr Trp Arg Trp Leu Glu Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly
    450

<210> SEQ ID NO 151
<211> LENGTH: 450
<212> TYPE: PRT
<213> ORGANISM: Artificial Sequence
<220> FEATURE:
<223> OTHER INFORMATION: FS22-053-008-AA/FS28-024-060 mAb2 heay chain
      with LALA

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly
   450

<210> SEQ ID NO 152
<211> LENGTH: 450
<212> TYPE: PRT
<213> ORGANISM: Artificial Sequence
<220> FEATURE:
<223> OTHER INFORMATION: FS22-053-008-AA/FS28-026 mAb2 heavy chain with
      LALA

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ser Ile Thr Pro Tyr Tyr Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Tyr Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu

```
                    180                 185                 190
Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 153
<211> LENGTH: 450
<212> TYPE: PRT
<213> ORGANISM: Artificial Sequence
<220> FEATURE:
<223> OTHER INFORMATION: FS22-053-008-AA/FS28-091 mAb2 heavy chain with
      LALA

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Lys Gly Leu Glu Trp Val
        35                  40                  45

Ser Ser Ile Lys Pro Tyr Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asn Arg Trp Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 154
<211> LENGTH: 457
<212> TYPE: PRT
<213> ORGANISM: Artificial Sequence
<220> FEATURE:
<223> OTHER INFORMATION: FS22-053-008-AA/FS28-185 mAb2 heavy chain with
```

LALA

<400> SEQUENCE: 154

| | | | | | | | | | | | | | | |
|---|---|---|---|---|---|---|---|---|---|---|---|---|---|---|
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Thr Ser
            20                  25                  30

Ala Met Ser Trp Val Arg Gln Ala Pro Gly Lys Gly Leu Glu Trp Val
        35                  40                  45

Ser Arg Ile Asn Pro Tyr Glu Gly Glu Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Ser Ile Ala Thr Tyr Tyr Lys Ser Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Asn Pro Pro Tyr
        355                 360                 365

Leu Phe Ser Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

```
Asn Tyr Lys Thr Thr Pro Val Leu Asp Ser Asp Gly Ser Phe Phe
                405                 410                 415

Leu Tyr Ser Lys Leu Thr Val Asp Tyr Trp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455

<210> SEQ ID NO 155
<211> LENGTH: 453
<212> TYPE: PRT
<213> ORGANISM: Artificial Sequence
<220> FEATURE:
<223> OTHER INFORMATION: FS22-053-008/FS28-256 mAb2 heavy chain without
      LALA

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 156
<211> LENGTH: 453
<212> TYPE: PRT
<213> ORGANISM: Artificial Sequence
<220> FEATURE:
<223> OTHER INFORMATION: FS22-053-008/FS28-256 mAb2 heavy chain with
      LALA

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
                    195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Asn Pro Pro Tyr Leu Phe Ser Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Tyr Trp Arg Trp Leu Glu Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly
    450

<210> SEQ ID NO 157
<211> LENGTH: 453
<212> TYPE: PRT
<213> ORGANISM: Artificial Sequence
<220> FEATURE:
<223> OTHER INFORMATION: FS22-053-008/FS28-256-001 mAb2 heavy chain
      without LALA

<400> SEQUENCE: 157

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Thr Glu Thr
            20                  25                  30
Tyr Met Ser Trp Val Arg Gln Ala Pro Gly Lys Gly Leu Glu Trp Val
        35                  40                  45
Ser Asn Ile Ser Pro Thr Tyr Ser Thr Thr Asn Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

```
Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
        450

<210> SEQ ID NO 158
<211> LENGTH: 453
<212> TYPE: PRT
<213> ORGANISM: Artificial Sequence
<220> FEATURE:
<223> OTHER INFORMATION: FS22-053-008/FS28-256-001 mAb2 heavy chain with
      LALA

<400> SEQUENCE: 158
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                     135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                     215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                     295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
370                     375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415
```

```
Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
            450

<210> SEQ ID NO 159
<211> LENGTH: 453
<212> TYPE: PRT
<213> ORGANISM: Artificial Sequence
<220> FEATURE:
<223> OTHER INFORMATION: FS22-053-008/FS28-256-005 mAb2 heavy chain
      without LALA

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
            35                  40                  45

Ser Asn Ile Ser Pro Thr Tyr Ser Thr Thr Asn Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Asn Pro Pro Tyr Leu Phe Ser Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
        450

<210> SEQ ID NO 160
<211> LENGTH: 453
<212> TYPE: PRT
<213> ORGANISM: Artificial Sequence
<220> FEATURE:
<223> OTHER INFORMATION: FS22-053-008/FS28-256-005 mAb2 heavy chain with
      LALA

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
            210                 215                 220
Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Asn Pro Pro Tyr Leu Phe Ser Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Tyr Trp Arg Trp Leu Glu Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 161
<211> LENGTH: 447
<212> TYPE: PRT
<213> ORGANISM: Artificial Sequence
<220> FEATURE:
<223> OTHER INFORMATION: FS28m-228 mAb (with LALA) heavy chain

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Phe Met Val Trp Val Arg Gln Ala Pro Gly Lys Gly Leu Glu Trp Val
            35                  40                  45

Ser Met Ile Ser Pro Lys Ser Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Phe Thr Pro Ala Arg Phe Asp Tyr Trp Gly Gln Gly Thr
            100                 105                 110

Leu Val Thr Val Ser Ser Ala Ser Thr Lys Gly Pro Ser Val Phe Pro
```

```
                115             120             125
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 162
<211> LENGTH: 215
<212> TYPE: PRT
<213> ORGANISM: Artificial Sequence
<220> FEATURE:
<223> OTHER INFORMATION: FS28m-228 mAb light chain

<400> SEQUENCE: 162

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
                    35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Pro Phe Pro Phe Ser
                 85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 163
<211> LENGTH: 447
<212> TYPE: PRT
<213> ORGANISM: Artificial Sequence
<220> FEATURE:
<223> OTHER INFORMATION: FS22-063-AA/FS28m-228 mAb2 heavy chain with
      LALA

<400> SEQUENCE: 163

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Phe Met Val Trp Val Arg Gln Ala Pro Gly Lys Gly Leu Glu Trp Val
         35                  40                  45

Ser Met Ile Ser Pro Lys Ser Ser Asn Thr Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Trp Phe Thr Pro Ala Arg Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 164
<211> LENGTH: 215
<212> TYPE: PRT
<213> ORGANISM: Artificial Sequence
<220> FEATURE:
<223> OTHER INFORMATION: FS22-063-AA/FS28m-228 mAb2 light chain

<400> SEQUENCE: 164

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Pro Phe Pro Phe Ser
                85                  90                  95
```

```
Phe Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
            210             215

<210> SEQ ID NO 165
<211> LENGTH: 445
<212> TYPE: PRT
<213> ORGANISM: Artificial Sequence
<220> FEATURE:
<223> OTHER INFORMATION: G1-AA/HelD1.3 mAb heavy chain with LALA

<400> SEQUENCE: 165

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 166
<211> LENGTH: 214
<212> TYPE: PRT
<213> ORGANISM: Artificial Sequence
<220> FEATURE:
<223> OTHER INFORMATION: G1-AA/HelD1.3 mAb light chain

<400> SEQUENCE: 166

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 167
<211> LENGTH: 448
<212> TYPE: PRT
<213> ORGANISM: Artificial Sequence
<220> FEATURE:
<223> OTHER INFORMATION: G1-AA/SS1 mAb (with LALA) heavy chain

<400> SEQUENCE: 167

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 168
<211> LENGTH: 213
<212> TYPE: PRT
<213> ORGANISM: Artificial Sequence
<220> FEATURE:
<223> OTHER INFORMATION: G1-AA/SS1 mAb light chain

<400> SEQUENCE: 168

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 169
<211> LENGTH: 303
<212> TYPE: PRT
<213> ORGANISM: Homo sapiens

<400> SEQUENCE: 169

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Val Ala Thr Leu Ile Asp Arg Phe Val Lys Gly Arg Gly
        115                 120                 125

Gln Leu Asp Lys Asp Thr Leu Asp Thr Leu Thr Ala Phe Tyr Pro Gly
130                 135                 140

Tyr Leu Cys Ser Leu Ser Pro Glu Glu Leu Ser Ser Val Pro Pro Ser
145                 150                 155                 160

Ser Ile Trp Ala Val Arg Pro Gln Asp Leu Asp Thr Cys Asp Pro Arg
                165                 170                 175

Gln Leu Asp Val Leu Tyr Pro Lys Ala Arg Leu Ala Phe Gln Asn Met
            180                 185                 190

Asn Gly Ser Glu Tyr Phe Val Lys Ile Gln Ser Phe Leu Gly Gly Ala
        195                 200                 205

Pro Thr Glu Asp Leu Lys Ala Leu Ser Gln Gln Asn Val Ser Met Asp
210                 215                 220

Leu Ala Thr Phe Met Lys Leu Arg Thr Asp Ala Val Leu Pro Leu Thr
225                 230                 235                 240

Val Ala Glu Val Gln Lys Leu Leu Gly Pro His Val Glu Gly Leu Lys
                245                 250                 255

Ala Glu Glu Arg His Arg Pro Val Arg Asp Trp Ile Leu Arg Gln Arg
            260                 265                 270

Gln Asp Asp Leu Asp Thr Leu Gly Leu Gly Leu Gln Gly Gly Ile Pro
        275                 280                 285

Asn Gly Tyr Leu Val Leu Asp Leu Ser Met Gln Glu Ala Leu Ser
290                 295                 300

<210> SEQ ID NO 170
<211> LENGTH: 303
<212> TYPE: PRT
<213> ORGANISM: Macaca fascicularis

<400> SEQUENCE: 170

Asp Val Glu Arg Thr Thr Cys Pro Pro Glu Lys Glu Val His Glu Ile
1               5                   10                  15

Asp Glu Ser Leu Ile Phe Tyr Lys Lys Arg Glu Leu Glu Ala Cys Val
            20                  25                  30

```
Asp Ala Ala Leu Leu Ala Ala Gln Met Asp Arg Val Asp Ala Ile Pro
             35                  40                  45

Phe Thr Tyr Glu Gln Leu Asp Val Leu Lys His Lys Leu Asp Glu Leu
 50                  55                  60

Tyr Pro Gln Gly Tyr Pro Glu Ser Val Ile Arg His Leu Gly His Leu
 65                  70                  75                  80

Phe Leu Lys Met Ser Pro Glu Asp Ile Arg Lys Trp Asn Val Thr Ser
                 85                  90                  95

Leu Glu Thr Leu Lys Ala Leu Leu Lys Val Ser Lys Gly His Glu Met
            100                 105                 110

Ser Ala Gln Val Ala Thr Leu Ile Asp Arg Val Val Gly Arg Gly
            115                 120                 125

Gln Leu Asp Lys Asp Thr Ala Asp Thr Leu Thr Ala Phe Cys Pro Gly
            130                 135                 140

Cys Leu Cys Ser Leu Ser Pro Glu Arg Leu Ser Ser Val Pro Pro Ser
145                 150                 155                 160

Ile Ile Gly Ala Val Arg Pro Gln Asp Leu Asp Thr Cys Gly Pro Arg
                165                 170                 175

Gln Leu Asp Val Leu Tyr Pro Lys Ala Arg Leu Ala Phe Gln Asn Met
            180                 185                 190

Ser Gly Ser Glu Tyr Phe Val Lys Ile Arg Pro Phe Leu Gly Gly Ala
            195                 200                 205

Pro Thr Glu Asp Leu Lys Ala Leu Ser Gln Gln Asn Val Ser Met Asp
            210                 215                 220

Leu Ala Thr Phe Met Lys Leu Arg Arg Glu Ala Val Leu Pro Leu Ser
225                 230                 235                 240

Val Ala Glu Val Gln Lys Leu Leu Gly Pro His Val Glu Gly Leu Lys
                245                 250                 255

Val Glu Glu Gln His Ser Pro Val Arg Asp Trp Ile Leu Lys Gln Arg
            260                 265                 270

Gln Asp Asp Leu Asp Thr Leu Gly Leu Gly Leu Gln Gly Gly Ile Pro
            275                 280                 285

Asn Gly Tyr Leu Ile Leu Asp Leu Ser Val Arg Glu Ala Leu Ser
            290                 295                 300

<210> SEQ ID NO 171
<211> LENGTH: 303
<212> TYPE: PRT
<213> ORGANISM: Mus musculus

<400> SEQUENCE: 171

Asp Ala Glu Gln Lys Ala Cys Pro Pro Gly Lys Glu Pro Tyr Lys Val
1                5                  10                  15

Asp Glu Asp Leu Ile Phe Tyr Gln Asn Trp Glu Leu Glu Ala Cys Val
             20                  25                  30

Asp Gly Thr Met Leu Ala Arg Gln Met Asp Leu Val Asn Glu Ile Pro
             35                  40                  45

Phe Thr Tyr Glu Gln Leu Ser Ile Phe Lys His Lys Leu Asp Lys Thr
 50                  55                  60

Tyr Pro Gln Gly Tyr Pro Glu Ser Leu Ile Gln Gln Leu Gly His Phe
 65                  70                  75                  80

Phe Arg Tyr Val Ser Pro Glu Asp Ile His Gln Trp Asn Val Thr Ser
                 85                  90                  95

Pro Asp Thr Val Lys Thr Leu Leu Lys Val Ser Lys Gly Gln Lys Met
            100                 105                 110
```

Asn Ala Gln Ala Ile Ala Leu Val Ala Cys Tyr Leu Arg Gly Gly Gly
            115                 120                 125

Gln Leu Asp Glu Asp Met Val Lys Ala Leu Gly Asp Ile Pro Leu Ser
        130                 135                 140

Tyr Leu Cys Asp Phe Ser Pro Gln Asp Leu His Ser Val Pro Ser Ser
145                 150                 155                 160

Val Met Trp Leu Val Gly Pro Gln Asp Leu Asp Lys Cys Ser Gln Arg
                165                 170                 175

His Leu Gly Leu Leu Tyr Gln Lys Ala Cys Ser Ala Phe Gln Asn Val
            180                 185                 190

Ser Gly Leu Glu Tyr Phe Glu Lys Ile Lys Thr Phe Leu Gly Gly Ala
        195                 200                 205

Ser Val Lys Asp Leu Arg Ala Leu Ser Gln His Asn Val Ser Met Asp
    210                 215                 220

Ile Ala Thr Phe Lys Arg Leu Gln Val Asp Ser Leu Val Gly Leu Ser
225                 230                 235                 240

Val Ala Glu Val Gln Lys Leu Gly Pro Asn Ile Val Asp Leu Lys
                245                 250                 255

Thr Glu Glu Asp Lys Ser Pro Val Arg Asp Trp Leu Phe Arg Gln His
            260                 265                 270

Gln Lys Asp Leu Asp Arg Leu Gly Leu Gly Leu Gln Gly Ile Pro
        275                 280                 285

Asn Gly Tyr Leu Val Leu Asp Phe Asn Val Arg Glu Ala Phe Ser
    290                 295                 300

<210> SEQ ID NO 172
<211> LENGTH: 107
<212> TYPE: PRT
<213> ORGANISM: Artificial Sequence
<220> FEATURE:
<223> OTHER INFORMATION: wild-type CH3 domain

<400> SEQUENCE: 172

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 173
<211> LENGTH: 110
<212> TYPE: PRT
<213> ORGANISM: Artificial Sequence
<220> FEATURE:
<223> OTHER INFORMATION: CH2 domain containing LALA mutation

<400> SEQUENCE: 173

Ala Pro Glu Ala Ala Gly Gly Pro Ser Val Phe Leu Phe Pro Pro Lys

```
  1               5                  10                 15
Pro Lys Asp Thr Leu Met Ile Ser Arg Thr Pro Glu Val Thr Cys Val
              20                 25                 30

Val Val Asp Val Ser His Glu Asp Pro Glu Val Lys Phe Asn Trp Tyr
              35                 40                 45

Val Asp Gly Val Glu Val His Asn Ala Lys Thr Lys Pro Arg Glu Glu
 50                  55                 60

Gln Tyr Asn Ser Thr Tyr Arg Val Val Ser Val Leu Thr Val Leu His
 65                  70                 75                  80

Gln Asp Trp Leu Asn Gly Lys Glu Tyr Lys Cys Lys Val Ser Asn Lys
                 85                 90                 95

Ala Leu Pro Ala Pro Ile Glu Lys Thr Ile Ser Lys Ala Lys
                100                105                110

<210> SEQ ID NO 174
<211> LENGTH: 110
<212> TYPE: PRT
<213> ORGANISM: Artificial Sequence
<220> FEATURE:
<223> OTHER INFORMATION: CH2 domain containing LALA-PA mutation

<400> SEQUENCE: 174

Ala Pro Glu Ala Ala Gly Gly Pro Ser Val Phe Leu Phe Pro Pro Lys
 1               5                  10                 15

Pro Lys Asp Thr Leu Met Ile Ser Arg Thr Pro Glu Val Thr Cys Val
              20                 25                 30

Val Val Asp Val Ser His Glu Asp Pro Glu Val Lys Phe Asn Trp Tyr
              35                 40                 45

Val Asp Gly Val Glu Val His Asn Ala Lys Thr Lys Pro Arg Glu Glu
 50                  55                 60

Gln Tyr Asn Ser Thr Tyr Arg Val Val Ser Val Leu Thr Val Leu His
 65                  70                 75                  80

Gln Asp Trp Leu Asn Gly Lys Glu Tyr Lys Cys Lys Val Ser Asn Lys
                 85                 90                 95

Ala Leu Ala Ala Pro Ile Glu Lys Thr Ile Ser Lys Ala Lys
                100                105                110

<210> SEQ ID NO 175
<211> LENGTH: 1901
<212> TYPE: DNA
<213> ORGANISM: Homo sapiens

<400> SEQUENCE: 175
aagcttgaat cgccgccac  catggccctg cctaccgcta ggcctctgct cggatcctgc      60
ggcacacctg ccctgggaag cctcctgttc ctgctgttct ccctgggctg ggtgcagccc     120
tccagaacac tggccggcga acaggacaa  gaggctgccc ctctcgatgg cgtgctcgct     180
aaccccccca acatcagctc cctgtcccct aggcagctcc tgggctttcc ctgtgccgag     240
gtcagcggcc tctccaccga gagggtgagg gagctggctg tggccctggc tcagaagaac     300
gtgaaactga gcaccgagca actcaggtgc ctggctcata ggctgtccga gcccccgag      360 gatctggatg ccctgcctct cgacctgctg ctgttcctga accccgacgc ttttagcggc     420
ccccaggcct gcacaaggtt cttcagcaga atcaccaagg ccaacgtgga tctgctgccc     480
agaggcgctc ccgagaggca aagactgctg ccgccgctc  tcgcctgttg gggcgtcaga     540
ggatccctgc tgagcgaggc cgacgtgaga gccctgggcg gcctggcttg tgatctgccc     600
```

```
ggcaggtttg tcgctgagag cgccgaagtg ctcctgccca gactggtgag ctgccctgga      660
cctctggacc aggatcaaca ggaggccgcc agagctgctc tgcagggagg aggaccccc       720 tacggacctc ctagcacctg gtccgtgagc acaatggacg ccctgagagg cctgctgcct      780
gtgctgggac agcccatcat taggagcatt ccccagggca ttgtggccgc ctggagacag      840
aggagcagca gggaccccctc ctggaggcag cctgagagaa caatcctgag gcccagattc     900
agaagagagg tggagaaaac cgcctgccct agcggcaaga aggccagaga gattgacgag      960
agcctgatct tctataaaaa gtgggagctc gaagcctgcg tggatgctgc cctgctggcc     1020
acacagatgg acagggtgaa cgccatcccc ttcacctacg agcagctgga cgtcctgaag     1080
cacaagctcg atgagctgta ccccagggc taccccgagt ccgtgattca gcatctcggc      1140
tacctgttcc tgaaaatgag ccccgaagac atcaggaagt ggaacgtgac aagcctggag     1200
accctcaagg ccctgctgga agtgaacaag ggacacgaga tgagccccca ggtggccacc     1260
ctcatcgaca gatttgtgaa gggaaggggga cagctggata aggacaccct cgacaccctg     1320
accgccttct accctggata cctctgcagc ctgtccccg aagagctgtc cagcgtgcct      1380
ccctcctcca tctgggccgt cagaccccag gatctcgaca catgcgaccc cagacagctg     1440
gatgtgctgt accccaaggc taggctggcc ttccagaaca tgaacggatc cgaatatttc     1500
gtcaaaatcc agagctttct gggcggagcc cccacagagg acctcaaagc cctgagccag     1560
cagaacgtca gcatggacct ggccaccttt atgaaactga gaaccgacgc cgtcctccct     1620
ctgacagtgg ccgaagtgca gaagctcctg ggccccatg tggaaggcct gaaggccgag      1680
gagagacaca gacccgtgag agactggatt ctgaggcaga ggcaggacga tctggatacc     1740
ctgggcctgg gactgcaggg cggcattcct aacggatacc tggtcctcga cctgagcatg     1800
caggaagccc tgagcggcac accttgtctg ctgggacctg ccctgtcct caccgtgctc      1860 gctctgctgc tggcttccac cctcgcctga tgagcggccg c                         1901
```

<210> SEQ ID NO 176
<211> LENGTH: 448
<212> TYPE: PRT
<213> ORGANISM: Artificial Sequence
<220> FEATURE:
<223> OTHER INFORMATION: FS28-256-271 mAb heavy chain without LALA

<400> SEQUENCE: 176

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ala Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

| | | | | | | | | | | | | | | |
|---|---|---|---|---|---|---|---|---|---|---|---|---|---|---|
| | | | | 130 | | | | | 135 | | | | | 140 |

Gly Cys Leu Val Lys Asp Tyr Phe Pro Glu Pro Val Thr Val Ser Trp
145                              150                            155                            160

Asn Ser Gly Ala Leu Thr Ser Gly Val His Thr Phe Pro Ala Val Leu
                    165                            170                            175

Gln Ser Ser Gly Leu Tyr Ser Leu Ser Ser Val Val Thr Val Pro Ser
                180                            185                            190

Ser Ser Leu Gly Thr Gln Thr Tyr Ile Cys Asn Val Asn His Lys Pro
            195                            200                            205

Ser Asn Thr Lys Val Asp Lys Lys Val Glu Pro Lys Ser Cys Asp Lys
210                            215                            220

Thr His Thr Cys Pro Pro Cys Pro Ala Pro Glu Leu Leu Gly Gly Pro
225                            230                            235                            240

Ser Val Phe Leu Phe Pro Pro Lys Pro Lys Asp Thr Leu Met Ile Ser
                    245                            250                            255

Arg Thr Pro Glu Val Thr Cys Val Val Val Asp Val Ser His Glu Asp
                260                            265                            270

Pro Glu Val Lys Phe Asn Trp Tyr Val Asp Gly Val Glu Val His Asn
            275                            280                            285

Ala Lys Thr Lys Pro Arg Glu Glu Gln Tyr Asn Ser Thr Tyr Arg Val
290                            295                            300

Val Ser Val Leu Thr Val Leu His Gln Asp Trp Leu Asn Gly Lys Glu
305                            310                            315                            320

Tyr Lys Cys Lys Val Ser Asn Lys Ala Leu Pro Ala Pro Ile Glu Lys
                    325                            330                            335

Thr Ile Ser Lys Ala Lys Gly Gln Pro Arg Glu Pro Gln Val Tyr Thr
                340                            345                            350

Leu Pro Pro Ser Arg Asp Glu Leu Thr Lys Asn Gln Val Ser Leu Thr
            355                            360                            365

Cys Leu Val Lys Gly Phe Tyr Pro Ser Asp Ile Ala Val Glu Trp Glu
370                            375                            380

Ser Asn Gly Gln Pro Glu Asn Asn Tyr Lys Thr Thr Pro Pro Val Leu
385                            390                            395                            400

Asp Ser Asp Gly Ser Phe Phe Leu Tyr Ser Lys Leu Thr Val Asp Lys
                    405                            410                            415

Ser Arg Trp Gln Gln Gly Asn Val Phe Ser Cys Ser Val Met His Glu
                420                            425                            430

Ala Leu His Asn His Tyr Thr Gln Lys Ser Leu Ser Leu Ser Pro Gly
            435                            440                            445

<210> SEQ ID NO 177
<211> LENGTH: 1344
<212> TYPE: DNA
<213> ORGANISM: Artificial Sequence
<220> FEATURE:
<223> OTHER INFORMATION: FS28-256-271 mAb heavy chain without LALA

<400> SEQUENCE: 177

```
gaagtgcaac tgctggagtc cggtggtggt ctggtacagc cgggtggttc tctgcgtctg    60
agttgcgcgg ccagtggctt taccttcact catacttata tgagctgggt cgtcaggct    120 ccgggcaaag gtctggaatg ggttagcgcg atttctccga cttatagcac taccaactat    180
gcggatagcg tgaaaggccg ttttaccatt tctcgcgaca acaacaagaa cacgctgtac    240
ctgcagatga actcactgcg tgccgaagat acggccgtgt attactgtgc gagatacaac    300
```

```
gcgtatcatg ctgctctgga ctactggggc cagggaaccc tggtcaccgt ctcgagtgct    360
agcactaagg gcccgtcggt gttcccgctg gccccatcgt ccaagagcac atcaggggt     420
accgccgccc tgggctgcct tgtgaaggat tactttcccg agcccgtcac agtgtcctgg    480
aacagcggag ccctgacctc cggagtgcat actttcccgg ctgtgcttca gtcctctggc    540
ctgtactcat tgtcctccgt ggtcaccgtc ccttcgtcct ccctgggcac ccagacctat    600
atctgtaatg tcaaccataa gcccctcgaac accaaggtcg acaagaaggt cgagccgaag    660
tcgtgcgaca agactcacac ttgcccgcct tgcccagccc cggaactgct gggtggtcct    720
tcggtgttcc tcttcccgcc caagccgaag gatacccctga tgatctcacg gacccccgaa    780
gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca agtgtccaa caaggcgctg cctgccccaa ttgagaaaac tatctcgaaa   1020
gccaagggcc agcctcgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gatccttctt cctctacagc aagctcaccg tggacaagag caggtggcag   1260
caggggaacg tcttctcctg cagcgtgatg catgaggctc tgcacaacca ctacacacag   1320
aagagcctct ccctgtctcc gggt                                          1344

<210> SEQ ID NO 178
<211> LENGTH: 448
<212> TYPE: PRT
<213> ORGANISM: Artificial Sequence
<220> FEATURE:
<223> OTHER INFORMATION: FS28-256-271 mAb heavy chain with LALA

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ala Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 179
<211> LENGTH: 1344
<212> TYPE: DNA
<213> ORGANISM: Artificial Sequence
<220> FEATURE:
<223> OTHER INFORMATION: FS28-256-271 mAb heavy chain with LALA

<400> SEQUENCE: 179
gaagtgcaac tgctggagtc cggtggtggt ctggtacagc cgggtggttc tctgcgtctg      60
agttgcgcgg ccagtggctt taccttcact catacttata tgagctgggt cgtcaggct     120 ccgggcaaag gtctggaatg ggttagcgcg atttctccga cttatagcac taccaactat     180
gcggatagcg tgaaaggccg ttttaccatt tctcgcgaca caacaagaa cacgctgtac      240 ctgcagatga actcactgcg tgccgaagat acggccgtgt attactgtgc gagatacaac     300
gcgtatcatg ctgctctgga ctactggggc cagggaaccc tggtcaccgt ctcgagtgct     360
agcactaagg gcccgtcggt gttcccgctg gccccatcgt ccaagagcac atcggggggt     420
accgccgccc tgggctgcct tgtgaaggat tactttcccg agcccgtcac agtgtcctgg     480
aacagcggag ccctgacctc cggagtgcat actttcccgg ctgtgcttca gtcctctggc     540
```

```
ctgtactcat tgtcctccgt ggtcaccgtc ccttcgtcct ccctgggcac ccagacctat    600
atctgtaatg tcaaccataa gccctcgaac accaaggtcg acaagaaggt cgagccgaag    660
tcgtgcgaca agactcacac ttgcccgcct tgcccagccc cggaagctgc cggtggtcct    720
tcggtgttcc tcttcccgcc caagccgaag gatacccctga tgatctcacg gaccccgaa     780 gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca aagtgtccaa caaggcgctg cctgccccaa ttgagaaaac tatctcgaaa   1020
gccaagggcc agcctcgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gatccttctt cctctacagc aagctcaccg tggacaagag caggtggcag   1260
caggggaacg tcttctcctg cagcgtgatg catgaggctc tgcacaacca ctacacacag   1320
aagagcctct ccctgtctcc gggt                                         1344
```

<210> SEQ ID NO 180
<211> LENGTH: 119
<212> TYPE: PRT
<213> ORGANISM: Artificial Sequence
<220> FEATURE:
<223> OTHER INFORMATION: FS28-256-271 mAb variable domain

<400> SEQUENCE: 180

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ala Ile Ser Pro Thr Tyr Ser Thr Thr Asn Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser
        115
```

<210> SEQ ID NO 181
<211> LENGTH: 357
<212> TYPE: DNA
<213> ORGANISM: Artificial Sequence
<220> FEATURE:
<223> OTHER INFORMATION: FS28-256-271 mAb variable domain

<400> SEQUENCE: 181

```
gaagtgcaac tgctggagtc cggtggtggt ctggtacagc cgggtggttc tctgcgtctg     60
agttgcgcgg ccagtggctt taccttcact catacttata tgagctgggt gcgtcaggct    120
ccgggcaaag gtctggaatg ggttagcgcg atttctccga cttatagcac taccaactat    180
gcggatagcg tgaaaggccg ttttaccatt tctcgcgaca acaacaagaa cacgctgtac    240
```
ctgcagatga actcactgcg tgccgaagat acggccgtgt attactgtgc gagatacaac    300
gcgtatcatg ctgctctgga ctactggggc cagggaaccc tggtcaccgt ctcgagt        357

<210> SEQ ID NO 182
<211> LENGTH: 17
<212> TYPE: PRT
<213> ORGANISM: Artificial Sequence
<220> FEATURE:
<223> OTHER INFORMATION: FS28-256-271 mAb CDR2 (Kabat)

<400> SEQUENCE: 182

Ala Ile Ser Pro Thr Tyr Ser Thr Thr Asn Tyr Ala Asp Ser Val Lys
1               5                   10                  15

Gly

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187
<211> LENGTH: 453
<212> TYPE: PRT
<213> ORGANISM: Artificial Sequence
<220> FEATURE:
<223> OTHER INFORMATION: FS22-172-003-AA/FS28-256-271 mAb2 heavy chain
      with LALA

<400> SEQUENCE: 187

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
                20                  25                  30

Tyr Met Ser Trp Val Arg Gln Ala Pro Gly Lys Gly Leu Glu Trp Val
            35                  40                  45

Ser Ala Ile Ser Pro Thr Tyr Ser Thr Thr Asn Tyr Ala Asp Ser Val
        50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Pro Tyr Ile Ile Pro Pro Tyr Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Gly Ala Asp Arg Trp Leu Glu Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly
    450

<210> SEQ ID NO 188
<211> LENGTH: 215
<212> TYPE: PRT
<213> ORGANISM: Artificial Sequence
<220> FEATURE:
<223> OTHER INFORMATION: FS22-172-003-AA/FS28-256-271 mAb2 light chain

<400> SEQUENCE: 188

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Thr Val Pro Tyr Pro
                 85                  90                  95

Tyr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 189
<211> LENGTH: 448
<212> TYPE: PRT
<213> ORGANISM: Artificial Sequence
<220> FEATURE:
<223> OTHER INFORMATION: OX40 (FS20-022-049)/FS28-256-271 mAb2 heavy
      chain with LALA

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ala Ile Ser Pro Thr Tyr Ser Thr Thr Asn Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp

-continued

```
            145                 150                 155                 160
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Tyr Trp Asp Gln Glu Val Ser Leu Thr
                355                 360                 365

Cys Leu Val Lys Gly Phe Tyr Pro Ser Asp Ile Ala Val Glu Trp Glu
                370                 375                 380

Ser Asn Gly Asp Glu Gln Phe Ala Tyr Lys Thr Thr Pro Pro Val Leu
385                 390                 395                 400

Asp Ser Asp Gly Ser Phe Phe Leu Tyr Ser Lys Leu Thr Val Asp Gln
                405                 410                 415

Tyr Arg Trp Asn Pro Ala Asp Tyr Phe Ser Cys Ser Val Met His Glu
                420                 425                 430

Ala Leu His Asn His Tyr Thr Gln Lys Ser Leu Ser Leu Ser Pro Gly
                435                 440                 445
```

<210> SEQ ID NO 190
<211> LENGTH: 215
<212> TYPE: PRT
<213> ORGANISM: Artificial Sequence
<220> FEATURE:
<223> OTHER INFORMATION: OX40 (FS20-022-049)/FS28-256-271 mAb2 light
      chain

<400> SEQUENCE: 190

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Thr Val Pro Tyr Pro
                 85                  90                  95

Tyr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 191
<211> LENGTH: 445
<212> TYPE: PRT
<213> ORGANISM: Artificial Sequence
<220> FEATURE:
<223> OTHER INFORMATION: FS22m-063-AA/HelD1.3 mAb2  heavy chain with
      LALA

<400> SEQUENCE: 191

Gln Val Gln Leu Gln Glu Ser Gly Pro Gly Leu Val Arg Pro Ser Gln
  1               5                  10                  15

Thr Leu Ser Leu Thr Cys Thr Val Ser Gly Ser Thr Phe Ser Gly Tyr
             20                  25                  30

Gly Val Asn Trp Val Arg Gln Pro Pro Gly Arg Gly Leu Glu Trp Ile
         35                  40                  45

Gly Met Ile Trp Gly Asp Gly Asn Thr Asp Tyr Asn Ser Ala Leu Lys
     50                  55                  60

Ser Arg Val Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

```
Lys Val Asp Lys Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Pro Tyr Trp Ser Tyr Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Met Asn Tyr Arg Trp
                405                 410                 415

Glu Leu Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 192
<211> LENGTH: 214
<212> TYPE: PRT
<213> ORGANISM: Artificial Sequence
<220> FEATURE:
<223> OTHER INFORMATION: FS22m-063-AA/HelD1.3 mAb2 light chain

<400> SEQUENCE: 192

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 193
<211> LENGTH: 447
<212> TYPE: PRT
<213> ORGANISM: Artificial Sequence
<220> FEATURE:
<223> OTHER INFORMATION: FS22m-063-AA/4420 mAb2 heavy chain with LALA

<400> SEQUENCE: 193

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 194
<211> LENGTH: 219
<212> TYPE: PRT
<213> ORGANISM: Artificial Sequence
<220> FEATURE:
<223> OTHER INFORMATION: FS22m-063-AA/4420 mAb2 light chain

<400> SEQUENCE: 194

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 195
<211> LENGTH: 216
<212> TYPE: PRT
<213> ORGANISM: Artificial Sequence
<220> FEATURE:
<223> OTHER INFORMATION: FS28-185 mAb light chain

<400> SEQUENCE: 195

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Tyr Ser Ala
                85                  90                  95

Pro Val Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 196
<211> LENGTH: 447
<212> TYPE: PRT
<213> ORGANISM: Artificial Sequence
<220> FEATURE:
<223> OTHER INFORMATION: FS22m-063-AA/FS28m-228-010 mAb2 heavy chain
      with LALA

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Phe Met Val Trp Val Arg Gln Ala Pro Gly Lys Gly Leu Glu Trp Val
        35                  40                  45

```
Ser Met Ile Ser Pro Lys Ser Ser Asn Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Tyr His Ile Ser Pro Arg Phe Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Pro Tyr Trp Ser Tyr Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Met Asn Tyr
                405                 410                 415
Arg Trp Glu Leu Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 197
<211> LENGTH: 215
<212> TYPE: PRT
```

<213> ORGANISM: Artificial Sequence
<220> FEATURE:
<223> OTHER INFORMATION: FS22m-063-AA/FS28m-228-010 mAb2 light chain

<400> SEQUENCE: 197

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Pro Phe Pro Phe Ser
                85                  90                  95
Phe Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 198
<211> LENGTH: 7
<212> TYPE: PRT
<213> ORGANISM: Artificial Sequence
<220> FEATURE:
<223> OTHER INFORMATION: Fcab FS22-172-003 CH3 domain structural loop
      sequence

<400> SEQUENCE: 198

```
Pro Tyr Ile Ile Pro Pro Tyr
1               5
```

<210> SEQ ID NO 199
<211> LENGTH: 7
<212> TYPE: PRT
<213> ORGANISM: Artificial Sequence
<220> FEATURE:
<223> OTHER INFORMATION: Fcab FS22-172-003 CH3 domain structural loop
      sequence

<400> SEQUENCE: 199

```
Gly Ala Asp Arg Trp Leu Glu
1               5
```

<210> SEQ ID NO 200
<211> LENGTH: 217

```
<212> TYPE: PRT
<213> ORGANISM: Artificial Sequence
<220> FEATURE:
<223> OTHER INFORMATION: FS22-172-003-AA/FS28-256-271 light chain

<400> SEQUENCE: 200

Ala Ala Glu Ile Val Leu Thr Gln Ser Pro Gly Thr Leu Ser Leu Ser
1               5                   10                  15

Pro Gly Glu Arg Ala Thr Leu Ser Cys Arg Ala Ser Gln Ser Val Ser
            20                  25                  30

Ser Ser Tyr Leu Ala Trp Tyr Gln Gln Lys Pro Gly Gln Ala Pro Arg
        35                  40                  45

Leu Leu Ile Tyr Gly Ala Ser Ser Arg Ala Thr Gly Ile Pro Asp Arg
50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Gln Thr Val Pro
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
210                 215

<210> SEQ ID NO 201
<211> LENGTH: 453
<212> TYPE: PRT
<213> ORGANISM: Artificial Sequence
<220> FEATURE:
<223> OTHER INFORMATION: FS22-172-003-AA/FS28-256-271 heavy chain with
      LALA

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ala Ile Ser Pro Thr Tyr Ser Thr Thr Asn Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
```

```
                100             105             110
Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
        130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
        210             215             220

Thr His Thr Cys Pro Pro Cys Pro Ala Pro Glu Ala Ala Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
        290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Asp Glu Leu Pro Tyr Ile Ile Pro Pro Tyr Asn
        355             360             365

Gln Val Ser Leu Thr Cys Leu Val Lys Gly Phe Tyr Pro Ser Asp Ile
        370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Lys
            405             410             415

Leu Thr Val Gly Ala Asp Arg Trp Leu Glu Gly Asn Val Phe Ser Cys
            420             425             430

Ser Val Met His Glu Ala Leu His Asn His Tyr Thr Gln Lys Ser Leu
        435             440             445

Ser Leu Ser Pro Gly
    450
```

ANTI-MESOTHELIN ANTIBODIES

RELATED APPLICATION

This application is a national stage filing under 35 U.S.C. 371 of International Patent Application Serial No. PCT/EP2019/068800, filed Jul. 12, 2019, the entire contents of which is incorporated herein by reference in its entirety.

REFERENCE TO AN ELECTRONIC SEQUENCE LISTING

The content of the electronic sequence listing (F083170007US00-SUBSEQ-ZJG.txt; Size: 413,955 bytes; and Date of Creation: Feb. 22, 2021) is herein incorporated by reference in its entirety.

FIELD OF THE INVENTION

The present invention relates to antibody molecules that bind mesothelin (MSLN). The antibody molecules find application in the treatment and diagnosis of diseases and disorders, such as cancer.

BACKGROUND TO THE INVENTION

MSLN is expressed at relatively low levels on mesothelial cells lining the pleura, peritoneum, and pericardium (Hassan et al., 2005) of healthy individuals, but is highly expressed in several different cancers, including mesotheliomas, squamous cell carcinomas, pancreatic cancer, lung, gastric, breast, endometrial and ovarian cancer. The normal biological function of mesothelin is not known. In the context of cancer, high expression levels of MSLN have been correlated with poor prognosis in ovarian cancer, cholangiocarcinoma, lung adenocarcinoma and triple-negative breast cancer. The limited expression of MSLN on normal cells versus the high expression on tumour cells makes it an attractive therapeutic target using monoclonal antibodies (Hassan et al., 2016).

MSLN is expressed as a 69-kDa precursor protein (628 amino acids). The precursor protein is then cleaved by the endoprotease furin to release the secreted N-terminal region called megakaryocyte-potentiating factor (MPF), whereas the 40-kDa protein mature MSLN remains attached to the cell membrane via a glycosylphosphatidylinositol (GPI) linker. Human MSLN shares 60% and 87% amino acid identity with the murine and cynomolgus orthologs of MSLN, respectively.

Membrane bound, mature MSLN is shed from cells as a result of alternative splicing, by creating variants lacking the membrane-anchor sequence, or protease cleavage by tumour necrosis factor α-converting enzyme (TACE) (Sapede et al., 2008, Zhang et al., 2011). Soluble shed MSLN is found in patient's sera and in stroma of tumours including malignant mesothelioma, ovarian cancers or highly metastatic cancers. Measuring soluble MSLN levels in the blood and effusions of mesothelioma patients has been approved by the US FDA for monitoring patient response to treatment and progression (Hollevoet et al., 2012, Creany et al., 2015).

Several antibody-based therapies targeting MSLN have been developed and tested in clinical trials, predominantly in mesothelioma, pancreatic and non-small cell lung cancer (Hassan et al., 2016). The strategies employed include direct tumour cell killing through the use of anti-MSLN antibodies, such as amatuximab, with antibody-dependent cellular cytotoxicity (ADCC) activity, as well as the use of antibody drug conjugates (ADCs), such as SS1P-PE38 and anetumab-ravtansine, comprising an antibody or antibody fragment conjugated to a toxin. In addition, anti-MSLN binding Fv fragments have been used in chimeric antigen receptor T cell therapies and bispecifics, such as ABBV-428, are emerging from preclinical studies to clinical trials.

Amatuximab is a mouse chimeric IgG1 kappa mAb that blocks the MSLN-MUC16 interaction and relies on ADCC function to eliminate tumour cells. Phase I trials showed a good safety profile but limited clinical efficacy when combined with chemotherapy (gemcitabine or pemetrexed/cisplatin) with minimal/no improvement in progression free survival in malignant mesothelioma (NCT00738582, Hassan et al., 2014) and no overall response compared to comparator arm in pancreatic cancer (NCT00570713). SS1-PE-38 is a recombinant immunotoxin, containing the anti-MSLN scFv present in amatuximab, linked to the protein synthesis inhibitor PE38. Despite high anti-tumour activity observed in phase I trials (77% partial response when combined with chemotherapy, NCT01445392), the clinical use of SS1P is limited by immunogenicity and a dose-limiting vascular leak syndrome. LMB-100, an optimised version of SS1P-PE38 with reduced immunogenicity in vitro, is currently being tested in phase I and II trials alone and in combination with chemotherapy (NCT02798536, NCT02810418).

Anti-MSLN targeting is most often used to deliver cytotoxic drugs to tumour cells. Anetumab-ravtansine, a fully human IgG1 covalently linked to the anti-mitotic agent DM4, showed a 31% overall response rate (ORR) in a phase I trials with ovarian, primary peritoneal, fallopian tube cancer and advanced predominantly epithelioid peritoneal mesothelioma (NCT01439152). In mesothelioma, anetumab-ravtansine showed a 50% ORR in combination with standard dosing of chemotherapy (NCT02639091). Like another ADC antibody drug, RG7600, anetumab-ravtansine showed a tolerable safety profile but dose limiting toxicities have been observed in these studies in line with those reported for the respective ADC moieties. To date, phase I data from BMS86148 is not yet available.

In summary, unconjugated antibodies targeting MSLN have shown favourable safety profiles but their therapeutic efficacy has been limited, whereas ADCs have shown more potent in anti-tumour activity but were associated with dose limiting toxicities. With regard to safety, ADCs might have a bigger therapeutic window than the immunotoxin therapies (Zhao et al., 2016). For a number of these antibody-based MSLN therapeutics, phase II clinical trials combining the therapeutic with either chemotherapy or with immune checkpoint inhibitors such as PD-1 or PD-L1 are ongoing. Several bispecific molecules intended to engage the immune system are also in development, including ABBV-428, which targets MSLN as well as the costimulatory protein CD40, the MSLN-CD3 bispecific T cell engager (BITE), and a MSLN-CD47 bispecific molecule.

STATEMENTS OF INVENTION

As explained above, mature MSLN, like other tumour-associated antigens (TAAs), is known to be shed from the cell surface by enzymatic cleavage. The shed/soluble portion of MSLN is then cleared away from the tumour site. This represents a challenge for therapeutics targeting MSLN, as the shed/soluble portion can act as a sink for the therapeutic, clearing the therapeutic away from the tumour site before it binds to the tumour.

The present inventors conducted an extensive selection program to isolate antibody molecules that bind with higher affinity to immobilised MSLN than to MSLN in solution.

'Affinity' as referred to herein may refer to the strength of the binding interaction between an antibody molecule and its cognate antigen as measured by $K_D$. As would be readily apparent to the skilled person, where the antibody molecule is capable of forming multiple binding interactions with an antigen (e.g. where the antibody molecule is capable of binding the antigen bivalently and, optionally, the antigen is dimeric) the affinity, as measured by $K_D$, may also be influenced by avidity, whereby avidity refers to the overall strength of an antibody-antigen complex.

Specifically, it is thought that the antibody molecules of the invention bind to MSLN with high avidity and thus bind MSLN more strongly where the antibody is able to bind to two MSLN molecules, as is the case where multiple copies of the antigen are immobilised at a surface, than where the MSLN is in monomeric form, as is expected to be the case with MSLN in solution. Without wishing to be bound by theory, it is therefore thought that the antibody molecules of the invention will not remain bound to shed MSLN in solution in vivo due to the low affinity of the antibodies for monomeric MSLN, thus will not be cleared from the tumour site as quickly, and hence will have longer to exert their therapeutic effect by binding MSLN on the surface of tumour cells. Preferential targeting of membrane-bound MSLN has been reported previously, although the molecules in question were isolated using different approaches to that employed by the present inventors. Specifically, preferential targeting of membrane-bound MSLN has been reported through isolation of molecules targeting different regions of MSLN (Asgarov et al., 2017; Tang et al., 2013). For example, a single domain (VH domain only) antibody fused to human Fc, SD1-Fc, has been reported which targets an epitope close to the cell membrane to promote CDC activity (Tang et al., 2013). It is however unclear how exposed such epitopes are in different cancer settings. In addition, the MSLN-CD3 bispecific T cell engager (BITE) has also been reported to preferentially bind to cell-bound MSLN. However, neither of these molecules are full IgG molecules and neither is capable of binding to MSLN bivalently as both have monovalent binding to the target (via the VH domain in SD1-Fc or the scFv of the BITE).

The antibody molecules isolated by the present inventors bind different epitopes/regions on MSLN. This evident from the fact that some of the antibody molecules are capable of blocking binding of the ligand MUC16 to MSLN while others are not. Blocking MUC16 to MSLN is thought to be advantageous for inhibiting metastasis of MUC16 expressing cancer cells to MSLN expressing surfaces in the pleura and peritoneum (Chen et al., 2013). Other binding regions closer to the cell membrane might facilitate ADCC and CDC activity.

The anti-MSLN antibody molecules of the invention have been shown to have ADCC activity and thus are expected to find application in cancer treatment. Specifically, the antibody molecules have been shown to be capable of targeting tumour cells comprising MSLN on their cell surface and mediating killing of the tumour cell via ADCC.

The antibody molecules of the invention may also be useful for preparing ADCs comprising the antibody molecule of the invention and a bioactive molecule, such as a toxin. Such molecules are also expected to find application in the treatment of cancers comprising MSLN on their cell surface through targeted delivery of the bioactive molecule to the tumour cell.

The present inventors have recognised that the anti-MSLN antibodies of the invention can be used to prepare multispecific, e.g. bispecific, molecules which bind a second antigen in addition to MSLN. Preferably the multispecific molecule binds the second antigen bivalently. In particular, the present inventors have prepared anti-MSLN antibody molecules comprising an additional antigen-binding site in each of the CH3 domains of the antibody molecule which are able to bind a second antigen bivalently.

The second antigen bound by the antibody molecule may be an immune cell antigen, such as a member of the tumour necrosis factor receptor superfamily (TNFRSF). Tumour necrosis factor (TNF) receptors require clustering for activation. Specifically, initial ligation of a TNF receptor ligand to its receptor initiates a chain of events that leads to TNF receptor trimerisation, followed by receptor clustering, activation the NFkB intracellular signalling pathway and subsequent immune cell activation. For a therapeutic agent to efficiently activate a TNFR receptor, several TNF receptor monomers therefore need to be bridged together in a way that mimics the trimeric ligand. Many anti-TNF receptor agonist antibodies either require crosslinking by Fcγ receptors for their agonist activity or exhibit agonist activity in the absence of crosslinking. In both cases, the agonist activity of the antibody is not limited to a particular site, as Fcγ receptors are found throughout the human body.

Bispecific anti-MSLN antibody molecules comprising constant domain binding sites for an immune cell antigen are expected to be capable of activating the immune cell antigen conditionally in the presence of MSLN without the need for e.g. Fcγ receptor-mediated crosslinking, as required by conventional antibody molecules. It is thought that binding of the antibody molecules to MSLN will cause crosslinking of the antibody molecules at the site of MSLN, which in turn will lead to clustering and activation of immune cell antigen on the immune cell surface. The agonistic activity of the antibody molecules is therefore expected to be dependent on both the immune cell antigen and MSLN being present. In other words, the agonistic activity is expected to be conditional. In addition, crosslinking of the antibodies in the presence of MSLN is thought to assist with clustering of the immune cell antigen bound via the constant domain antigen-binding sites of the antibody molecule. As MSLN is a tumour antigen, the antibody molecules are therefore expected to be capable of activating immune cells in a disease-dependent manner, e.g. in the tumour microenvironment. This targeted activation of immune cells is expected to be beneficial in avoiding off-target side effects. The present inventors have shown that bispecific antibody molecules comprising an anti-MSLN and an anti-CD137 binding site were capable of inhibiting tumour growth and increasing survival in the absence of Fcγ receptor binding in a mouse tumour model.

Antibody molecules comprising an anti-MSLN Fab and CH3 domain binding sites specific for a second antigen bind both MSLN and the second antigen bivalently. Where the second antigen is an immune cell antigen, the bivalent binding of both targets is expected to make the bridging between the immune cell expressing the immune cell antigen and MSLN more stable and thereby extend the time during which the immune cell is localised at a particular site, such as a tumour microenvironment, and can act on the disease, e.g. the tumour. This is different to the vast majority of conventional bispecific antibody formats which are heterodimeric and bind each target antigen monovalently via one Fab arm. Such a monovalent interaction is expected to be not only less stable but in many cases is insufficient to induce clustering of immune cell antigens such as TNF receptors in the first place.

A further feature of the anti-MSLN antibody molecules of the invention comprising CH3 domain binding sites specific for a second antigen is that the two antigen binding sites for MSLN and the second antigen are both contained within the antibody structure itself. In particular, the antibody molecules do not require other proteins to be fused to the antibody molecule via linkers or other means to result in molecule that binds bivalently to both of its targets. This has a number of advantages. Specifically, the antibody molecules can be produced using methods similar to those employed for the production of standard antibodies, as they do not comprise any additional fused portions. The structure is also expected to result in improved antibody stability, as linkers may degrade over time, resulting in a heterogeneous population of antibody molecules. Those antibodies in the population having only one protein fused may not be able to induce conditional agonism of immune cell antigens, such as TNF receptors, as efficiently as those having two fused proteins. Cleavage/degradation of the linker could take place prior to administration or after administration of the therapeutic to the patient (e.g. through enzymatic cleavage or the in vivo pH of the patient), thereby resulting in a reduction of its effectiveness whilst circulating in the patient. As there are no linkers in the antibody molecules, the antibody molecules are expected to retain the same number of binding sites both before and after administration. Furthermore, the structure of the antibody molecules is also preferred from the perspective of immunogenicity of the molecules, as the introduction of fused proteins or linkers or both may induce immunogenicity when the molecules are administered to a patient, resulting in reduced effectiveness of the therapeutic.

Thus, the present invention provides:

[1] An antibody molecule that binds to mesothelin (MSLN), wherein the antigen-binding site of the antibody molecule comprises complementarity determining regions (CDRs) 1-6 of antibody:
  (i) FS28-256-271 set forth in SEQ ID NO: 98, 73, 99, 20, 21, and 44, respectively;
  (ii) FS28-024-052 set forth in SEQ ID NO: 10, 11, 41, 20, 21 and 22, respectively;
  (iii) FS28-256-021 set forth in SEQ ID NO: 98, 73, 99, 20, 21 and 34, respectively;
  (iv) FS28-256-012 set forth in SEQ ID NO: 98, 73, 99, 20, 21 and 25, respectively;
  (v) FS28-256-023 set forth in SEQ ID NO: 101, 73, 103, 20, 21 and 34, respectively;
  (vi) FS28-256-024 set forth in SEQ ID NO: 98, 73, 99, 20, 21 and 43, respectively;
  (vii) FS28-256-026 set forth in SEQ ID NO: 101, 73, 103, 20, 21 and 43, respectively;
  (viii) FS28-256-027 set forth in SEQ ID NO: 98, 73, 99, 20, 21 and 44, respectively;
  (ix) FS28-256-001 set forth in SEQ ID NO: 85, 73, 75, 20, 21 and 34, respectively;
  (x) FS28-256-005 set forth in SEQ ID NO: 85, 73, 75, 20, 21 and 43, respectively;
  (xi) FS28-256-014 set forth in SEQ ID NO: 111, 73, 113, 20, 21 and 25, respectively;
  (xii) FS28-256-018 set forth in SEQ ID NO: 101, 73, 103, 20, 21 and 25, respectively;
  (xiii) FS28-256 set forth in SEQ ID NO: 71, 73, 75, 20, 21 and 25, respectively;
  (xiv) FS28-024-051 set forth in SEQ ID NO: 10, 11, 32, 20, 21 and 22, respectively;
  (xv) FS28-024-053 set forth in SEQ ID NO: 10, 11, 51, 20, 21 and 22, respectively; or
  (xvi) FS28-024 set forth in SEQ ID NO: 10, 11, 12, 20, 21 and 22, respectively; and
wherein the CDR sequences are defined according to the ImMunoGeneTics (IMGT) numbering scheme.

[2] An antibody molecule that binds to MSLN, wherein the antigen-binding site of the molecule comprises CDRs 1-6 of antibody:
  (i) FS28-256-271 set forth in SEQ ID NO: 97, 182, 100, 23, 24, and 44, respectively;
  (ii) FS28-024-052 set forth in SEQ ID NO: 13, 14, 42, 23, 24 and 22, respectively;
  (iii) FS28-256-021 set forth in SEQ ID NO: 97, 74, 100, 23, 24 and 34, respectively;
  (iv) FS28-256-012 set forth in SEQ ID NO: 97, 74, 100, 23, 24 and 25, respectively;
  (v) FS28-256-023 set forth in SEQ ID NO: 102, 74, 104, 23, 24 and 34, respectively;
  (vi) FS28-256-024 set forth in SEQ ID NO: 97, 74, 100, 23, 24 and 43, respectively;
  (vii) FS28-256-026 set forth in SEQ ID NO: 102, 74, 104, 23, 24 and 43, respectively;
  (viii) FS28-256-027 set forth in SEQ ID NO: 97, 74, 100, 23, 24 and 44, respectively;
  (ix) FS28-256-001 set forth in SEQ ID NO: 86, 74, 76, 23, 24 and 34, respectively;
  (x) FS28-256-005 set forth in SEQ ID NO: 86, 74, 76, 23, 24 and 43, respectively;
  (xi) FS28-256-014 set forth in SEQ ID NO: 112, 74, 114, 23, 24 and 25, respectively;
  (xii) FS28-256-018 set forth in SEQ ID NO: 102, 74, 104, 23, 24 and 25, respectively;
  (xiii) FS28-256 set forth in SEQ ID NO: 72, 74, 76, 23, 24 and 25, respectively;
  (xiv) FS28-024-051 set forth in SEQ ID NO: 13, 14, 33, 23, 24 and 22, respectively;
  (xiv) FS28-024-053 set forth in SEQ ID NO: 13, 14, 52, 23, 24 and 22, respectively; or
  (xvi) FS28-024 set forth in SEQ ID NO: 13, 14, 15, 23, 24 and 22, respectively; and
wherein the CDR sequences are defined according to the Kabat numbering scheme.

[3] The antibody molecule according to [1] or [2], wherein the antibody molecule comprises a heavy chain variable (VH) domain and/or light chain variable (VL) domain, preferably a VH domain and a VL domain.

[4] The antibody molecule according to any one of [1] to [3], wherein the antibody molecule comprises an immunoglobulin heavy chain and/or an immunoglobulin light chain, preferably an immunoglobulin heavy chain and an immunoglobulin light chain.

[5] The antibody molecule according to any one of [3] to [4], wherein the antibody molecule comprises the VH domain and/or VL domain, preferably the VH domain and the VL domain, of antibody:
  (i) FS28-256-271 set forth in SEQ ID NO: 180, and 56, respectively;
  (ii) FS28-024-052 set forth in SEQ ID NO: 39 and 18, respectively;
  (iii) FS28-256-021 set forth in SEQ ID NO: 109 and 93, respectively;
  (iv) FS28-256-012 set forth in SEQ ID NO: 109 and 79, respectively;
  (v) FS28-256-023 set forth in SEQ ID NO: 121 and 93, respectively;

(vi) FS28-256-024 set forth in SEQ ID NO: 109 and 53, respectively;
(vii) FS28-256-026 set forth in SEQ ID NO: 121 and 53, respectively;
(viii) FS28-256-027 set forth in SEQ ID NO: 109 and 56, respectively;
(ix) FS28-256-001 set forth in SEQ ID NO: 63 and 93, respectively;
(x) FS28-256-005 set forth in SEQ ID NO: 63 and 53, respectively;
(xi) FS28-256-014 set forth in SEQ ID NO: 115 and 79, respectively;
(xii) FS28-256-018 set forth in SEQ ID NO: 121 and 79, respectively;
(xiii) FS28-256 set forth in SEQ ID NO: 69 and 79, respectively;
(xiv) FS28-024-051 set forth in SEQ ID NO: 30 and 18, respectively;
(xv) FS28-024-053 set forth in SEQ ID NO: 49 and 18, respectively; or
(xvi) FS28-024 set forth in SEQ ID NO: 8 and 18, respectively.

[6] The antibody molecule according to any one of [1] to [5], wherein the antibody molecule comprises the heavy chain [without LALA] and light chain of antibody:
(i) FS28-256-271 set forth in SEQ ID NO: 176, and 95, respectively;
(ii) FS28-024-052 set forth in SEQ ID NO: 35 and 16, respectively;
(iii) FS28-256-021 set forth in SEQ ID NO: 105 and 83, respectively;
(iv) FS28-256-012 set forth in SEQ ID NO: 105 and 77, respectively;
(v) FS28-256-023 set forth in SEQ ID NO: 123 and 83, respectively;
(vi) FS28-256-024 set forth in SEQ ID NO: 105 and 90, respectively;
(vii) FS28-256-026 set forth in SEQ ID NO: 123 and 90, respectively;
(viii) FS28-256-027 set forth in SEQ ID NO: 105 and 95, respectively;
(ix) FS28-256-001 set forth in SEQ ID NO: 81 and 83, respectively;
(x) FS28-256-005 set forth in SEQ ID NO: 87 and 90, respectively;
(xi) FS28-256-014 set forth in SEQ ID NO: 117 and 77, respectively;
(xii) FS28-256-018 set forth in SEQ ID NO: 123 and 77, respectively;
(xiii) FS28-256 set forth in SEQ ID NO: 65 and 77, respectively;
(xiv) FS28-024-051 set forth in SEQ ID NO: 26 and 16, respectively;
(xv) FS28-024-053 set forth in SEQ ID NO: 45 and 16, respectively; or
(xvi) FS28-024 set forth in SEQ ID NO: 4 and 16, respectively.

[7] The antibody molecule according to any one of [1] to [5], wherein the antibody molecule comprises the heavy chain [with LALA] and light chain of antibody:
(i) FS28-256-271 set forth in SEQ ID NO: 178, and 95, respectively;
(ii) FS28-024-052 set forth in SEQ ID NO: 37 and 16, respectively;
(iii) FS28-256-021 set forth in SEQ ID NO: 107 and 83, respectively;
(iv) FS28-256-012 set forth in SEQ ID NO: 107 and 77, respectively;
(v) FS28-256-023 set forth in SEQ ID NO: 125 and 83, respectively;
(vi) FS28-256-024 set forth in SEQ ID NO: 107 and 90, respectively;
(vii) FS28-256-026 set forth in SEQ ID NO: 125 and 90, respectively;
(viii) FS28-256-027 set forth in SEQ ID NO: 107 and 95, respectively;
(ix) FS28-256-001 set forth in SEQ ID NO: 89 and 83, respectively;
(x) FS28-256-005 set forth in SEQ ID NO: 89 and 90, respectively;
(xi) FS28-256-014 set forth in SEQ ID NO: 119 and 77, respectively;
(xii) FS28-256-018 set forth in SEQ ID NO: 125 and 77, respectively;
(xiii) FS28-256 set forth in SEQ ID NO: 67 and 77, respectively;
(xiv) FS28-024-051 set forth in SEQ ID NO: 28 and 16, respectively;
(xv) FS28-024-053 set forth in SEQ ID NO: 47 and 16, respectively; or
(xvi) FS28-024 set forth in SEQ ID NO: 5 and 16, respectively.

[8] The antibody molecule according to any one of [1] to [7], wherein the antibody molecule comprises CDRs 1-6, the VH domain, VL domain, light chain and/or heavy chain of antibody FS28-256-271.

[9] The antibody molecule according to any one of [1] to [7], wherein the antibody molecule comprises CDRs 1-6, the VH domain, VL domain, light chain and/or heavy chain of antibody FS28-024-052.

[10] The antibody molecule according to any one of [1] to [9], wherein the MSLN is cell-surface bound MSLN.

[11] The antibody molecule according to [10], wherein the antibody molecule binds to immobilised MSLN with a higher affinity than to MSLN in solution.

[12] The antibody molecule according to [11], wherein the antibody molecule binds to immobilised MSLN with an affinity (kD) of 8 nM or with a higher affinity.

[13] The antibody molecule according to [11] or [12], wherein the antibody molecule binds to MSLN in solution with an affinity (kD) of 15 nM or with a lower affinity.

[14] The antibody molecule according to any one of [1] to [13], wherein the MSLN is human MSLN.

[15] The antibody molecule according to [14], wherein the MSLN consists of or comprises the sequence set forth in SEQ ID NO: 169.

[16] The antibody molecule according to any one of [1] to [13], wherein the MSLN is cynomolgus MSLN.

[17] The antibody molecule according to [16], wherein the MSLN consists of or comprises the sequence set forth in SEQ ID NO: 170. [18] The antibody molecule according to any one of [1] to [17], wherein the antibody molecule comprises CDRs 1-6, the VH domain, VL domain, light chain and/or heavy chain of antibody FS28-024-051, FS28-024-052, FS28-024-053, or FS28-024, and wherein the antibody blocks binding of MUC16 to MSLN.

[19] The antibody molecule according to any one of [1] to [17], wherein the antibody molecule comprises CDRs 1-6, the VH domain, VL domain, light chain and/or heavy chain of antibody FS28-256-271, FS28-256-021, FS28-256-012, FS28-256-023, FS28-256-024, FS28-256-026, or FS28-256-027, FS28-256-001, FS28-256-005, FS28-256-014, FS28-

256-018, or FS28-256, and wherein the antibody does not block binding of MUC16 to MSLN.

[20] The antibody molecule according to [18] or [19], wherein the MUC16 is human MUC16. [21] The antibody molecule according to any one of [1] to [20], wherein antibody molecule is a multispecific antibody molecule and comprises a second antigen-binding site that binds a second antigen.

[22] The antibody molecule according to [21], wherein antibody molecule is a bispecific, trispecific, or tetraspecific antibody molecule.

[23] The antibody molecule according to [22], wherein antibody molecule is a bispecific molecule.

[24] The antibody molecule according to any one of [21] to [23], wherein the second antigen-binding site is located in a constant domain of the antibody molecule.

[25] The antibody molecule according to any one of [21] to [24], wherein the second antigen is an immune cell antigen.

[26] The antibody molecule according to [25], wherein the immune cell antigen is a member of the tumour necrosis factor receptor superfamily (TNFRSF).

[27] The antibody molecule according to [26], wherein the member of the TNFRSF is OX40 or CD137.

[28] The antibody molecule according to any one of [21] to [27], wherein the second antigen-binding site comprises a first sequence, a second sequence, and/or a third sequence, wherein the first sequence, second sequence and third sequence are located in the AB structural loop, the CD structural loop and the EF structural loop of the constant domain, respectively.

[29] The antibody molecule according to any one of [24] to [28], wherein the constant domain is a CH3 domain.

[30] The antibody molecule according to any one of [26] to [29], wherein the antibody molecule is capable of activating the TNFRSF member on an immune cell in the presence of tumour cell-surface bound MSLN.

[31] The antibody molecule according to any one of [26] to [30] wherein binding of the antibody molecule to the TNFRSF member and to tumour cell-surface bound MSLN, causes clustering of the TNFRSF member on the immune cell surface.

[32] The antibody molecule according to [30] or [31], wherein the immune cell is a T cell, B cell, natural killer (NK) cell, natural killer T (NKT) cell, or dendritic cell (DC).

[33] The antibody molecule according to [32], wherein the immune cell is a T cell.

[34] The antibody molecule according to any one of [1] to [33], wherein the antibody molecule has, or is capable of eliciting, antibody-dependent cellular cytotoxicity (ADCC).

[35] The antibody molecule according to any one of [1] to [33], wherein the antibody molecule has been modified to reduce or abrogate binding of the CH2 domain of the antibody molecule to one or more Fcγ receptors.

[36] The antibody molecule according to any one of [1] to [33] or [35] wherein the antibody molecule does not bind to Fcγ receptors.

[37] The antibody molecule according to [35] or [36], wherein the Fcγ receptor is selected from the group consisting of: FcγRI, FcγRIIa, FcγRIIb and FcγRIII.

[38] A conjugate comprising the antibody molecule according to any one of [1] to [37] and a bioactive molecule.

[39] A conjugate comprising the antibody molecule according to any one of [1] to [37] and a detectable label.

[40] A nucleic acid molecule or molecules encoding the antibody molecule according to any one of [1] to [37]. [41] The nucleic acid molecule(s) according to [40], wherein the nucleic acid molecule(s) comprise(s) the VH domain and/or the VL domain nucleic acid sequence of antibody:
(i) FS28-256-271 set forth in SEQ ID NO: 181, and 57, respectively;
(ii) FS28-024-052 set forth in SEQ ID NO: 40 and 19, respectively;
(iii) FS28-256-021 set forth in SEQ ID NO: 110 and 94, respectively;
(iv) FS28-256-012 set forth in SEQ ID NO: 110 and 80, respectively;
(v) FS28-256-023 set forth in SEQ ID NO: 122 and 94, respectively;
(vi) FS28-256-024 set forth in SEQ ID NO: 110 and 54, respectively;
(vii) FS28-256-026 set forth in SEQ ID NO: 122 and 54, respectively;
(viii) FS28-256-027 set forth in SEQ ID NO: 110 and 57, respectively;
(ix) FS28-256-001 set forth in SEQ ID NO: 64 and 94, respectively;
(x) FS28-256-005 set forth in SEQ ID NO: 64 and 54, respectively;
(xi) FS28-256-014 set forth in SEQ ID NO: 116 and 80, respectively;
(xii) FS28-256-018 set forth in SEQ ID NO: 122 and 80, respectively;
(xiii) FS28-256 set forth in SEQ ID NO: 70 and 80, respectively;
(xiv) FS28-024-051 set forth in SEQ ID NO: 31 and 19, respectively;
(xv) FS28-024-053 set forth in SEQ ID NO: 50 and 19, respectively; or
(xvi) FS28-024 set forth in SEQ ID NO: 9 and 19, respectively.

[42] The nucleic acid molecule(s) according to [40] or [41], wherein the nucleic acid molecule(s) comprise(s):
(i) the heavy chain nucleic acid sequence of antibody FS28-256-271 set forth in SEQ ID NO: 179 or 177, and/or the light chain nucleic acid sequence of antibody FS28-256-271 set forth in SEQ ID NO: 96;
(ii) the heavy chain nucleic acid sequence of antibody FS28-024-052 set forth in SEQ ID NO: 38 or 36, and/or the light chain nucleic acid sequence of antibody FS28-024-052 set forth in SEQ ID NO: 17;
(iii) the heavy chain nucleic acid sequence of antibody FS28-256-021 set forth in SEQ ID NO: 108 or 106, and/or the light chain nucleic acid sequence of antibody FS28-256-021 set forth in SEQ ID NO: 92;
(iv) the heavy chain nucleic acid sequence of antibody FS28-256-012 set forth in SEQ ID NO: 108 or 106, and/or the light chain nucleic acid sequence of antibody FS28-256-012 set forth in SEQ ID NO: 78;
(v) the heavy chain nucleic acid sequence of antibody FS28-256-023 set forth in SEQ ID NO: 126 or 124, and/or the light chain nucleic acid sequence of antibody FS28-256-023 set forth in SEQ ID NO: 92;
(vi) the heavy chain nucleic acid sequence of antibody FS28-256-024 set forth in SEQ ID NO: 108 or 106, and/or the light chain nucleic acid sequence of antibody FS28-256-024 set forth in SEQ ID NO: 91;
(vii) the heavy chain nucleic acid sequence of antibody FS28-256-026 set forth in SEQ ID NO: 126 or 124, and/or the light chain nucleic acid sequence of antibody FS28-256-026 set forth in SEQ ID NO: 91;
(viii) the heavy chain nucleic acid sequence of antibody FS28-256-027 set forth in SEQ ID NO: 108 or 106, and/or the light chain nucleic acid sequence of antibody FS28-256-027 set forth in SEQ ID NO: 96;
(ix) the heavy chain nucleic acid sequence of antibody FS28-256-001 set forth in SEQ ID NO: 84 or 82, and/or the light chain nucleic acid sequence of antibody FS28-256-001 set forth in SEQ ID NO: 92;
(x) the heavy chain nucleic acid sequence of antibody FS28-256-005 set forth in SEQ ID NO: 84 or 88, and/or the light chain nucleic acid sequence of antibody FS28-256-005 set forth in SEQ ID NO: 91;
(xi) the heavy chain nucleic acid sequence of antibody FS28-256-014 set forth in SEQ ID NO: 120 or 118, and/or the light chain nucleic acid sequence of antibody FS28-256-014 set forth in SEQ ID NO: 78;
(xii) the heavy chain nucleic acid sequence of antibody FS28-256-018 set forth in SEQ ID NO: 126 or 124, and/or the light chain nucleic acid sequence of antibody FS28-256-018 set forth in SEQ ID NO: 78;
(xiii) the heavy chain nucleic acid sequence of antibody FS28-256 set forth in SEQ ID NO: 68 or 66, and/or the light chain nucleic acid sequence of antibody FS28-256 set forth in SEQ ID NO: 78;
(xiv) the heavy chain nucleic acid sequence of antibody FS28-024-051 set forth in SEQ ID NO: 29 or 27, and/or the light chain nucleic acid sequence of antibody FS28-024-051 set forth in SEQ ID NO: 17;
(xv) the heavy chain nucleic acid sequence of antibody FS28-024-053 set forth in SEQ ID NO: 48 or 46, and/or the light chain nucleic acid sequence of antibody FS28-024-053 set forth in SEQ ID NO: 17; or
(xvi) the heavy chain nucleic acid sequence of antibody FS28-024 set forth in SEQ ID NO: 7 or 6, and/or the light chain nucleic acid sequence of antibody FS28-024 set forth in SEQ ID NO: 17.

[43] A vector or vectors comprising the nucleic acid molecule or molecules according to any one of [40] to [42].

[44] A recombinant host cell comprising the nucleic acid molecule(s) according to any one of [40] to [42], or the vector(s) according to [43].

[45] A method of producing the antibody molecule according to any one of [1] to [37] comprising culturing the recombinant host cell of [44] under conditions for production of the antibody molecule.

[46] The method according to [45] further comprising isolating and/or purifying the antibody molecule.

[47] A pharmaceutical composition comprising the antibody molecule or conjugate according to any one of [1] to [39] and a pharmaceutically acceptable excipient.

[48] The antibody molecule or conjugate according to any one of [1] to [39] for use in a method of treating cancer in an individual.

[49] A method of treating cancer in an individual comprising administering to the individual a therapeutically effective amount of the antibody molecule or conjugate according to any one of [1] to [39].

[50] The use of the antibody molecule or conjugate according to any one of [1] to [39] in the preparation of a medicament for the treatment of cancer.

[51] The antibody molecule or conjugate for use, the method, or the use according to any one of [48] to [50], wherein cells of the cancer express MSLN on their cell surface.

[52] The antibody molecule or conjugate for use, the method, or the use according to any one of [48] to [50], wherein the cancer is selected from the group consisting of: mesothelioma, pancreatic cancer, ovarian cancer, and lung cancer.

[53] The antibody molecule or conjugate for use according to [48], where the method of treatment comprises administering the antibody molecule or conjugate to the individual in combination with a second therapeutic.

[54] The method according to [49], wherein the method further comprises administering a therapeutically effective amount of a second therapeutic to the individual.

[55] The antibody molecule or conjugate according to any one of [1] to [37] or [39] for use in a method of detecting, diagnosing, prognosis or monitoring the prognosis of cancer in an individual.

[56] A method of detecting, diagnosing, prognosis or monitoring the prognosis of a cancer in an individual, the method comprising the use of the antibody molecule or conjugate according to any one of [1] to [37] or [39].

[57] The use of the antibody molecule or conjugate according to any one of [1] to [37] or [39] in the manufacture of a diagnostic product for detecting, diagnosing, prognosis or monitoring the prognosis of cancer in an individual.

[58] A kit for use in a method of detecting, diagnosing, prognosis, or monitoring the prognosis of cancer in an individual, the kit comprising an antibody molecule or conjugate according to any one of [1] to [37] or [39]. [59] The antibody molecule or conjugate for use, the method, the use, or the kit according to any one of [55] to [58], wherein the cancer is selected from the group consisting of: mesothelioma, pancreatic cancer, ovarian cancer, and lung cancer.

Figure 1:
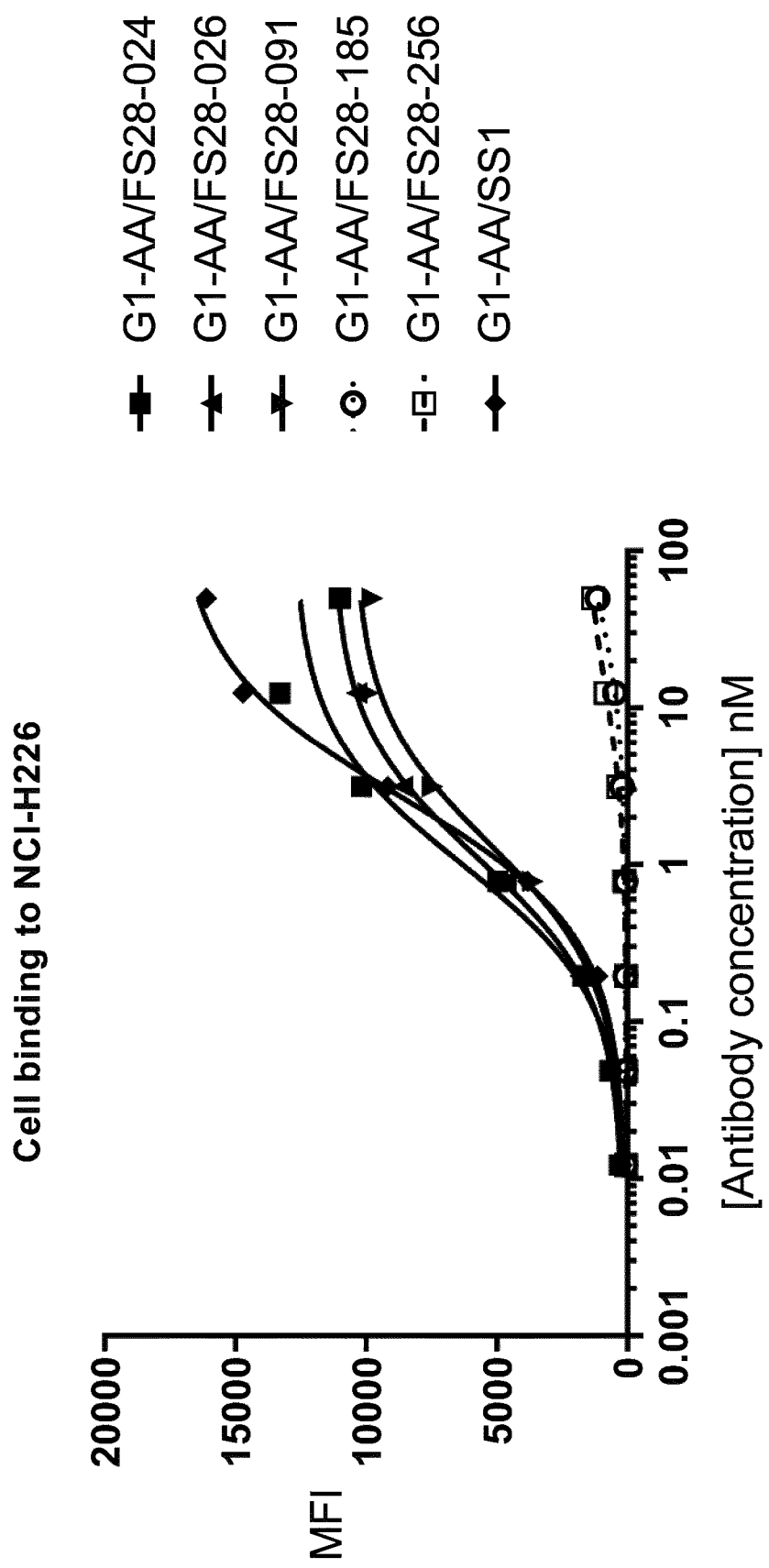
FIG. 1 shows binding of the anti-MSLN mAbs to NCI-H226 cells. The anti-human MSLN mAbs FS28-024, FS28-026, FS28-091, FS28-185 and FS28-256 (all in IgG1 LALA format) showed dose-dependent binding to NCI-H226 cells. FS28-024, FS28-026 and FS28-091 showed high affinity binding to cell surface MSLN with low nanomolar $EC_{50}$ values, similar to the positive control anti-MSLN mAb SS1. mAbs FS28-185 and FS28-256 showed weaker binding to cell surface MSLN with $EC_{50}$ values over 30 nM and lower $E_{max}$ values compared with FS28-024, FS28-026 and FS28-091.

(anti-mouse CD137 Fcab in mAb² format), G1-AA/FS28m-228-010 (anti-mouse MSLN Fab), combination of FS22m-063-AA/HeID1.3 and G1-AA/FS28m-228-010 (anti-mouse CD137 Fcab plus anti-mouse MSLN Fab), and FS22m-063-AA/FS28m-228-010 (anti-mouse CD137/MSLN mAb²). The results show that FS22m-063-AA/FS28m-228-010 treatment resulted in significantly improved survival compared to mice treated with the isotype control or other treatment groups.

DETAILED DESCRIPTION

The present invention relates to antibody molecules that bind MSLN. The antibody molecule preferably binds human MSLN, more preferably human and cynomolgus MSLN. The antibody molecule of the present invention is preferably capable of binding to MSLN expressed on the surface of a cell. The cell is preferably a tumour cell.

The antibody molecule preferably binds MSLN specifically. The term "specific" may refer to the situation in which the antibody molecule will not show any significant binding to molecules other than its specific binding partner(s), here MSLN. The term "specific" is also applicable where the antibody molecule is specific for particular epitopes, such as epitopes on MSLN, that are carried by a number of antigens, in which case the antibody molecule will be able to bind to the various antigens carrying the epitope. The antibody molecule preferably does not bind, or does not show any significant binding, to other molecules involved in cell adhesion, such as CEACAM-5, E-Cadherin, thrombomodulin and/or EpCAM.

As explained in the background section above, mature MSLN is shed from tumour cells and is cleared from the tumour site. This shed MSLN can act as a sink for anti-MSLN binding molecules which after binding to the shed MSLN are also cleared from the tumour site. In order to select for molecules which preferentially bind to MSLN present on the surface of tumour cells, the present inventors selected for antibody molecules with high avidity for MSLN. Specifically, the present inventors selected antibody molecules which bound to immobilised MSLN with higher affinity than to MSLN in solution. Antibody molecules which bind to MSLN with high avidity are thought to preferentially bind to MSLN present on tumour cells where multiple copies of MSLN are expected to be present and available for bivalent binding by the antibody molecule, as opposed to mesothelin shed from the tumour cells which is expected to be in monomeric form. Without wishing to be bound by theory, the antibody molecules of the invention are therefore expected to be cleared from the tumour site less quickly, and hence to have a longer time window in which to exert their therapeutic effect.

The antibody molecule preferably binds to immobilised MSLN with a higher affinity than to MSLN in solution. Immobilised MSLN may be MSLN immobilised at a surface, such as chip for use in surface plasmon resonance. MSLN in solution is also referred to as soluble MSLN herein and is not immobilised. The soluble MSLN is preferably in monomeric form, i.e. monomeric mesothelin.

The affinity of an antibody for its cognate antigen can be expressed as the equilibrium dissociation constant ($K_D$) with which the antibody binds said antigen. The higher the $K_D$ value, the lower the affinity of the antibody molecule for the antigen.

The antibody molecule preferably binds to immobilised MSLN with an affinity ($K_D$) of at least 9 nM, 8 nM, 7 nM, or 6 nM or with a higher affinity. Preferably, the antibody molecule binds to immobilised MSLN with an affinity ($K_D$) of at least 7 nM, 6 nM or with a higher affinity.

The antibody molecule preferably binds to immobilised MSLN with an affinity ($K_D$) of 15 nM or with an affinity that is lower. More preferably, the antibody molecule binds to immobilised MSLN with an affinity ($K_D$) of 16 nM, 17 nM, or 18 nM, or with an affinity that is lower.

In a preferred embodiment, the antibody molecule binds immobilised MSLN with an affinity ($K_D$) of 6 nM or with a higher affinity, and binds MSLN in solution with an affinity ($K_D$) of 18 nM or with a lower affinity.

The binding affinity of an antibody molecule for cells comprising surface-bound MSLN may be measured by determining the concentration of the antibody molecule needed to achieve half-maximal binding ($EC_{50}$) of the antibody molecule to the cells. Suitable methods for determining the concentration of an antibody molecule needed to achieve half-maximal binding of an antibody molecule to cells are known in the art and disclosed in the present Examples (see e.g. Example 4). As explained above, antibody molecules whose binding to tumour cells comprising surface-bound MSLN is not affected or less affected by the presence of soluble mesothelin are preferred in view of the presence of shed MSLN in the tumour environment. Thus, in a preferred embodiment, the concentration of the antibody molecule needed to achieve half-maximal binding ($EC_{50}$) of the antibody to cells (e.g. tumour cells) comprising surface-bound MSLN in the presence of soluble MSLN is less than 20-fold, less than 15-fold, less than 10-fold, less than 9-fold, less than 8-fold, less than 7-fold, less than 6-fold, less than 5-fold, less than 4-fold, or less than 3-fold higher than the concentration of the antibody molecule needed to achieve half-maximal binding ($EC_{50}$) of the antibody to the cells in the absence of soluble MSLN.

The binding of antibody molecules, which do not block binding of MUC16 to MSLN, to cells comprising cell-bound MSLN has been shown to be less affected by the presence of soluble MSLN. Thus, an antibody molecule which is not capable of, or does not block, binding of MUC16 to MSLN may be preferred.

Alternatively, the antibody molecule may block binding of MUC16 to MSLN.

The immobilised MSLN may have the sequence set forth in SEQ ID NO: 169. The MSLN in solution may have the sequence set forth in SEQ ID NO: 169.

The antibody molecules of the invention have also been shown to bind cynomolgus MSLN. Binding to cynomolgus MSLN as well as human MSLN is thought to be beneficial for carrying out efficacy and toxicity studies with the antibody molecule in cynomolgus monkeys, which may be predictive of the efficacy and toxicity of the antibody molecule in humans.

The antibody molecule may bind to immobilised human MSLN and immobilised cynomolgus MSLN with similar affinity. In addition, the antibody molecule may bind to human MSLN in solution and cynomolgus MSLN in solution with similar affinity. This is thought to be beneficial for ensuring that efficacy and toxicity studies carried out with the antibody molecule in cynomolgus monkeys are predictive of the efficacy and toxicity of the antibody molecule in humans.

Thus, in a preferred embodiment, the antibody molecule binds to immobilised cynomolgus MSLN with an affinity which is no more than 10-fold, preferably no more than 5-fold, more preferably no more than 2-fold lower or higher than the affinity with which the antibody molecule binds immobilised human MSLN. In addition, the antibody molecule preferably binds to cynomolgus MSLN in solution with an affinity which is no more than 10-fold, preferably no more than 5-fold, more preferably no more than 2-fold lower or higher than the affinity with which the antibody molecule binds human MSLN in solution.

The binding affinity of an antibody molecule to a cognate antigen, such as human or cynomolgus MSLN can be determined by surface plasmon resonance (SPR), such as Biacore, for example.

The antibody molecule may be chimeric, humanised or human. Preferably, the antibody molecule is a human antibody molecule.

The antibody molecule is preferably monoclonal.

The antibody molecule may be isolated, in the sense of being free from contaminants, such as antibodies able to bind other polypeptides and/or serum components.

The antibody molecule may be natural or partly or wholly synthetically produced. For example, the antibody molecule may be a recombinant antibody molecule.

The antibody molecule comprises one or more CDR-based antigen-binding sites for MSLN.

The antibody molecule may be an immunoglobulin or an antigen-binding fragment thereof. For example, the antibody molecule may be an IgG, IgA, IgE or IgM molecule, preferably an IgG molecule, such as an IgG1, IgG2, IgG3 or IgG4 molecule, more preferably an IgG1 or IgG2 molecule, most preferably an IgG1 molecule, or a fragment thereof. In a preferred embodiment, the antibody molecule is a complete immunoglobulin molecule.

In other embodiments, the antibody molecule may be an antigen-binding fragment comprising a CDR-based antigen-binding site for MSLN. For example, the antigen-binding fragment may be a fragment antigen-binding (Fab), IgGΔCH2, F(ab')$_2$, single-chain Fab (scFab), a disulphide stabilized variable fragment (dsFv), a single-chain variable fragment (scFv), (scFv)$_2$, an scFv-CH3 (minibody), scFv-Fc, scFv-zipper, a diabody, a triabody, a tetrabody, or a single-domain antibody (sdAb), such as a V$_H$H domain or nanobody. Preferred antigen-binding fragments comprise more than one CDR-based antigen-binding site for MSLN, i.e. they may be multivalent. Thus, the antigen-binding fragment may preferably be an IgGΔCH2, F(ab')$_2$, a diabody, a triabody, or a tetrabody. (Brinkmann and Kontermann, (2017) and Powers et al, (2012))

Antibodies and methods for their construction and use are well-known in the art and are described in, for example, Holliger and Hudson, 2005. It is possible to take monoclonal and other antibodies and use techniques of recombinant DNA technology to produce other antibodies or chimeric molecules which retain the specificity of the original antibody. Such techniques may involve introducing CDRs or variable regions of one antibody molecule into a different antibody molecule (EP-A-184187, GB 2188638A and EP-A-239400).

A CDR-based antigen-binding site is an antigen-binding site in an antibody variable region. A CDR-based antigen-binding site, may be formed by three CDRs, such as the three light chain variable domain (VL) CDRs or three heavy chain variable domain (VH) CDRs. Preferably the CDR-based antigen-binding site is formed by six CDRs, three VL CDRs and three VH CDRs. The contributions of the different CDRs to the binding of the antigen may vary in different antigen binding sites.

The three VH domain CDRs of the antigen-binding site may be located within an immunoglobulin VH domain and the three VL domain CDRs may be located within an immunoglobulin VL domain. For example, the CDR-based antigen-binding site may be located in an antibody variable region.

The antibody molecule has one or preferably more than one, for example two, CDR-based antigen binding sites for MSLN. The antibody molecule thus may comprise one VH and one VL domain but preferably comprises two VH and two VL domains, i.e. two VH/VL domain pairs, as is the case in naturally-occurring IgG molecules, for example.

The CDR-based antigen-binding site may comprise the three VH CDRs or three VL CDRs, preferably the three VH CDRs and the three VL CDRs, of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, or FS28-024, preferably antibody FS28-256-271, or FS28-024-052, most preferably antibody FS28-256-271.

The sequences of the CDRs may be readily determined from the VH and VL domain sequences of an antibody molecule using routine techniques. The VH and VL domain sequences of antibodies FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024, are described herein, and the three VH and three VL domain CDRs of said antibodies may thus be determined from said sequences. The CDR sequences may, for example, be determined according to Kabat et al., 1991 or the international ImMunoGeneTics information system (IMGT) (Lefranc et al., 2015).

The VH domain CDR1, CDR2 and CDR3 sequences of the antibody molecule according to IMGT numbering may be the sequences located at positions 27-38, 56-65, and 105-117, of the VH domain of the antibody molecule, respectively.

The VH domain CDR1, CDR2 and CDR3 sequences of the antibody molecule according to Kabat numbering may be the sequences at located positions 31-35, 50-65, and 95-102 of the VH domain, respectively.

The VL domain CDR1, CDR2 and CDR3 sequences of the antibody molecule according to IMGT numbering may be the sequences located at positions 27-38, 56-65, and 105-117, of the VL domain, respectively.

The VL domain CDR1, CDR2 and CDR3 sequences of the antibody molecule according to Kabat numbering may be the sequences at located positions 24-34, 50-56, and 89-97 of the VL domain, respectively.

For example, the sequence of the VH domain CDR1, CDR2 and CDR3 of:
(i) FS28-256-271 may be as set forth in SEQ ID NO: 98, 73, and 99, respectively;
(ii) FS28-024-052 may be as set forth in SEQ ID NO: 10, 11, and 41, respectively;
(iii) FS28-256-021 may be as set forth in SEQ ID NO: 98, 73 and 99, respectively;
(iv) FS28-256-012 may be as set forth in SEQ ID NO: 98, 73 and 99, respectively;
(v) FS28-256-023 may be as set forth in SEQ ID NO: 101, 73 and 103, respectively;
(vi) FS28-256-024 may be as set forth in SEQ ID NO: 98, 73 and 99, respectively;
(vii) FS28-256-026 may be as set forth in SEQ ID NO: 101, 73 and 103, respectively;
(viii) FS28-256-027 may be as set forth in SEQ ID NO: 98, 73 and 99, respectively;

(ix) FS28-256-001 may be as set forth in SEQ ID NO: 85, 73 and 75, respectively;
(x) FS28-256-005 may be as set forth in SEQ ID NO: 85, 73 and 75, respectively;
(xi) FS28-256-014 may be as set forth in SEQ ID NO: 111, 73 and 113, respectively;
(xii) FS28-256-018 may be as set forth in SEQ ID NO: 101, 73 and 103, respectively;
(xiii) FS28-256 may be as set forth in SEQ ID NO: 71, 73 and 75, respectively;
(xiv) FS28-024-051 may be as set forth in SEQ ID NO: 10, 11 and 32, respectively;
(xv) FS28-024-053 may be as set forth in SEQ ID NO: 10, 11 and 51, respectively; and
(xvi) FS28-024 may be as set forth in SEQ ID NO: 10, 11 and 12, respectively;
wherein the CDR sequences are defined according to the IMGT numbering scheme.

The sequence of the VL domain CDR1, CDR2 and CDR3 of:
(i) FS28-256-271 may be as set forth in SEQ ID NO: 20, 21, and 44, respectively;
(ii) FS28-024-052 may be as set forth in SEQ ID NO: 20, 21 and 22, respectively;
(iii) FS28-256-021 may be as set forth in SEQ ID NO: 20, 21 and 34, respectively;
(iv) FS28-256-012 may be as set forth in SEQ ID NO: 20, 21 and 25, respectively;
(v) FS28-256-023 may be as set forth in SEQ ID NO: 20, 21 and 34, respectively;
(vi) FS28-256-024 may be as set forth in SEQ ID NO: 20, 21 and 43, respectively;
(vii) FS28-256-026 may be as set forth in SEQ ID NO: 20, 21 and 43, respectively;
(viii) FS28-256-027 may be as set forth in SEQ ID NO: 20, 21 and 44, respectively;
(ix) FS28-256-001 may be as set forth in SEQ ID NO: 20, 21 and 34, respectively;
(x) FS28-256-005 may be as set forth in SEQ ID NO: 20, 21 and 43, respectively;
(xi) FS28-256-014 may be as set forth in SEQ ID NO: 20, 21 and 25, respectively;
(xii) FS28-256-018 may be as set forth in SEQ ID NO: 20, 21 and 25, respectively;
(xiii) FS28-256 may be as set forth in SEQ ID NO: 20, 21 and 25, respectively;
(xiv) FS28-024-051 may be as set forth in SEQ ID NO: 20, 21 and 22, respectively;
(xv) FS28-024-053 may be as set forth in SEQ ID NO: 20, 21 and 22, respectively; and
(xvi) FS28-024 may be as set forth in SEQ ID NO: 20, 21 and 22, respectively;
wherein the CDR sequences are defined according to the IMGT numbering scheme.

For example, the sequence of the VH domain CDR1, CDR2 and CDR3 of:
(i) FS28-256-271 may be as set forth in SEQ ID NO: 97,182, and 100, respectively;
(ii) FS28-024-052 may be as set forth in SEQ ID NO: 13, 14 and 42, respectively;
(iii) FS28-256-021 may be as set forth in SEQ ID NO: 97, 74 and 100, respectively;
(iv) FS28-256-012 may be as set forth in SEQ ID NO: 97, 74 and 100, respectively;
(v) FS28-256-023 may be as set forth in SEQ ID NO: 102, 74 and 104, respectively;
(vi) FS28-256-024 may be as set forth in SEQ ID NO: 97, 74 and 100, respectively;
(vii) FS28-256-026 may be as set forth in SEQ ID NO: 102, 74 and 104, respectively;
(viii) FS28-256-027 may be as set forth in SEQ ID NO: 97, 74 and 100, respectively;
(ix) FS28-256-001 may be as set forth in SEQ ID NO: 86, 74 and 76, respectively;
(x) FS28-256-005 may be as set forth in SEQ ID NO: 86, 74 and 76, respectively;
(xi) FS28-256-014 may be as set forth in SEQ ID NO: 112, 74 and 114, respectively;
(xii) FS28-256-018 may be as set forth in SEQ ID NO: 102, 74 and 104, respectively;
(xiii) FS28-256 may be as set forth in SEQ ID NO: 72, 74 and 76, respectively;
(xiv) FS28-024-051 may be as set forth in SEQ ID NO: 13, 14 and 33, respectively;
(xv) FS28-024-053 may be as set forth in SEQ ID NO: 13, 14 and 52, respectively; and
(xvi) FS28-024 may be as set forth in SEQ ID NO: 13, 14 and 15, respectively;
wherein the CDR sequences are defined according to the Kabat numbering scheme.

The sequence of the VL domain CDR1, CDR2 and CDR3 of:
(i) FS28-256-271 may be as set forth in SEQ ID NO: 23, 24, and 44, respectively;
(ii) FS28-024-052 may be as set forth in SEQ ID NO: 23, 24 and 22, respectively;
(iii) FS28-256-021 may be as set forth in SEQ ID NO: 23, 24 and 34, respectively;
(iv) FS28-256-012 may be as set forth in SEQ ID NO: 23, 24 and 25, respectively;
(v) FS28-256-023 may be as set forth in SEQ ID NO: 23, 24 and 34, respectively;
(vi) FS28-256-024 may be as set forth in SEQ ID NO: 23, 24 and 43, respectively;
(vii) FS28-256-026 may be as set forth in SEQ ID NO: 23, 24 and 43, respectively;
(viii) FS28-256-027 may be as set forth in SEQ ID NO: 23, 24 and 44, respectively;
(ix) FS28-256-001 may be as set forth in SEQ ID NO: 23, 24 and 34, respectively;
(x) FS28-256-005 may be as set forth in SEQ ID NO: 23, 24 and 43, respectively;
(xi) FS28-256-014 may be as set forth in SEQ ID NO: 23, 24 and 25, respectively;
(xii) FS28-256-018 may be as set forth in SEQ ID NO: 23, 24 and 25, respectively;
(xiii) FS28-256 may be as set forth in SEQ ID NO: 23, 24 and 25, respectively;
(xiv) FS28-024-051 may be as set forth in SEQ ID NO: 23, 24 and 22, respectively;
(xv) FS28-024-053 may be as set forth in SEQ ID NO: 23, 24 and 22, respectively; and
(xvi) FS28-024 may be as set forth in SEQ ID NO: 23, 24 and 22, respectively;
wherein the CDR sequences are defined according to the Kabat numbering scheme.

The CDR-based antigen-binding site may comprise the VH or VL domains, preferably the VH and VL domains, of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-

024-053, or FS28-024, preferably antibody FS28-256-271, or FS28-024-052, most preferably antibody FS28-256-271.

The VH domain of antibodies FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024, may have the sequence set forth in SEQ ID NO: 180, 39, 109, 109, 121, 109, 121, 109, 63, 63, 115, 121, 69, 30, 49, and 8 respectively.

The VL domain of antibodies FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024 may have the sequence set forth in SEQ ID NO: 56, 18, 93, 79, 93, 53, 53, 56, 93, 53, 79, 79, 79, 18, 18, and 18, respectively.

The antibody molecule may comprise the heavy or light chain, preferably the heavy and light chain, of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, or FS28-024, preferably antibody FS28-256-271, or FS28-024-052, most preferably antibody FS28-256-271.

The heavy chain (with LALA mutation) of antibodies FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024, may have the sequence set forth in SEQ ID NO: 178, 37, 107, 107, 125, 107, 125, 107, 89, 89, 119, 125, 67, 28, 47, 5, respectively.

The heavy chain (without LALA mutation) of antibodies FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024, may have the sequence set forth in SEQ ID NO: 176, 35, 105, 105, 123, 105, 123, 105, 81, 87, 117, 123, 65, 26, 45, and 4, respectively.

The light chain of antibodies FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024, may have the sequence set forth in SEQ ID NO: 95, 16, 83, 77, 83, 90, 90, 95, 83, 90, 77, 77, 77, 16, 16, and 16, respectively.

The antibody molecule may also comprise a variant of a CDR, VH domain, VL domain, heavy chain or light chain sequence as described herein. Suitable variants can be obtained by means of methods of sequence alteration, or mutation, and screening. In a preferred embodiment, an antibody molecule comprising one or more such variant sequences retains one or more of the functional characteristics of the parent antibody molecule, such as binding specificity and/or binding affinity for MSLN, preferably human and/or cynomolgus MSLN. For example, an antibody molecule comprising one or more variant sequences preferably binds to MSLN with the same affinity as, or a higher affinity than, the (parent) antibody molecule. The parent antibody molecule is antibody molecule which does not comprise the amino acid substitution(s), deletion(s), and/or insertion(s) which has (have) been incorporated into the variant antibody molecule.

An antibody molecule which comprises CDRs 1-6, the VH domain, and/or the heavy chain of antibody FS28-256-021, FS28-256-012, FS28-256-023, FS28-256-024, FS28-256-026, FS28-256-027, FS28-256-001, FS28-256-005, FS28-256-014, FS28-256-018, or FS28-256, may comprise an amino acid substitution at position 55 or 57 of the VH domain, wherein the amino acid residue numbering is according to the IMGT numbering scheme.

For example, the antibody molecule may comprise CDRs 1-6, the VH domain, and/or the heavy chain of antibody FS28-256-027, wherein the antibody molecule comprises an amino acid substitution at position 55 of the VH domain, wherein the amino acid residue numbering is according to the IMGT numbering scheme.

The antibody molecule of the invention may comprise a VH domain, VL domain, heavy chain, or light chain, which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the VH domain, VL domain, heavy chain, or light chain of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, or FS28-024, preferably antibody FS28-256-271, or FS28-024-052, most preferably antibody FS28-256-271.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equaling 12 and a gap extension penalty equaling 4. Use of GAP may be preferred but other algorithms may be used, e.g. BLAST (which uses the method of Altschul et al., 1990, FASTA (which uses the method of Pearson and Lipman, 1988), or the Smith-Waterman algorithm (Smith and Waterman, 1981), or the TBLASTN program, of Altschul et al., 1990 supra, generally employing default parameters. In particular, the psi-Blast algorithm (Altschul et al., 1997) may be used.

The antibody molecule may comprise a VH CDR1, VH CDR2, VH CDR3, VL CDR1, VL CDR2, and/or VL CDR3 which has one or more amino acid sequence alterations (addition, deletion, substitution and/or insertion of an amino acid residue), preferably 3 alterations or fewer, 2 alterations or fewer, or 1 alteration compared with the VH CDR1, VH CDR2, VH CDR3, VL CDR1, VL CDR2, and/or VL CDR3 of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, or FS28-024, preferably antibody FS28-256-271, or FS28-024-052, most preferably antibody FS28-256-271.

The antibody molecule may comprise a VH domain, VL domain, heavy chain, or light chain, which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the VH domain, VL domain, heavy chain, or light chain of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, or FS28-024, preferably antibody FS28-256-271, or FS28-024-052, most preferably antibody FS28-256-271. In particular, amino acid sequence alterations may be located in one or more framework regions of the antibody molecules, such as one or more framework regions of the heavy and/or light chains of the antibody molecule.

In preferred embodiments in which one or more amino acids are substituted with another amino acid, the substitutions may conservative substitutions, for example according to the following Table. In some embodiments, amino acids in the same category in the middle column are substituted for one another, i.e. a non-polar amino acid is substituted with another non-polar amino acid, for example. In some embodiments, amino acids in the same line in the rightmost column are substituted for one another.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. binding affinity) of the antibody molecule comprising the substitution as compared to the equivalent unsubstituted antibody molecule.

The heavy chain of the antibody molecule may optionally comprise an additional lysine residue (K) at the immediate C-terminus of the heavy chain CH3 domain sequence.

The CH2 domain is known bind to Fcγ receptors and complement. Binding of the CH2 domain to Fcγ receptors is required antibody-dependent cell-mediated cytotoxicity (ADCC), while binding to complement is required complement-dependent cytotoxicity (CDC). Where the antibody molecule is used in the treatment of cancer and is not in the form of an ADC, ADCC activity is expected to lead to killing of the cancer cells and should therefore preferably be retained. However, where the antibody molecule is in the form of an ADC and is conjugated to a bioactive molecule, mutations to reduce or abrogate ADCC activity are expected to be beneficial to avoid killing of the target cancer cells via ADCC before the bioactive molecule is delivered to the cell. In addition, mutations to reduce or abrogate ADCC and/or CDC activity is expected to be useful where the antibody molecule comprises a second antigen-binding site for an immune cell antigen as described herein, where ADCC and/or CDC-mediated killing of immune cells bound by the antibody molecule should be avoided.

The CH2 domain of the antibody molecule may thus comprise one or more mutations that reduce or abrogate binding of the CH2 domain to one or more Fcγ receptors, such as FcγRI, FcγRIIa, FcγRIIb, FcγRIII, and/or to complement. The inventors postulate that reducing or abrogating binding to Fcγ receptors will decrease or eliminate ADCC mediated by the antibody molecule. Similarly, reducing or abrogating binding to complement is expected to reduce or eliminate CDC mediated by the antibody molecule. Mutations to decrease or abrogate binding of the CH2 domain to one or more Fcγ receptors and/or complement are known in the art (Wang et al., 2018). These mutations include the "LALA mutation" described in Bruhns et al., 2009 and Hezareh et al., 2001, which involves substitution of the leucine residues at positions 1.3 and 1.2 of the CH2 domain with alanine (L1.3A and L1.2A). Alternatively, the generation of a-glycosyl antibodies through mutation of the conserved N-linked glycosylation site by mutating the aparagine (N) at position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at position 114 of the CH2 domain to alanine or glycine (P114A or P114G) (Idusogie et al., 2000; Klein et al., 2016). These mutations may also be combined in order to generate antibody molecules with further reduced or no ADCC or CDC activity.

Thus, the antibody molecule may comprise a CH2 domain, wherein the CH2 domain preferably comprises:
  (i) alanine residues at positions 1.3 and 1.2; and/or
  (ii) an alanine or glycine at position 114; and/or
  (iii) an alanine, glutamine or glycine at position 84.4;
  wherein the amino acid residue numbering is according to the IMGT numbering scheme.

In a preferred embodiment, the antibody molecule comprises a CH2 domain, wherein the CH2 domain comprises:
  (i) an alanine residue at position 1.3; and
  (ii) an alanine residue at position 1.2;
  wherein the amino acid residue numbering is according to the IMGT numbering scheme.

For example, the CH2 domain may comprise a LALA mutation and have the sequence set forth in SEQ ID NO: 173.

In an alternative preferred embodiment, the antibody molecule comprises a CH2 domain, wherein the CH2 domain comprises:
  (i) an alanine residue at position 1.3;
  (ii) an alanine residue at position 1.2; and
  (iii) an alanine at position 114;
  wherein the amino acid residue numbering is according to the IMGT numbering scheme.

For example, the CH2 domain may comprise a LALA-PA mutation and have the sequence set forth in SEQ ID NO: 174.

Also contemplated is antibody molecule which comprises a CDR-based antigen binding site for MSLN and which competes with an antibody molecule as described herein, or that binds to the same epitope on MSLN as an antibody molecule as described herein. Methods for determining competition for an antigen by two antibodies are known in the art. For example, competition of binding to an antigen by two antibodies can be determined by surface plasmon resonance, e.g. using a Biacore instrument. Methods for mapping the epitope bound by an antibody are similarly known.

The N-terminal region of MSLN has been reported to interact with MUC16. It has been reported that this interaction may play a role in cancer cell adhesion.

The antibody molecules have been shown to have range of activities on ligand binding. For example, the antibody molecule may be capable of blocking, or may not be capable of blocking binding of MUC16 to MSLN. Alternatively, the antibody molecule may be capable of enhancing binding of MUC16 to MSLN. For example, the antibody molecule may comprise CDRs 1-6, the VH domain, VL domain, heavy chain and/or light chain of antibody FS28-024-051, FS28-024-052, FS28-024-053, or FS28-024, or a variant thereof, wherein the antibody molecule blocks binding of MUC16 to MSLN.

In a preferred embodiment, the antibody molecule does not block binding of MUC16 to MSLN. For example, the antibody molecule may comprise CDRs 1-6, the VH domain, VL domain, heavy chain and/or light chain of antibody FS28-256-271, FS28-256-021, FS28-256-012, FS28-256-023, FS28-256-024, FS28-256-026, FS28-256-027, FS28-256-001, FS28-256-005, FS28-256-014, FS28-256-018, FS28-256, or a variant thereof, wherein the antibody molecule does not block binding of MUC16 to MSLN.

Methods which are suitable for determining the ability of an antibody molecule to block the binding of MUC16 to MSLN are known in the art and include ELISAs and cell-based assays, for example an assay where the antibody competes for binding with MUC16 for binding to cells expressing MSLN, such as NCI-H226 cells In a preferred embodiment, the antibody molecule may comprise one or more further antigen-binding sites that bind one or more further antigens, in addition to the CDR-based antigen binding site for MSLN. The one or more further antigen-binding sites preferably bind their cognate antigens specifically.

The one or more further antigen-binding sites preferably do not bind MSLN. The antibody molecule may thus be a multispecific, for example a bispecific, trispecific, or tetraspecific molecule, preferably a bispecific molecule. In a preferred embodiment, the antibody molecule is capable of simultaneously binding to MSLN and the one or more further antigens.

Antibody molecules are known to have a modular architecture comprising discrete domains, which can be combined in a multitude of different ways to create multispecific, e.g. bispecific, trispecific, or tetraspecific antibody formats. Exemplary multispecific antibody formats are described in Spiess et al. (2015) and Kontermann (2012), for example. The antibody molecules of the present invention may be employed in such multispecific formats.

For example, the antibody molecule of the invention may be a heterodimeric antibody molecule, such as a heterodimeric complete immunoglobulin molecule, or a fragment thereof. In this case, one part of the antibody molecule will have a sequence or sequences as described herein. For example, where the antibody molecule of the invention is a bispecific heterodimeric antibody molecule, the antibody molecule may comprise a heavy chain and light chain as described herein paired with a heavy chain and light chain comprising a VH domain and a VL domain, respectively, which bind an antigen other than MSLN or additionally binds to another epitope on MSLN. Techniques for preparing heterodimeric antibodies are known in the art and include knobs-into-holes (KIHs) technology, which involves engineering the CH3 domains of an antibody molecule to create either a "knob" or a "hole" to promote chain heterodimerization. Alternatively, heterodimeric antibodies can be prepared through the introduction of charge pairs into the antibody molecule to avoid homodimerization of CH3 domains by electrostatic repulsion and to direct heterodimerization by electrostatic attraction. Examples of heterodimeric antibody formats include CrossMab, mAb-Fv, SEEDbody, and kih IgG.

Alternatively, a multispecific antibody molecule may comprise a complete immunoglobulin molecule or a fragment thereof and an additional antigen-binding moiety or moieties. The antigen-binding moiety may for example be an Fv, scFv or single domain antibody, and may be fused to the complete immunoglobulin molecule or a fragment thereof. Examples of multispecific antibody molecules comprising additional antigen-binding moieties fused to a complete immunoglobulin molecule include DVD-IgG, DVI-IgG, scFv4-IgG, IgG-scFv, and scFv-IgG molecules (Spiess et al., 2015; FIG. 1). Examples of multispecific antibody molecules comprising additional antigen-binding moieties fused to an immunoglobulin fragment include BiTE molecules, diabodies, and DART molecules, for example (Spiess et al., 2015; FIG. 1). Other suitable formats would be readily apparent to the skilled person.

In a preferred embodiment, the antibody molecule comprises a second antigen-binding site that binds a second antigen, wherein the second antigen-binding site is located in a constant domain of the antibody molecule. For example, the antibody molecule may be a $mAb^2$ (™) bispecific antibody. A $mAb^2$ bispecific antibody, as referred to herein, is an IgG immunoglobulin which includes a CDR-based antigen binding site in each of its variable regions and at least one antigen binding site in a constant domain of the antibody molecule.

In a preferred embodiment, the antibody is an antibody molecule that binds MSLN and a second antigen, the antibody molecule comprising:
(i) two CDR-based antigen-binding sites for MSLN, each formed by an immunoglobulin VH domain and an immunoglobulin VL domain; and
(ii) two antigen-binding sites that bind a second antigen located in the two CH3 domains of the antibody molecule.

In a more preferred embodiment, the antibody is a complete immunoglobulin molecule, e.g. a complete IgG1 molecule that binds MSLN and a second antigen, the antibody molecule comprising:
(i) two CDR-based antigen-binding sites for MSLN, each formed by an immunoglobulin VH domain and an immunoglobulin VL domain; and
(ii) two antigen-binding sites that bind a second antigen located in the two CH3 domains of the antibody molecule; and
wherein the immunoglobulin molecule further comprises CH1, CH2 and CL domains.

The antigen-binding site for the second antigen may be located in any constant domain of the antibody molecule. For example, the antigen-binding site for the second antigen may be located in one or more of the CH4, CH3, CH2, CH1 or CL domains, preferably the CH3 or CH2 domain, most preferably the CH3 domain.

The antigen binding site may be composed of one or more, for example one, two, three or more, structural loops of the constant domain of the antibody molecule.

The structural loops of an antibody constant domain include the AB, BC, CD, DE, EF, and FG structural loops. The antigen binding site may comprise two or more of the AB, BC, CD, DE, EF, and FG structural loops of the constant domain, preferably the AB and EF structural loops, or the AB, CD and EF structural loops.

The positions of the structural loops in antibody constant domains are well-known in the art. For example, the structural loops of the CH3 domain are located between positions 10 and 19 (AB loop), 28 and 39 (BC loop), 42 and 79 (CD loop), 82 and 85 (DE loop), 91 and 102 (EF loop) and 106 and 117 (FG loop) of the CH3 domain, wherein the residues are numbered according to IMGT numbering scheme. The locations of the structural loop positions in other constant domains may be easily determined.

The structural loops of the constant domain may comprise one or more amino acid modifications in order to form the antigen-binding site for the second antigen. One or more amino acid modifications may include amino acid substitutions, additions, or deletions. The introduction of amino acid modifications into the structural loop regions of antibody constant domains to create antigen-binding sites for target antigens is well-known in the art and is described, for example, in Wozniak-Knopp G et al., 2010, WO2006/072620 and WO2009/132876. Examples of constant domain binding sites are provided below.

In a preferred embodiment, the antibody molecule comprises one or more amino acid modifications (substitutions, additions, and/or deletions) in the AB, CD and/or EF structural loops, preferably the AB and EF structural loops or the AB, CD and EF structural loops. For example, the antibody molecule may comprise one or more amino acid modifications (substitutions, additions, and/or deletions) at positions 11-18, 43-78 and/or 92-101 of the CH3 domain, preferably at positions 11-18 and 92-101, or at positions 11-18, 43-78 and 92-101 of the CH3 domain to provide an antigen-binding site for a second antigen as set out herein. More preferably, the antibody molecule comprises one or more amino acid modifications (substitutions, additions, and/or deletions) at positions 12-18, 45.1 to 78, 92 to 94, and/or 97-98 of the CH3 domain, more preferably at positions 12-18, 92 to 94, and 97-98, or at positions 12-18, 45.1 to 78, 92 to 94, and 97-98 of the CH3 domain to provide an antigen-binding site for a second antigen as set out herein. The unmodified CH3 domain preferably comprises or consists of the sequence set forth in SEQ ID NO: 172. The residue numbering is according to IMGT numbering scheme.

The second antigen bound by the second antigen-binding site of the antibody molecule may be an immune cell antigen, preferably a member of the tumour necrosis factor receptor superfamily (TNFRSF). TNFRSF receptors are membrane-bound cytokine receptors that comprise an extracellular cysteine rich domain that binds one or more ligands of the tumour necrosis factor superfamily (TNFSF).

The TNFRSF receptor is preferably located on the surface of an immune cell, such as a T cell, an antigen presenting cell (APC), an NK cell and/or a B cell, preferably a T cell. Upon binding of a TNFRSF ligand, TNFRSF receptors form clusters on the immune cell surface which activates the immune cell. For example, ligand bound TNFRSF receptors may form multimers, such as trimers, or clusters of multimers. The presence of clusters of ligand-bound TNFRSF receptors stimulates intracellular signalling pathways which activate the immune cell.

Without wishing to be bound by theory it is thought that by engaging both MSLN on a tumour cell surface and a TNFRSF receptor on an immune cell surface, the antibody molecules will be crosslinked through binding to MSLN and thereby drive clustering and activation of the TNFRSF receptor and hence activation of the immune cell(s). In other words, the antibody molecule will act as a TNFRSF receptor agonist when both targets are bound. The activated immune cells may then then initiate, promote or take part in an immune response against the cancer expressing cell-surface bound MSLN. An overview of the role the immune system plays in recognizing and eradicating cancer cells is provided by Chen and Mellman (2013).

Antibody molecule can be crosslinked through binding to Fcγ receptors but this is both inefficient and cannot be targeted to a particular location e.g. the site of a disease, as Fcγ receptor expressing cells are present throughout the human body. In a preferred embodiment, an antibody molecule comprising a second antigen-binding site for a TNFRSF receptor therefore comprises one or mutation to reduce or abrogate binding to one or more Fcγ receptors as described herein.

The present inventors have shown using bispecific molecules comprising binding sites for both MSLN and TNFRSF receptor, specifically mAb$^2$ molecules comprising two constant domain binding sites for a TNFRSF receptor, and two CDR-based antigen binding sites for MSLN that binding of the antibody molecule to both MSLN and the TNFRSF receptor, induces or enhances, T cell activation.

An antibody molecule comprising a second antigen-binding site for a TNFRSF receptor that activates immune cells, such as T cells, only on binding to the MSLN and the TNFRSF receptor, or whose immune cell activation activity is enhanced on binding to MSLN and the TNFRSF receptor, is also referred to as a conditional agonist. This immune cell activation activity is independent of binding of the antibody molecule to Fcγ receptors and/or external crosslinking agents, such as protein A or G or secondary antibodies, and therefore allows the conditional agonist activity of the antibody molecule to be targeted to sites where both MSLN and the TNFRSF are present. As MSLN is a tumour antigen, the antibody molecule may activate immune cells, such as T cells, selectively at the site of the tumour and not elsewhere in an individual.

An antibody molecule which activates immune cells, such as T cells, only on binding to a MSLN and the TNFRSF receptor, may have increased immune cell activation activity compared with antibody molecules that rely on crosslinking by other mechanisms, such as external crosslinking agents, or crosslinking via Fcγ receptor interaction. Because the activation of the TNFRSF receptor is more efficient, immune cell activation may be achieved at lower concentrations of antibody molecules described herein relative to other anti-TNFRSF antibody molecules.

Where the antibody molecule of the invention comprises a second antigen binding site for a TNFRSF receptor present on a T cell, the antibody molecule preferably induces increased activation of immune cells, such as T cells, when the antibody molecule is crosslinked, e.g. through binding to MSLN, than when the antibody molecule is not crosslinked.

The ability of an antibody molecule to activate T cells may be measured using a T cell activation assay. T cells release IL-2 on activation. A T cell activation assay may therefore measure IL-2 release to determine the level of T cell activation induced by the antibody molecule.

For example, the ability of the antibody molecule to activate T cells may be determined by measuring the concentration of the antibody molecule required to achieve half-maximal release of IL-2 by the T cells in a T cells activation assay when the antibody molecule is crosslinked. This is also referred to as the $EC_{50}$ of the antibody molecule. A lower $EC_{50}$ indicates that a lower concentration of the antibody molecule is needed to achieve half-maximal release of IL-2 by the T cells in the T cells activation assay, and thus that the antibody molecule has a higher T cell activation activity. The antibody molecule may be crosslinked using and anti-CH2 antibody, for example.

In addition, or alternatively, the ability of an antibody molecule to activate T cells may be determined by measuring the maximum concentration of IL-2 released by the T cells in a T cell activation assay in the presence of the antibody molecule, wherein the antibody molecule is crosslinked.

In a preferred embodiment, the antibody molecule (e.g. in mAb$^2$ format comprising Fcab FS22-172-003) when crosslinked e.g. via binding to NCI-H226 cells has an $EC_{50}$ in a T cell activation assay which is within 50-fold, 40-fold, 30-fold, 20-fold, 10-fold, or 5-fold of the $EC_{50}$ of FS22-172-003-AA/FS28-256-271 in the same assay, wherein FS22-172-003-AA/FS28-256-271 consists of the heavy chain of SEQ ID NO: 187 and the light chain of SEQ ID NO: 188.

For example, the antibody molecule when crosslinked may have an $EC_{50}$ in a primary T cell activation assay of 30 nM or less, 25 nM or less, 20 nM or less, 14 nM or less, 10 nM or less, 5 nM or less, 4 nM or less, 3 nM or less, 2 nM or less, 1.5 nM, 1 nM or 0.5 nM or less, preferably 1.5 nM or less, more preferably 1 nM, most preferably 0.5 nM or less when crosslinked.

In addition, or alternatively, the ability of an antibody molecule to activate T cells may be determined by measuring the maximum concentration of IL-2 released by the T cells in a T cell activation assay in the presence of the crosslinked antibody molecule.

In a preferred embodiment, the maximum concentration of IL-2 released by the T cells in a T cell activation assay in the presence of the antibody molecule (e.g. in $mAb^2$ format comprising Fcab FS22-172-003) when crosslinked e.g. via binding to NCI-H226 cells is within 20%, or 10% of the maximum concentration of IL-2 released by the T cells in the presence of FS22-172-003-AA/FS28-256-271 in the same assay, FS22-172-003-AA/FS28-256-271 consists of the heavy chain of SEQ ID NO: 187 and the light chain of SEQ ID NO: 188.

For example, the T cell assay may be a pan-T cell activation assay or a CD8+ T activation cell assay, depending on the TNFRSF receptor bound by the second antigen binding site. For example, a pan-T cell assay is suitable where the TNFRSF receptor is OX40, while a CD8+ T cell assay is suitable where the TNFRSF receptor is CD137.

For example, a pan-T cell activation assay may comprise isolating human PBMCs from leucocyte depletion cones. Methods for isolating PBMCs are known in the art. The T cells may then be isolated from the PBMCs. Methods for isolating T cells from PBMCs are also known in the art.

The T cell activation assay may comprise preparing the required number of T cells for example in a suitable medium, such as a T cell medium. The required number of T cells may be prepared at a concentration of $1.0 \times 10^6$ cells/ml. T cells may then be stimulated using a suitable T cell activation reagent that provides the signals required for T cell activation. For example, the T cell activation reagent may be a reagent comprising CD3 and CD28, such as beads comprising CD3 and CD28. Isolated T cells may be incubated overnight with the T cell activation reagent to activate the T cells. Following this, the activated T cells may be washed to separate the T cells from the T cell activation reagent and resuspended in T cell medium at a suitable concentration, such as $2.0 \times 10^6$ cells/ml. Activated T cells may then be added to plates coated with an anti-human CD3 antibody.

A suitable dilution of each test antibody molecule may be prepared and added to the wells. The T cells may then be incubated at 37° C., 5% $CO_2$ for 24 hours with the test antibody.

Supernatants may be collected and assayed to determine the concentration of IL-2 in the supernatant. Methods for determining the concentration of IL-2 in a solution are known in the art and are described in the present examples. The concentration of human IL-2 may be plotted versus the log concentration of the antibody molecule. The resulting curves may be fitted using the log (agonist) versus response equation.

For example, a CD8+ T cell activation assay may comprise isolating human PBMCs from leucocyte depletion cones. Methods for isolating PBMCs are known in the art. The CD8+ T cells may then be isolated from the PBMCs. Methods for isolating CD8+ T cells from PBMCs are also known in the art.

The CD8+ T cells may then be added to multiwall plates coated with an anti-human CD3 antibody. A suitable dilution of each test antibody molecule may be prepared and added to the wells. The T cells may then be incubated at 37° C., 5% $CO_2$ for 24 hours with the test antibody. Supernatants may be collected and assayed to determine the concentration of IL-2 in the supernatant. Methods for determining the concentration of IL-2 in a solution are known in the art and are described in the present examples. The concentration of human IL-2 may be plotted versus the log concentration of the antibody molecule. The resulting curves may be fitted using the log (agonist) versus response equation.

TNFRSF receptors include CD27, CD40, EDA2R, EDAR, FAS, LTBR, RELT, TNFRSF1A, TNFRSF1B, TNFRSF4 (OX40), TNFRSF6B, TNFRSF8, TNFRSF9 (CD137), TNFRSF10A-10D, TNFRSF11A, TNFRSF11B, TNFRSF12A, TNFRSF13B, TNFRSF13C, TNFRSF14, TNFRSF17, TNFRSF18, TNFRSF19, TNFRSF21 and TNFRSF25.

In a preferred embodiment, the TNFRSF receptor is TNFRSF4 (OX40).

In an alternative preferred embodiment, the TNFRSF receptor is TNFRSF9 (CD137).

CD27 (TNFRSF7: Gene ID 939) has the reference amino acid sequence of NP_001233.1 and may be encoded by the reference nucleotide sequence of NM_001242.4. CD40 (TNFRSF5: Gene ID 958) has the reference amino acid sequence of NP_001241.1 and may be encoded by the reference nucleotide sequence of NM_001250.5. EDA2R (TNFRSF27: Gene ID 60401) has the reference amino acid sequence of NP_001186616.1 and may be encoded by the reference nucleotide sequence of NM_001199687.2. EDAR (Gene ID 10913) has the reference amino acid sequence of NP_071731.1 and may be encoded by the reference nucleotide sequence of NM_022336, 3. FAS (TNFRSF6: Gene ID 355) has the reference amino acid sequence of NP_000034.1 and may be encoded by the reference nucleotide sequence of NM_000043.5. LTBR (TNFRSF3: Gene ID 4055) has the reference amino acid sequence of NP_001257916.1 and may be encoded by the reference nucleotide sequence of NM_001270987.1. RELT (TNFRSF19L: Gene ID 84957) has the reference amino acid sequence of NP_116260.2 and may be encoded by the reference nucleotide sequence of NM_032871.3. TNFRSF1A (Gene ID 7132) has the reference amino acid sequence of NP_001056.1 and may be encoded by the reference nucleotide sequence of NM_001065.3. TNFRSF1B (Gene ID 7133) has the reference amino acid sequence of NP_001057.1 and may be encoded by the reference nucleotide sequence of NM_001066.2. TNFRSF4 (Gene ID 7293) has the reference amino acid sequence of NP_003318 and may be encoded by the reference nucleotide sequence of NM_003327). TNFRSF6B (Gene ID 8771) has the reference amino acid sequence of NP_003814.1 and may be encoded by the reference nucleotide sequence of NM_003823.3. TNFRSF8 (Gene ID 943) has the reference amino acid sequence of NP_001234.3 and may be encoded by the reference nucleotide sequence of NM_001243.4. TNFRSF9 (Gene ID 3604) has the reference amino acid sequence of NP_001552 and may be encoded by the reference nucleotide sequence of NM001561). TNFRSF10A (Gene ID 8797) has the reference amino acid sequence of NP_003835.3 and may be encoded by the reference nucleotide sequence of NM_003844.3. TNFRSF10B (Gene ID 8795) has the reference amino acid sequence of NP_003833.4 and may be encoded by the reference nucleotide sequence of NM_003842.4. TNFRSF10C (Gene ID 8794) has the reference amino acid sequence of NP_003832.2 and may be encoded by the reference nucleotide sequence of NM_003841.4. TNFRSF10D (Gene ID 8793) has the reference amino acid sequence of NP_003831.2 and may be encoded by the reference nucleotide sequence of NM_003840.4. TNFRSF11 A (Gene ID 8792) has the reference amino acid sequence of XP_011524547.1 and may be encoded by the reference nucleotide sequence of XM_11526245.2. TNFRSF11B (Gene ID 4982) has the reference amino acid sequence of NP_002537.3 and may be encoded by the reference nucleotide sequence of NM_002546.3. TNFRSF12A (Gene ID 51330) has the reference amino acid sequence of NP_057723.1 and may be encoded by the reference nucleotide sequence of NM_016639.2. TNFRSF13B (Gene ID 23495) has the reference amino acid sequence of NP_0036584.1 and may be encoded by the reference nucleotide sequence of NM_012452.2. TNFRSF13C (Gene ID 115650) has the reference amino acid sequence of NP_443177.1 and may be encoded by the reference nucleotide sequence of NM_052945.3. TNFRSF14 (Gene ID 8764) has the reference amino acid sequence of NP_001284534.1 and may be encoded by the reference nucleotide sequence of NM_001297605.1. TNFRSF17 (Gene ID 608) has the reference amino acid sequence of NP_001183.2 and may be encoded by the reference nucleotide sequence of NM_001192.2. TNFRSF18 (Gene ID 8784) has the reference amino acid sequence of NP_004195.2 and may be encoded by the reference nucleotide sequence of NM_004186.1. TNFRSF19 (Gene ID 55504) has the reference amino acid sequence of NP_001191387.1 and may be encoded by the reference nucleotide sequence of NM_001204458.1. NFRSF21 (Gene ID 27242) has the reference amino acid sequence of NP_055267.1 and may be encoded by the reference nucleotide sequence of NM_014452.4. TNFRSF25 (DR3: Gene ID 8718) binds to ligand TNFSF15 (TL1A) has the reference amino acid sequence of NP_001034753.1 and may be encoded by the reference nucleotide sequence of NM_001039664.1.

In some embodiments, the antibody molecule may not comprise an antigen-binding site in a constant domain, e.g. a CH3 domain of the antibody molecule. For example, the antibody molecule may not comprise an antigen-binding site that binds to CD137 in a constant domain, such as a CH3 domain, of the antibody molecule. In particular, the antibody molecule may not comprise a CD137 antigen-binding site in a constant domain of the antibody molecule, wherein the antigen-binding site comprises modifications in one or more structural loops of the constant domain, such as one or more modifications in the AB, CD and/or EF structural loops of the constant domain. In a particular embodiment, the antibody molecule may not comprise a CD137 antigen-binding site located in a CH3 domain of the antibody molecule comprising a first sequence and a second sequence located in the AB and EF structural loops of the CH3 domain, respectively, wherein the first and second sequence have the sequence set forth in SEQ ID NO: 198 and 199, respectively [FS22-172-003]. For example the antibody molecule may not comprise the light and heavy chain sequences set forth in SEQ ID NO: 200 and 201 [FS22-172-003-AA/FS28-256-271].

The antibody molecule may be conjugated to a bioactive molecule or a detectable label. In this case, the antibody molecule may be referred to as a conjugate. Such conjugates find application in the treatment and/or diagnosis of diseases as described herein.

For example, the bioactive molecule may be an immune system modulator, such as a cytokine, preferably a human cytokine. For example, the cytokine may be a cytokine which stimulates T cell activation and/or proliferation. Examples of cytokines for conjugation to the antibody molecule include IL-2, IL-10, IL-12, IL-15, IL-21, GM-CSF and IFN-gamma.

Alternatively, the bioactive molecule may be a ligand trap, such as a ligand trap of a cytokine, e.g. of TGF-beta or IL-6.

As a further alternative, the bioactive molecule may be a ligand such as CD137L, OX40L, TRAIL, CD40L, CD27L, or GITRL.

As a further alternative, the bioactive molecule may be a drug such as an inhibitor of tubulin polymerisation (e.g. an auristatin), a tubulin depolymerisation agent (e.g. a maytansine), a DNA strand scission inducing agent (e.g. calicheamicin), a DNA alkylating agent (e.g. duocarmycin), or an RNA polymerase inhibitor (such as alpha-amanitin).

As a yet further alternatively, the bioactive molecule may be a therapeutic radioisotope.

Radioimmunotherapy is used in cancer treatment, for example. Therapeutic radioisotopes suitable for radioimmunotherapy are known in the art and include yttrium-90, iodine-131, bismuth-213, astatine-211, lutetium 177, rhenium-188, copper-67, actinium-225, iodine-125.

Suitable detectable labels which may be conjugated to antibody molecules are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g. labelled avidin.

The antibody molecule may be conjugated to the bioactive molecule or detectable label by means of any suitable covalent or non-covalent linkage, such as a disulphide or peptide bond. Where the bioactive molecule is a cytokine, the cytokine may be joined to the antibody molecule by means of a peptide linker. Suitable peptide linkers are known in the art and may be 5 to 25, 5 to 20, 5 to 15, 10 to 25, 10 to 20, or 10 to 15 amino acids in length.

In some embodiments, the bioactive molecule may be conjugated to the antibody molecule by a cleavable linker. The linker may allow release of the bioactive molecule from the antibody molecule at a site of therapy. Linkers may include amide bonds (e.g. peptidic linkers), disulphide bonds or hydrazones. Peptide linkers for example may be cleaved by site specific proteases, disulphide bonds may be cleaved by the reducing environment of the cytosol and hydrazones may be cleaved by acid-mediated hydrolysis.

The conjugate may be a fusion protein comprising the antibody molecule and the bioactive molecule. In this case the bioactive molecule may be conjugated to the antibody molecule by means of a peptide linker or peptide bond. Where the antibody molecule is a multichain molecule, such as where the antibody molecule is or comprises an Fcab or is a mAb$^2$, the bioactive molecule may be conjugated to one or more chains of the antibody molecule. For example, the bioactive molecule may be conjugated to one or both of the heavy chains of the mAb² molecule. Fusion proteins have the advantage of being easier to produce and purify, facilitating the production of clinical-grade material.

The invention also provides an isolated nucleic acid molecule or molecules encoding an antibody molecule of the invention. The skilled person would have no difficulty in preparing such nucleic acid molecules using methods well-known in the art.

The nucleic acid molecule or molecules may encode the VH domain and/or VL domain, preferably the VH domain and VL domain of: antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, or FS28-024, preferably antibody FS28-256-271, or FS28-024-052, most preferably antibody FS28-256-271.

For example, a nucleic acid molecule which encodes the VH domain of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024 is set forth in SEQ ID NO:: 181, 40, 110, 110, 122, 110, 122, 110, 64, 64, 116, 122, 70, 31, 50, and 9, respectively.

A nucleic acid molecule which encodes the VL domain of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024 is set forth in SEQ ID NO:: 57, 19, 94, 80, 94, 54, 54, 57, 94, 54, 80, 80, 19, 19, and 19 respectively.

In a preferred embodiment, the nucleic acid molecule(s) encode the heavy chain and/or light chain, preferably the heavy chain and light chain of: antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, or FS28-024, preferably antibody FS28-256-271, or FS28-024-052, most preferably antibody FS28-256-271.

For example, a nucleic acid molecule which encodes the heavy chain (with LALA mutation) of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024 is set forth in SEQ ID NO:: 179, 38, 108, 108, 126, 108, 126, 108, 84, 84, 120, 126, 68, 29, 48, and 7, respectively.

For example, a nucleic acid molecule which encodes the heavy chain (without LALA mutation) of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024 is set forth in SEQ ID NO:: 177, 36, 106, 106, 124, 106, 124, 106, 82, 88, 118, 124, 66, 27, 46, and 6 respectively.

A nucleic acid molecule which encodes the light chain of antibody FS28-256-271, FS28-024-052, FS28-256-021, FS28-256-012, FS28-256-023, FS28-256-024, FS28-256-026, FS28-256-027, FS28-256-001, FS28-256-005, FS28-256-014, FS28-256-018, FS28-256, FS28-024-051, FS28-024-053, and FS28-024 is set forth in SEQ ID NO:: 96, 17, 92, 78, 92, 91, 91, 96, 92, 91, 78, 78, 78, 17, 17, and 17, respectively.

Where the nucleic acid encodes the VH and VL domain, or heavy and light chain, of an antibody molecule of the invention, the two domains or chains may be encoded on two separate nucleic acid molecules.

An isolated nucleic acid molecule may be used to express an antibody molecule of the invention. The nucleic acid will generally be provided in the form of a recombinant vector for expression. Another aspect of the invention thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids, viral e.g. phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant antibody molecules are known in the art, and include bacterial, yeast, insect or mammalian host cells. A preferred host cell is a mammalian cell, such as a CHO, NS0, or HEK cell, for example a HEK293 cell.

Another aspect of the invention provides a method of producing an antibody molecule of the invention comprising expressing a nucleic acid encoding the antibody molecule in a host cell and optionally isolating and/or purifying the antibody molecule thus produced. Methods for culturing host cells are well-known in the art. The method may further comprise isolating and/or purifying the antibody molecule. Techniques for the purification of recombinant antibody molecules are well-known in the art and include, for example HPLC, FPLC or affinity chromatography, e.g. using Protein A or Protein L. In some embodiments, purification may be performed using an affinity tag on antibody molecule. The method may also comprise formulating the antibody molecule into a pharmaceutical composition, optionally with a pharmaceutically acceptable excipient or other substance as described below.

As explained above, MSLN is expressed on the surface of tumour cells and high expression levels of soluble MSLN have been correlated with poor prognosis in several cancers. Anti-MSLN antibodies have been investigated as anti-cancer therapeutics. These anti-MSLN antibodies either induce direct cell killing through their ADCC activity or are used in the form of ADCs.

The antibody molecules described herein are therefore expected to find application in the treatment of cancer. Related aspects of the invention thus provide:
(i) an antibody molecule described herein for use in a method of treating cancer in an individual,
(ii) the use of an antibody molecule described herein in the manufacture of a medicament for use in the treatment of cancer in an individual; and,
(iv) a method of treating cancer in an individual, wherein the method comprises administering to the individual a therapeutically effective amount of an antibody molecule as described herein.

The individual may be a patient, preferably a human patient.

The antibody molecules of the invention have been shown to preferentially bind to MSLN present on the surface of a cancer cell as compared to soluble MSLN. The cancer to be treated using an antibody molecule of the invention therefore preferably expresses, or has been determined to express, MSLN. More preferably, cells of the cancer to be treated comprise, or have been determined to comprise, MSLN at their cell surface, i.e. to comprise cell-surface bound MSLN.

Where the antibody molecule comprises a second antigen-binding site for an immune cell antigen, such as a TNFRSF member, e.g. in a constant domain of the antibody molecule, the cancer preferably comprises, or has been determined to comprise, tumour infiltrating lymphocytes (TILs) that express the TNFRSF member. Specifically, the TILs preferably comprise, or have been determined to comprise, the TNFRSF member on their cell surface.

Methods for determining the presence of an antigen on a cell surface are known in the art and include, for example, flow cytometry.

The cancer may be a primary or a secondary cancer. Thus, an antibody molecule as described herein may be for use in a method of treating cancer in an individual, wherein the cancer is a primary tumour and/or a tumour metastasis.

The cancer to be treated using an antibody molecule of the invention may be a solid cancer. The cancer may be selected from the group consisting of: mesothelioma, pancreatic cancer, ovarian cancer, lung cancer (such as small-cell lung cancer and non-small cell lung cancer), oesophageal cancer, breast cancer, gastric cancer, cholangiocarcinoma, colon cancer, thymic carcinoma, endometrial cancer, head and neck cancer, sarcoma (such as biphasic synovial sarcoma, Kaposi's sarcoma, osteogenic sarcoma, rhabdomyosarcoma, or soft-tissue sarcoma), desmoplastic small round cell tumours, leukaemia (such as acute lymphocytic leukaemia, chronic lymphocytic leukaemia, acute granulocytic leukaemia, chronic granulocytic leukaemia, hairy cell leukaemia, or myeloid leukaemia), adrenal cortex cancer, bladder cancer, brain cancer, cervical cancer, cervical hyperplasia, testicular choriocarcinoma, essential thrombocytosis, genitourinary carcinoma, glioma, glioblastoma, lymphoma (such as Hodgkin's disease or non-Hodgkin's lymphoma), malignant carcinoid carcinoma, malignant hypercalcemia, melanoma (also referred to as malignant melanoma), malignant pancreatic insulinoma, medullary thyroid carcinoma, multiple myeloma, mycosis fungoides, neuroblastoma, polycythemia vera, primary brain carcinoma, primary macroglobulinemia, prostate cancer, renal cell cancer, skin cancer, squamous cell cancer, stomach cancer, testicular cancer, thyroid cancer, and Wilms' tumor.

Preferably, the cancer is selected from the group consisting of: mesothelioma, pancreatic cancer, ovarian cancer, lung cancer, oesophageal cancer, breast cancer, gastric cancer, cholangiocarcinoma, colon cancer, thymic carcinoma, endometrial cancer, head and neck cancer, biphasic synovial sarcomas, and desmoplastic small round cell tumours.

More preferably, the cancer is selected from the group consisting of: mesothelioma, pancreatic cancer, ovarian cancer, and lung cancer.

Cancer is characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

In the context of cancer, treatment may include inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens. Activating or enhancing immune responses to cancerous tumours in an individual may improve the capacity of the individual to resist cancer growth, in particular growth of a cancer already present in the subject and/or decrease the propensity for cancer growth in the individual.

Whilst an antibody molecule may be administered alone, antibody molecules will usually be administered in the form of a pharmaceutical composition, which may comprise at least one component in addition to the antibody molecule. Another aspect of the invention therefore provides a pharmaceutical composition comprising an antibody molecule as described herein. A method comprising formulating an antibody molecule into a pharmaceutical composition is also provided.

Pharmaceutical compositions may comprise, in addition to the antibody molecule, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by infusion, injection or any other suitable route, as discussed below.

For parenteral, for example subcutaneous or intravenous administration, e.g. by injection, the pharmaceutical composition comprising the antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/ or non-ionic surfactants, such as TWEEN™, PLURON-ICS™ or polyethylene glycol (PEG).

In some embodiments, antibody molecules may be provided in a lyophilised form for reconstitution prior to administration. For example, lyophilised antibody molecules may be re-constituted in sterile water and mixed with saline prior to administration to an individual.

Administration may be in a "therapeutically effective amount", this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of antibody molecule, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody molecules are well known in the art (Ledermann et al., 1991; Bagshawe et al., 1991). Specific dosages indicated herein, or in the Physician's Desk Reference (2003) as appropriate for an antibody molecule being administered, may be used. A therapeutically effective amount or suitable dose of an antibody molecule can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the antibody molecule.

A typical antibody dose is in the range 100 µg to 1 g for systemic applications, and 1 µg to 1 mg for topical applications. An initial higher loading dose, followed by one or more lower doses, may be administered. This is a dose for a single treatment of an adult individual, which may be proportionally adjusted for children and infants, and also adjusted for other antibody formats in proportion to molecular weight.

Treatments may be repeated at daily, twice-weekly, weekly or monthly intervals, at the discretion of the physician. The treatment schedule for an individual may be dependent on the pharmacokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Suitable formulations and routes of administration are described above.

In the context of cancer treatment, an antibody molecule as described herein may be administered to an individual in combination with another anti-cancer therapy or therapeutic agent, such as an anti-cancer therapy or therapeutic agent which has been shown to be suitable, or is expected to be suitable, for the treatment of the cancer in question. For example, the antibody molecule may be administered to the individual in combination with a chemotherapeutic agent, radiotherapy, an immunotherapeutic agent, an anti-tumour vaccine, an oncolytic virus, an adoptive cell transfer (ACT) therapy (such as adoptive NK cell therapy or therapy with chimeric antigen receptor (CAR) T-cells, autologous tumour infiltrating lymphocytes (TILs), or gamma/delta T cells, or an agent for hormone therapy.

Without wishing to be bound by theory, it is thought that the antibody molecule as described herein, wherein the antibody molecules comprises a second antigen-binding site for an immune cell antigen, such as a TNFRSF receptor, may act as an adjuvant in anti-cancer therapy. Specifically, it is thought that administration of the antibody molecule to an in individual in combination with chemotherapy and/or radiotherapy, or in combination with an anti-tumour vaccine, for example, will trigger a greater immune response against the cancer than is achieved with chemotherapy and/or radiotherapy, or with an anti-tumour vaccine, alone.

One or more chemotherapeutic agents for administration in combination with an antibody molecule as described herein may be selected from the group consisting of: taxanes, cytotoxic antibiotics, tyrosine kinase inhibitors, PARP inhibitors, B-Raf enzyme inhibitors, MEK inhibitors, c-MET inhibitors, VEGFR inhibitors, PDGFR inhibitors, alkylating agents, platinum analogues, nucleoside analogues, antifolates, thalidomide derivatives, antineoplastic chemotherapeutic agents and others. Taxanes include docetaxel, paclitaxel and nab-paclitaxel; cytotoxic antibiotics include actinomycin, bleomycin, and anthracyclines such as doxorubicin, mitoxantrone and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide and temozolomide; platinum analogues include carboplatin, cisplatin and oxaliplatin; nucleoside analogues include azacitidine, capecitabine, fludarabine, fluorouracil and gemcitabine; antifolates include methotrexate and pemetrexed. Other chemotherapeutic agents suitable for use in the present invention include defactinib, entinostat, eribulin, irinotecan and vinblastine.

Preferred therapeutic agents for administration with an antibody molecule as described herein are pentostatin, cyclophosphamide, cis-platin, pemetrexed, paclitaxel, carboplatin, gemcitabine, doxorubicin, vinorelbine, docetaxel, or etoposide A radiotherapy for administration in combination with an antibody molecule as described herein may be external beam radiotherapy (such as intensity-modulated radiotherapy (IMRT), stereotactic body radiotherapy (SBRT), image-guided radiotherapy (IGRT), intra-operative radiotherapy (IORT), electron therapy or electron beam therapy (EBT), superficial radiotherapy (SRT)), or internal radiotherapy (such as brachytherapy, radioisotope or radionuclide therapy, SIRT. Preferably, the radiotherapy is conventional external beam radiotherapy, external beam radiation therapy (EBRT), stereotactic radiotherapy, or brachytherapy An immunotherapeutic agent for administration in combination with an antibody molecule as described herein may be a therapeutic antibody molecule, nucleic acid, cytokine, or cytokine-based therapy. For example, the therapeutic antibody molecule may bind to an immune regulatory molecule, e.g. an inhibitory checkpoint molecule or an immune costimulatory molecule, a receptor of the innate immune system, or a tumour antigen, e.g. a cell surface tumour antigen or a soluble tumour antigen. Examples of immune regulatory molecules to which the therapeutic antibody molecule may bind include inhibitory checkpoint molecules, such as CTLA-4, LAG-3, TIGIT, TIM-3, VISTA, PD-L1, PD-1, or KIR, immune costimulatory molecules, such as OX40, CD40, CD137, GITR, CD27, or ICOS, other immune regulatory molecules such as CD47, CD73, CSF-1R, HVEM, TGFB, or CSF-1.

Examples of receptors of the innate immune system to which the therapeutic antibody molecule may bind include TLR1, TLR2, TLR4, TLR5, TLR7, TLR9, RIG-1-like receptors (e.g. RIG-1 and MDA-5), and STING.

The nucleic acid for administration in combination with an antibody molecule as described herein may be an siRNA.

The cytokines or cytokine-based therapy may be selected from the group consisting of: IL-2, prodrug of conjugated IL-2, GM-CSF, IL-7, IL-12, IL-9, IL-15, IL-18, IL-21, and type I interferon.

Anti-tumour vaccines for the treatment of cancer have both been implemented in the clinic and discussed in detail within scientific literature (such as Rosenberg, S. 2000). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

The chemotherapeutic agent, radiotherapy, immunotherapeutic agent, anti-tumour vaccine, oncolytic virus, ACT therapy, or agent for hormone therapy is preferably a chemotherapeutic agent, radiotherapy, immunotherapeutic agent, anti-tumour vaccine, oncolytic virus, ACT therapy, or agent for hormone therapy for the cancer in question, i.e. a chemotherapeutic agent, radiotherapy, immunotherapeutic agent, anti-tumour vaccine, oncolytic virus, ACT therapy, or agent for hormone therapy which has been shown to be effective in the treatment of the cancer in question. The selection of a suitable chemotherapeutic agent, radiotherapy, immunotherapeutic agent, anti-tumour vaccine, oncolytic virus, ACT therapy, or agent for hormone therapy which has been shown to be effective for the cancer in question is well within the capabilities of the skilled practitioner.

The antibody molecules of the invention may be useful in the detection MSLN, in particular in the detection of immobilised MSLN, such as cell-surface bound MSLN. The antibody molecule may be conjugated to a detectable label as described elsewhere herein.

Thus, the present invention relates to the use of an antibody molecule for detecting the presence of immobilised MSLN, preferably the presence of cells comprising MSLN at their cell surface, in a sample.

Also provided is an in vitro method of detecting MSLN, wherein the method comprises incubating the antibody molecule with a sample of interest, and detecting binding of the antibody molecule to the sample, wherein binding of the antibody to the sample indicates the presence of immobilised MSLN. Binding of the antibody molecule to a sample may be detected using an ELISA, for example.

In a preferred embodiment, the present invention relates to an in vitro method of detecting cells comprising MSLN at their cell surface, wherein the method comprises incubating the antibody molecule with a cell sample of interest, and determining binding of the antibody molecule to cells present in the sample, wherein binding of the antibody to cells present in sample indicates the presence of cells comprising MSLN at their cell surface. Methods for detecting binding of an antibody molecule to cells are known in the art and include ELISAs, and flow-cytometry.

The antibody molecules of the invention may find application in the detection, diagnosis, and/or prognosis of cancer. The cancer may be a cancer which can be treated with an antibody molecule of the invention as described herein.

Related aspects of the invention thus provide;
(i) an antibody molecule described herein for use in a method of detecting cancer, diagnosing cancer, determining cancer prognosis, or monitoring cancer prognosis in an individual;
(ii) the use of an antibody molecule described herein in the manufacture of a diagnostic product for use in the detecting cancer, diagnosing cancer, determining cancer prognosis, or monitoring cancer prognosis;
(iii) a method of detecting cancer, diagnosing cancer, determining cancer prognosis, or monitoring cancer prognosis in an individual using an antibody molecule as described herein; and
(iv) a kit for use in a method of detecting, diagnosing, prognosis, or monitoring the prognosis of cancer in an individual, the kit comprising an antibody molecule as described herein.

The method may comprise administering an antibody molecule of the invention to an individual and determining the presence of the antibody molecule at a site in the body of the individual, wherein the presence of the antibody molecule at a site in the body indicates the presence of a tumour, in particular the presence of a tumour comprising cells expressing MSLN at their cell surface.

In a preferred embodiment, the method comprises determining the presence of cells expressing MSLN at their cell surface in a sample obtained from an individual, wherein the presence of cells expressing MSLN at their cell surface indicates that the individual has cancer.

In an alternative preferred embodiment, the method comprises determining the presence of tumour cells expressing MSLN at their cell surface in a tumour sample obtained from an individual, wherein the presence of tumour cells expressing MSLN at their cell surface indicates that the individual has a worse prognosis, such as a higher risk of cancer metastasis, than an individual with the same cancer which does not comprise cells expressing MSLN at their cell surface.

The cancer may be a cancer as referred to herein. Preferably, the cancer is selected from the group consisting of: mesothelioma, pancreatic cancer, ovarian cancer, lung cancer, oesophageal cancer, breast cancer, gastric cancer, cholangiocarcinoma, colon cancer, thymic carcinoma, endometrial cancer, head and neck cancer, biphasic synovial sarcomas, and desmoplastic small round cell tumours. More preferably, the cancer is selected from the group consisting of: mesothelioma, pancreatic cancer, ovarian cancer, and lung cancer.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Other aspects and embodiments of the invention provide the aspects and embodiments described above with the term "comprising" replaced by the term "consisting of" or "consisting essentially of", unless the context dictates otherwise.

Certain aspects and embodiments of the invention will now be illustrated by way of example and with reference to the figures described above.

EXAMPLES

Example 1: Isolation of Anti-Human MSLN Antibodies: Antigens, Selections and Screeninq Mesothelin is a glycosylphosphatidylinositol (GPI)-linked glycoprotein synthesized as a 69 kDa precursor and proteolytically processed into a 30 kDa NH2-terminal secreted form (referred to as megakaryocyte potentiating factor or MPF) and a 40 kDa membrane-bound mesothelin (MSLN). Soluble forms of MSLN, shed from the tumour cell surface and generated by alternative splicing or tumour necrosis factor-α-converting enzymes (TACE) of the membrane-bound MSLN, are found in patient serum. This tumour-shed antigen is known to create a 'sink' which can act as a decoy for therapeutic antibodies (Lee et al, 2018) such that this must be overcome to allow the antibodies to bind to MSLN on the tumour. To avoid this sink effect, the inventors set out to isolate novel anti-mesothelin antibodies that preferentially bound to immobilised MSLN compared to soluble MSLN, with the intention that this would translate to preferential binding to membrane-bound MSLN over soluble MSLN. To this end, different forms of MSLN antigens were employed in phage selections and subsequent screening campaigns.

1.1 Production of Human, Cynomolgus and Mouse Mesothelin Antigens

Recombinant biotinylated human MSLN-His antigen, designated 'hMSLN-His Acro', was obtained from Acrobiosystems (cat no MSN-H8223) which lacks the C-terminal 18 amino acids. To maximise the diversity of binders selected across the whole of the antigen, full-length monomeric human MSLN antigen was generated and biotinylated in house for phage selections. Cynomolgus and mouse MSLN were produced to allow the isolation of binders that were capable of binding to human as well as cyno MSLN, and also for the isolation of murine MSLN binders respectively.

Briefly, MSLN antigens were produced by cloning DNA encoding human (SEQ ID NO: 169) (hMSLN-His-Avi), cynomolgus (SEQ ID NO: 170) (cMSLN-His-Avi) or mouse (SED ID NO: 171) (mMSLN-His-Avi) MSLN along with six C-terminal histidine residues and an Avi sequence into modified pFUSE vectors (Invivogen cat no pfuse-mg2afc2) using EcoRI-HF and BamHI-HF restriction enzymes. The vectors were transfected into HEK293-6E cells (National Research Council of Canada), and expressed MSLN was purified using a HisTrap™ excel nickel column (GE LifeSciences, 29048586). Each of the antigens was biotinylated using a BirA biotin-biotin protein ligase reaction kit (Avidity LLC, BirA500) to produce monomeric MSLN antigens labelled with a single biotin molecule. Specifically, five to ten mg of antigen was mixed with BirA enzyme mix to a molar ratio of enzyme to substrate of 1:50. Additives were then added in accordance to the manufacturer's recommendations, incubated overnight at room temperature and recombinant human, cyno or mouse MSLN was subsequently purified using a HisTrap™ excel nickel column (GE LifeSciences, 29048586) to remove excess free biotin.

The biophysical properties of each antigen were characterised by SEC-HPLC analysis to determine whether aggregates were present and by PAGE to verify the size of the molecules. SEC-HPLC of these antigens showed less than 10% aggregation and PAGE verified that the antigens were monomeric. ELISA and surface plasmon resonance (SPR) were used to confirm that the biotinylated MSLN antigens could be bound by MSLN-specific positive control antibodies (SS1, see section 1.3; Hassan et al 2002 and MOR6626 see section 7.1, Patent Publication No. WO 2009/068204 A1). Based on this data all antigens were deemed suitable for naïve selections.

1.2 Phagemid Library Selections

Synthetic naïve phagemid libraries displaying the human Fab domain of germlines with randomised amino acids in the CDR1, CDR2 and CDR3 (MSM Technologies) were used for selections with the MSLN antigens described in section 1.1.

Fab libraries were initially selected in multiple campaigns each in three or four rounds using Streptavidin Dynabeads (Thermo Fisher, 11205D), Neutravidin-binding protein coupled to Dynabeads (Thermo Fisher, 31000) or anti-His Dynabeads (Thermo Fisher, 10103D) to isolate the phage bound to biotinylated human, cyno or mouse MSLN-His-Avi or hMSLN-His Acro. Selection campaigns were also performed using full-length MSLN antigens produced in-house in which human MSLN selection rounds were alternated with cyno MSLN antigen with an aim to isolate human and cyno cross-reactive clones. Selections for binders to mouse MSLN (R&D mMSLN-His 8604-MS) were also performed. Standard phage selection and phage recovery procedures were used.

In an effort to obtain clones that bind to different regions of MSLN antigen, an epitope masking strategy was adopted using anti-MSLN antibodies from the initial selection campaigns described above. Briefly, a first round of selection of the naïve Fab libraries was performed using biotinylated human MSLN-His-Avi at 500 nM. In round 2 and 3 the phage binding of biotinylated cyno MSLN-His-Avi at 500 nM (round 2) or 100 nM (round 3) was tested in the presence of a mixture of naïve anti-mesothelin mAb proteins isolated from the initial selection campaign (FS28-004, FS28-024, FS28-026, FS28-091 and FS28-97, 500 nM of each mAb). These epitope masking selections resulted in reduced output titers, indicating that the selection strategy was working as fewer binders were identified. This led to the identification of clones (FS28-243, FS28-255 and FS28-256, see section 2.1.3) that target additional areas of MSLN compared to the clones from the earlier selection campaign.

1.3 Screening to Identify Anti-MSLN Antibodies

About 2000 clones from round 3 and 4 outputs of all selections were screened by phage ELISA for binding to 25 nM immobilised biotinylated hMSLN-His Acro, full-length biotinylated human or cyno MSLN-His-Avi, consistent with the antigen used in the round of selections.

Streptavidin plates or plates immobilised with irrelevant biotinylated His tagged antigens were included as negative controls. Clones which had a MSLN binding signal at least 4-fold higher than signal to negative controls were selected and their variable regions sequenced, leading to the identification of 156 unique VH/VL sequence combinations, which were subsequently selected for soluble expression. Clones were chosen from all selection campaigns including the epitope masking selections. For each clone, the VH and VL were individually cloned into a pTT5 expression vector (National Research Council of Canada) containing either CH1, CH2 (with a LALA mutation in the CH2 domain (Bruhns et al., 2009; Hezareh et al., 2001) and CH3 domain, or CL domains respectively. The resulting pTT5-FS28 VH with LALA mutation (AA) and pTT5-FS28 VL vectors were transiently cotransfected into HEK293-6E cells and the clones were produced as complete IgG1 molecules. The antibodies were either kept in supernatant or purified by mAb Select SuRe Protein A columns and subjected to further testing as described below. Using the same method, the VH and VL regions of SS1 and anti-hen egg white lysozyme antibody HeID1.3 were cloned and expressed in IgG1 LALA format, yielding G1-AA/SS1 (SEQ ID No 167 and 168) and G1-AA/HeID1.3 (SEQ ID No 165 and 166), to serve as positive and negative controls respectively.

Example 2: Identification of Panel of Naïve Anti-MSLN mAbs

Anti-mesothelin mAbs have a broad range of potential applications including their use as therapeutics capable of inducing ADCC, as a tumour targeting arm for the delivery of immunotoxin, ADC and for the generation of bispecific antibodies, amongst others. The desired characteristics of the anti-mesothelin mAbs are dependent on the application and the inventors therefore set out to identify a panel of mAbs that bound to membrane-bound human and cyno MSLN, with a variety of affinities, and that were able to target different areas of MSLN. To this end, a set of screening assays including ELISA, Biacore blocking assays and cell binding were performed as well as assays in which the binding regions to MSLN were compared.

2.1 Screening for Binding to Recombinant MSLN 2.1.1 Binding ELISA

HEK293-6E supernatants containing soluble anti-MSLN binding clones or purified clones were screened for binding to human MSLN-His Acro, hMSLN-His-Avi and, for some campaigns, cMSLN-His-Avi by ELISA. Briefly, hMSLN-His Acro, hMSLN-His-Avi, cMSLN-His-Avi or an irrelevant His tagged antigen were coated on maxisorp plates at 25 nM overnight at 4° C. The next day, plates were blocked with 300 µl PBS containing 0.05% Tween20 and 2% Marvel milk (Marvel dried milk). Anti-MSLN mAb containing supernatants or purified proteins were incubated for 1 hour at room temperature and their binding was detected with a mouse anti human Fc-IgG antibody conjugated to horse radish peroxidase (HRP). Clones that showed binding to the irrelevant antigen or were not cross reactive to both the human and cynomolgus antigens were discarded. In addition, clones that bound to the truncated MSLN antigen, hMSLN-His Acro, but not to the full length MSLN antigen, MSLN-His-Avi, were also not taken forward as it was expected that the full-length antigen would be more representative of antigen conformation on the cell surface of MSLN-expressing cells.

Mesothelin is a glycoprotein and its glycosylation pattern might vary depending on species and tissue. To ensure that the antibodies had specificity for binding to MSLN, the anti-MSLN binding clones were also tested for differential binding to glycosylated and deglycosylated MSLN. Biotinylated hMSLN-His-Avi was deglycosylated using PNGase F enzyme (NEB, P0704L) for 24 hr at 37° C., purified using Amicon ultra centrifugal filters (Millipore, UFC901024) and coated on maxisorp plates at 25 nM. ELISA binding of the unique anti-mesothelin mAbs to MSLN was detected using mouse anti-human Fc-IgG-HRP (Sigma, A0170). Clones that showed a more than 2-fold reduction in binding signal to deglycosylated compared to glycosylated MSLN antigen were excluded from the panel of naïve anti-MSLN binding mAbs.

2.1.2 BIAcore Screening

Human MSLN-His-Avi was immobilised on flow cell 2 on a CM5 Series S BIAcore sensor chip (GE Healthcare, BR10530) using an amine coupling kit (GE Healthcare, BR10050) to approximately 200 response units (RU). Flow cell 1 was left blank for subtraction. HEK293-6E supernatants or purified proteins were adjusted with HBS-EP+(GE Healthcare) to approximately 50 nM anti-MSLN mAb per sample. Samples were injected over flow cell 1 and 2 for 2.5 min at 30 µl/min and then allowed to dissociate in HBS-EP buffer for 2.5 min. Regeneration was achieved by injecting 10 mM glycine pH 1.5 (GE Healthcare, BR100354) for 30 seconds at a rate of 30 µl/min. Subtracted data (flow cell 2—flow cell 1) were analysed using BIAevaluation 3.2 Software (GE Healthcare). Of the 86 clones tested in this assay from the binding ELISA, 39 clones showed a binding response of greater than 10 RU at 50 nM and were therefore selected for re-expression, purification and further screening.

2.1.3 Binning of Antibodies Based on the Region of MSLN Bound

Based on the ELISA and Biacore screening data, clones were then tested in binning assays in which the binding of the mAbs to human MSLN was tested in the presence of another mAb by Bio-Layer Interferometry (BLI) on an Octet (ForteBio).

Briefly, biotinylated hMSLN-His-Avi (5 µg/ml) was bound to streptavidin tips (ForteBIO, 18-5020) for 5 min. G1-AA/SS1 was diluted to 200 nM in 1× kinetic buffer (ForteBIO, 18-1092) and allowed to bind to hMSLN-His-Avi for 5 minutes. Next, binding of a mixture containing 200 nM of the test mAb and 200 nM of G1-AA/SS1, was assessed for 5 minutes. This was compared with the binding of the test mAb to hMSLN-His-Avi in the absence of bound G1-AA/SS1 to determine the maximal extent of possible binding in the absence of SS1 (i.e. where there was no competition for binding). If both antibodies competed for binding to the same region of MSLN, the test antibody would not be able to bind.

These binning experiments with G1-AA/SS1 revealed that the majority (19 out of 23) of the FS28-lineage antibodies tested were unable to bind MSLN in the presence of G1-AA/SS1 and could therefore be attributed to bind a similar region as G1-AA/SS1. The MSLN binding site for the SS1 antibody in Fab format has been reported (Ma et al., 2012) and is defined as an N-terminal region comprising amino acids 7 to 64 that are also involved in MUC16 binding. The fact that most anti-MSLN binders isolated bound to this or a similar region suggests that these amino acids are well exposed in the recombinant antigens. Four other clones, FS28-185, FS28-243, FS28-255 and FS28-256, were identified that showed partial or no competition with G1-AA/SS1 for binding to MSLN Binning of these clones against each other revealed that these clones represented two additional independent bins, i.e. were capable of binding to a further two different regions of MSLN. FS28-185, FS28-243 and FS28-255 were all assigned to one bin ('bin 2') whereas FS28-256 was assigned to a separate bin ('bin 3'). These results showed that the epitope masking selections in section 1.2 were successful as antibodies which bound to multiple regions of MSLN were identified.

2.1.4 Affinities

For each bin described in 2.1.3, the binding kinetics were determined using the same method as described in section 2.1.2, except that human or cyno MSLN-His-Avi was immobilised at 50 or 100 RU. Clones were tested at a concentration range of 81 nM to 0.33 nM in 3-fold dilutions. The binders were ranked and the best from each bin were selected: FS28-024, FS28-026 and FS28-091 all from bin 1, FS28-185 from bin 2 and FS28-256 from bin 3. All of these clones were shown to be cyno cross-reactive, but affinities were not calculated under these test conditions. The affinities of the selected antibodies are shown in Table 1, which shows that affinities obtained at 50 RU of immobilised MSLN were lower than those at 100 RU of immobilised MSLN antigen, showing increased binding at higher levels of MSLN.

TABLE 1

Affinities of naïve anti-mesothelin mAbs to immobilised human mesothelin

| mAb (in G1-AA format) | Affinity to immobilised human MSLN-His-Avi $K_D$ (nM) | |
| --- | --- | --- |
| | 50 RU | 100 RU |
| FS28-024 | 0.77 | 0.23 |
| FS28-026 | 0.21 | 0.12 |
| FS28-091 | 1.24 | 0.76 |
| FS28-185 | 37.00 | 29.57 |
| FS28-256 | 26.20 | 23.16 |

2.2 MUC16-MSLN Blocking Assays

The N-terminal region of MSLN (amino acids 296-359) has been reported to interact with glycoprotein MUC16 and this interaction may play a role in cancer cell adhesion (Kaneko et al., 2009). FS28-024, FS28-026, FS28-091, FS28-185 and FS28-256 were tested for their ability to block the binding of MUC16 to mesothelin in a blocking assay. SS1 is known from the literature to block MUC16 binding to MSLN (Ma et al., 2012). As previously described, we converted this to a G1-AA/SS1 format with the expectation that this would not impact its ability to block MUC16 binding. G1-AA/SS1 and a control IgG1 antibody (G1-AA/HeID1.3) were included as positive and negative controls respectively.

Briefly, recombinant human MUC16 (R&D Systems, 5809-MU-050) was coated on maxisorp plates at 0.65 μg/ml in 1×PBS overnight at 4° C. Plates were washed 3 times with 1×PBS and blocked with 300 μl PBS containing 2% Tween20 and 2% Marvel Milk. A concentration of anti-MSLN mAbs (0.23 nM to 500 nM, 3-fold dilutions) were pre-mixed with biotinylated hMSLN-His-Avi antigen (final concentration 2 μg/ml) in a volume of 100 μl for 1 hr at room temperature. After removal of the blocking solution, the mAb/MSLN mixture was added to the plates and incubated for 1 hr at room temperature. Plates were washed 3 times with PBST (1×PBS and 0.05% Tween20) and incubated with streptavidin-HRP (Thermo Scientific, 21126, 1:1000 dilution in 1×PBS) for 1 hr at room temperature. Finally, plates were washed 3 times with PBST and 3 times with PBS. MSLN bound to MUC16 was visualised by adding 100 μl TMB for 15 min, followed by 100 μl 1 M sulphuric acid solution. Absorbances were read at 450-630 nm (Gen5 software, BioTek).

TABLE 2

Activity of naïve anti-mesothelin mAbs in MUC16-MSLN blocking assay

| mAb (in G1-AA format) | MUC16-MSLN blocking activity $IC_{50}$ (nM) |
| --- | --- |
| FS28-024 | 2.9 |
| FS28-026 | 5.2 |
| FS28-091 | 4.4 |
| FS28-185 | Enhanced binding |
| FS28-256 | No activity |
| SS1 | 4.8 |
| HeID1.3 | No activity |

Bin 1 clones FS28-024, FS28-026 and FS28-091 showed dose-dependent blocking of the MUC16-MSLN interaction with $IC_{50}$ of 2.9 nM, 5.2 nM and 4.4 nM respectively (Table 2). The observed blocking activity was similar to that of G1-AA/SS1. FS28-256 did not show any blocking activity similarly to the negative control G1-AA/HeID1.3. Whereas FS28-185 promoted the binding of MUC16 to MSLN. This phenomenon has been reported (Patent nr. U.S. Pat. No. 8,911,732B2). These results were consistent with the binning data in section 2.1.3 in that clones which bound to three different regions of MSLN showed three different behaviours in the ligand blocking assay.

In conclusion, the results show that a panel of clones was selected that bind to 3 different regions (bins) of MSLN; antibodies binding to one region of MSLN block the binding of MUC16 to MSLN, whereas antibodies binding to the other two regions do not.

2.3 Specificity

In light of the different areas of MSLN bound by the panel of antibodies, their specificity for binding to MSLN was tested. Specificity of FS28-024, FS28-026, FS28-091, FS28-185 and FS28-256 was tested by ELISA by comparing the binding to MSLN with binding to other molecules involved in cell adhesion such as CEACAM-5, E-Cadherin, Thrombomodulin and EpCAM.

A similar protocol was used as described in section 1.2.1 in which maxisorp plates were coated with 1 μg/ml of recombinant human MSLN-His-Avi, human CEACAM-5-His-Fc (Sino Biological, 1077-H03H), human E-Cadherin (R&D systems, 8505-EC), human Thrombomodulin (Peprotech, 100-58) or human EpCAM-hFc (in-house production). Binding of the anti-MSLN mAbs, tested at a concentration range of 0.02 to 1000 nM (3-fold dilutions) was detected using anti-human Fab-HRP (Sigma, A0293). Positive controls for the respective molecules included human EpCAM antibody (clone 2G8 from patent no. U.S. Pat. No. 8,236,308B2) CEACAM-5 antibody (clone hMN15 from patent no. U.S. Pat. No. 8,771,690B2), human E-Cadherin antibody, mouse IgG2b clone 180215 (R&D systems, MAB1838), human Thrombomodulin antibody, mouse IgG1, clone 501733 (R&D systems, MAB3947). The latter two were detected using goat anti mouse Fc-HRP (Sigma, A9309) as secondary mAb.

FS28-024, FS28-026, FS28-091 and FS28-185 bound to human MSLN-His-Avi ($EC_{50}$ around 0.5 nM and maximum binding signal of 3) but no binding was observed to any of the cell adhesion molecules tested up to 1000 nM. Positive control antibodies bound to their respective targets, as expected. Thus, the anti-MSLN antibodies showed a high level of specificity.

2.4 Cell Binding

The panel of five selected anti-mesothelin mAbs was analysed for binding to endogenous cell surface MSLN on the human lung cancer cell line NCI-H226.

Briefly, NCI-H226 cells (ATCC CRL-5826) were harvested from T175 cell culture flasks using StemPro Accutase (Gibco, A11105-01). Cells were centrifuged at 1200 rpm for 3 min and resuspended in ice cold FACS buffer made up of DPBS (Life Technologies, 14190169) and 1% BSA (Sigma-Aldrich, A7906) at 2×10⁶ cells/ml and 50 µl per well was seeded in a 96-well V-bottom plate (Costar, 3894). All mAbs tested were diluted in FACS buffer in 120 µl at a concentration range of 0.01-200 nM (4-fold dilutions). The NCI-H226 cells were then centrifuged, supernatant removed and cells resuspended in 100 µl of each mAb dilution and incubated at 4° C. for 45 min. Cells were washed twice by centrifugation with 150 µl FACS buffer, resuspended in 100 µl containing goat anti-human IgG (γ-chain specific) F(ab')2 fragment-R-Phycoerythrin antibody (Sigma, P8047) diluted 1:1000 in FACS buffer and incubated at 4° C. for 45 min. The cells were washed once with 150 µl FACS buffer and then with 150 µl DPBS, resuspended in 150 µl DPBS containing DAPI (Biotium, 40043) at 1:10.000 and read on the BDCantoII or iQue (Intellicyt). Data was analysed using FlowJo v10 to determine the signal geometric mean for PE for live cells in each well.

The cell binding data (Table 3) showed that FS28-024, FS28-026 and FS28-091 all bound to cell surface cell surface MSLN on NCI-H226 with $EC_{50}$ in a range of 0.62 to 1.22 nM, as did the positive control G1-AA/SS1. In comparison, FS28-185 and FS28-256 demonstrated weak binding with $EC_{50}$ greater than 30 nM and a low maximum binding signal ($E_{max}$). A representative binding assay is shown in FIG. 1.

TABLE 3

Cell binding of naïve anti-mesothelin mAbs to NCI-H226 cancer cells

| mAb (in G1-AA format) | Cell binding to NCI-H226 (n = 3) | |
|---|---|---|
| | $EC_{50}$ (nM) | $E_{max}$ (MFI signal) |
| FS28-024 | 0.62 | 14647 |
| FS28-026 | 1.08 | 13650 |
| FS28-091 | 1.22 | 11926 |
| FS28-185 | 37.47 | 2435 |
| FS28-256 | 33.13 | 4246 |
| SS1 | 0.90 | 19385 |

2.5 Summary of Naïve Screening Procedure

From the 156 mAbs identified by the initial screen of the naïve phage libraries, five anti-human MSLN mAb clones (FS28-024, FS28-026, FS28-091, FS28-185 and FS28-256) were selected based on a set of screening assays that first confirmed binding to full-length, deglycosylated recombinant MSLN as well as the ability to bind to cyno MSLN. Secondly, clones were grouped based on diversity of the region of MSLN they bound (bins) and MUC16 blocking activity and from within these groups, the highest affinity binders were selected. The resulting panel of mAb clones FS28-024, FS28-026, FS28-091, FS28-185 and FS28-256 bound three different regions of MSLN, one of which (bin 1, including FS28-024, FS28-026 and FS28-091) blocks the binding of MUC16 to MSLN in vitro. The panel of five anti-MSLN mAbs showed specific binding to MSLN, different affinities for recombinant and cell-surface MSLN and were selected for further characterisation and/or optimisation as described in Examples 3 and 4 below.

Example 3: Affinity Maturation and Sequence Optimisation of Naïve Anti-MSLN mAbs 3.1 Affinity Maturation of FS28-185 and FS28-256

In comparison to FS28-024, FS28-026 and FS28-091, FS28-185 and FS28-256 had weaker affinity for both recombinant and cell surface MSLN and were therefore subjected to affinity maturation.

3.1.1 Affinity Maturation and Screening of FS28-185 and FS28-256

The VH and VL CDR3 regions were affinity matured in parallel in scFv format by randomizing overlapping cassettes of five to six amino acids using NNK primers. The regions randomised for FS28-185 were VH G95-M100F and VL S91-A95 and for FS28-256 they were VH Y95-L100B and VL S91-196 (Kabat numbering). Before library generation, parsimonious mutagenesis was performed on potential methionine oxidation and deamidation sites in the CDR1 and CDR3 regions (except for the FS28-256 VL CDR3 library). Phagemid libraries were generated independently and pooled to produce one VH CDR3 and one VL CDR3 library for each clone. Two rounds of selections were performed as described for the naïve campaigns, using 20 nM biotinylated human MSLN-His-Avi in round 1 and either 20 or 2 nM cyno MSLN-His-Avi in round 2. Soluble scFv (single point concentration) were then tested for binding to an ovarian cancer cell line OVCAR-3 (ATCC® HTB-161™). OVCAR-3 cells were harvested using StemPro Accutase (Gibco, A11105-01), centrifuged at 1200 rpm for 3 min and resuspended in FACS buffer (DPBS containing 2% BSA) at 2×10⁶ cells/ml. 100 µl of OVCAR-3 cells were added to 96-well V-bottom plates. Plates were centrifuged at 1200 rpm for 3 mins and the buffer was discarded. 150 µl of scFv was added to the cells and incubated at 4° C. for one hour. ScFvs of parental clones FS28-185 and 256 were included as controls. After washing, cells were resuspended in 100 µl of Penta His Alexa-Fluor 647 (Qiagen, 109-546-098), and washed before being resuspended in 100 µl DPBS containing Sytox Green Nucleic Acid Stain (Invitrogen S7020, 1:10000 dilution). Samples were run on the iQue (Intellicyt Corporation, IQue Plus) and the geometric mean for APC was recorded.

For both FS28-185 and FS28-256, affinity matured clones with improved binding to OVCAR-3 cells were identified. On the basis of cell binding (MFI greater than 850) and sequence diversity, 10 clones were selected from the FS28-256 VH CDR3 and 9 from the VL CDR3 selections. Of the 38 FS28-185 affinity matured clones tested in this assay, 14 were selected from the VH CDR3 selections and one from the VL CDR3 selections. Selected clones were further characterised in a mAb² bispecific antibody format.

3.1.2 Generation of FS28-185 and FS28-256 Based mAb²

For further characterisation of the anti-MSLN binders, the affinity matured VH or VL region of FS28-185 or FS28-256, as well as the parental clones, were produced in mAb² format. The resulting mAb² are IgG1 antibodies comprising of the CDRs of either FS28-185 or FS28-256 clones or the affinity matured variants derived from them, the LALA mutation in the CH2 domain, and a human CD137 receptor-binding site in the CH3 domain. These mAb² molecules were designated FS22-053-008-AA/FS28-185 (SEQ ID NO: 154 and 195) and FS22-053-008-AA/FS28-256 (SEQ ID NO: 156 and 77) and FS22-053-008-AA/FS28-256-x for the affinity matured progeny. The mAb² were produced by transient expression in HEK293-6E cells and, where indicated, purified using mAb Select SuRe protein A columns.

3.1.3 Affinity Screening of FS28-185 and FS28-256 Affinity Matured Clones to Immobilised MSLN The binding of the mAb² containing affinity matured CDR regions were next screened for binding to immobilised human and cyno MSLN-His-Avi by Biacore. HEK293-6E supernatants containing FS22-053-008-AA/FS28-185 and FS22-053-008-AA/FS28-256 affinity matured clones were analysed for binding to immobilised MSLN at 200 RU as described in section 2.1.2. Two concentrations of mAb² were tested, i.e. 50 and 100 nM, and the binding was compared to the binding of the parental antibody also in mAb² format. Binders were ranked and the best six cyno cross-reactive binders of each lineage were re-expressed, purified and tested in cell binding assays as described in section 3.1.4 below. For the FS28-256 lineage, clones with improved VH CDR3 were then shuffled with clones with improved VL CDR3s, creating an additional nine VH/VL pairings, which were produced as mAb² and were also tested.

3.1.4 Cell Binding in the Presence of Soluble MSLN

As previously discussed in section 1, soluble MSLN can act as a decoy for the binding of any anti-MSLN antibody. The affinity matured clones were therefore screened for binding to recombinant and cell surface MSLN in the presence and absence of soluble human MSLN. Since soluble, shed MSLN lacks either 7 or 13 C-terminal residues (Zhang et al., 2011), a commercially available human MSLN antigen, MSLN-His Acro, which lacks 18 C-terminal amino acids was used as a mimic. This antigen was used at a 20 nM concentration, which is about 10-20 times the level of soluble MSLN found to be of diagnostic value for defining malignant mesothelioma and lung cancer patients as MSLN positive (Cui et al., 2014).

Cell binding assays using OVCAR-3 cells were performed similarly to the assays described in section 2.4. The effect of the presence of soluble MSLN was tested by pre-incubating the antibodies in the presence or absence of soluble MSLN before mixing with cells and determining if the pre-incubation affected binding to MSLN on the cell surface. The affinity matured clones and parental molecules (all in mAb² format as previously described) were diluted in FACS buffer to give a 2× final concentration in a 96-well V-bottom plate. 60 µl from each well was then added to either FACS buffer alone or to FACS buffer containing 60 µl of 40 nM recombinant hMSLN (R&D systems, 3265-MS-050) (to give a final concentration of 20 nM hMSLN) and pre-incubated at room temperature for 1 hour before 100 µl was added to the cells. Bound antibody was detected using goat anti-human anti-Fcγ Alexa-Fluor 488 (Jackson Immunoresearch, 109-546-098).

For the FS28-185 lineage, all affinity matured clones showed improved cell binding to OVCAR-3 (about 7-fold in $EC_{50}$) in comparison to binding by the parental clone. This binding was however reduced in the presence of 20 nM soluble MSLN, resulting in a 3 to 7-fold higher $EC_{50}$ (from 1.6-1.8 nM to approximately 5-7.8 nM). As for the FS28-256 lineage, five clones were selected as representatives of that lineage, all of which had a range of $EC_{50}$ varying from 0.9 to 8.6 nM. Most importantly, the binding affinity was retained and there was less than a 2-fold change in binding in the presence of 20 nM soluble MSLN compared to when it was absent. From this data, the clones selected for further testing included FS28-256-012, FS28-256-021, FS28-256-023 and FS28-256-024.

3.2 Affinity Maturation of Clone FS28-024 Using NNK Walk Strategy

Whereas FS28-024 bound to human MSLN with a subnanomolar affinity, its affinity for cyno MSLN was about 5-fold lower (see Example 4, Table 4). To improve binding to cyno MSLN, an NNK walk strategy on five residues in the VH CDR3 region was used. The sequence of the FS28-024 VH and VL was optimised in the same mAb² format as described in section 3.1.2. Parsimonious mutagenesis libraries were generated by diversifying one amino acid residue at a time of the RATLF residues (kabat numbering 95-99) in the VH CDR3, leading to a total of five individual libraries. The libraries were made with low redundancy NNK codons to represent all possible amino acids in the position of interest. Forward and reverse primers were designed according to the guidelines of Quickchange Lightning Site-Directed Mutagenesis Kit (Agilent, 200518), which was used to create the libraries. Each mutant was expressed in small scale in HEK293-6E cells and supernatants were screened by BIAcore for retained or improved binding to human and cyno MSLN-His-Avi. Of the 84 clones screened, few retained binding, most of them being substitutes of T98 residue. Four clones, FS28-024-51, FS28-024-52, FS28-024-53 and FS28-024-060 were re-expressed, purified and their affinities for human and cyno MSLN determined. Only one clone, FS28-024-53 showed an improvement in cyno cross-reactivity which was achieved by a single T98V mutation (Kabat numbering, see Table 4, Example 4). All four clones were taken forward as they might provide alternative sequences and characteristics depending on the application.

3.3 Summary of Affinity Maturation

Overall, the affinity maturation and sequence optimisation strategies for the FS28-024, FS28-185 and FS28-256 lineages were successful by further expanding the panel and diversity of anti-MSLN mAbs.

Example 4: Characterisation of Anti-MSLN Clones

4.1 Affinities

Binding of the selected anti-MSLN clones in mAb² format, to recombinant human and cyno MSLN-His-Avi antigen was measured by SPR using a Biacore T200 processing unit (GE Healthcare). As previously described, it was desirable to bind more strongly to immobilised antigen than to soluble antigen. To assess the binding properties of the clones, binding kinetics to immobilised MSLN antigen were determined as described in section 2.1.2 and compared to the kinetics obtained when MSLN antigens in solution bound to captured clones.

For the capture experiments, clones in mAb² format were captured using a BIAcore sensor series S chip Protein G (GE Healthcare, 29179315). mAb² diluted in HBS-EP buffer (GE Healthcare, BR100188) containing 900 mM $NaCl_2$ at 1 µg/ml, were injected individually on flow cell 2, 3 and 4 at 30 µl/min to achieve a response of approximately 100 RU. G1-AA/HelD1.3 was captured on flow cell 1. The recombinant human and cyno MSLN-His-Avi (section 1.1), diluted in HBS-EP buffer containing 900 mM $NaCl_2$, were injected on flow cell 1, 2, 3 or 4 as appropriate at a concentration range of 1000 nM to 0.051 nM with 3-fold dilutions for 5 minutes at 70 µl/min and then allowed to dissociate in buffer for 5 minutes. Regeneration was achieved by injecting 10 mM glycine pH1.5 (GE Healthcare, BR100354) and surfactant P20 (GE Healthcare, BR-1000-54) for 20 seconds at a rate of 30 µl/min. Subtracted data (flow cell 2—flow cell 1, flow cell 3—flow cell 1, or flow cell 4—flow cell 1) were analysed using BIAevaluation 3.2 Software (GE Healthcare) to identify binding using the model 1:1 binding, local Rmax and with refractive index (RI) constant 0.

TABLE 4

Affinities to immobilised and in-solution human mesothelin as well as cyno crossreactivity

| Clone (in FS22-053-008-AA mAb² format) | Affinity to immobilised human MSLN-His-Avi $K_D$ (nM) | Affinity to human MSLN-His-Avi in solution $K_D$ (nM) | Ratio of $K_D$ in solution/immobilised for human MSLN-His-Avi | Affinity to cyno MSLN-His-Avi in solution $K_D$ (nM) |
|---|---|---|---|---|
| FS28-024 | 0.39 | 46.5 | 119.2 | 240.0 |
| FS28-024-51 | 0.31 | 47.5 | 154.2 | 148.1 |
| FS28-024-52 | 0.36 | 33.1 | 92.3 | 185.4 |
| FS28-024-53 | 0.89 | 49.2 | 55.3 | 78.3 |
| FS28-024-060 | 0.07 | 5.2 | 78.6 | 265.9 |
| FS28-026 | 0.14 | 700.2 | 5001.4 | 886.0 |
| FS28-091 | 1.1 | 614.9 | 580.1 | >1000 |
| FS28-185 | 30.1 | 452.4 | 15 | 361.5 |
| FS28-256 | 23.7 | 888.8 | 37.5 | 737.9 |
| FS28-256-012 | 4.1 | 861.1 | 209 | 716.7 |
| FS28-256-021 | 3.3 | 23.2 | 7.0 | 16.2 |
| FS28-256-023 | 3.3 | 68.6 | 20.8 | 32.6 |
| FS28-256-024 | 6.7 | 95.4 | 14.3 | 56.7 |
| FS28-256-026 | 3.2 | 62.3 | 19.5 | 33.2 |
| FS28-256-027 | 1.1 | 6.0 | 5.3 | 0.7 |

*Affinity of FS28-026 to 100 RU immobilised MSLN is likely overestimated as the on-rate measurements are outside the limits of the Biacore T200.

The kinetic data demonstrated that all clones tested, with the exception of FS28-024-060, were crossreactive to cyno MSLN-His-Avi, having affinity to the cyno antigen within 5-fold of that to human MSLN-His-Avi.

In addition, for each group of clones that bound to a different MSLN binding region, clones were identified that bound with low nanomolar affinity to immobilised human MSLN-His-Avi.

Progeny clones of FS28-256 had a higher affinity than their respective parental antibodies, confirming that the affinity maturation of these clones had been successful. Of interest, all clones had a higher affinity for immobilised MSLN than for in-solution human MSLN-His-Avi, a characteristic that was quantified by calculating the fold difference of the in-solution $K_D$ versus the immobilised $K_D$ (see Table 4). It can therefore be hypothesised that the anti-MSLN antibodies are not binding with high affinity to the target, as observed by the low affinity for binding to soluble MSLN, but are thought to be binding more strongly to immobilised MSLN due to enhanced avidity interactions with the immobilised antigen. The avidity appears to be antibody specific.

4.2 Cell Binding to NCI-H226 in the Presence of Soluble MSLN

All selected clones, supplemented with other non-shuffled FS28-256 affinity matured clones (see Table 5), were then tested for binding to cell surface MSLN on NCI-H226 cells in the absence and presence of 20 nM MSLN. The method used was exactly as described in section 3.1.4. Both $EC_{50}$ and $E_{max}$ values were determined (Table 5).

TABLE 5

Cell binding in the absence and presence of soluble mesothelin

| Clone (in CD137 mAb₂ format) | NCI-H226 | | NCI-H226 + 20 nM soluble | |
|---|---|---|---|---|
| | $EC_{50}$ (nM) | $E_{max}$ (MFI) | $EC_{50}$ (nM) | $E_{max}$ (MFI) |
| FS28-024 | 1.47 | 980955 | 5.04 | 1023695 |
| FS28-024-051 | 0.78 | 800589 | 7.47 | 1100503 |
| FS28-024-052 | 1.32 | 957685 | 4.28 | 985916 |
| FS28-024-053 | 1.19 | 914344 | 7.52 | 964941 |
| FS28-024-060 | 1.46 | 1011600 | 25.69 | 1225277 |
| FS28-026 | 1.91 | 729876 | 2.65 | 701999 |
| FS28-091 | 2.72 | 739899 | 3.97 | 744939 |
| FS28-185* | 16.3 | 5155 | 14.3 | 5031 |
| FS28-256 | 15.78 | 275841 | 39.41 | 351430 |
| FS28-256-001 | 4.98 | 703342 | 5.36 | 608248 |
| FS28-256-005 | 5.30 | 759574 | 3.91 | 653731 |
| FS28-256-012 | 8.48 | 968727 | 4.83 | 790055 |
| FS28-256-014 | 3.11 | 771117 | 2.72 | 616427 |
| FS28-256-018 | 6.98 | 637266 | 4.60 | 493728 |
| FS28-256-021 | 3.29 | 919116 | 7.65 | 838717 |
| FS28-256-023 | 3.29 | 856041 | 3.90 | 716321 |
| FS28-256-024 | 3.88 | 812760 | 3.91 | 668584 |
| FS28-256-026 | 2.43 | 741080 | 4.59 | 714886 |
| FS28-256-027 | 3.93 | 986870 | 21.82 | 964426 |

* FS28-185 data were obtained on the BD Cantoll instead of iQue (Intellicyt) resulting in lower $E_{max}$ values due to differences in PMT voltages between machines.

The data showed that the anti-MSLN binding Fab arms of the mAb² tested bound with varying affinities to NCI-H226 cells ranging from 0.78 to greater than 16 nM, with the majority of clones exhibiting low nanomolar cell binding affinities, consistent with the affinities reported for the recombinant immobilised MSLN. The ranking of cell binding affinities of the naïve FS28-024, FS28-026, FS28-091, FS28-185 and FS28-256 was also consistent with the ranking data obtained in mAb format (Table 3, section 2.4). Of interest, the effect of 20 nM recombinant MSLN on cell binding affinity was low with minimal (less than 2.5-fold) increases in $EC_{50}$ observed for most clones. In particular, the cell binding affinities of FS28-256 derived clones, such as FS28-256-001, FS28-256-005, FS28-256-012, FS28-256-014, FS28-256-018, FS28-256-023, FS28-256-024 and FS28-256-026 were not affected by the presence of soluble MSLN. This demonstrated that even in the presence of an excess of soluble MSLN, most clones bound preferentially to the membrane bound form of MSLN.

For clones derived from FS28-024, a more variable effect of soluble MSLN was observed with increases in $EC_{50}$ ranging from 3.4 to 17.6 fold.

Two clones with the highest affinity for recombinant soluble MSLN (see Table 4), i.e. FS28-024-060 and FS28-256-027 (both having single digit nM $K_D$ to MSLN-His-Avi in solution), were most affected when binding to cells in the presence of soluble MSLN, indicating that higher affinity binders are more likely to be affected by shed MSLN. As a result, increases in $EC_{50}$ in the presence of soluble MSLN are less preferred, since it is the final $EC_{50}$ in the presence of soluble MSLN that is thought to be most reflective of the affinity of the mAb for these tumour cells in the patient. The actual required affinity of the anti-MSLN antibodies is application dependent.

Example 5: Sequence Optimisation of FS28-256 Affinity Matured Clones 5.1 Sequence Optimisation of FS28-256 Affinity Matured Clones All FS28-256 lineage clones contained a potential N-linked glycosylation site in the VH CDR2 (IMGT numbering N55-X-S57, wherein X is any residue). Moreover, FS28-256-001, FS28-256-021 and FS28-256-023 harboured a potential deamidation site in the VL CDR3 region at position N116-T117 (IMGT numbering). Similar to the procedure described in section 3.2 an NNK walk strategy was employed to identify amino acid substitutions in clone FS28-256-021 which would remove these potential glycosylation and deamidation sites. Initially the VH CDR2 residue N55 and the VL CDR3 N116 residue were mutated in the respective clones, and mutants were screened for retained for optimised binding to human and cyno MSLN. For FS28-256-021, changes to the VL CDR3 N116 residue resulted in a loss of antigen binding. Of the changes in the VH CDR2 at N55, only four mutants (N55A, N55H, N55S, and N55T) retained binding to human MSLN, though their binding was weaker compared with the parental clone.

Since it was not possible to remove the potential deamidation site in the VL CDR3 by mutating the sequence, alternative strategies were adopted. Since some of the other affinity matured clones derived from FS28-256 shared the same heavy chain sequence as FS28-256-021 but had different light chain sequences, these other clones were explored further. Specifically, FS28-256-027 was selected for testing. As previously described, FS28-256-027 had a higher affinity to soluble MSLN than FS28-256-021 (6.0 nM, Table 4), resulting in reduced binding to cell surface expressed MSLN in the presence of soluble MSLN (Table 5) and consequently was not selected as a preferred clone at the time. To explore whether this clone could be optimised for binding to cell surface expressed MSLN, the N55A, N55H, N55S or N55T mutations identified for the FS28-256-021 clone were introduced into the heavy chain of FS28-256-027 and the binding of the 4 resulting clones was measured by SPR, in a similar manner to the protocol used in Example 4.1 but with an RU of approximately 40 instead of 100, for binding to immobilised and in-solution MSLN. The results are shown in Table 6. Introduction of mutation N55T into FS28-256-027 resulted in a clone, FS28-256-274, which had a much weaker affinity for immobilised MSLN than the other clones and was therefore not progressed further. Introduction of mutations N55H and N55S into FS28-256-027, resulted in clones FS28-256-272 and FS28-256-273, respectively, which bound to soluble MSLN either with a higher or comparable affinity as to immobilised MSLN. Consequently, it was considered likely that binding of both of these clones to cell surface expressed MSLN would be negatively impacted by the presence of soluble MSLN. In contrast, introduction of mutation N55A into FS28-256-027 resulted in a clone, FS28-256-271, which showed the highest affinity for immobilised MSLN of the four clones tested and weaker binding to soluble MSLN. These results showed that, surprisingly, the N55A mutation in the VH CDR2 of the parental clone FS28-256-027 reduced the affinity of binding to both immobilised and soluble MSLN such that FS28-258-271 preferentially targeted immobilised MSLN over soluble MSLN. Consistent with other clones, such as FS28-256-021, which bound with a $K_D$ of at 10 nM or less to immobilised MSLN and 10 nM or greater $K_D$ to soluble MSLN, it is expected that binding of FS28-258-271 to MSLN on cell surfaces will be less impacted by the presence of soluble MSLN.

TABLE 6

Affinities to immobilised and in-solution human mesothelin

| Clone (in CD137 mAb² format) | Mutation in Heavy Chain CDR2 | Affinity to immobilised human MSLN-His-Avi $K_D$ (nM) | Affinity to human MSLN-His-Avi in solution $K_D$ (nM) | Ratio of $K_D$ in solution/immobilised for human MSLN-His-Avi |
|---|---|---|---|---|
| FS28-256-027 | — | 4.7 | 3.2 | 0.68 |
| FS28-256-271 | N55A | 5.9 | 18.2 | 3 |
| FS28-256-272 | N55H | 10.7 | 7.6 | 0.7 |
| FS28-256-273 | N55S | 6.0 | 7.4 | 1.2 |
| FS28-256-274 | N55T | 19.8 | 55.9 | 2.8 |

For mAb² FS22-172-003-AA/FS28-256-271, cyno cross-reactivity was determined by SPR using a steady-state kinetic analysis. A CM5 chip (GE Healthcare BR-1005-30) was coated with hMSLN-His-Avi or cMSLN-His-Avi at approximately 50RU according to manufacturer's instructions. mAb² were injected at a range of concentrations in a three-fold dilution series starting at 243 nM, at a flow rate of 10 µl/min. The association time was 1000 sec to steady state and the dissociation time was 30 sec. Running buffer was HBS-EP (GE Healthcare BR100188). Flow cells were regenerated by injecting Glycine-HCl pH1.5 at a flow rate of 30 µl/min for 30 seconds. Data were analysed by double referencing against a flow cell which was intentionally left blank (no antigen coating). Steady state affinity model was used to analyse kinetic data using the BiaEvaluation software version 3.2. Binding to cyno MSLN was within 3 fold of binding to human MSLN.

5.2 Antibody-Dependent Cellular Cytotoxicity (ADCC) Activity

To assess effector function of the MLSN mAbs, the molecules were tested in an ADCC in vitro assay. For this purpose, FS28-256-271 and FS28-024-052 antibodies were produced in human IgG1 format with or without LALA mutations (LALA or G1, respectively).

Raji cells expressing human MSLN (Raji.hMSLN cells) were generated by lentiviral transduction using the Lenti-X HTX Packaging system (Takara, cat. No. 631253). Lenti-X expression vector (pLVX) (Takara, cat. No. 631253) containing cDNA encoding human MLSN was co-transfected with a Lenti-X HTX Packaging Mix into the Lenti-X 293T cell line (Takara, cat. No. 632180) to generate virus. A Raji cell line (ATCC@CCL-86™) was then transduced with these lentiviral vectors. Expression of human MLSN on these cells was confirmed by binding of G1/SS1 positive control antibody for 1 hour and then a fluorescently-labelled anti-human Fc detection antibody (Stratech Scientific Ltd, cat. no. 109-546-098-JIR) was used to detect cell binding.

Figure 2:
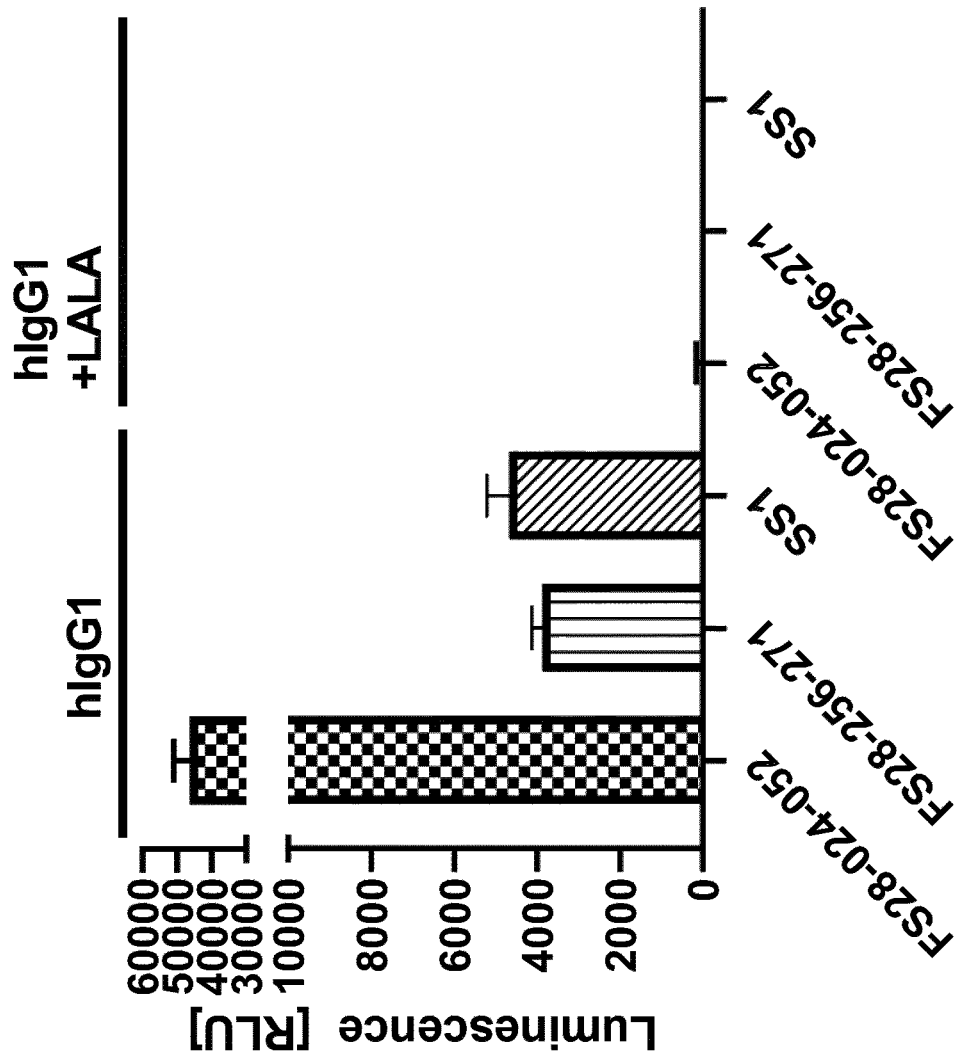
FIG. 2 shows the ADCC activity of anti-MSLN $mAb^2$. The anti-human MSLN $mAb^2$ FS28-024-052 and FS28-256-271, as well as the positive control antibody SS1, were tested in hIgG1 LALA format (no effector function) and effector competent backbone hIgG1. FS28-024-052 had the highest ADCC activity of the tested antibodies, with FS28-256-271 having comparable ADCC activity to the control antibody. In all cases, introduction of the LALA mutations into the IgG1 backbone completely abrogated any ADCC activity, as expected.

An ADCC reporter bioassay kit (Promega, cat. No. G7010) was used following the manufacturer's protocol. Effector cells from the ADCC kit were mixed in a 20:1 ratio with Raji.hMSLN cells. mAb² or control antibody SS1 were titrated on a 96-well plate and incubated at 37° C. 5% $CO_2$ for 6 hours. ADCC activity was measured by adding a luciferase substrate from the Bio-Glo assay system kit (Promega, cat. No. G7941) as per the manufacturer's instructions. Luminescence signal was plotted vs the log concentration of antibody and the resulting curves were fitted using the log (agonist) vs response equation in Graph-Pad Prism. The results are shown in FIG. 2 and demonstrate that both FS28-256-271 and FS28-024-052 were able to elicit ADCC activity when in human IgG1 format. As expected ADCC activity was lost when the LALA mutation was introduced into the hIgG1 backbone of these antibodies. This data demonstrates that the MSLN antibodies described here can be used to elicit effector functions to modulate immune responses.

5.3 Potency of FS28-256-271 in Primary T Cell Assays 5.3.1 Potency of FS28-256-271 in an OX40 mAb$^2$ Format In Vitro in a Primary T Cell Assay Pan T cells were isolated from peripheral blood mononuclear cells (PBMCs) obtained from leucocyte depletion cones, a by-product of platelet donations. Briefly, leucocyte cone contents were flushed with PBS and overlaid on a Ficoll gradient (GE Lifesciences cat no 17144002). PBMCs were isolated by centrifugation and recovery of cells that did not cross the Ficoll gradient. PBMCs were further washed with PBS and the remaining red blood cells were lysed through the addition of 10 ml red blood cell lysis buffer (eBioscience) according to the manufacturer's instructions. PBMCs were counted and resuspended to 2.0×10^6 cells/ml in T cell medium (RPMI medium (Life Technologies) with 10% FBS (Life Technologies), 1× Penicillin Streptomycin (Life Technologies), Sodium Pyruvate (Gibco), 10 mM Hepes (Gibco), 2 mM L-Glutamine (Gibco) and 50 µM 2-mercaptoethanol (Gibco).

T cells were then isolated from the PBMCs using a Pan T Cell Isolation Kit II (Miltenyi Biotec Ltd) according to the manufacturer's instructions. Human T-Activator CD3/CD28 Dynabeads (Invitrogen 111.32D) were resuspended by vortexing. Beads were washed twice with T cell medium (RPMI medium (Life Technologies) with 10% FBS (Life Technologies), 1× Penicillin Streptomycin (Life Technologies), Sodium Pyruvate (Gibco), 10 mM Hepes (Gibco), 2 mM L-Glutamine (Gibco) and 50 µM 2-mercaptoethanol (Gibco). T cells at a concentration of $1.0×10^6$ cells/ml in T cell medium were stimulated with the washed human T-Activator CD3/CD28 Dynabeads at a 2:1 cell to bead ratio in a T-25 flask (Sigma) and incubated overnight at 37° C., 5% $CO_2$ to activate the T cells. Activated T cells were washed from the Dynabeads and resuspended in T cell medium at a concentration of $2.0×10^6$ cells/ml. 96-well flat-bottomed plates were coated with anti-human CD3 antibody through incubation with 2.5 µg/ml anti-human CD3 antibody (R&D Systems clone UHCT1) diluted in PBS for 2 hours at 37° C., 5% $CO_2$ and then washed twice with PBS. Activated T cells were added to the plates at $6×10^5$ cells/well. Mesothelin expressing cells, NCI-H226, were added at 20,000 cells\well. A mAb$^2$ comprising an anti-OX40 Fcab as well as the anti-MSLN Fab FS28-256-271 was tested in this assay, together with control antibodies. The assay plates were incubated at 37° C., 5% $CO_2$ for 72 hours. Supernatants were collected and IL-2 release was measured by Human IL-2 ELISA (Life Technologies, 88-7025-88). The concentration of human IL-2 (hIL-2) was plotted vs the log concentration of antibody and the resulting curves were fitted using the log (agonist) vs response equation in GraphPad Prism. The results are shown in Table 7 and demonstrate that FS28-256-271 in a mAb$^2$ format is able to bind to MSLN expressed on a cell surface and crosslink the antibody such that the OX40 binding site can bind to and activate OX40.

5.3.2 Potency of FS28-256-271 in a CD137 mAb$^2$ Format in an In Vitro Primary T Cell Assay Peripheral blood mononuclear cells (PBMCs) were obtained as described in 5.2. CD8$^+$ T cells were isolated using the CD8$^+$ T cell isolation kit II (Miltenyi Biotec Ltd, 130-096-495) according to the manufacturer's instructions. 96-well flat bottom tissue culture plates were coated with 8 µg/ml anti-CD3 antibody (Clone UCHT1, R&D Systems, MAB100-SP) in PBS overnight at 4° C. The plates were then washed 3 times with 200 µl PBS. NCI-H226 cells were plated at $2×10^4$ cells per well on to anti-CD3 antibody-coated (8 µg/ml) 96 well flat bottom plates in 100 µl T cell culture medium (RPMI medium (Life Technologies, 61870-044) with 10% FBS (Life Technologies), 1× Penicillin Streptomycin (Life Technologies, 15140122), 1 mM Sodium Pyruvate (Gibco, 11360-070), 10 mM Hepes (Sigma-Aldrich, H0887), 2 mM L-Glutamine (Sigma-Aldrich, G7513) and 50 µM 2-mercaptoethanol (Gibco, M6250)). Once cells had adhered after 4 hours incubation, all T cell culture medium was removed and replaced with 50 µl T cell culture medium containing T cells at a concentration of $4.0×10^5$ cells/ml resulting in $2.0×10^4$ cells/well. Control antibodies or a mAb$^2$ comprising a CD137 Fcab and the MSLN Fab FS28-256-271 were diluted in T cell medium at a 4× final concentration starting at 60 nM and 1:3 or 1:7 serial dilutions were carried out. 50 µl of antibody titration was added to the cells for a total assay volume of 200 µl and 1× concentration of antibody. The assay was incubated at 37° C. 5% $CO_2$ for 72 hours.

Supernatants were collected and assayed with a V-PLEX IL-2 kit from Meso Scale Discovery (K151QQD-4) following the manufacturer's instructions. The concentration of human IL-2 (hIL-2) was plotted vs the log concentration of antibody and the resulting curves were fitted using the log (agonist) vs response equation in GraphPad Prism. The results are shown in Table 7 and demonstrate that FS28-256-271 in a mAb$^2$ format is able to bind to MSLN on the cell surface and crosslink the antibody such that the CD137 binding site can bind to and activate CD137.

5.3.3 Summary of Sequence Optimised MSLN Clone FS28-256-271 and its Use to Drive Agonism of TNFRSF Members.

Table 7 shows the results of the T cell assays described in 5.3.1 and 5.3.2 which demonstrate the ability of anti-MSLN Fabs such as FS28-256-271 in a mAb$^2$ format to crosslink and activate different TNFSFRs such as OX40- or CD137 to induce agonism in T cells.

TABLE 7

T cell activation assay using FS28-256-271 as mesothelin-binding Fab in a mAb$^2$ format, and using NCI-H226 cells for crosslinking

| Clone | $EC_{50}$ (nM) | Emax (pg/ml IL-2) |
|---|---|---|
| OX40/FS28-256-271 mAb$^2$ | 0.11 | 6509 |
| CD137/FS28-256-271 mAb$^2$ | 0.096 | 4871 |

Summary of Isolation Anti-Human Mesothelin mAbs (Examples 1 to 5)

Phage selection and antibody screening strategies aimed at isolating anti-human MSLN antibodies that bind to cell surface MSLN, led to the identification of a panel of specific anti-mesothelin binding antibodies with a range of affinities, MUC16-MSLN blocking activities, MSLN region binding bins and cell binding characteristics. Due to the screening cascade performed, most anti-MSLN binding Fabs, whether tested in mAb or mAb$^2$ format, preferentially bound to cell surface MSLN.

Example 6: Selection and Characterisation of Anti-Mouse MSLN Antibodies 6.1 Naïve Selection of Anti-Mouse MSLN mAbs The amino acid identity between mouse and human MSLN is low (60%). To enable in vivo Proof of Concept (PoC) studies in mice, the inventors set out to isolate anti-mouse MSLN mAbs with similar properties as the anti-human MSLN mAbs described in Example 1 to 5. Phage selections, using the synthetic naive phagemid libraries displaying the Fab domain of human IgG1 germlines with randomisation in the CDR1, CDR2 and CDR3 (MSM Technologies) were used for selections with biotinylated mouse MSLN-His-Avi (SEQ ID NO 171, see section 1.1) as described in section 1.2. Four rounds of selections were performed with decreasing concentrations of biotinylated mMSLN-His-Avi and similarly to the anti-human MSLN selections, epitope masking strategies were performed in a subsequent campaign. In addition, after a first round of using recombinant antigen, HEK293-mMSLN cells were generated and used in round 2, 3 and 4.

Briefly, mouse MSLN sequence was subcloned into the pcDNA5/FRT/TO vector (Life technologies, V652020) and then co-transfected with the FIp recombinase expression plasmid, pOG44 (Life Technologies, V600520) into FIp-In TREx 293 cell lines (Life Technologies, R78007). Cells were grown in DMEM containing 10% FBS, 100 µg/ml Hygromycin B (Melford Laboratories Ltd, Z2475) and 15 µg/ml Blasticidin (Melford Laboratories Ltd, B1105) for 3-4 weeks until colonies of stably transformed cells had formed. These colonies were amplified in the presence of 1 µg/ml Doxycyclin (Sigma Aldrich, D9891) and tested for expression of MSLN using anti-mouse MSLN (LS Bio, LS-C179484).

In total 47 individual mAbs from enriched populations were screened for antigen binding and 45 unique positive binders were subcloned and expressed as soluble mAbs in IgG1 LALA format as previously described in Example 1.3. mAbs were characterised for specific binding to immobilised mMSLN-His-Avi by ELISA and ranked based on affinity to about 50 or 200 RU of immobilized mMSLN-His-Avi in kinetic experiments using Biacore analysis. This identified a panel of mAbs, including FS28m-194, FS28m-201, FS28m-209, FS28m-216, FS28m-228, FS28m-261 and FS28m-265 with affinities ranging from 1 to 25 nM. In addition, binding to different regions of MSLN was tested as described in section 2.1.3. A mouse cross-reactive mAb G1-AA/MOR6626, generated by cloning the VH and VL of MOR6626 clone (Patent publication no WO 2009/068204 A1) was used as a positive control. Most clones, amongst which FS28m-228 failed to bind to MSLN that was already bound to MOR6626, whereas others like FS28-194 or FS28-026 showed partial or full binding respectively. Thus, clones binding to different regions (bins) were isolated. The anti-MSLN binding regions of MOR6626 have been used for in vivo PoC studies (Patent publication no. US 2017/0342169 A1). Based on the obtained data, FS28m-228 might bind to a similar region on MSLN as MOR6626.

6.2 Affinity Maturation of Anti-Mouse MSLN mAbs

The VH and VL CDR3 regions of FS28m-228 were optimised in parallel in scFv format by randomizing overlapping cassettes of five amino acids using NNK primers as described in example 3.1.1. Two rounds of selections were performed using 50 nM biotinylated mMSLN-His-Avi in round 1 and 0.2 nM mMSLN-His-Avi in round 2. For the second round, an off-rate selection pressure was also applied by adding a 1000-fold excess (200 nM) of mMSLN-His-Avi (non-biotinylated) and incubating the antigen/phage mixture for 2.5 hours at room temperature. Soluble scFv (single point concentration) were then tested for binding to mMSLN-His-Avi using Octet. Briefly, streptavidin sensors (ForteBio, 18-5019) were incubated with mMSLN-His-Avi (10 µg/ml) for 5 min. Association of soluble scFv, diluted with 10× kinetic buffer to final concentration of 1× buffer (ForteBio, 18-1092), to mMSLN was analysed for 5 min, followed by a dissociation step of 5 min. Compared to the parental FS28m-228 scFv, about 66 out of 85 clones tested showed improved binding. Nine clones were taken forward for expression into mAb$^2$ format, combining the Fab arms with an Fcab which binds to mouse CD137, called FS22-063-AA, using the same cloning and expression method as described (section 3.1.2). The resulting mAb$^2$ designated were tested for their MSLN binding affinities.

6.3 Binding Affinity of Anti-Mouse MSLN mAb$^2$ to Immobilised and Soluble Mouse MSLN Like the anti-human MSLN binders, the affinity matured variants derived from FS28m-228 were tested for binding to immobilised and soluble MSLN using the Biacore. The procedure for binding to immobilised MSLN was similar to the method described in section 2.1.4 with mMSLN-His-Avi immobilised at 50 RU. To determine the affinity for soluble MSLN the mAb$^2$ were captured via anti-human Fc. Briefly, 25 µg/ml anti-human IgG (Fc) antibody (GE Healthcare, Human Antibody Capture Kit, BR100839) was coated on flow cells 1, 2, 3 and 4 of a Biacore sensor chip CM5 (GE Healthcare, BR100530) achieving a final response of approximately 750 RU. The mAb$^2$ clones, diluted in HBS-EP buffer (GE Healthcare, BR100188) at 50 nM, were injected individually on flows cell 2, 3 and 4 at 30 µl/min to achieve a response of approximately 100 RU. The recombinant mMSLN-His-Avi antigens, diluted in HBS-EP buffer, were injected on flow cell 1, 2, 3 or 4 as appropriate at a concentration range of 243 nM to 0.11 nM with 3-fold dilutions for 5 minutes at 70 µl/min and then allowed to dissociate in buffer for 5 minutes. Regeneration was achieved by injecting 3 M magnesium chloride (GE Healthcare, Human Antibody Capture Kit, BR100839) for 30 seconds at a rate of 30 µl/min.

The kinetic data of both the immobilised and in-solution affinities (Table 8) showed that in comparison to the parental FS28m-228 Fab arm, the affinity matured clones showed improved binding to mouse MSLN-His-Avi antigen. Moreover, all clones showed binding kinetics with an affinity to immobilised which was higher than to soluble MSLN, with varying ratios. Like the human clones described in sections 4.1 and 5.1, it was thought that these clones would have stronger binding to membrane bound than soluble shed MSLN due to enhanced avid binding interactions. Thus, the affinity maturation of FS28m-228 led to a panel of affinity matured clones that had increased affinity towards mouse MSLN and all bound more strongly to immobilised MSLN than soluble MSLN. Clone FS28m-228-010 was selected as the preferred clone, as it had the highest affinity to immobilised mouse MSLN and low affinity to in-solution mouse MSLN.

TABLE 8

Affinities to immobilised and in-solution human mesothelin

| Clone (in FS22-063AA mAb$^2$ format) | Affinity to immobilised mMSLN-His-Avi $K_D$ (nM) | Affinity to in-solution mMSLN-His-Avi $K_D$ (nM) | Ratio of $K_D$ in solution/ immobilised for mouse MSLN-His-Avi |
|---|---|---|---|
| FS28m-228 | 7.90 | 252 | 31.9 |
| FS28m-228-010 | 2.6 | 60.24 | 23.2 |

6.4 Summary of Isolation Anti-Mouse Mesothelin mAbs

Phage selection and antibody screening strategies led to the identification of a panel of anti-mouse mesothelin binding clones with a range of affinities and which bind to different regions of mMSLN. Like the anti-human MSLN binders, the clones showed binding characteristics favouring binding to immobilised mMSLN than soluble mMSLN rendering them suitable molecules for studying in murine in vivo PoC studies.

6.5 In Vivo Efficacy of mAb$^2$ Containing the Anti-Mouse MSLN mAb FS28m-228-010 Having shown that anti-MLSN mAbs in hIgG1 isotype were able to elicit ADCC activity, it was desirable to demonstrate that the anti-MLSN mAbs were able to drive MLSN-dependent crosslinking in vivo in a CD137 mAb$^2$ format.

A syngeneic mouse tumour model expressing mouse MSLN was constructed. CT26 colon carcinoma cells (ATCC, CRL-2638) expressing full-length mouse mesothelin (SEQ ID NO: 171), were produced by lipofection (Lipofectamine 3000, Thermo Fisher Scientific, catalogue number L3000008) using the pcDNA3.1 vector (+) (Thermo Fisher Scientific, catalogue number V79020). Following the manufacturer's protocol, the CT26 cells were transfected with the pcDNA3.1 vectors containing the mouse MSLN cDNA. A stable transfection was achieved using geneticin as the selection antibiotic (at 600 µg/ml) in complete media (RPMI, 10% FBS). Expression of mouse MSLN on the CT26 cells was confirmed by flow cytometry by using the positive control antibody MOR6626 (WO 2009/068204 A1). Specifically, cells were incubated with the positive control antibody for 1 hour and then a fluorescently-labelled anti-human IgG detection antibody (Stratech Scientific Ltd, catalogue no. 109-546-098-JIR) was used to detect cell binding. Clonal populations were expanded and subsequently analysed to determine the relative expression levels using the same flow cytometric procedure, after which one clone was selected and denominated CT26.G10.

CT26.G10 tumour growth was confirmed in vivo. Balb/c female mice (Charles River) aged 8-10 weeks were micro-chipped and given a unique identifier. Each cohort had 17 mice and each animal received 1×10$^5$ cells injected subcutaneously in the dorsal left flank in 100 µl serum free medium. Tumour volume measurements were taken three times per week with callipers to determine the longest axis and the shortest axis of the longest axis and the shortest axis of the tumour. The following formula was used to calculate the tumour volume:

Volume=$L \times S2 2$

Where $L$=longest axis; $S$=shortest axis

The trial was halted when tumour volume reached the humane endpoint in accordance with the United Kingdom Animal (Scientific Procedures) Act and EU Directive EU86/609. Tumour tissues were collected at the termination of the study, and expression of membrane-bound mesothelin was confirmed by immunohistochemical staining in formalin fixed paraffin embedded (FFPE) tumour tissues as follows: 4 µm FFPE tissue sections were deparaffinised and antigen retrieved using low pH 6.1 at 97° C. (Dako PT Link) followed by a peroxidase block and protein block prior to incubation with a primary anti-mesothelin antibody (LifeSpan Biosciences, catalogue no. LS-C407883) at a concentration of 1 µg/ml. The anti-mesothelin antibody was detected using a labelled polymer-HRP anti-rabbit secondary reagent and a DAB (3,3'-diaminobenzidine) chromogenic endpoint (Dako EnVision+ System).

To assess antibody FS28m-228-010, the following molecules or combinations were tested in vivo: FS28m-228-010 antibody in human IgG1 isotype with LALA mutations (G1-AA/FS28m-228-010), two "mock" CD137 mAb$^2$ (FS22m-063-AA/HeID1.3 and FS22m-063-AA/4420), a combination of the FS28m-228-010 antibody with a mock CD137 mAb$^2$ with LALA mutations (G1-AA/FS28m-228-010+FS22m-063-AA/HeID1.3), a human isotype control antibody (G1-AA/HeID1.3), and finally a CD137/MSLN mAb$^2$ (FS22m-063-AA/FS28m-228-010) with LALA mutations (SEQ ID NO: 196 and 197).

Balb/c female mice (Charles River) aged 8-10 weeks and weighing 20-25 g each were acclimatized for one week prior to the study start. All animals were micro-chipped and given a unique identifier. With the exception of FS22m-063-AA/4420 (n=10 mice), each cohort comprised 20 mice. The CT26.G10 colon carcinoma cell line was expanded and cell banks generated. Each animal received 1×10$^5$ cells injected subcutaneously in the left flank in 100 µl serum free media. Any mice which did not have tumours 12 days following tumour cell inoculation were removed from the study.

200 µg doses of each antibody (~10 mg/kg) were prepared and injected intraperitoneally (IP) into mice. In addition, both the G1-AA/FS28m-228-010+FS22m-063-AA/HeID1.3 were each prepared at 200 µg per dose (~10 mg/kg) for the combination group. 200 µl doses were administered to the mice on days 12, 14 and 16 (q2d×3), following tumour inoculation. Tumour volume measurements were made three times per week using callipers and mice were monitored closely. The study endpoint was determined by humane endpoints based on tumour volume and condition of the mice.

Figure 3:
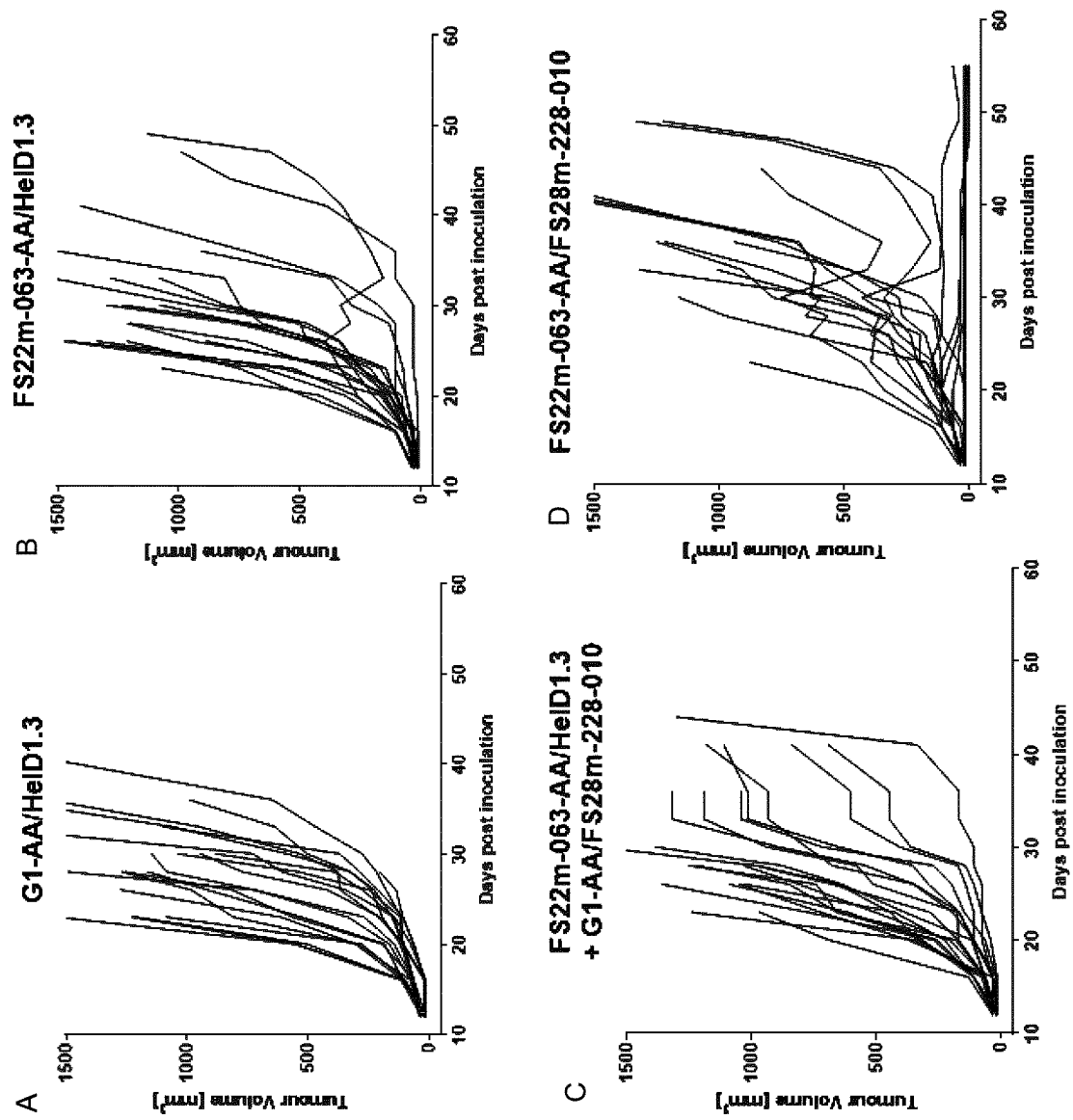
FIG. 3 shows individual tumour volume measurements in the CT26.G10 syngeneic tumour model treated with (A) G1-AA/HeID1.3 (human IgG1 control), (B) FS22m-063-AA/HeID1.3 (anti-mouse CD137 Fcab in $mAb^2$ format), (C) combination of FS22m-063-AA/HeID1.3 and G1-AA/FS28m-228-010 (anti-mouse CD137 Fcab plus anti-mouse MSLN Fab), (D) FS22m-063-AA/FS28m-228-010 (anti-mouse CD137/MSLN $mAb^2$) (E) FS22m-063-AA/4420 (anti-mouse CD137 Fcab in $mAb^2$ format), and (F) G1-AA/FS28m-228-010 (anti-mouse MSLN Fab). FS22m-063-AA/FS28m-228-010 showed reduced tumour growth compared to the isotype control, as well as other treatment groups.
Figure 3:
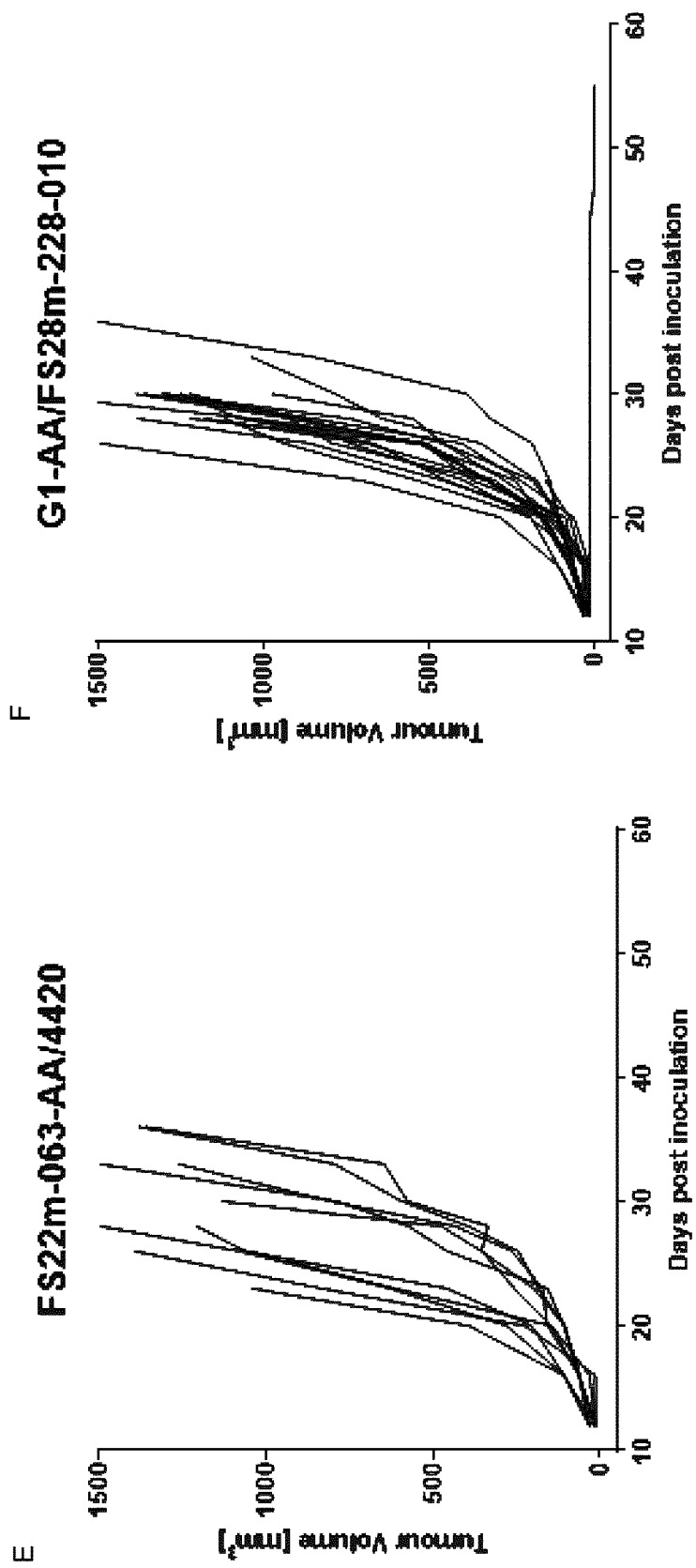

As shown in FIG. 3, the FS22m-063-AA/FS28m-228-010 mAb$^2$ significantly inhibited tumour growth compared to the G1-AA/HeID1.3 isotype control. Table 9 shows pairwise comparison of the tumour growth rates for all treatment groups over the full course of the study using Mixed Model analysis, comparing all groups to the G1-AA/HeID1.3 isotype control.

All animals bearing tumours measuring equal or below 62.5 mm$^3$ at the end of the study were counted as fully responding animals (see Table 10). 35% of anti-CD137/MSLN mAb$^2$-treated animals were complete responders to treatment at the end of study, compared to 0% in the G1-AA/HeID1.3 isotype control, FS22m-063-AA/HeID1.3, FS22m-063-AA/4420, and FS22m-063-AA/HeID1.3 and G1-AA/FS28m-228-010 combination groups.

Figure 4:
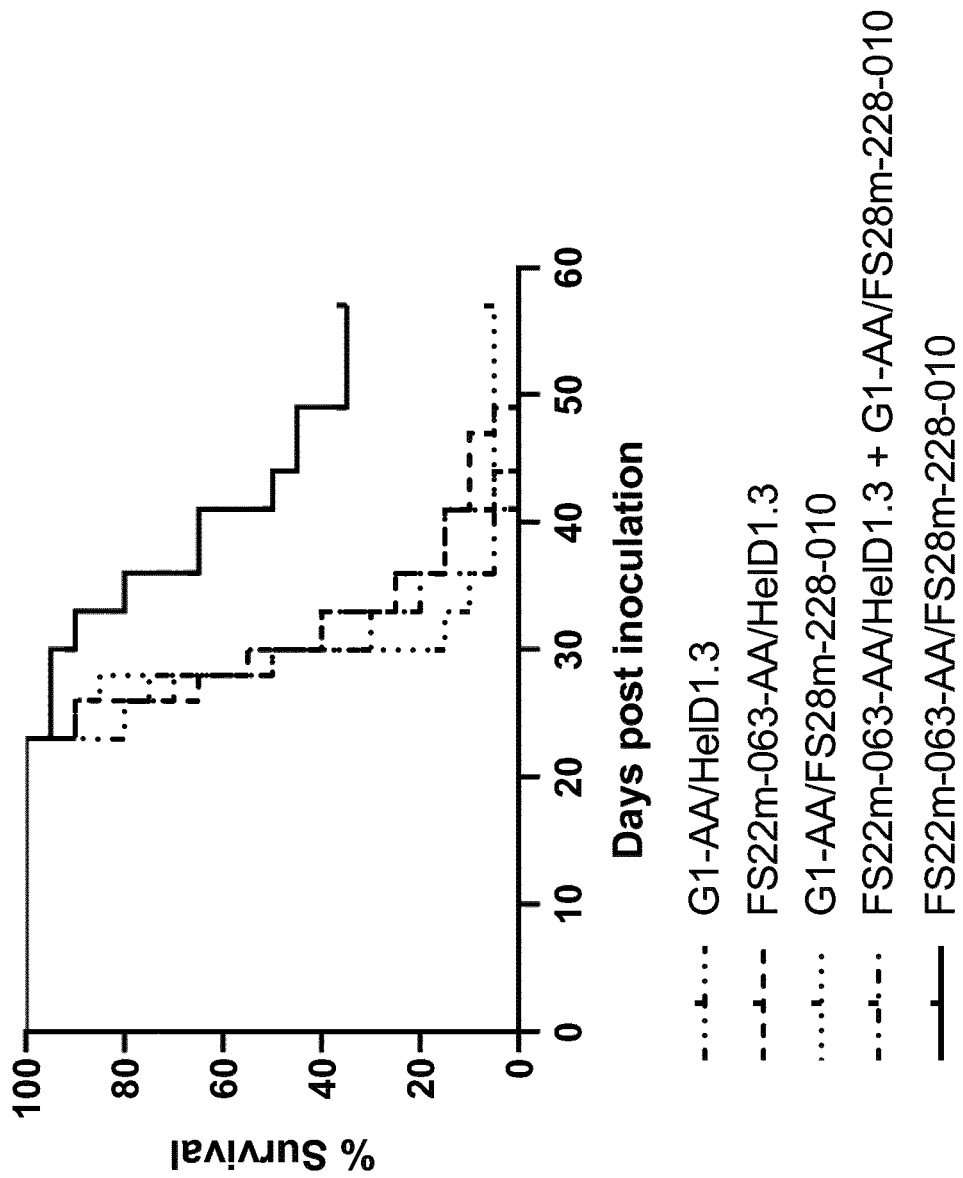
FIG. 4 shows a Kaplan Meier survival curve for the CT26.G10 syngeneic tumour model treated with G1-AA/HeID1.3 (IgG control), FS22m-063-AA/HeID1.3 (anti-mouse CD137 Fcab in $mAb^2$ format), FS22m-063-AA/4420

Survival analysis (FIG. 4 and Table 11) showed that the FS22m-063-AA/FS28m-228-010 mAb$^2$ induced a significant survival benefit compared with the G1-AA/HeID1.3 antibody, whereas the G1-AA/FS28m-228-010, FS22m-063-AA/HeID1.3 and FS22m-063-AA/4420) did not demonstrate a survival advantage. In addition, the FS22m-063-AA/FS28m-228-010 mAb$^2$ resulted in an improved median survival time of 42.5 days compared with G1-AA/HeID1.3 (29 days), FS22m-063-AA/HeID1.3 (30 days), FS22m-063-AA/4420 (29 days), G1-AA0FS28m-228-010 (30 days) and combination of FS22m-063-AA/HeID1.3 with G1-AA/FS28m-228-010 (29 days).

These data suggest that crosslinking of the mAb$^2$ via MSLN is capable of driving CD137 agonism in the tumour; an action of the bispecific antibody which is superior to targeting CD137 and/or MSLN alone (and even in combination), resulting in significantly improved survival in tumour-bearing mice. The mAb on its own (G1-AA/FS28m-228-010) with LALA mutation showed no intrinsic activity in this study. Without wishing to be bound by theory, it expected that an effector-competent version of antibody FS28m-228-010 (excluding the LALA mutation) would show ADCC activity and anti-tumour efficacy consistent with the in vitro results observed in section 5.2.

TABLE 9

Results of pairwise comparison of the tumour growth using Mixed Model analysis, comparing all groups to the G1-AA/HelD1.3 isotype control.

| Groups | Mixed Model Analysis | |
|---|---|---|
| G1-AA/HelD1.3 10 mg/kg (negative control) | P-value | Significance |
| G1-AA/FS28m-228-010 10 mg/kg | 0.4367 | NS |
| FS22m-063-AA/HelD1.3 10 mg/kg | 0.0017 | *** |
| FS22m-063-AA/4420 10 mg/kg | 0.7067 | NS |
| G1-AA/FS28m-228-010 10 mg/kg + FS22m-063-AA/HelD1.3 10 mg/kg | 0.2093 | NS |
| FS22m-063-AA/FS28m-228-010 10 mg/kg | 0.0000 | **** |

NS-not significant $p \geq 0.05$;
****-p-value < 0.0001;
***-p-value 0.0001-0.001

TABLE 10

Number and percentage of tumour-free mice (tumours $\leq 62.mm^3$) by the end of study in the CT26.G10 syngeneic tumour model.

| Groups | Tumour-free mice at study end |
|---|---|
| G1-AA/HelD1.3 10 mg/kg (negative control) | 0/20 (0%) |
| G1-AA/FS28m-228-010 10 mg/kg | 1/20 (5%) |
| FS22m-063-AA/HelD1.3 10 mg/kg | 0/20 (0%) |
| FS22m-063-AA/4420 10 mg/kg | 0/10 (0%) |
| G1-AA/FS28m-228-010 10 mg/kg + FS22m-063-AA/HelD1.3 10 mg/kg | 0/20 (0%) |
| FS22m-063-AA/FS28m-228-010 10 mg/kg | 7/20 (35%) |

TABLE 11

Median survival times for animals treated with each compound, and results of pairwise statistical analyses (Log-rank) in CT26.G10 syngeneic tumour model

| Groups | Median Survival (Days) | Log-rank | |
|---|---|---|---|
| G1-AA/HelD1.3 10 mg/kg | 29 | P-value | Significance |
| G1-AA/FS28m-228-010 10 mg/kg | 30 | 0.993 | NS |
| FS22m-063-AA/HelD1.3 10 mg/kg | 30 | 0.3952 | NS |
| FS22m-063-AA/4420 10 mg/kg | 29 | 0.9645 | NS |
| G1-AA/FS28m-228-010 10 mg/kg + FS22m-063-AA/HelD1.3 10 mg/kg | 29 | 0.4706 | NS |
| FS22m-063-AA/FS28m-228-010 10 mg/kg | 42.5 | <0.0001 | **** |

NS-not significant $p \geq 0.05$;
****-p-value < 0.0001

6.6 Mechanism of Action of an Anti-Mouse CD137/MSLN mAb$^2$ Containing the Anti-Mouse MLSN Mab Fs28m-228-010

To further understand the pharmacology of the anti-tumour response observed with FS22m-063-AA/FS28m-228-010 containing the anti-mouse MSLN mAb FS28m-228-010, the mechanism of action of CD137/MSLN mAb$^2$ in a MSLN-positive syngeneic tumour model was investigated.

Mice were prepared as described in Example 6.5, and inoculated with the CT26.G10 colon carcinoma cell line. Each cohort consisted of 20 mice. FS22m-063-AA/FS28-228-010 (CD137/MSLN) mAb$^2$, human IgG1 isotype control (G1-AA/4420) and an anti-CD137 agonist antibody (clone 3H3; G1/3H3; Rickert et al., 2016) was also included for comparison. All three antibodies were prepared at 134 µg per dose (approximately 6.7 mg/kg in a 20 g mouse) in DPBS+1 mM arginine+0.05% Tween 80 and injected intraperitoneally (IP) into mice. Each mouse received the antibodies by one 200 µl intraperitoneal injection at a fixed dose of 134 µg on day 20 following tumour inoculation. Tumour volume measurements were made three times per week using callipers as described in Example 6.5, and mice were monitored closely.

Six mice per group were necropsied 24, 72, 144 and 192 hours post dose at day 20 following tumour inoculation. Spleen, blood and tumour tissue were taken for analysis from CT26.G10 tumour-bearing mice treated with either FS22m-063-AA/FS28-228-010, G1-AA/4420, or G1/3H3. All samples were investigated for T cell abundance and proliferation by flow cytometry, as T cell activation and proliferation markers are known to be downstream effects of CD137 agonism (Fisher et al., 2012). In addition, serum from blood was also collected for detection and quantification of soluble MSLN expression. Spleen and tumour tissue were disaggregated to single cell suspension by standard mechanical and enzymatic methods, and red blood cells were lysed once in red blood cell lysis buffer (Miltenyi Biotec Ltd., 130-094-183). Blood was collected by terminal cardiac bleed, and half collected into EDTA-containing tubes for single cell analysis by flow cytometry and half of blood was collected into clotting activator/serum tubes for analysis of soluble MSLN. Whole blood collected in EDTA-containing tubes were lysed three times in red blood cell lysis buffer (Miltenyi Biotec Ltd., 130-094-183) according to Manufacturer's instructions. Blood collected in serum tubes was fractionated by centrifugation and serum removed for analysis of soluble MSLN.

Single cells from spleen, tumour and blood were then treated the same, and cells were washed once with PBS and samples stained with fixable viability dye (eBioscience, 65-0865-14). Cells were subsequently stained for cell surface markers with an antibody staining panel shown in Table 12 (all but intracellular markers, Ki67 and FoxP3), in the presence of Fc block (eBioscience, 16-0161-85 at 1:25) for 45 minutes at 4° C. Cells were then fixed and permeabilised with the eBioscience FoxP3 staining kit (eBioscience, 00-5523-00) according to manufacturer's instructions. Cells were resuspended in 100 µl permeabilization buffer with intracellular markers Ki67 and FoxP3 antibodies and incubated overnight at 4° C. in the dark. Prior to acquisition on a BD Fortessa flow cytometer, cells were washed once with permeabilization buffer and resuspended in 120 µl PBS containing 0.5% BSA. Data was acquired using BD FACS Diva software, and analysed with FlowJo (V10), and Microsoft Excel. The data shows the abundance and proliferation of CD8$^+$ T cells at 144 hours following dosing, as a percentage of the parental population.

TABLE 12

| Flow Cytometry panel | | | | |
|---|---|---|---|---|
| Target | Clone | Fluorophore | Manufacturer | Cat No. |
| CD45 | 30-F11 | Alexa700 | eBioscience | 56-0451 |
| CD3e | 145-2C11 | PE-Cy7 | eBioscience | 25-0031-82 |
| CD8 | 53-6.7 | BUV737 | BD Bioscience | 564297 |
| CD4 | RM4-5 | BUV395 | BD Bioscience | 740208 |
| FoxP3 | FJK-16s | PerCP-0y5.5 | eBioscience | 45-5773 |

TABLE 12-continued

Flow Cytometry panel

| Target | Clone | Fluorophore | Manufacturer | Cat No. |
|---|---|---|---|---|
| CD49b | DX5 | BV421 | Biolegend | 563063 |
| CD103 | M290 | BV786 | BD Bioscience | 564322 |
| CD137 | 1765 | APC | eBioscience | 106110 |
| CD69 | H1.2F3 | BV510 | Biolegend | 104505 |
| PDI | 29F.1A12 | FITC | Biolegend | 135220 |
| Ki67 | SolA15 | PE | eBioscience | 12-5698-82 |
| Viability | N/A | eFluor780 | eBioscience | 65-0865-14 |

As shown in Table 13, an increase in the percentage of CD8+ T cells in the tumour was observed at 144 hours following dosing with G1/3H3 and FS22m-063-AA/FS28-228-010 mAb$^2$, compared to the control treatment group (G1-AA/4420). The mean percentage of CD8+ T cells in the tumour increased from 32.1% (G1-AA/4420) to 56.1% with G1/3H3 and 58.4% with FS22m-063-AA/FS28m-228-010 at 144 hours post dose.

In addition, an increase in the abundance of CD8+ T cells was also observed in the blood and spleen, but only with G1/3H3 in comparison to IgG1 control. In the blood at 144 hours post dose, the mean percentage of CD8+ T cells increased from 22.6% (G1-AA/4420) to 57.0% (G1/3H3), yet this increase was not observed with FS22m-063-AA/FS28m-228-010 (25.8%). Similarly, in the spleen, the mean percentage of CD8+ T cells increased from 28.8% (G1-AA/4420) to 38.0% with G1/3H3, yet this increase was not observed with FS22m-063-AA/FS28m-228-010 (29%).

This suggests that the FS22m-063-AA/FS28m-228-010 mAb$^2$ increases CD8+ T cells specifically in the tumour, where MSLN is expressed, whereas the CD137-targeting antibody, G1/3H3, also demonstrates peripheral (blood and spleen) increases in CD8+ T cells.

To identify whether there were any differences in the proliferation of CD8+ T cells following dosing, proliferation marker, Ki67, was analysed on CD8+ T cells in tumour, blood and spleen. As shown in Table 14, a high proportion of CD8+ T cells expressed Ki67+ in the control group (mean expression of 75.1%), suggesting a high level of proliferating CD8+ T cells in the tumour in the CT26.G10 model. This may contribute to the unclear differences in Ki67 expression on CD8+ T cells between dose groups in the tumour.

In comparison, a clear increase in Ki67+ expression on CD8+ T cells in the blood and spleen was observed at 144 hours post dosing with G1/3H3 in comparison to the IgG1 control. In the blood, whereas the isotype control-treated mice show a mean Ki67+ expression on CD8+ T cells of 10.4%, the mean expression of Ki67 on CD8+ T cells following dosing with G1/3H3 is shown to be 86.3% at 144 hours post dose. In comparison, this increase was not observed with FS22m-063-AA/FS28m-228-010, where the mean Ki67+ expression on CD8+ T cells was observed at 13.1% following dosing with mAb$^2$ in the blood. Similarly, in the spleen, mean Ki67+ expression was observed on 36.1% of CD8+ T cells following dosing with G1/3H3, in comparison to 8.1% observed following dosing with isotype control and 11.4% observed with FS22m-063-AA/FS28m-228-010.

TABLE 13

The mean percentage of CD8+ T cells of total CD3+ cells in the tumour, blood and spleen at 144 hours post dosing with G1-AA/4420, G1/3H3 or FS22m-063-AA/FS28m-228-010. Data shows mean percentage CD8+ T cells of total CD3+ T cells ± standard error of the mean.

|  | G1-AA/4420 % ± SEM | G1/3H3 % ± SEM | FS22m-063-AA/FS28m-228-010 % ± SEM |
|---|---|---|---|
| Tumour | 32.1 ± 5.8 | 56.1 ± 2.8 | 58.4 ± 5.0 |
| Blood | 22.6 ± 0.6 | 57.0 ± 1.6 | 25.8 ± 0.6 |
| Spleen | 28.8 ± 0.4 | 38.0 ± 0.8 | 29.0 ± 0.9 |

TABLE 14

The mean percentage of Ki67 expressed on CD8+ T cells in the tumour, blood and spleen at 144 hours post dosing with G1-AA/4420, G1/3H3 or FS22m-063-AA/FS28m-228-010. Data shows mean percentage of Ki67+ of total CD8+ T cells ± standard error of the mean.

|  | G1-AA/4420 % ± SEM | G1/3H3 % ± SEM | FS22m-063-AA/FS28m-228-010 % ± SEM |
|---|---|---|---|
| Tumour | 75.1% ± 2.9 | 85.1% ± 2.8 | 77.6% ± 5.0 |
| Blood | 10.4% ± 1.0 | 86.3% ± 0.7 | 13.1 ± 3.4 |
| Spleen | 8.1% ± 0.3 | 36.1 ± 1.7 | 11.4% ± 1.4 |

Taken together, these data show that the mAb$^2$ containing the anti-mouse MLSN mAb FS28m-228-010, FS22m-063-AA/FS28m-228-010, mediates a tumour-specific increase in cytotoxic CD8+ T cells in the tumour. Although this is also observed with G1/3H3, this CD137-targeted agonist also promotes a peripheral increase in CD8+ T cells in the blood and spleen. Furthermore, these CD8+ T cells also show increased proliferation following dosing with G1/3H3.

SEQUENCE LISTING

Heavy chain amino acid sequence of parent clone FS28-256 showing "master" CDR2 sequence applicable to the parent clone and affinity matured clones FS28-256-001, FS28-256-005, FS28-256-012, FS28-256-014, FS28-256-018, FS28-256-021, FS28-256-023, FS28-256-024, FS28-256-026 and FS28-256-027. The "X"s double underlined represent all potential substitutions to remove a possible N-linked glycosylation. Resulting clones can either contain one or the other substitution, or both

```
Heavy chain AA (without LALA)
                                   SEQ ID NO: 1
EVQLLESGGGLVQPGGSLRLSCAASGFTFTETYMSWVRQAPGKGLEW

VSXIXPTYSTTNYADSVKGRFTISRDNSKNTLYLQMNSLRAEDTAVY

YCARYNSYQGGLDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHN
```

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPG

Heavy chain AA (with LALA)
SEQ ID NO: 2
EVQLLESGGGLVQPGGSLRLSCAASGFTGTETYMSWVRQAPGKGLEW

VSXIXPTYSTTNYADSVKGRFTISRDNSKNTLYLQMNSLRAEDTAVY

YCARYNSYQGGLDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAAG

GPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKS

LSLSPG

Master Light Chain amino acid sequence applicable to clones FS28-256-001, FS28-256-021 and FS28-256-023. The "X"s double underlined represent all potential substitutions to remove a possible deamidation site. Resulting clones can either contain one or the other substitution, or both.

Light chain
SEQ ID NO: 3
EIVLTQSPGTLSLSPGERATLSCRASQSVSSSYLAWYQQKPGQAPRL

LIYGASSRATGIPDRFSGSGSGTDFTLTISRLEPEDFAVYYC

QQHNQYPXXFGQGTKVEIKRTVAAPSVFIFPPSDEQLKSGTASVVCLL

NNFYPREAKVQWKVDNALQSGNSQESVTEQDSKDSTYSLSSTLTLSKAD

YEKHKVYACEVTHQGLSSPVTKSFNRGEC

Amino Acid and cDNA Sequences of Heavy Chain of FS28-024 mAb and its Variable Domain and Amino Acid Sequence of CDRs Heavy chain AA (without LALA)
SEQ ID NO: 4
EVQLLESGGGLVQPGGSLRLSCAASGFTLSYSSMSWVR

QAPGKGLEWVSFITPSTGYTHYADSVKGRFTISRDNSK

NTLYLQMNSLRAEDTAVYYCARRALTFDYWGQGTLVTV

SSASTKGPSVFPLAPSSKSTSGGTAALGCLVKDYFPEPVTV

SWNSGALTSGVHTFPAVLQSSGLYSLSSVVTVPSSSLGTQT

YICNVNHKPSNTKVDKKVEPKSCDKTHTCPPCPAPELLGGP

SVFLFPPKPKDTLMISRTPEVTCVVVDVSHEDPEVKFNWYV

DGVEVHNAKTKPREEQYNSTYRVVSVLTVLHQDWLNGKEYK

CKVSNKALPAPIEKTISKAKGQPREPQVYTLPPSRDELTKN

QVSLTCLVKGFYPSDIAVEWESNGQPENNYKTTPPVLDSDG

SFFLYSKLTVDKSRWQQGNVFSCSVMHEALHNHYTQKSLSL

SPG

Heavy chain DNA (without LALA)
SEQ ID NO: 6
GAAGTGCAACTGCTGGAGTCCGGTGGTGGTCTGGTACAGCC

GGGTGGTTCTCTGCGTCTGAGTTGCGCGGCCAGTGGCTTTA

CCCTCAGTTATTCTTCTATGTCATGGGTGCGTCAGGCTCCG

GGCAAAGGTCTGGAATGGGTTAGCTTTATTACTCCGTCTAC

TGGCTATACCCACTATGCGGATAGCGTGAAAGGCCGTTTTA

CCATTTCTCGCGACAACAGCAAGAACACGCTGTACCTGCAG

ATGAACTCACTGCGTGCCGAAGATACGGCCGTGTATTACTG

TGCGAGACGGGCGCTGACGTTCGACTACTGGGGCCAGGGAA

CCTTGGTCACCGTCTCGAGTGCTAGCACTAAGGGCCCGTCG

GTGTTCCCGCTGGCCCCATCGTCCAAGAGCACATCAGGGGG

TACCGCCGCCCTGGGCTGCCTTGTGAAGGATTACTTTCCCG

AGCCCGTCACAGTGTCCTGGAACAGCGGAGCCCTGACCTCC

GGAGTGCATACTTTCCCGGCTGTGCTTCAGTCCTCTGGCCT

GTACTCATTGTCCTCCGTGGTCACCGTCCCTTCGTCCTCCC

TGGGCACCCAGACCTATATCTGTAATGTCAACCATAAGCCC

TCGAACACCAAGGTCGACAAGAAGGTCGAGCCGAAGTCGTG

CGACAAGACTCACACTTGCCCGCCTTGCCCAGCCCCGGAAC

TGCTGGGTGGTCCTTCGGTGTTCCTCTTCCCGCCCAAGCCG

AAGGATACCCTGATGATCTCACGGACCCCCGAAGTGACCTG

TGTGGTGGTGGACGTGTCCCACGAGGACCCGGAAGTGAAAT

TCAATTGGTACGTGGATGGAGTGGAAGTGCACAACGCCAAG

ACCAAGCCACGGGAAGAACAGTACAACTCTACCTACCGCGT

GGTGTCCGTGCTCACTGTGCTGCACCAAGACTGGCTGAACG

GGAAGGAGTACAAGTGCAAAGTGTCCAACAAGGCGCTGCCT

GCCCCAATTGAGAAAACTATCTCGAAAGCCAAGGGACAGCC

TCGAGAGCCTCAAGTGTACACCCTGCCTCCCTCTCGGGACG

AGCTGACCAAGAACCAAGTCTCCCTGACCTGTCTGGTCAAG

GGATTCTACCCATCGGATATCGCCGTGGAATGGGAAAGCAA

CGGACAGCCCGAGAACAACTACAAGACGACTCCGCCCGTGC

TGGATTCCGACGGGAGCTTCTTCTTGTACTCCAAGCTGACC

GTCGACAAGAGCAGATGGCAGCAGGGAAACGTGTTCTCCTG

CTCCGTGATGCATGAGGCGCTGCACAACCACTACACTCAGA

AGAGCTTGTCCCTGTCGCCCGGA

Heavy chain AA (with LALA)
SEQ ID NO: 5
EVQLLESGGGLVQPGGSLRLSCAASGFTLSYSSMSWVR

QAPGKGLEWVSFITPSTGYTHYADSVKGRFTISRDNSKN

-continued

TLYLQMNSLRAEDTAVYYCARRALTFDYWGQGTLVTVS
SASTKGPSVFPLAPSSKS TSGGTAALGCLVKDYFPEPVTV
SWNSGALTSGVHTFPAVLQSSGLYSLSSVVTVPSSSLGTQT
YICNVNHKPSNTKVDKKVEPKSCDKTHTCPPCPAPEAA
GGPSVFLFPPKPKDTLMISRTPEVTCVVVDVSH EDPEVKF
NWYVDGVEVHNAKTKPREEQYNSTYRVVSVLTVLHQDWLNG
KEYKCKVSNKALPAPIEKTISKAKGQPREPQVYTLPPSRDE
LTKNQVSLTCLVKGFYPSDIAVEWESNGQPENNYKTTPPVL
DSDGSFFLYSKLTVDKSRWQQGNVFSCSVMHEALHNHYTQK
SLSLSPG

Heavy chain DNA (with LALA)
SEQ ID NO: 7
GAAGTGCAACTGCTGGAGTCCGGTGGTGGTCTGGTACAGCC
GGGTGGTTCTCTGCGTCTGAGTTGCGCGGCCAGTGGCTTTA
CCCTCAGTTATTCTTCTATGTCATGGGTGCGTCAGGCTCCG
GGCAAAGGTCTGGAATGGGTTAGCTTTATTACTCCGTCTAC
TGGCTATACCCACTATGCGGATAGCGTGAAAGGCCGTTTTA
CCATTTCTCGCGACAACAGCAAGAACACGCTGTACCTGCAG
ATGAACTCACTGCGTGCCGAAGATACGGCCGTGTATTACTG
TGCGAGACGGGCGCTGACGTTCGACTACGGGGCCAGGGAA
CCTTGGTCACCGTCTCGAGTGCTAGCACTAAGGGCCCGTCG
GTGTTCCCGCTGGCCCCATCGTCCAAGAGCACATCAGGGGG
TACCGCCGCCCTGGGCTGCCTTGTGAAGGATTACTTTCCCG
AGCCCGTCACAGTGTCCTGGAACAGCGGAGCCCTGACCTCC
GGAGTGCATACTTTCCCGGCTGTGCTTCAGTCCTCTGGCCT
GTACTCATTGTCCTCCGTGGTCACCGTCCCTTCGTCCTCCC
TGGGCACCCAGACCTATATCTGTAATGTCAACCATAAGCCC
TCGAACACCAAGGTCGACAAGAAGGTCGAGCCGAAGTCGTG
CGACAAGACTCACACTTGCCCGCCTTGCCCAGCCCCGGAAG
CTGCCGGTGGTCCTTCGGTGTTCCTCTTCCCGCCCAAGCCG
AAGGATACCCTGATGATCTCACGGACCCCCGAAGTGACCTG
TGTGGTGGTGGACGTGTCCCACGAGGACCCGGAAGTGAAAT
TCAATTGGTACGTGGATGGAGTGGAAGTGCACAACGCCAAG
ACCAAGCCACGGGAAGAACAGTACAACTCTACCTACCGCGT
GGTGTCCGTGCTCACTGTGCTGCACCAAGACTGGCTGAACG
GGAAGGAGTACAAGTGCAAAGTGTCCAACAAGGCGCTGCCT
GCCCCAATTGAGAAAACTATCTCGAAAGCCAAGGGACAGCC
TCGAGAGCCTCAAGTGTACACCCTGCCTCCCTCTCGGGACG
AGCTGACCAAGAACCAAGTCTCCCTGACCTGTCTGGTCAAG
GGATTCTACCCATCGGATATCGCCGTGGAATGGGAAAGCAA
CGGACAGCCCGAGAACAACTACAAGACGACTCCGCCCGTGC
TGGATTCCGACGGGAGCTTCTTCTTGTACTCCAAGCTGACC GTCGACAAGAGCAGATGGCAGCAGGGAAACGTGTTCTCCTG
CTCCGTGATGCATGAGGCGCTGCACAACCACTACACTCAGA
AGAGCTTGTCCCTGTCGCCCGGA Variable domain AA
SEQ ID NO: 8
EVQLLESGGGLVQPGGSLRLSCAASGFTLSYSSMSWVR
QAPGKGLEWVSFITPSTGYTHYADSVKGRFTISRDNSK
NTLYLQMNSLRAEDTAVYYCARRALTFDYWGQGTLVTV
SS Variable domain DNA
SEQ ID NO: 9
GAAGTGCAACTGCTGGAGTCCGGTGGTGGTCTGGTACAGCC
GGGTGGTTCTCTGCGTCTGAGTTGCGCGGCCAGTGGCTTTA
CCCTCAGTTATTCTTCTATGTCATGGGTGCGTCAGGCTCCG
GGCAAAGGTCTGGAATGGGTTAGCTTTATTACTCCGTCTAC
TGGCTATACCCACTATGCGGATAGCGTGAAAGGCCGTTTTA
CCATTTCTCGCGACAACAGCAAGAACACGCTGTACCTGCAG
ATGAACTCACTGCGTGCCGAAGATACGGCCGTGTATTACTG
TGCGAGACGGGCGCTGACGTTCGACTACGGGGCCAGGGAA
CCTTGGTCACCGTCTCGAGT

CDR1 (AA) (IMGT)
SEQ ID NO: 10
GFTLSYSS

CDR1 (AA) (Kabat)
SEQ ID NO: 13
YSSMS

CDR2 (AA) (IMGT)
SEQ ID NO: 11
ITPSTGYT

CDR2 (AA) Kabat)
SEQ ID NO: 14
FITPSTGYTHYADSVKG

CDR3 (AA) (IMGT)
SEQ ID NO: 12
ARRALTFDY

CDR3 (AA) (Kabat)
SEQ ID NO: 15
RALTFDY

Amino Acid and cDNA Sequences of Light Chain of FS28-024 mAb and its Variable Domain and Amino Acid Sequence of CDRs Light chain AA
SEQ ID NO: 16
EIVLTQSPGTLSLSPGERATLSCRASQSVSSSYLAWYQQKPGQAPR
LLIYGASSRATGIPDRFSGSGSGTDFTLTISRLEPEDFAVYYC
FGQGTKVEIKRTVAAPSVFIFPPSDEQLKSGTASVVCL
LNNFYPREAKVQWKVDNALQSGNSQESVTEQDSKDSTYSLSSTLTLSKA
DYEKHKVYACEVTHQGLSSPVTKSFNRGEC -continued Light chain DNA
SEQ ID NO: 17
GAAATTGTGCTGACCCAGTCTCCGGGCACGTTATCTCTGAGCCCTGGTG
AGCGCGCCACTCTGTCATGCCGGGCTTCTCAAAGTGTTAGCAGTAGCTA
CCTGGCGTGGTATCAGCAAAAACCGGGCCAGGCCCCGCGTCTGCTGATT
TACGGTGCATCCAGCCGTGCCACCGGCATTCCAGATCGTTTTTCCGGTA
GTGGTTCTGGGACGGACTTCACTCTGACAATCTCACGCCTGGAACCGGA
GGATTTTGCGGTGTATTACTGCCAGCAAGCTTCTTCTTATCCTCTCACG
TTCGGCCAAGGGACCAAGGTGGAAATCAAACGTACTGTGGCCGCTCCTA
GCGTGTTCATTTTTCCGCCATCCGACGAGCAGCTCAAGTCCGGCACCGC
CTCCGTGGTCTGCCTGCTCAACAACTTCTACCCTCGCGAAGCTAAGGTC
CAGTGGAAGGTCGACAATGCCCTGCAGTCCGGAAACTCGCAGGAAAGCG
TGACTGAACAGGACTCCAAGGACTCCACCTATTCACTGTCCTCGACTCT
GACCCTGAGCAAGGCGGATTACGAAAAGCACAAAGTGTACGCATGCGAA
GTGACCCACCAGGGTCTTTCGTCCCCCGTGACCAAGAGCTTCAACAGAG
GAGAGTGT Variable domain AA
SEQ ID NO: 18
EIVLTQSPGTLSLSPGERATLSCRASQSVSSSYLAWYQQKPGQAPR
LLIYGASSRATGIPDRFSGSGSGTDFTLTISRLEPEDFAVYYC
QQASSYPLTFGQGTKVEIK Variable domain DNA
SEQ ID NO: 19
GAAATTGTGCTGACCCAGTCTCCGGGCACGTTATCTCTGAGCCCTGGTG
AGCGCGCCACTCTGTCATGCCGGGCTTCTCAAAGTGTTAGCAGTAGCTA
CCTGGCGTGGTATCAGCAAAAACCGGGCCAGGCCCCGCGTCTGCTGATT
TACGGTGCATCCAGCCGTGCCACCGGCATTCCAGATCGTTTTTCCGGTA
GTGGTTCTGGGACGGACTTCACTCTGACAATCTCACGCCTGGAACCGGA
GGATTTTGCGGTGTATTACTGCCAGCAAGCTTCTTCTTATCCTCTCACG
TTCGGCCAAGGGACCAAGGTGGAAATCAAA

CDR1 (AA) (IMGT)
SEQ ID NO: 20
QSVSSSY

CDR1 (AA) (Kabat)
SEQ ID NO: 23
RASQSVSSSYLA

CDR2 (AA) (IMGT)
SEQ ID NO: 21
GAS

CDR2 (AA) (Kabat)
SEQ ID NO: 24
GASSRAT

CDR3 (AA) (IMGT)
SEQ ID NO: 22
QQASSYPLT

CDR3 (AA) (Kabat)
SEQ ID NO: 22
QQASSYPLT

Amino Acid and cDNA Sequences of Heavy Chain of FS28-024-051 mAb and its Variable Domain and Amino Acid Sequence of CDRs Heavy chain AA (without LALA)
SEQ ID NO: 26
EVQLLESGGGLVQPGGSLRLSCAASGFTLSYSSMSWVRQAPGKGLEW
VSFITPSTGYTHYADSVKGRFTISRDNSKNTLYLQMNSLRAEDTAVY
YCARRALIFDYWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPG Heavy chain DNA (without LALA)
SEQ ID NO: 27
GAAGTGCAACTGCTGGAGTCCGGTGGTGGTCTGGTACAGCCGGGTGGTT
CTCTGCGTCTGAGTTGCGCGGCCAGTGGCTTTACCCTCAGTTATTCTTC
TATGTCATGGGTGCGTCAGGCTCCGGGCAAAGGTCTGGAATGGGTTAGC
TTTATTACTCCGTCTACTGGCTATACCCACTATGCGGATAGCGTGAAAG
GCCGTTTTACCATTTCTCGCGACAACAGCAAGAACACGCTGTACCTGCA
GATGAACTCACTGCGTGCCGAAGATACGGCCGTGTATTACTGTGCGAGA
CGGGCGCTGATTTTCGACTACTGGGGCCAGGGAACCCTGGTCACCGTCT
CGAGTGCTAGCACTAAGGGCCCGTCGGTGTTCCCGCTGGCCCCATCGTC
CAAGAGCACATCAGGGGGTACCGCCGCCCTGGGCTGCCTTGTGAAGGAT
TACTTTCCCGAGCCCGTCACAGTGTCCTGGAACAGCGGAGCCCTGACCT
CCGGAGTGCATACTTTCCCGGCTGTGCTTCAGTCCTCTGGCCTGTACTC
ATTGTCCTCCGTGGTCACCGTCCCTTCGTCCTCCCTGGGCACCCAGACC
TATATCTGTAATGTCAACCATAAGCCCTCGAACACCAAGGTCGACAAGA
AGGTCGAGCCGAAGTCGTGCGACAAGACTCACACTTGCCCGCCTTGCCC
AGCCCCGGAACTGCTGGGTGGTCCTTCGGTGTTCCTCTTCCCGCCCAAG
CCGAAGGATACCCTGATGATCTCACGGACCCCCGAAGTGACCTGTGTGG
TGGTGGACGTGTCCCACGAGGACCCGGAAGTGAAATTCAATTGGTACGT
GGATGGAGTGGAAGTGCACAACGCCAAGACCAAGCCACGGGAAGAACAG
TACAACTCTACCTACCGCGTGGTGTCCGTGCTCACTGTGCTGCACCAAG
ACTGGCTGAACGGGAAGGAGTACAAGTGCAAAGTGTCCAACAAGGCGCT
GCCTGCCCCAATTGAGAAAACTATCTCGAAAGCCAAGGGACAGCCTCGA
GAGCCTCAAGTGTACACCCTGCCTCCCTCTCGGGACGAGCTGACCAAGA
ACCAAGTCTCCCTGACCTGTCTGGTCAAGGGATTCTACCCATCGGATAT
CGCCGTGGAATGGGAAAGCAACGGACAGCCCGAGAACAACTACAAGACG
ACTCCGCCCGTGCTGGATTCCGACGGGAGCTTCTTCTTGTACTCCAAGC
TGACCGTCGACAAGAGCAGATGGCAGCAGGGAAACGTGTTCTCCTGCTC

```
CGTGATGCATGAGGCGCTGCACAACCACTACACTCAGAAGAGCTTGTCC

CTGTCGCCCGGA
```

Heavy chain AA (with LALA)

SEQ ID NO: 28

```
EVQLLESGGGLVQPGGSLRLSCAASGFTLSYSSMSWVRQAPGKGLEW
VSFITPSTGYTHYADSVKGRFTISRDNSKNTLYLQMNSLRAEDTAV
YYCARRALIFDYWGQGTLVTVSSASTKGPSVFPLAPSSKSTSGGTA
ALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPEAA
GGPSVFLFPPKPKDTLMISRTPEVTCVVVDVSH EDPEVKFNWYVDGVE
VHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHE
ALHNHYTQKSLSLSPG
```

Heavy chain DNA (with LALA)

SEQ ID NO: 29

```
GAAGTGCAACTGCTGGAGTCCGGTGGTGGTCTGGTACAGCCGGGTGGTT
CTCTGCGTCTGAGTTGCGCGGCCAGTGGCTTTACCCTCAGTTATTCTTC
TATGTCATGGGTGCGTCAGGCTCCGGGCAAAGGTCTGGAATGGGTTAGC
TTTATTACTCCGTCTACTGGCTATACCCACTATGCGGATAGCGTGAAAG
GCCGTTTTACCATTTCTCGCGACAACAGCAAGAACACGCTGTACCTGCA
GATGAACTCACTGCGTGCCGAAGATACGGCCGTGTATTACTGTGCGAGA
CGGGCGCTGATTTTCGACTACTGGGGCCAGGGAACCCTGGTCACCGTCT
CGAGTGCTAGCACTAAGGGCCCGTCGGTGTTCCCGCTGGCCCCATCGTC
CAAGAGCACATCAGGGGGTACCGCCGCCCTGGGCTGCCTTGTGAAGGAT
TACTTTCCCGAGCCCGTCACAGTGTCCTGGAACAGCGGAGCCCTGACCT
CCGGAGTGCATACTTTCCCGGCTGTGCTTCAGTCCTCTGGCCTGTACTC
ATTGTCCTCCGTGGTCACCGTCCCTTCGTCCTCCCTGGGCACCCAGACC
TATATCTGTAATGTCAACCATAAGCCCTCGAACACCAAGGTCGACAAGA
AGGTCGAGCCGAAGTCGTGCGACAAGACTCACACTTGCCCGCCTTGCC
AGCCCCGGAAGCTGCCGGTGGTCCTTCGGTGTTCCTCTTCCCGCCCAAG
CCGAAGGATACCCTGATGATCTCACGGACCCCCGAAGTGACCTGTGTGG
TGGTGGACGTGTCCCACGAGGACCCGGAAGTGAAATTCAATTGGTACGT
GGATGGAGTGGAAGTGCACAACGCCAAGACCAAGCCACGGGAAGAACAG
TACAACTCTACCTACCGCGTGGTGTCCGTGCTCACTGTGCTGCACCAAG
ACTGGCTGAACGGGAAGGAGTACAAGTGCAAAGTGTCCAACAAGGCGCT
GCCTGCCCCAATTGAGAAAACTATCTCGAAAGCCAAGGGACAGCCTCGA
GAGCCTCAAGTGTACACCCTGCCTCCCTCTCGGGACGAGCTGACCAAGA
ACCAAGTCTCCCTGACCTGTCTGGTCAAGGGATTCTACCCATCGGATAT
CGCCGTGGAATGGGAAAGCAACGGACAGCCCGAGAACAACTACAAGACG
ACTCCGCCCGTGCTGGATTCCGACGGGAGCTTCTTCTTGTACTCCAAGC
TGACCGTCGACAAGAGCAGATGGCAGCAGGGAAACGTGTTCTCCTGCTC
CGTGATGCATGAGGCGCTGCACAACCACTACACTCAGAAGAGCTTGTCC
CTGTCGCCCGGA
```

Variable domain AA

SEQ ID NO: 30

```
EVQLLESGGGLVQPGGSLRLSCAASGFTLSYSSMSWVRQAPGKGLE
WVSFITPSTGYTHYADSVKGRFTISRDNSKNTLYLQMNSLRAEDT
AVYYCARRALIFDYWGQGTLVTVSS
```

Variable domain DNA

SEQ ID NO: 31

```
GAAGTGCAACTGCTGGAGTCCGGTGGTGGTCTGGTACAGCCGGGTGGTT
CTCTGCGTCTGAGTTGCGCGGCCAGTGGCTTTACCCTCAGTTATTCTTC
TATGTCATGGGTGCGTCAGGCTCCGGGCAAAGGTCTGGAATGGGTTAGC
TTTATTACTCCGTCTACTGGCTATACCCACTATGCGGATAGCGTGAAAG
GCCGTTTTACCATTTCTCGCGACAACAGCAAGAACACGCTGTACCTGCA
GATGAACTCACTGCGTGCCGAAGATACGGCCGTGTATTACTGTGCGAGA
CGGGCGCTGATTTTCGACTACTGGGGCCAGGGAACCCTGGTCACCGTCT
CGAGT
```

CDR1 (AA) (IMGT)

SEQ ID NO: 10

GFTLSYSS

CDR1 (AA) (Kabat)

SEQ ID NO: 13

*YSSMS*

CDR2 (AA) (IMGT)

SEQ ID NO: 11

ITPSTGYT

CDR2 (AA) Kabat

SEQ ID NO: 14

*FITPSTGYTHYADSVKG*

CDR3 (AA) (IMGT)

SEQ ID NO: 32

ARRALIFDY

CDR3 (AA) (Kabat)

SEQ ID NO: 33

*RALIFDY*

Amino Acid and cDNA Sequences of Light Chain of FS28-024-051 mAb and its Variable Domain and Amino Acid Sequence of CDRs Light chain AA

SEQ ID NO: 16

```
EIVLTQSPGTLSLSPGERATLSCRASQSVSSSYLAWYQQKPGQAPR
LLIYGASSRATGIPDRFSGSGSGTDFTLTISRLEPEDFAVYYC
QQASSYPLTFGQGTKVEIKRTVAAPSVFIFPPSDEQLKSGTASVVCL
LNNFYPREAKVQWKVDNALQSGNSQESVTEQDSKDSTYSLSSTLTLSKA
DYEKHKVYACEVTHQGLSSPVTKSFNRGEC
```

Light chain DNA

SEQ ID NO: 17

```
GAAATTGTGCTGACCCAGTCTCCGGGCACGTTATCTCTGAGCCCTGGTG
AGCGCGCCACTCTGTCATGCCGGGCTTCTCAAAGTGTTAGCAGTAGCTA
```

-continued
CCTGGCGTGGTATCAGCAAAAACCGGGCCAGGCCCCGCGTCTGCTGATT
TACGGTGCATCCAGCCGTGCCACCGGCATTCCAGATCGTTTTTCCGGTA
GTGGTTCTGGGACGGACTTCACTCTGACAATCTCACGCCTGGAACCGGA
GGATTTTGCGGTGTATTACTGCCAGCAAGCTTCTTCTTATCCTCTCACG
TTCGGCCAAGGGACCAAGGTGGAAATCAAACGTACTGTGGCCGCTCCTA
GCGTGTTCATTTTTCCGCCATCCGACGAGCAGCTCAAGTCCGGCACCGC
CTCCGTGGTCTGCCTGCTCAACAACTTCTACCCTCGCGAAGCTAAGGTC
CAGTGGAAGGTCGACAATGCCCTGCAGTCCGGAAACTCGCAGGAAAGCG
TGACTGAACAGGACTCCAAGGACTCCACCTATTCACTGTCCTCGACTCT
GACCCTGAGCAAGGCGGATTACGAAAAGCACAAAGTGTACGCATGCGAA
GTGACCCACCAGGGTCTTTCGTCCCCGTGACCAAGAGCTTCAACAGAG
GAGAGTGT Variable domain AA
SEQ ID NO: 18
EIVLTQSPGTLSLSPGERATLSCRASQSVSSSYLAWYQQKPGQAPR
LLIYGASSRATGIPDRFSGSGSGTDFTLTISRLEPEDFAVYYC
QQASSYPLTFGQGTKVEIK Variable domain DNA
SEQ ID NO: 19
GAAATTGTGCTGACCCAGTCTCCGGGCACGTTATCTCTGAGCCCTGGTG
AGCGCGCCACTCTGTCATGCCGGGCTTCTCAAAGTGTTAGCAGTAGCTA
CCTGGCGTGGTATCAGCAAAAACCGGGCCAGGCCCCGCGTCTGCTGATT
TACGGTGCATCCAGCCGTGCCACCGGCATTCCAGATCGTTTTTCCGGTA
GTGGTTCTGGGACGGACTTCACTCTGACAATCTCACGCCTGGAACCGGA
GGATTTTGCGGTGTATTACTGCCAGCAAGCTTCTTCTTATCCTCTCACG
TTCGGCCAAGGGACCAAGGTGGAAATCAAA

CDR1 (AA) (IMGT)
SEQ ID NO: 20
QSVSSSY

CDR1 (AA) (Kabat)
SEQ ID NO: 23
RASQSVSSSYLA

CDR2 (AA) (IMGT)
SEQ ID NO: 21
GAS

CDR2 (AA) (Kabat)
SEQ ID NO: 24
GASSRAT

CDR3 (AA) (IMGT)
SEQ ID NO: 22
QQASSYPLT

CDR3 (AA) (Kabat)
SEQ ID NO: 22
QQASSYPLT

Amino Acid and cDNA Sequences of Heavy Chain of FS28-024-052 mAb and its Variable Domain and Amino Acid Sequence of CDRs Heavy chain AA (without LALA)
SEQ ID NO: 35
EVQLLESGGGLVQPGGSLRLSCAASGFTLSYSSMSWVRQAPGKGLE
WVSFITPSTGYTHYADSVKGRFTISRDNSKNTLYLQMNSLRAEDTA
VYYCARRALIFDYWGQGTLVTVSSASTKGPSVFPLAPSSKSTSGGT
AALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALH
NHYTQKSLSLSPG Heavy chain DNA (without LALA)
SEQ ID NO: 36
GAAGTGCAACTGCTGGAGTCCGGTGGTGGTCTGGTACAGCCGGGTGGTT
CTCTGCGTCTGAGTTGCGCGGCCAGTGGCTTTACCCTCAGTTATTCTTC
TATGTCATGGGTGCGTCAGGCTCCGGGCAAAGGTCTGGAATGGGTTAGC
TTTATTACTCCGTCTACTGGCTATACCCACTATGCGGATAGCGTGAAAG
GCCGTTTTACCATTTCTCGCGACAACAGCAAGAACACGCTGTACCTGCA
GATGAACTCACTGCGTGCCGAAGATACGGCCGTGTATTACTGTGCGAGA
CGGGCGCTGCTTTTCGACTACTGGGGCCAGGGAACCCTGGTCACCGTCT
CGTCGGCTAGCACTAAGGGCCCGTCGGTGTTCCCGCTGGCCCCATCGTC
CAAGAGCACATCAGGGGGTACCGCCGCCCTGGGCTGCCTTGTGAAGGAT
TACTTTCCCGAGCCCGTCACAGTGTCCTGGAACAGCGGAGCCCTGACCT
CCGGAGTGCATACTTTCCCGGCTGTGCTTCAGTCCTCTGGCCTGTACTC
ATTGTCCTCCGTGGTCACCGTCCCTTCGTCCTCCCTGGGCACCCAGACC
TATATCTGTAATGTCAACCATAAGCCCTCGAACACCAAGGTCGACAAGA
AGGTCGAGCCGAAGTCGTGCGACAAGACTCACACTTGCCCGCCTTGCCC
AGCCCCGGAACTGCTGGGTGGTCCTTCGGTGTTCCTCTTCCCGCCCAAG
CCGAAGGATACCCTGATGATCTCACGGACCCCCGAAGTGACCTGTGTGG
TGGTGGACGTGTCCCACGAGGACCCGGAAGTGAAATTCAATTGGTACGT
GGATGGAGTGGAAGTGCACAACGCCAAGACCAAGCCACGGGAAGAACAG
TACAACTCTACCTACCGCGTGGTGTCCGTGCTCACTGTGCTGCACCAAG
ACTGGCTGAACGGGAAGGAGTACAAGTGCAAAGTGTCCAACAAGGCGCT
GCCTGCCCCAATTGAGAAAACTATCTCGAAAGCCAAGGGACAGCCTCGA
GAGCCTCAAGTGTACACCCTGCCTCCCTCTCGGGACGAGCTGACCAAGA
ACCAAGTCTCCCTGACCTGTCTGGTCAAGGGATTCTACCCATCGGATAT
CGCCGTGGAATGGGAAAGCAACGGACAGCCCGAGAACAACTACAAGACG
ACTCCGCCCGTGCTGGATTCCGACGGGAGCTTCTTCTTGTACTCCAAGC
TGACCGTCGACAAGAGCAGATGGCAGCAGGGAAACGTGTTCTCCTGCTC

```
CGTGATGCATGAGGCGCTGCACAACCACTACACTCAGAAGAGCTTGTCC

CTGTCGCCCGGA
```

Heavy chain AA (with LALA)

SEQ ID NO: 37

EVQLLESGGGLVQPGGSLRLSCAASGFTLSYSSMSWVRQAPGKGLE

WVSFITPSTGYTHYADSVKGRFTISRDNSKNTLYLQMNSLRAEDTA

VYYCARRALLFDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAA

GGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEA

LHNHYTQKSLSLSPG

Heavy chain DNA (with LALA)

SEQ ID NO: 38

```
GAAGTGCAACTGCTGGAGTCCGGTGGTGGTCTGGTACAGCCGGGTGGTT

CTCTGCGTCTGAGTTGCGCGGCCAGTGGCTTTACCCTCAGTTATTCTTC

TATGTCATGGGTGCGTCAGGCTCCGGGCAAAGGTCTGGAATGGGTTAGC

TTTATTACTCCGTCTACTGGCTATACCCACTATGCGGATAGCGTGAAAG

GCCGTTTTACCATTTCTCGCGACAACAGCAAGAACACGCTGTACCTGCA

GATGAACTCACTGCGTGCCGAAGATACGGCCGTGTATTACTGTGCGAGA

CGGGCGCTGCTTTTCGACTACTGGGGCCAGGGAACCCTGGTCACCGTCT

CGTCGGCTAGCACTAAGGGCCCGTCGGTGTTCCCGCTGGCCCCATCGTC

CAAGAGCACATCAGGGGGTACCGCCGCCCTGGGCTGCCTTGTGAAGGAT

TACTTTCCCGAGCCCGTCACAGTGTCCTGGAACAGCGGAGCCCTGACCT

CCGGAGTGCATACTTTCCCGGCTGTGCTTCAGTCCTCTGGCCTGTACTC

ATTGTCCTCCGTGGTCACCGTCCCTTCGTCCTCCCTGGGCACCCAGACC

TATATCTGTAATGTCAACCATAAGCCCTCGAACACCAAGGTCGACAAGA

AGGTCGAGCCGAAGTCGTGCGACAAGACTCACACTTGCCCGCCTTGCCC

AGCCCCGGAAGCTGCCGGTGGTCCTTCGGTGTTCCTCTTCCCGCCCAAG

CCGAAGGATACCCTGATGATCTCACGGACCCCCGAAGTGACCTGTGTGG

TGGTGGACGTGTCCCACGAGGACCCGGAAGTGAAATTCAATTGGTACGT

GGATGGAGTGGAAGTGCACAACGCCAAGACCAAGCCACGGGAAGAACAG

TACAACTCTACCTACCGCGTGGTGTCCGTGCTCACTGTGCTGCACCAAG

ACTGGCTGAACGGGAAGGAGTACAAGTGCAAAGTGTCCAACAAGGCGCT

GCCTGCCCCAATTGAGAAAACTATCTCGAAAGCCAAGGGACAGCCTCGA

GAGCCTCAAGTGTACACCCTGCCTCCCTCTCGGGACGAGCTGACCAAGA

ACCAAGTCTCCCTGACCTGTCTGGTCAAGGGATTCTACCCATCGGATAT

CGCCGTGGAATGGGAAAGCAACGGACAGCCCGAGAACAACTACAAGACG

ACTCCGCCCGTGCTGGATTCCGACGGGAGCTTCTTCTTGTACTCCAAGC

TGACCGTCGACAAGAGCAGATGGCAGCAGGGAAACGTGTTCTCCTGCTC

CGTGATGCATGAGGCGCTGCACAACCACTACACTCAGAAGAGCTTGTCC

CTGTCGCCCGGA
```

Variable domain AA

SEQ ID NO: 39

EVQLLESGGGLVQPGGSLRLSCAASGFTLSYSSMSWVRQAPGKGLE

WVSFITPSTGYTHYADSVKGRFTISRDNSKNTLYLQMNSLRAEDTA

VYYCARRALLFDYWGQGTLVTVSS

Variable domain DNA

SEQ ID NO: 40

```
GAAGTGCAACTGCTGGAGTCCGGTGGTGGTCTGGTACAGCCGGGTGGTT

CTCTGCGTCTGAGTTGCGCGGCCAGTGGCTTTACCCTCAGTTATTCTTC

TATGTCATGGGTGCGTCAGGCTCCGGGCAAAGGTCTGGAATGGGTTAGC

TTTATTACTCCGTCTACTGGCTATACCCACTATGCGGATAGCGTGAAAG

GCCGTTTTACCATTTCTCGCGACAACAGCAAGAACACGCTGTACCTGCA

GATGAACTCACTGCGTGCCGAAGATACGGCCGTGTATTACTGTGCGAGA

CGGGCGCTGCTTTTCGACTACTGGGGCCAGGGAACCCTGGTCACCGTCT

CGTCG
```

CDR1 (AA) (IMGT)

SEQ ID NO: 10

GFTLSYSS

CDR1 (AA) (Kabat)

SEQ ID NO: 13

YSSMS

CDR2 (AA) (IMGT)

SEQ ID NO: 11

ITPSTGYT

CDR2 (AA) Kabat)

SEQ ID NO: 14

FITPSTGYTHYADSVKG

CDR3 (AA) (IMGT)

SEQ ID NO: 41

ARRALLFDY

CDR3 (AA) (Kabat)

SEQ ID NO: 42

RALLFDY

Amino Acid and cDNA Sequences of Light Chain of FS28-024-052 mAb and its Variable Domain and Amino Acid Sequence of CDRs Light chain AA

SEQ ID NO: 16

EIVLTQSPGTLSLSPGERATLSCRASQSVSSSYLAWYQQKPGQAPRL

LIYGASSRATGIPDRFSGSGSGTDFTLTISRLEPEDFAVYYC

QQASSYPLTFGQGTKVEIKRTVAAPSVFIFPPSDEQLKSGTASVVCL

LNNFYPREAKVQWKVDNALQSGNSQESVTEQDSKDSTYSLSSTLTLSKA

DYEKHKVYACEVTHQGLSSPVTKSFNRGEC

Light chain DNA

SEQ ID NO: 17

```
AAATTGTGCTGACCCAGTCTCCGGGCACGTTATCTCTGAGCCCTGGTGA

GCGCGCCACTCTGTCATGCCGGGCTTCTCAAAGTGTTAGCAGTAGCTAC
```

-continued
CTGGCGTGGTATCAGCAAAAACCGGGCCAGGCCCCGCGTCTGCTGATTT

ACGGTGCATCCAGCCGTGCCACCGGCATTCCAGATCGTTTTTCCGGTAG

TGGTTCTGGGACGGACTTCACTCTGACAATCTCACGCCTGGAACCGGAG

GATTTTGCGGTGTATTACTGCCAGCAAGCTTCTTCTTATCCTCTCACGT

TCGGCCAAGGGACCAAGGTGGAAATCAAACGTACTGTGGCCGCTCCTAG

CGTGTTCATTTTTCCGCCATCCGACGAGCAGCTCAAGTCCGGCACCGCC

TCCGTGGTCTGCCTGCTCAACAACTTCTACCCTCGCGAAGCTAAGGTCC

AGTGGAAGGTCGACAATGCCCTGCAGTCCGGAAACTCGCAGGAAAGCGT

GACTGAACAGGACTCCAAGGACTCCACCTATTCACTGTCCTCGACTCTG

ACCCTGAGCAAGGCGGATTACGAAAAGCACAAAGTGTACGCATGCGAAG

TGACCCACCAGGGTCTTTCGTCCCCGTGACCAAGAGCTTCAACAGAGG

AGAGTGT

Variable domain AA

SEQ ID NO: 18
EIVLTQSPGTLSLSPGERATLSCRASQSVSSSYLAWYQQKPGQAPRL
LIYGASSRATGIPDRFSGSGSGTDFTLTISRLEPEDFAVYYC
QQASSYPLTFGQGTKVEIK

Variable domain DNA

SEQ ID NO: 19
GAAATTGTGCTGACCCAGTCTCCGGGCACGTTATCTCTGAGCCCTGGTG

AGCGCGCCACTCTGTCATGCCGGGCTTCTCAAAGTGTTAGCAGTAGCTA

CCTGGCGTGGTATCAGCAAAAACCGGGCCAGGCCCCGCGTCTGCTGATT

TACGGTGCATCCAGCCGTGCCACCGGCATTCCAGATCGTTTTTCCGGTA

GTGGTTCTGGGACGGACTTCACTCTGACAATCTCACGCCTGGAACCGGA

GGATTTTGCGGTGTATTACTGCCAGCAAGCTTCTTCTTATCCTCTCACG

TTCGGCCAAGGGACCAAGGTGGAAATCAAA

CDR1 (AA) (IMGT)

SEQ ID NO: 20
QSVSSSY

CDR1 (AA) (Kabat)

SEQ ID NO: 23
RASQSVSSSYLA

CDR2 (AA) (IMGT)

SEQ ID NO: 21
GAS

CDR2 (AA) (Kabat)

SEQ ID NO: 24
GASSRAT

CDR3 (AA) (IMGT)

SEQ ID NO: 22
QQASSYPLT

CDR3 (AA) (Kabat)

SEQ ID NO: 22
QQASSYPLT

Amino Acid and cDNA Sequences of Heavy Chain of FS28-024-053 mAb and its Variable Domain and Amino Acid Sequence of CDRs Heavy chain AA (without LALA)

SEQ ID NO: 45
EVQLLESGGGLVQPGGSLRLSCAASGFTLSYSSMSWVRQAPGKGL
EWVSFITPSTGYTHYADSVKGRFTISRDNSKNTLYLQMNSLRAED
TAVYYCARRALLFDYWGQGTLVTVSSASTKGPSVFPLAPSSKSTS
GGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHE
ALHNHYTQKSLSLSPG

Heavy chain DNA (without LALA)

SEQ ID NO: 46
GAAGTGCAACTGCTGGAGTCCGGTGGTGGTCTGGTACAGCCGGGTGGTT

CTCTGCGTCTGAGTTGCGCGGCCAGTGGCTTTACCCTCAGTTATTCTTC

TATGTCATGGGTGCGTCAGGCTCCGGGCAAAGGTCTGGAATGGGTTAGC

TTTATTACTCCGTCTACTGGCTATACCCACTATGCGGATAGCGTGAAAG

GCCGTTTTACCATTTCTCGCGACAACAGCAAGAACACGCTGTACCTGCA

GATGAACTCACTGCGTGCCGAAGATACGGCCGTGTATTACTGTGCGAGA

CGGGCGCTGGTGTTCGACTACTGGGGCCAGGGAACCCTGGTCACCGTCT

CGTCGGCTAGCACTAAGGGCCCGTCGGTGTTCCCGCTGGCCCCATCGTC

CAAGAGCACATCAGGGGGTACCGCCGCCCTGGGCTGCCTTGTGAAGGAT

TACTTTCCCGAGCCCGTCACAGTGTCCTGGAACAGCGGAGCCCTGACCT

CCGGAGTGCATACTTTCCCGGCTGTGCTTCAGTCCTCTGGCCTGTACTC

ATTGTCCTCCGTGGTCACCGTCCCTTCGTCCTCCCTGGGCACCCAGACC

TATATCTGTAATGTCAACCATAAGCCCTCGAACACCAAGGTCGACAAGA

AGGTCGAGCCGAAGTCGTGCGACAAGACTCACACTTGCCCGCCTTGCCC

AGCCCCGGAACTGCTGGGTGGTCCTTCGGTGTTCCTCTTCCCGCCCAAG

CCGAAGGATACCCTGATGATCTCACGGACCCCCGAAGTGACCTGTGTGG

TGGTGGACGTGTCCCACGAGGACCCGGAAGTGAAATTCAATTGGTACGT

GGATGGAGTGGAAGTGCACAACGCCAAGACCAAGCCACGGGAAGAACAG

TACAACTCTACCTACCGCGTGGTGTCCGTGCTCACTGTGCTGCACCAAG

ACTGGCTGAACGGGAAGGAGTACAAGTGCAAAGTGTCCAACAAGGCGCT

GCCTGCCCCAATTGAGAAAACTATCTCGAAAGCCAAGGGACAGCCTCGA

GAGCCTCAAGTGTACACCCTGCCTCCCTCTCGGGACGAGCTGACCAAGA

ACCAAGTCTCCCTGACCTGTCTGGTCAAGGGATTCTACCCATCGGATAT

CGCCGTGGAATGGGAAAGCAACGGACAGCCCGAGAACAACTACAAGACG

ACTCCGCCCGTGCTGGATTCCGACGGGAGCTTCTTCTTGTACTCCAAGC

TGACCGTCGACAAGAGCAGATGGCAGCAGGGAAACGTGTTCTCCTGCTC

```
CGTGATGCATGAGGCGCTGCACAACCACTACACTCAGAAGAGCTTGTCC

CTGTCGCCCGGA
```

Heavy chain AA (with LALA)
SEQ ID NO: 47
EVQLLESGGGLVQPGGSLRLSCAASGFTLSYSSMSWVRQAPGKGLE

WVSFITPSTGYTHYADSVKGRFTISRDNSKNTLYLQMNSLRAEDTA

VYYCARRALVFDYWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAA

GGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEA

LHNHYTQKSLSLSPG

Heavy chain DNA (with LALA)
SEQ ID NO: 48
```
GAAGTGCAACTGCTGGAGTCCGGTGGTGGTCTGGTACAGCCGGGTGGTT

CTCTGCGTCTGAGTTGCGCGGCCAGTGGCTTTACCCTCAGTTATTCTTC

TATGTCATGGGTGCGTCAGGCTCCGGGCAAAGGTCTGGAATGGGTTAGC

TTTATTACTCCGTCTACTGGCTATACCCACTATGCGGATAGCGTGAAAG

GCCGTTTTACCATTTCTCGCGACAACAGCAAGAACACGCTGTACCTGCA

GATGAACTCACTGCGTGCCGAAGATACGGCCGTGTATTACTGTGCGAGA

CGGGCGCTGGTGTTCGACTACGGGGCCAGGGAACCCTGGTCACCGTCT

CGTCGGCTAGCACTAAGGGCCCGTCGGTGTTCCCGCTGGCCCCATCGTC

CAAGAGCACATCAGGGGGTACCGCCGCCCTGGGCTGCCTTGTGAAGGAT

TACTTTCCCGAGCCCGTCACAGTGTCCTGGAACAGCGGAGCCCTGACCT

CCGGAGTGCATACTTTCCCGGCTGTGCTTCAGTCCTCTGGCCTGTACTC

ATTGTCCTCCGTGGTCACCGTCCCTTCGTCCTCCCTGGGCACCCAGACC

TATATCTGTAATGTCAACCATAAGCCCTCGAACACCAAGGTCGACAAGA

AGGTCGAGCCGAAGTCGTGCGACAAGACTCACACTTGCCCGCCTTGCC

AGCCCCGGAAGCTGCCGGTGGTCCTTCGGTGTTCCTCTTCCCGCCCAAG

CCGAAGGATACCCTGATGATCTCACGGACCCCCGAAGTGACCTGTGTGG

TGGTGGACGTGTCCCACGAGGACCCGGAAGTGAAATTCAATTGGTACGT

GGATGGAGTGGAAGTGCACAACGCCAAGACCAAGCCACGGGAAGAACAG

TACAACTCTACCTACCGCGTGGTGTCCGTGCTCACTGTGCTGCACCAAG

ACTGGCTGAACGGGAAGGAGTACAAGTGCAAAGTGTCCAACAAGGCGCT

GCCTGCCCCAATTGAGAAAACTATCTCGAAAGCCAAGGGACAGCCTCGA

GAGCCTCAAGTGTACACCCTGCCTCCCTCTCGGGACGAGCTGACCAAGA

ACCAAGTCTCCCTGACCTGTCTGGTCAAGGGATTCTACCCATCGGATAT

CGCCGTGGAATGGGAAAGCAACGGACAGCCCGAGAACAACTACAAGACG

ACTCCGCCCGTGCTGGATTCCGACGGGAGCTTCTTCTTGTACTCCAAGC

TGACCGTCGACAAGAGCAGATGGCAGCAGGGAAACGTGTTCTCCTGCTC

CGTGATGCATGAGGCGCTGCACAACCACTACACTCAGAAGAGCTTGTCC

CTGTCGCCCGGA
```

Variable domain AA
SEQ ID NO: 49
EVQLLESGGGLVQPGGSLRLSCAASGFTLSYSSMSWVRQAPGKGLE

WVSFITPSTGYTHYADSVKGRFTISRDNSKNTLYLQMNSLRAEDTA

VYYCARRALVFDYWGQGTLVTVSS

Variable domain DNA
SEQ ID NO: 50
```
GAAGTGCAACTGCTGGAGTCCGGTGGTGGTCTGGTACAGCCGGGTGGTT

CTCTGCGTCTGAGTTGCGCGGCCAGTGGCTTTACCCTCAGTTATTCTTC

TATGTCATGGGTGCGTCAGGCTCCGGGCAAAGGTCTGGAATGGGTTAGC

TTTATTACTCCGTCTACTGGCTATACCCACTATGCGGATAGCGTGAAAG

GCCGTTTTACCATTTCTCGCGACAACAGCAAGAACACGCTGTACCTGCA

GATGAACTCACTGCGTGCCGAAGATACGGCCGTGTATTACTGTGCGAGA

CGGGCGCTGGTGTTCGACTACGGGGCCAGGGAACCCTGGTCACCGTCT

CGTCG
```

CDR1 (AA) (IMGT)
SEQ ID NO: 10
GFTLSYSS

CDR1 (AA) (Kabat)
SEQ ID NO: 13
YSSMS

CDR2 (AA) (IMGT)
SEQ ID NO: 11
ITPSTGYT

CDR2 (AA) Kabat)
SEQ ID NO: 14
FITPSTGYTHYADSVKG

CDR3 (AA) (IMGT)
SEQ ID NO: 51
ARRALVFDY

CDR3 (AA) (Kabat)
SEQ ID NO: 52
RALVFDY

Amino Acid and cDNA Sequences of Light Chain of FS28-024-053 mAb and its Variable Domain and Amino Acid Sequence of CDRs Light chain AA
SEQ ID NO: 16
EIVLTQSPGTLSLSPGERATLSCRASQSVSSSYLAWYQQKPGQAPR

LLIYGASSRATGIPDRFSGSGSGTDFTLTISRLEPEDFAVYYC

QQASSYPLTFGQGTKVEIKRTVAAPSVFIFPPSDEQLKSGTASVVCL

NNFYPREAKVQWKVDNALQSGNSQESVTEQDSKDSTYSLSSTLTLSKAD

YEKHKVYACEVTHQGLSSPVTKSFNRGEC

Light chain DNA
SEQ ID NO: 17
```
GAAATTGTGCTGACCCAGTCTCCGGGCACGTTATCTCTGAGCCCTGGTG

AGCGCGCCACTCTGTCATGCCGGGCTTCTCAAAGTGTTAGCAGTAGCTA
```

-continued
CCTGGCGTGGTATCAGCAAAAACCGGGCCAGGCCCCGCGTCTGCTGATT

TACGGTGCATCCAGCCGTGCCACCGGCATTCCAGATCGTTTTTCCGGTA

GTGGTTCTGGGACGGACTTCACTCTGACAATCTCACGCCTGGAACCGGA

GGATTTTGCGGTGTATTACTGCCAGCAAGCTTCTTCTTATCCTCTCACG

TTCGGCCAAGGGACCAAGGTGGAAATCAAACGTACTGTGGCCGCTCCTA

GCGTGTTCATTTTTCCGCCATCCGACGAGCAGCTCAAGTCCGGCACCGC

CTCCGTGGTCTGCCTGCTCAACAACTTCTACCCTCGCGAAGCTAAGGTC

CAGTGGAAGGTCGACAATGCCCTGCAGTCCGGAAACTCGCAGGAAAGCG

TGACTGAACAGGACTCCAAGGACTCCACCTATTCACTGTCCTCGACTCT

GACCCTGAGCAAGGCGGATTACGAAAAGCACAAAGTGTACGCATGCGAA

GTGACCCACCAGGGTCTTTCGTCCCCCGTGACCAAGAGCTTCAACAGAG

GAGAGTGT

Variable domain AA
SEQ ID NO: 18
*EIVLTQSPGTLSLSPGERATLSCRASQSVSSSYLAWYQQKPGQAPRL*

*LIYGASSRATGIPDRFSGSGSGTDFTLTISRLEPEDFAVYYC*

*QQASSYPLTFGQGTKVEIK*

Variable domain DNA
SEQ ID NO: 19
GAAATTGTGCTGACCCAGTCTCCGGGCACGTTATCTCTGAGCCCTGGTG

AGCGCGCCACTCTGTCATGCCGGGCTTCTCAAAGTGTTAGCAGTAGCTA

CCTGGCGTGGTATCAGCAAAAACCGGGCCAGGCCCCGCGTCTGCTGATT

TACGGTGCATCCAGCCGTGCCACCGGCATTCCAGATCGTTTTTCCGGTA

GTGGTTCTGGGACGGACTTCACTCTGACAATCTCACGCCTGGAACCGGA

GGATTTTGCGGTGTATTACTGCCAGCAAGCTTCTTCTTATCCTCTCACG

TTCGGCCAAGGGACCAAGGTGGAAATCAAA

CDR1 (AA) (IMGT)
SEQ ID NO: 20
*QSVSSSY*

CDR1 (AA) (Kabat)
SEQ ID NO: 23
*RASQSVSSSYLA*

CDR2 (AA) (IMGT)
SEQ ID NO: 21
*GAS*

CDR2 (AA) (Kabat)
SEQ ID NO: 24
*GASSRAT*

CDR3 (AA) (IMGT)
SEQ ID NO: 22
*QQASSYPLT*

CDR3 (AA) (Kabat)
SEQ ID NO: 22
*QQASSYPLT*

Amino Acid Sequences of the Heavy and Light Chain of FS28-024-060 mAb (with LALA)

Heavy chain AA (with LALA)
SEQ ID NO: 55
*EVQLLESGGGLVQPGGSLRLSCAASGFTLSYSSMSWVRQAPGKGLE*

*WVSFITPSTGYTHYADSVKGRFTISRDNSKNTLYLQMNSLRAEDTA*

*VYYCARRALVFDYWGQGTLVTVSSASTKGPSVFPLAPSSKSTSGGT*

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAA

GGPSVFLFPPKPKDTLMISRTPEVTCVVVDVS HEDPEVKFNWYVDGVE

VHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPG

Light chain AA
SEQ ID NO: 16
*EIVLTQSPGTLSLSPGERATLSCRASQSVSSSYLAWYQQKPGQAPR*

*LLIYGASSRATGIPDRFSGSGSGTDFTLTISRLEPEDFAVYYC*

*QQASSYPLTFGQGTKVEIKRTVAAPSVFIFPPSDEQLKSGTASVVCL*

LNNFYPREAKVQWKVDNALQSGNSQESVTEQDSKDSTYSLSSTLTLSKA

DYEKHKVYACEVTHQGLSSPVTKSFNRGEC

Amino acid sequences of the heavy and light chain of FS28-026 mAb (with LALA)
Heavy chain AA (with LALA)
SEQ ID NO: 58
*EVQLLESGGGLVQPGGSLRLSCAASGFTFSNYAMTWVRQAPGKGLE*

*WVSSITPYYSKTDYADSVKGRFTISRDNSKNTLYLQMNSLRAEDTA*

*VYYCARNWYRFDYWGQGTLVTVSSASTKGPSVFPLAPSSKSTSGGT*

AALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPEAA

GGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEA

LHNHYTQKSLSLSPG

Light chain AA
SEQ ID NO: 59
*EIVLTQSPGTLSLSPGERATLSCRASQSVSSSYLAWYQQKPGQAPR*

*LLIYGASSRATGIPDRFSGSGSGTDFTLTISRLEPEDFAVYYC*

*QQYSSYPITFGQGTKVEIKRTVAAPSVFIFPPSDEQLKSGTASVVCL*

LNNFYPREAKVQWKVDNALQSGNSQESVTEQDSKDSTYSLSSTLTLSKA

DYEKHKVYACEVTHQGLSSPVTKSFNRGEC

Amino Acid Sequences of the Heavy and Light Chain of
FS28-091 mAb (with LALA)

```
Heavy chain AA (with LALA)
                                                     SEQ ID NO: 60
EVQLLESGGGLVQPGGSLRLSCAASGFTGTNYAMSWVRQAPGKGLEWVSSIKPYDGNTYYADSVK

GRFTISRDNSKNTLYLQMNSLRAEDTAVYYCARNRWVFDYWGQGTLVTVSSASTKGPSVFPLAPSS

KSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Light chain AA
                                                       SEQ ID NO 61
EIVLTQSPGTLSLSPGERATLSCRASQSVSSSYLAWYQQKPGQAPRLLIYGASSRATGIPDRFSGSG

SGTDFTLTISRLEPEDFAVYYCQQYSSSPFTFGQGTKVEIKRTVAAPSVFIFPPSDEQLKSGTASVVCL

LNNFYPREAKVQWKVDNALQSGNSQESVTEQDSKDSTYSLSSTLTLSKADYEKHKVYACEVTHQGL

SSPVTKSFNRGEC
```

Amino Acid Sequences of the Heavy and Light Chain of
FS28-185 mAb (with LALA)

```
Heavy chain AA (with LALA)
                                                     SEQ ID NO: 62
EVQLLESGGGLVQPGGSLRLSCAASGFTGTTSAMSWVRQAPGKGLEWVSRINPYEGETNYADSVK

GRFTISRDNSKNTLYLQMNSLRAEDTAVYYCARGWSIATYYKSAMDYWGQGTLVTVSSASTKGPSV

FPLAPSSKSTSGGTAALGCLVKDYFPEPVTVSWNSGALTSGVHTFPAVLQSSGLYSLSSVVTVPSSS

LGTQTYICNVNHKPSNTKVDKKVEPKSCDKTHTCPPCPAPEAAGGPSVFLFPPKPKDTLMISRTPEVT

CVVVDVSHEDPEVKFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG

Light chain AA
                                                      SEQ ID NO: 195
EIVLTQSPGTLSLSPGERATLSCRASQSVSSSYLAWYQQKPGQAPRLLIYGASSRATGIPDRFSGSG

SGTDFTLTISRLEPEDFAVYYCQQYSSSPFTFGQGTKVEIKRTVAAPSVFIFPPSDEQLKSGTASVV

CLLNNFYPREAKVQWKVDNALQSGNSQESVTEQDSKDSTYSLSSTLTLSKADYEKHKVYACEVTHQ

GLSSPVTKSFNRGEC
```

Amino Acid and cDNA Sequences of Heavy Chain of
FS28-256 mAb and its Variable Domain and Amino Acid
Sequence of CDRs

```
Heavy chain AA (without LALA)
                                                     SEQ ID NO: 65
EVQLLESGGGLVQPGGSLRLSCAASGFTGTNYAMSWVRQAPGKGLEWVSNISPTYSTTNYADSVKG

RFTISRDNSKNTLYLQMNSLRAEDTAVYYCARYNSYQGGLDYWGQGTLVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP
```

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)

SEQ ID NO: 66

GAAGTGCAACTGCTGGAGTCCGGTGGTGGTCTGGTACAGCCGGGTGGTTCTCTGCGTCTGAGT

TGCGCGGCCAGTGGCTTTACCTTCACTAACACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACTCTTACCAGGGTGGCTTGGAC

TACTGGGGCCAGGGAACCTTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCCAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA

Heavy chain AA (with LALA)

SEQ ID NO: 67

*EVQLLESGGGLVQPGGSLRLSCAASGFTFTNTYMSWVRQAPGKGLEWVSNISPTYSTTNYADSVKG*

*RFTISRDNSKNTLYLQMNSLRAEDTAVYYCARYNSYQGGLDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Heavy chain DNA (with LALA)

SEQ ID NO: 68

GAAGTGCAACTGCTGGAGTCCGGTGGTGGTCTGGTACAGCCGGGTGGTTCTCTGCGTCTGAGT

TGCGCGGCCAGTGGCTTTACCTTCACTAACACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACTCTTACCAGGGTGGCTTGGAC

TACTGGGGCCAGGGAACCTTGGTCACCGTCTCGAGTGCTAGCACTAAGGGCCCGTCGGTGTTC

-continued

```
CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Variable domain AA

SEQ ID NO: 69

*EVQLLESGGGLVQPGGSLRLSCAAS*GFTFTNTYMSWVRQAPGKGLEWVSNISPTYSTTNYADSVKG*

*RFTISRDNSKNTLYLQMNSLRAEDTAVYYC*ARYNSYQGGLDYWGQGTLVTVSS*

Variable domain DNA

SEQ ID NO: 70

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTAACACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACTCTTACCAGGGTGGCTTGGAC

TACTGGGGCCAGGGAACCTTGGTCACCGTCTCGAGT
```

CDR1 (AA) (IMGT)

SEQ ID NO: 71

GFTFTNTY

CDR1 (AA) (Kabat)

SEQ ID NO: 72

NTYMS

CDR2 (AA) (IMGT)

SEQ ID NO: 73

ISPTYSTT

CDR2 (AA) Kabat

SEQ ID NO: 74

NISPTYSTTNYADSVKG

CDR3 (AA) (IMGT)

SEQ ID NO: 75

ARYNSYQGGLDY

CDR3 (AA) (Kabat)

SEQ ID NO: 76

YNSYQGGLDY

Amino Acid and cDNA Sequences of Light Chain of FS28-256 mAb and its Variable Domain and Amino Acid Sequence of CDRs Light chain AA

SEQ ID NO: 77

*EIVLTQSPGTLSLSPGERATLSCRASQSVSSSYLAWYQQKPGQAPRLLIYGASSRATGIPDRFSGSG*

*SGTDFTLTISRLEPEDFAVYYCQQSYYYPITFGQGTKVEIK*RTVAAPSVFIFPPSDEQLKSGTASVVCL

LNNFYPREAKVQWKVDNALQSGNSQESVTEQDSKDSTYSLSSTLTLSKADYEKHKVYACEVTHQGL

SSPVTKSFNRGEC

Light chain DNA

SEQ ID NO: 78

GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAATCTTATTATTATCCTATCACGTTCGGCCAAGGGACCAAGGTGGAAATC

AAACGTACTGTGGCCGCTCCTAGCGTGTTCATTTTTCCGCCATCCGACGAGCAGCTCAAGTCCG

GCACCGCCTCCGTGGTCTGCCTGCTCAACAACTTCTACCCTCGCGAAGCTAAGGTCCAGTGGAA

GGTCGACAATGCCCTGCAGTCCGGAAACTCGCAGGAAAGCGTGACTGAACAGGACTCCAAGGA

CTCCACCTATTCACTGTCCTCGACTCTGACCCTGAGCAAGGCGGATTACGAAAAGCACAAAGTGT

ACGCATGCGAAGTGACCCACCAGGGTCTTTCGTCCCCCGTGACCAAGAGCTTCAACAGAGGAGA

GTGT

Variable domain AA

SEQ ID NO: 79

*EIVLTQSPGTLSLSPGERATLSCRASQSVSSSYLAWYQQKPGQAPRLLIYGASSRATGIPDRFSGSG*

*SGTDFTLTISRLEPEDFAVYYCQQSYYYPITFGQGTKVEIK*

Variable domain DNA

SEQ ID NO: 80

GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAATCTTATTATTATCCTATCACGTTCGGCCAAGGGACCAAGGTGGAAATC

AAA

CDR1 (AA) (IMGT)

SEQ ID NO: 20

QSVSSSY

CDR1 (AA) (Kabat)

SEQ ID NO: 23

*RASQSVSSSYLA*

CDR2 (AA) (IMGT)

SEQ ID NO: 21

GAS

CDR2 (AA) (Kabat)

SEQ ID NO: 24

*GASSRAT*

```
CDR3 (AA) (IMGT)
                                                       SEQ ID NO: 25
QQSYYYPIT

CDR3 (AA) (Kabat)
                                                       SEQ ID NO: 25
QQSYYYPIT
```

Amino Acid and cDNA Sequences of Heavy Chain of FS28-256-001 mAb and its Variable Domain and Amino Acid Sequence of CDRs

```
Heavy chain AA (without LALA)
                                                       SEQ ID NO: 81
EVQLLESGGGLVQPGGSLRLSCAASGFTFTETYMSWVRQAPGKGLEWVSNISPTYSTTNYADSVKG

RFTISRDNSKNTLYLQMNSLRAEDTAVYYCARYNSYQGGLDYWGQGTLVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
                                                       SEQ ID NO: 82
GAAGTGCAACTGCTGGAGTCCGGTGGTGGTCTGGTACAGCCGGGTGGTTCTCTGCGTCTGAGT

TGCGCGGCCAGTGGCTTTACCTTCACTGAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACTCTTACCAGGGTGGCTTGGAC

TACTGGGGCCAGGGAACCTTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCCAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

-continued

Heavy chain AA (with LALA)
SEQ ID NO: 89
EVQLLESGGGLVQPGGSLRLSCAASGFTFTETYMSWVRQAPGKGLEWVSNISPTYSTTNYADSVKG
RFTISRDNSKNTLYLQMNSLRAEDTAVYYCARYNSYQGGLDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Heavy chain DNA (with LALA)
SEQ ID NO: 84
GAAGTGCAACTGCTGGAGTCCGGTGGTGGTCTGGTACAGCCGGGTGGTTCTCTGCGTCTGAGT
TGCGCGGCCAGTGGCTTTACCTTCACTGAGACTTATATGAGCTGGGTGCGTCAGGCTCCGGGCA
AAGGTCTGGAATGGGTTAGCAATATTTCTCCGACTTATAGCACTACCAACTATGCGGATAGCGTG
AAAGGCCGTTTTACCATTTCTCGCGACAACAGCAAGAACACGCTGTACCTGCAGATGAACTCACT
GCGTGCCGAAGATACGGCCGTGTATTACTGTGCGAGATACAACTCTTACCAGGGTGGCTTGGAC
TACTGGGGCCAGGGAACCTTGGTCACCGTCTCGAGTGCTAGCACTAAGGGCCCGTCGGTGTTC
CCGCTGGCCCCATCGTCCAAGAGCACATCAGGGGGTACCGCCGCCCTGGGCTGCCTTGTGAAG
GATTACTTTCCCGAGCCCGTCACAGTGTCCTGGAACAGCGGAGCCCTGACCTCCGGAGTGCATA
CTTTCCCGGCTGTGCTTCAGTCCTCTGGCCTGTACTCATTGTCCTCCGTGGTCACCGTCCCTTCG
TCCTCCCTGGGCACCCAGACCTATATCTGTAATGTCAACCATAAGCCCTCGAACACCAAGGTCGA
CAAGAAGGTCGAGCCCAAGTCGTGCGACAAGACTCACACTTGCCCGCCTTGCCCAGCCCCGGA
AGCTGCCGGTGGTCCTTCGGTGTTCCTCTTCCCGCCCAAGCCGAAGGATACCCTGATGATCTCA
CGGACCCCCGAAGTGACCTGTGTGGTGGTGGACGTGTCCCACGAGGACCCGGAAGTGAAATTC
AATTGGTACGTGGATGGAGTGGAAGTGCACAACGCCAAGACCAAGCCACGGGAAGAACAGTAC
AACTCTACCTACCGCGTGGTGTCCGTGCTCACTGTGCTGCACCAAGACTGGCTGAACGGGAAGG
AGTACAAGTGCAAAGTGTCCAACAAGGCGCTGCCTGCCCCAATTGAGAAAACTATCTCGAAAGC
CAAGGGACAGCCTCGAGAGCCTCAAGTGTACACCCTGCCTCCCTCTCGGGACGAGCTGACCAA
GAACCAAGTCTCCCTGACCTGTCTGGTCAAGGGATTCTACCCATCGGATATCGCCGTGGAATGG
GAAAGCAACGGACAGCCCGAGAACAACTACAAGACGACTCCGCCCGTGCTGGATTCCGACGGG
AGCTTCTTCTTGTACTCCAAGCTGACCGTCGACAAGAGCAGATGGCAGCAGGGAAACGTGTTCT
CCTGCTCCGTGATGCATGAGGCGCTGCACAACCACTACACTCAGAAGAGCTTGTCCCTGTCGCC
CGGA Variable domain AA
SEQ ID NO: 63
EVQLLESGGGLVQPGGSLRLSCAASGFTFTETYMSWVRQAPGKGLEWVSNISPTYSTTNYADSVKG
RFTISRDNSKNTLYLQMNSLRAEDTAVYYCARYNSYQGGLDYWGQGTLVTVSS Variable domain DNA
SEQ ID NO: 64
GAAGTGCAACTGCTGGAGTCCGGTGGTGGTCTGGTACAGCCGGGTGGTTCTCTGCGTCTGAGT
TGCGCGGCCAGTGGCTTTACCTTCACTGAGACTTATATGAGCTGGGTGCGTCAGGCTCCGGGCA
AAGGTCTGGAATGGGTTAGCAATATTTCTCCGACTTATAGCACTACCAACTATGCGGATAGCGTG

```
AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACTCTTACCAGGGTGGCTTGGAC

TACTGGGGCCAGGGAACCTTGGTCACCGTCTCGAGT

CDR1 (AA) (IMGT)
                                                        SEQ ID NO: 85
GFTFTETY

CDR1 (AA) (Kabat)
                                                        SEQ ID NO: 86
ETYMS CDR2 (AA) (IMGT)
                                                        SEQ ID NO: 73
ISPTYSTT CDR2 (AA) Kabat)
                                                        SEQ ID NO: 74
NISPTYSTTNYADSVKG CDR3 (AA) (IMGT)
                                                        SEQ ID NO: 75
ARYNSYQGGLDY CDR3 (AA) (Kabat)
                                                        SEQ ID NO: 76
YNSYQGGLDY
```

Amino Acid and cDNA Sequences of Light Chain of FS28-256-001 mAb and its Variable Domain and Amino Acid Sequence of CDRs

```
Light chain AA
                                                        SEQ ID NO: 83
EIVLTQSPGTLSLSPGERATLSCRASQSVSSSYLAWYQQKPGQAPRLLIYGASSRATGIPDRFSGSG

SGTDFTLTISRLEPEDFAVYYCQQHNQYPNTFGQGTKVEIKRTVAAPSVFIFPPSDEQLKSGTASVVC

LLNNFYPREAKVQWKVDNALQSGNSQESVTEQDSKDSTYSLSSTLTLSKADYEKHKVYACEVTHQG

LSSPVTKSFNRGEC

Light chain DNA
                                                        SEQ ID NO: 92
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAACATAATCAGTATCCGAATACGTTCGGCCAAGGGACCAAGGTGGAAATC

AAACGTACTGTAGCAGCTCCTTCCGTGTTCATCTTTCCGCCCAGTGATGAGCAGCTGAAGTCAG

GTACTGCTTCCGTGGTTTGCCTGCTCAACAACTTTTACCCCAGAGAAGCCAAAGTCCAGTGGAAA

GTGGACAATGCGTTGCAAAGCGGGAACTCTCAGGAATCCGTCACAGAGCAGGACTCTAAGGACT

CCACCTATAGCCTCTCTAGTACGCTGACACTGAGCAAAGCCGATTACGAGAAGCACAAGGTGTA

TGCCTGTGAGGTTACCCATCAAGGCCTTAGCTCACCAGTGACCAAGAGCTTCAATAGGGGAGAA

TGC

Variable domain AA
                                                        SEQ ID NO: 93
EIVLTQSPGTLSLSPGERATLSCRASQSVSSSYLAWYQQKPGQAPRLLIYGASSRATGIPDRFSGSG

SGTDFTLTISRLEPEDFAVYYCQQHNQYPNTFGQGTKVEIK
```

```
Variable domain DNA
                                                        SEQ ID NO: 94
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAACATAATCAGTATCCGAATACGTTCGGCCAAGGGACCAAGGTGGAAATC

AAA

CDR1 (AA) (IMGT)
                                                        SEQ ID NO: 20
QSVSSSY

CDR1 (AA) (Kabat)
                                                        SEQ ID NO: 23
RASQSVSSSYLA CDR2 (AA) (IMGT)
                                                        SEQ ID NO: 21
GAS CDR2 (AA) (Kabat)
                                                        SEQ ID NO: 24
GASSRAT CDR3 (AA) (IMGT)
                                                        SEQ ID NO: 34
QQHNQYPNT CDR3 (AA) (Kabat)
                                                        SEQ ID NO: 34
QQHNQYPNT
```

Amino Acid and cDNA Sequences of Heavy Chain of FS28-256-005 mAb and its Variable Domain and Amino Acid Sequence of CDRs

```
Heavy chain AA (without LALA)
                                                        SEQ ID NO: 87
EVQLLESGGGLVQPGGSLRLSCAASGFTFTETYMSWVRQAPGKGLEWVSNISPTYSTTNYADSVKG

RFTISRDNSKNTLYLQMNSLRAEDTAVYYCARYNSYQGGLDYWGQGTLVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
                                                        SEQ ID NO: 88
GAAGTGCAACTGCTGGAGTCCGGTGGTGGTCTGGTACAGCCGGGTGGTTCTCTGCGTCTGAGT

TGCGCGGCCAGTGGCTTTACCTTCACTGAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACTCTTACCAGGGTGGCTTGGAC

TACTGGGGCCAGGGAACCTTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG
```

-continued

```
TCCTCCCTGGGCACCCAGACCTATATCTGTAATGTCAACCATAAGCCCTCGAACACCAAGGTCGA
CAAGAAGGTCGAGCCGAAGTCGTGCGACAAGACTCACACTTGCCCGCCTTGCCCAGCCCCGGA
ACTGCTGGGTGGTCCTTCGGTGTTCCTCTTCCCGCCCAAGCCGAAGGATACCCTGATGATCTCA
CGGACCCCCGAAGTGACCTGTGTGGTGGTGGACGTGTCCCACGAGGACCCGGAAGTGAAATTC
AATTGGTACGTGGATGGAGTGGAAGTGCACAACGCCAAGACCAAGCCACGGGAAGAACAGTAC
AACTCTACCTACCGCGTGGTGTCCGTGCTCACTGTGCTGCACCAAGACTGGCTGAACGGGAAGG
AGTACAAGTGCAAAGTGTCCAACAAGGCGCTGCCTGCCCCAATTGAGAAAACTATCTCGAAAGC
CAAGGGACAGCCTCGAGAGCCTCAAGTGTACACCCTGCCTCCCTCTCGGGACGAGCTGACCAA
GAACCAAGTCTCCCTGACCTGTCTGGTCAAGGGATTCTACCCATCGGATATCGCCGTGGAATGG
GAAAGCAACGGACAGCCCGAGAACAACTACAAGACGACTCCGCCCGTGCTGGATTCCGACGGG
AGCTTCTTCTTGTACTCCAAGCTGACCGTCGACAAGAGCAGATGGCAGCAGGGAAACGTGTTCT
CCTGCTCCGTGATGCATGAGGCGCTGCACAACCACTACACTCAGAAGAGCTTGTCCCTGTCGCC
CGGA
```

Heavy chain AA (with LALA)
SEQ ID NO: 89

*EVQLLESGGGLVQPGGSLRLSCAASGFTFTETYMSWVRQAPGKGLEWVSNISPTYSTTNYADSVKG
RFTISRDNSKNTLYLQMNSLRAEDTAVYYCARYNSYQGGLDYWGQGTLVTVSS*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Heavy chain DNA (with LALA)
SEQ ID NO: 84

```
GAAGTGCAACTGCTGGAGTCCGGTGGTGGTCTGGTACAGCCGGGTGGTTCTCTGCGTCTGAGT
TGCGCGGCCAGTGGCTTTACCTTCACTGAGACTTATATGAGCTGGGTGCGTCAGGCTCCGGGCA
AAGGTCTGGAATGGGTTAGCAATATTTCTCCGACTTATAGCACTACCAACTATGCGGATAGCGTG
AAAGGCCGTTTTACCATTTCTCGCGACAACAGCAAGAACACGCTGTACCTGCAGATGAACTCACT
GCGTGCCGAAGATACGGCCGTGTATTACTGTGCGAGATACAACTCTTACCAGGGTGGCTTGGAC
TACTGGGGCCAGGGAACCTTGGTCACCGTCTCGAGTGCTAGCACTAAGGGCCCGTCGGTGTTC
CCGCTGGCCCCATCGTCCAAGAGCACATCAGGGGTACCGCCGCCCTGGGCTGCCTTGTGAAG
GATTACTTTCCCGAGCCCGTCACAGTGTCCTGGAACAGCGGAGCCCTGACCTCCGGAGTGCATA
CTTTCCCGGCTGTGCTTCAGTCCTCTGGCCTGTACTCATTGTCCTCCGTGGTCACCGTCCCTTCG
TCCTCCCTGGGCACCCAGACCTATATCTGTAATGTCAACCATAAGCCCTCGAACACCAAGGTCGA
CAAGAAGGTCGAGCCGAAGTCGTGCGACAAGACTCACACTTGCCCGCCTTGCCCAGCCCCGGA
AGCTGCCGGTGGTCCTTCGGTGTTCCTCTTCCCGCCCAAGCCGAAGGATACCCTGATGATCTCA
CGGACCCCCGAAGTGACCTGTGTGGTGGTGGACGTGTCCCACGAGGACCCGGAAGTGAAATTC
AATTGGTACGTGGATGGAGTGGAAGTGCACAACGCCAAGACCAAGCCACGGGAAGAACAGTAC
AACTCTACCTACCGCGTGGTGTCCGTGCTCACTGTGCTGCACCAAGACTGGCTGAACGGGAAGG
AGTACAAGTGCAAAGTGTCCAACAAGGCGCTGCCTGCCCCAATTGAGAAAACTATCTCGAAAGC
CAAGGGACAGCCTCGAGAGCCTCAAGTGTACACCCTGCCTCCCTCTCGGGACGAGCTGACCAA
GAACCAAGTCTCCCTGACCTGTCTGGTCAAGGGATTCTACCCATCGGATATCGCCGTGGAATGG
```

```
-continued
GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

```
Variable domain AA
                                                        SEQ ID NO: 63
EVQLLESGGGLVQPGGSLRLSCAASGFTFTETYMSWVRQAPGKGLEWVSNISPTYSTTNYADSVKG

RFTISRDNSKNTLYLQMNSLRAEDTAVYYCARYNSYQGGLDYWGQGTLVTVSS
```

```
Variable domain DNA
                                                        SEQ ID NO: 64
GAAGTGCAACTGCTGGAGTCCGGTGGTGGTCTGGTACAGCCGGGTGGTTCTCTGCGTCTGAGT

TGCGCGGCCAGTGGCTTTACCTTCACTGAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACTCTTACCAGGGTGGCTTGGAC

TACTGGGGCCAGGGAACCTTGGTCACCGTCTCGAGT
```

```
CDR1 (AA) (IMGT)
                                                        SEQ ID NO: 85
GFTFTETY
```

```
CDR1 (AA) (Kabat)
                                                        SEQ ID NO: 86
ETYMS
```

```
CDR2 (AA) (IMGT)
                                                        SEQ ID NO: 73
ISPTYSTT
```

```
CDR2 (AA) Kabat)
                                                        SEQ ID NO: 74
NISPTYSTTNYADSVKG
```

```
CDR3 (AA) (IMGT)
                                                        SEQ ID NO: 75
ARYNSYQGGLDY
```

```
CDR3 (AA) (Kabat)
                                                        SEQ ID NO: 76
YNSYQGGLDY
```

Amino Acid and cDNA Sequences of Light Chain of FS28-256-005 mAb and its Variable Domain and Amino Acid Sequence of CDRs)

```
Light chain AA
                                                        SEQ ID NO: 90
EIVLTQSPGTLSLSPGERATLSCRASQSVSSSYLAWYQQKPGQAPRLLIYGASSRATGIPDRFSGSG

SGTDFTLTISRLEPEDFAVYYCQQALGYPHTFGQGTKVEIKRTVAAPSVFIFPPSDEQLKSGTASVVC

LLNNFYPREAKVQWKVDNALQSGNSQESVTEQDSKDSTYSLSSTLTLSKADYEKHKVYACEVTHQG

LSSPVTKSFNRGEC
```

```
Light chain DNA
                                                        SEQ ID NO: 91
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAGCTTTGGGTTATCCTCATACGTTCGGCCAAGGGACCAAGGTGGAAATC
```

-continued

```
AAACGTACTGTAGCAGCTCCTTCCGTGTTCATCTTTCCGCCCAGTGATGAGCAGCTGAAGTCAG

GTACTGCTTCCGTGGTTTGCCTGCTCAACAACTTTTACCCCAGAGAAGCCAAAGTCCAGTGGAAA

GTGGACAATGCGTTGCAAAGCGGGAACTCTCAGGAATCCGTCACAGAGCAGGACTCTAAGGACT

CCACCTATAGCCTCTCTAGTACGCTGACACTGAGCAAAGCCGATTACGAGAAGCACAAGGTGTA

TGCCTGTGAGGTTACCCATCAAGGCCTTAGCTCACCAGTGACCAAGAGCTTCAATAGGGGAGAA

TGC
```

Variable domain AA
SEQ ID NO: 53
*EIVLTQSPGTLSLSPGERATLSCRASQSVSSSYLAWYQQKPGQAPRLLIYGASSRATGIPDRFSGSG*

*SGTDFTLTISRLEPEDFAVYYCQQALGYPHTFGQGTKVEIK*

Variable domain DNA
SEQ ID NO: 54
```
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAGCTTTGGGTTATCCTCATACGTTCGGCCAAGGGACCAAGGTGGAAATC

AAA
```

CDR1 (AA) (IMGT)
SEQ ID NO: 20
QSVSSSY

CDR1 (AA) (Kabat)
SEQ ID NO: 23
RASQSVSSSYLA

CDR2 (AA) (IMGT)
SEQ ID NO: 21
GAS

CDR2 (AA) (Kabat)
SEQ ID NO: 24
GASSRAT

CDR3 (AA) (IMGT)
SEQ ID NO: 43
QQALGYPHT

CDR3 (AA) (Kabat)
SEQ ID NO: 43
QQALGYPHT

Amino Acid and cDNA Sequences of Heavy Chain of FS28-256-012 mAb and its Variable Domain and Amino Acid Sequence of CDRs Heavy chain AA (without LALA)
SEQ ID NO: 105
*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCAR__YNAYHAALDY__WGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
SEQ ID NO: 106
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCCAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA

Heavy chain AA (with LALA)
SEQ ID NO: 107
*EVQLLESGGGLVQPGGSLRLSCAAS*GFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Heavy chain DNA (with LALA)
SEQ ID NO: 108
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

-continued
```
CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Variable domain AA

SEQ ID NO: 109

*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*

Variable domain DNA

SEQ ID NO: 110
```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGT
```

CDR1 (AA) (IMGT)

SEQ ID NO: 98

GFTFTHTY

CDR1 (AA) (Kabat)

SEQ ID NO: 97

<u>HTYMS</u>

CDR2 (AA) (IMGT)

SEQ ID NO: 73

ISPTYSTT

CDR2 (AA) Kabat

SEQ ID NO: 74

<u>NISPTYSTTNYADSVKG</u>

CDR3 (AA) (IMGT)

SEQ ID NO: 99

ARYNAYHAALDY

CDR3 (AA) (Kabat)

SEQ ID NO: 100

<u>YNAYHAALDY</u>

Amino Acid and cDNA Sequences of Light Chain of FS28-256-012 mAb and its Variable Domain and Amino Acid Sequence of CDRs Light chain AA
SEQ ID NO: 77
*EIVLTQSPGTLSLSPGERATLSCRASQSVSSSYLAWYQQKPGQAPRLLIYGASSRATGIPDRFSGSG*

*SGTDFTLTISRLEPEDFAVYYCQQSYYYPITFGQGTKVEIK*RTVAAPSVFIFPPSDEQLKSGTASVVCL

LNNFYPREAKVQWKVDNALQSGNSQESVTEQDSKDSTYSLSSTLTLSKADYEKHKVYACEVTHQGL

SSPVTKSFNRGEC

Light chain DNA
SEQ ID NO: 78
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAATCTTATTATTATCCTATCACGTTCGGCCAAGGGACCAAGGTGGAAATC

AAACGTACTGTGGCCGCTCCTAGCGTGTTCATTTTTCCGCCATCCGACGAGCAGCTCAAGTCCG

GCACCGCCTCCGTGGTCTGCCTGCTCAACAACTTCTACCCTCGCGAAGCTAAGGTCCAGTGGAA

GGTCGACAATGCCCTGCAGTCCGGAAACTCGCAGGAAAGCGTGACTGAACAGGACTCCAAGGA

CTCCACCTATTCACTGTCCTCGACTCTGACCCTGAGCAAGGCGGATTACGAAAAGCACAAAGTGT

ACGCATGCGAAGTGACCCACCAGGGTCTTTCGTCCCCCGTGACCAAGAGCTTCAACAGAGGAGA

GTGT

Variable domain AA
SEQ ID NO: 79
*EIVLTQSPGTLSLSPGERATLSCRASQSVSSSYLAWYQQKPGQAPRLLIYGASSRATGIPDRFSGSG*

*SGTDFTLTISRLEPEDFAVYYCQQSYYYPITFGQGTKVEIK*

Variable domain DNA
SEQ ID NO: 80
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAATCTTATTATTATCCTATCACGTTCGGCCAAGGGACCAAGGTGGAAATC

AAA

CDR1 (AA) (IMGT)
SEQ ID NO: 20
QSVSSSY

CDR1 (AA) (Kabat)
SEQ ID NO: 23
RASQSVSSSYLA

CDR2 (AA) (IMGT)
SEQ ID NO: 21
GAS

CDR2 (AA) (Kabat)
SEQ ID NO: 24
GASSRAT

-continued

CDR3 (AA) (IMGT)
SEQ ID NO: 25
QQSYYYPIT

CDR3 (AA) (Kabat)
SEQ ID NO: 25
QQSYYYPIT

Amino Acid and cDNA Sequences of Heavy Chain of FS28-256-014 mAb and its Variable Domain and Amino Acid Sequence of CDRs Heavy chain AA (without LALA)
SEQ ID NO: 117
*EVQLLESGGGLVQPGGSLRLSCAAS*GFTFTHTYMSWVRQAPGKGLEWVSNISPTYSTTNYADSVKG*

*RFTISRDNSKNTLYLQMNSLRAEDTAVYYC*ARYNAYAAGLDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
SEQ ID NO: 118
GAAGTGCAACTGCTGGAGTCCGGTGGTGGTCTGGTACAGCCGGGTGGTTCTCTGCGTCTGAGT

TGCGCGGCCAGTGGCTTTACCTTCACTGATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCGTATGCGGCGGGTCTTGA

CTACTGGGGCCAGGGAACCCTGGTCACCGTCTCGAGTGCTAGCACTAAGGGCCCGTCGGTGTT

CCCGCTGGCCCCATCGTCCAAGAGCACATCAGGGGGTACCGCCGCCCTGGGCTGCCTTGTGAA

GGATTACTTTCCCGAGCCCGTCACAGTGTCCTGGAACAGCGGAGCCCTGACCTCCGGAGTGCAT

ACTTTCCCGGCTGTGCTTCAGTCCTCTGGCCTGTACTCATTGTCCTCCGTGGTCACCGTCCCTTC

GTCCTCCCTGGGCACCCAGACCTATATCTGTAATGTCAACCATAAGCCCTCGAACACCAAGGTC

GACAAGAAGGTCGAGCCGAAGTCGTGCGACAAGACTCACACTTGCCCGCCTTGCCCAGCCCCG

GAACTGCTGGGTGGTCCTTCGGTGTTCCTCTTCCCGCCCAAGCCGAAGGATACCCTGATGATCT

CACGGACCCCCGAAGTGACCTGTGTGGTGGTGGACGTGTCCCACGAGGACCCGGAAGTGAAAT

TCAATTGGTACGTGGATGGAGTGGAAGTGCACAACGCCAAGACCAAGCCACGGGAAGAACAGTA

CAACTCTACCTACCGCGTGGTGTCCGTGCTCACTGTGCTGCACCAAGACTGGCTGAACGGGAAG

GAGTACAAGTGCAAAGTGTCCAACAAGGCGCTGCCTGCCCCAATTGAGAAAACTATCTCGAAAG

CCAAGGGACAGCCTCGAGAGCCTCAAGTGTACACCCTGCCTCCCTCTCGGGACGAGCTGACCA

AGAACCAAGTCTCCCTGACCTGTCTGGTCAAGGGATTCTACCCATCGGATATCGCCGTGGAATG

GGAAAGCAACGGACAGCCCGAGAACAACTACAAGACGACTCCGCCCGTGCTGGATTCCGACGG

GAGCTTCTTCTTGTACTCCAAGCTGACCGTCGACAAGAGCAGATGGCAGCAGGGAAACGTGTTC

TCCTGCTCCGTGATGCATGAGGCGCTGCACAACCACTACACTCAGAAGAGCTTGTCCCTGTCGC

CCGGA

Heavy chain AA (with LALA)

SEQ ID NO: 119

*EVQLLESGGGLVQPGGSLRLSCAASGFTFTDTYMSWVRQAPGKLEWVSNISPTYSTTNYADSVKG*
*RFTISRDNSKNTLYLQMNSLRAEDTAVYYCARYNAYAAGLDYWGQGTLVTVSS*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Heavy chain DNA (with LALA)

SEQ ID NO: 120

GAAGTGCAACTGCTGGAGTCCGGTGGTGGTCTGGTACAGCCGGGTGGTTCTCTGCGTCTGAGT
TGCGCGGCCAGTGGCTTTACCTTCACTGATACTTATATGAGCTGGGTGCGTCAGGCTCCGGGCA
AAGGTCTGGAATGGGTTAGCAATATTTCTCCGACTTATAGCACTACCAACTATGCGGATAGCGTG
AAAGGCCGTTTTACCATTTCTCGCGACAACAGCAAGAACACGCTGTACCTGCAGATGAACTCACT
GCGTGCCGAAGATACGGCCGTGTATTACTGTGCGAGATACAACGCGTATGCGGCGGGTCTTGA
CTACTGGGGCCAGGGAACCCTGGTCACCGTCTCGAGTGCTAGCACTAAGGGCCCGTCGGTGTT
CCCGCTGGCCCCATCGTCCAAGAGCACATCAGGGGGTACCGCCGCCCTGGGCTGCCTTGTGAA
GGATTACTTTCCCGAGCCCGTCACAGTGTCCTGGAACAGCGGAGCCCTGACCTCCGGAGTGCAT
ACTTTCCCGGCTGTGCTTCAGTCCTCTGGCCTGTACTCATTGTCCTCCGTGGTCACCGTCCCTTC
GTCCTCCCTGGGCACCCAGACCTATATCTGTAATGTCAACCATAAGCCCTCGAACACCAAGGTC
GACAAGAAGGTCGAGCCGAAGTCGTGCGACAAGACTCACACTTGCCCGCCTTGCCCAGCCCCG
GAAGCTGCCGGTGGTCCTTCGGTGTTCCTCTTCCCGCCCAAGCCGAAGGATACCCTGATGATCT
CACGGACCCCCGAAGTGACCTGTGTGGTGGTGGACGTGTCCCACGAGGACCCGGAAGTGAAAT
TCAATTGGTACGTGGATGGAGTGGAAGTGCACAACGCCAAGACCAAGCCACGGGAAGAACAGTA
CAACTCTACCTACCGCGTGGTGTCCGTGCTCACTGTGCTGCACCAAGACTGGCTGAACGGGAAG
GAGTACAAGTGCAAAGTGTCCAACAAGGCGCTGCCTGCCCCAATTGAGAAAACTATCTCGAAAG
CCAAGGGACAGCCTCGAGAGCCTCAAGTGTACACCCTGCCTCCCTCTCGGGACGAGCTGACCA
AGAACCAAGTCTCCCTGACCTGTCTGGTCAAGGGATTCTACCCATCGGATATCGCCGTGGAATG
GGAAAGCAACGGACAGCCCGAGAACAACTACAAGACGACTCCGCCCGTGCTGGATTCCGACGG
GAGCTTCTTCTTGTACTCCAAGCTGACCGTCGACAAGAGCAGATGGCAGCAGGGAAACGTGTTC
TCCTGCTCCGTGATGCATGAGGCGCTGCACAACCACTACACTCAGAAGAGCTTGTCCCTGTCGC
CCGGA

Variable domain AA

SEQ ID NO: 115

*EVQLLESGGGLVQPGGSLRLSCAASGFTFTDTYMSWVRQAPGKLEWVSNISPTYSTTNYADSVKG*
*RFTISRDNSKNTLYLQMNSLRAEDTAVYYCARYNAYAAGLDYWGQGTLVTVSS*

Variable domain DNA

SEQ ID NO: 116

GAAGTGCAACTGCTGGAGTCCGGTGGTGGTCTGGTACAGCCGGGTGGTTCTCTGCGTCTGAGT
TGCGCGGCCAGTGGCTTTACCTTCACTGATACTTATATGAGCTGGGTGCGTCAGGCTCCGGGCA
AAGGTCTGGAATGGGTTAGCAATATTTCTCCGACTTATAGCACTACCAACTATGCGGATAGCGTG

-continued

```
AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCGTATGCGGCGGGTCTTGA

CTACTGGGGCCAGGGAACCCTGGTCACCGTCTCGAGT
```

CDR1 (AA) (IMGT)
SEQ ID NO: 111
GFTFTDTY

CDR1 (AA) (Kabat)
SEQ ID NO: 112
<u>DTYMS</u>

CDR2 (AA) (IMGT)
SEQ ID NO: 73
ISPTYSTT

CDR2 (AA) Kabat)
SEQ ID NO: 74
<u>NISPTYSTTNYADSVKG</u>

CDR3 (AA) (IMGT)
SEQ ID NO: 113
ARYNAYAAGLDY

CDR3 (AA) (Kabat)
SEQ ID NO: 114
<u>YNAYAAGLDY</u>

Amino Acid and cDNA Sequences of Light Chain of FS28-256-014 mAb and its Variable Domain and Amino Acid Sequence of CDRs Light chain AA
SEQ ID NO: 77
*EIVLTQSPGTLSLSPGERATLSCRAS<u>QSVSSSY</u>LAWYQQKPGQAPRLLIY<u>GAS</u>SRATGIPDRFSGSG*

*SGTDFTLTISRLEPEDFAVYYC<u>QQSYYYPIT</u>FGQGTKVEIK*RTVAAPSVFIFPPSDEQLKSGTASVVCL

LNNFYPREAKVQWKVDNALQSGNSQESVTEQDSKDSTYSLSSTLTLSKADYEKHKVYACEVTHQGL

SSPVTKSFNRGEC

Light chain DNA
SEQ ID NO: 78
```
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAATCTTATTATTATCCTATCACGTTCGGCCAAGGGACCAAGGTGGAAATC

AAACGTACTGTGGCCGCTCCTAGCGTGTTCATTTTTCCGCCATCCGACGAGCAGCTCAAGTCCG

GCACCGCCTCCGTGGTCTGCCTGCTCAACAACTTCTACCCTCGCGAAGCTAAGGTCCAGTGGAA

GGTCGACAATGCCCTGCAGTCCGGAAACTCGCAGGAAAGCGTGACTGAACAGGACTCCAAGGA

CTCCACCTATTCACTGTCCTCGACTCTGACCCTGAGCAAGGCGGATTACGAAAAGCACAAAGTGT

ACGCATGCGAAGTGACCCACCAGGGTCTTTCGTCCCCCGTGACCAAGAGCTTCAACAGAGGAGA

GTGT
```

Variable domain AA
SEQ ID NO: 79
*EIVLTQSPGTLSLSPGERATLSCRAS<u>QSVSSSY</u>LAWYQQKPGQAPRLLIY<u>GAS</u>SRATGIPDRFSGSG*

*SGTDFTLTISRLEPEDFAVYYC<u>QQSYYYPIT</u>FGQGTKVEIK*

-continued

Variable domain DNA
SEQ ID NO: 80
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAATCTTATTATTATCCTATCACGTTCGGCCAAGGGACCAAGGTGGAAATC

AAA

CDR1 (AA) (IMGT)
SEQ ID NO: 20
QSVSSSY

CDR1 (AA) (Kabat)
SEQ ID NO: 23
<u>RASQSVSSSYLA</u>

CDR2 (AA) (IMGT)
SEQ ID NO: 21
GAS

CDR2 (AA) (Kabat)
SEQ ID NO: 24
<u>GASSRAT</u>

CDR3 (AA) (IMGT)
SEQ ID NO: 25
QQSYYYPIT

CDR3 (AA) (Kabat)
SEQ ID NO: 25
<u>QQSYYYPIT</u>

Amino Acid and cDNA Sequences of Heavy Chain of FS28-256-018 mAb and its Variable Domain and Amino Acid Sequence of CDRs Heavy chain AA (without LALA)
SEQ ID NO: 123
*EVQLLESGGGLVQPGGSLRLSCAASGFTFTDTYMSWVRQAPGKGLEWVSNISPTYSTTNYADSVKG*

*RFTISRDNSKNTLYLQMNSLRAEDTAVYYCARYNAYQIGLDYWGQGTLVTVSS*ASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
SEQ ID NO: 124
GAAGTGCAACTGCTGGAGTCCGGTGGTGGTCTGGTACAGCCGGGTGGTTCTCTGCGTCTGAGT

TGCGCGGCCAGTGGCTTTACCTTCACTGACACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

-continued

```
TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Heavy chain AA (with LALA)  
SEQ ID NO: 125

*EVQLLESGGGLVQPGGSLRLSCAAS*GFTFTQTYMSWVRQAPGKGLEWVSNISPTYSTTNYADSVKG

*RFTISRDNSKNTLYLQMNSLRAEDTAVYYC*ARYNAYQIGLDYWGQGTLVTVSSASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (with LALA)  
SEQ ID NO: 126

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG
```

-continued
```
GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Variable domain AA

SEQ ID NO: 121

*EVQLLESGGGLVQPGGSLRLSCAASGFTFTQTYMSWVRQAPGKGLEWVSNISPTYSTTNYADSVKG*

*RFTISRDNSKNTLYLQMNSLRAEDTAVYYCARYNAYQIGLDY**WGQGTLVTVSS*

Variable domain DNA

SEQ ID NO: 122

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGT
```

CDR1 (AA) (IMGT)

SEQ ID NO: 101

GFTFTQTY

CDR1 (AA) (Kabat)

SEQ ID NO: 102

*QTYMS*

CDR2 (AA) (IMGT)

SEQ ID NO: 73

ISPTYSTT

CDR2 (AA) Kabat

SEQ ID NO: 74

*NISPTYSTTNYADSVKG*

CDR3 (AA) (IMGT)

SEQ ID NO: 103

ARYNAYQIGLDY

CDR3 (AA) (Kabat)

SEQ ID NO: 104

*YNAYQIGLDY*

Amino Acid and cDNA Sequences of Light Chain of FS28-256-018 mAb and its Variable Domain and Amino Acid Sequence of CDRs Light chain AA

SEQ ID NO: 77

*EIVLTQSPGTLSLSPGERATLSCRASQSVSSSYLAWYQQKPGQAPRLLIYGASSRATGIPDRFSGSG*

*SGTDFTLTISRLEPEDFAVYYCQQSYYYPITFGQGTKVEIKRTVAAPSVFIFPPSDEQLKSGTASVVCL*

LNNFYPREAKVQWKVDNALQSGNSQESVTEQDSKDSTYSLSSTLTLSKADYEKHKVYACEVTHQGL

SSPVTKSFNRGEC

Light chain DNA

SEQ ID NO: 78

```
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACGGAGGATTTTGCGG

TGTATTACTGCCAGCAATCTTATTATTATCCTATCACGTTCGGCCAAGGGACCAAGGTGGAAATC
```

-continued

```
AAACGTACTGTGGCCGCTCCTAGCGTGTTCATTTTTCCGCCATCCGACGAGCAGCTCAAGTCCG

GCACCGCCTCCGTGGTCTGCCTGCTCAACAACTTCTACCCTCGCGAAGCTAAGGTCCAGTGGAA

GGTCGACAATGCCCTGCAGTCCGGAAACTCGCAGGAAAGCGTGACTGAACAGGACTCCAAGGA

CTCCACCTATTCACTGTCCTCGACTCTGACCCTGAGCAAGGCGGATTACGAAAAGCACAAAGTGT

ACGCATGCGAAGTGACCCACCAGGGTCTTTCGTCCCCGTGACCAAGAGCTTCAACAGAGGAGA

GTGT
```

Variable domain AA

SEQ ID NO: 79

*EIVLTQSPGTLSLSPGERATLSCRASQSVSSSYLAWYQQKPGQAPRLLIYGASSRATGIPDRFSGSG*

*SGTDFTLTISRLEPEDFAVYYCQQSYYYPITFGQGTKVEIK*

Variable domain DNA

SEQ ID NO: 80

```
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAATCTTATTATTATCCTATCACGTTCGGCCAAGGGACCAAGGTGGAAATC

AAA
```

CDR1 (AA) (IMGT)

SEQ ID NO: 20

QSVSSSY

CDR1 (AA) (Kabat)

SEQ ID NO: 23

RASQSVSSSYLA

CDR2 (AA) (IMGT)

SEQ ID NO: 21

GAS

CDR2 (AA) (Kabat)

SEQ ID NO: 24

GASSRAT

CDR3 (AA) (IMGT)

SEQ ID NO: 25

QQSYYYPIT

CDR3 (AA) (Kabat)

SEQ ID NO: 25

QQSYYYPIT

Amino Acid and cDNA Sequences of Heavy Chain of FS28-256-021 mAb and its Variable Domain and Amino Acid Sequence of CDRs Heavy chain AA (without LALA)

SEQ ID NO: 105

*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

-continued

Heavy chain DNA (without LALA)
SEQ ID NO: 106
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCCAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA

Heavy chain AA (with LALA)
SEQ ID NO: 107
*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Heavy chain DNA (with LALA)
SEQ ID NO: 108
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

```
-continued
CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Variable domain AA
                                                    SEQ ID NO: 109
*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*

Variable domain DNA
                                                    SEQ ID NO: 110
```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGT
```

CDR1 (AA) (IMGT)
                                                    SEQ ID NO: 98
GFTFTHTY

CDR1 (AA) (Kabat)
                                                    SEQ ID NO: 97
<u>HTYMS</u>

CDR2 (AA) (IMGT)
                                                    SEQ ID NO: 73
ISPTYSTT

CDR2 (AA) Kabat)
                                                    SEQ ID NO: 74
<u>NISPTYSTTNYADSVKG</u>

CDR3 (AA) (IMGT)
                                                    SEQ ID NO: 99
ARYNAYHAALDY

CDR3 (AA) (Kabat)
                                                    SEQ ID NO: 100
<u>YNAYHAALDY</u>

Amino Acid and cDNA Sequences of Light Chain of FS28-256-021 mAb and its Variable Domain and Amino Acid Sequence of CDRs Light chain AA
SEQ ID NO: 83
*EIVLTQSPGTLSLSPGERATLSCRASQSVSSSYLAWYQQKPGQAPRLLIYGASSRATGIPDRFSGSG*

*SGTDFTLTISRLEPEDFAVYYCQQHNQYPNTFGQGTKVEIK*RTVAAPSVFIFPPSDEQLKSGTASVVC

LLNNFYPREAKVQWKVDNALQSGNSQESVTEQDSKDSTYSLSSTLTLSKADYEKHKVYACEVTHQG

LSSPVTKSFNRGEC

Light chain DNA
SEQ ID NO: 92
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAACATAATCAGTATCCGAATACGTTCGGCCAAGGGACCAAGGTGGAAATC

AAACGTACTGTAGCAGCTCCTTCCGTGTTCATCTTTCCGCCCAGTGATGAGCAGCTGAAGTCAG

GTACTGCTTCCGTGGTTTGCCTGCTCAACAACTTTTACCCCAGAGAAGCCAAAGTCCAGTGGAAA

GTGGACAATGCGTTGCAAAGCGGGAACTCTCAGGAATCCGTCACAGAGCAGGACTCTAAGGACT

CCACCTATAGCCTCTCTAGTACGCTGACACTGAGCAAAGCCGATTACGAGAAGCACAAGGTGTA

TGCCTGTGAGGTTACCCATCAAGGCCTTAGCTCACCAGTGACCAAGAGCTTCAATAGGGGAGAA

TGC

Variable domain AA
SEQ ID NO: 93
*EIVLTQSPGTLSLSPGERATLSCRASQSVSSSYLAWYQQKPGQAPRLLIYGASSRATGIPDRFSGSG*

*SGTDFTLTISRLEPEDFAVYYCQQHNQYPNTFGQGTKVEIK*

Variable domain DNA
SEQ ID NO: 94
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAACATAATCAGTATCCGAATACGTTCGGCCAAGGGACCAAGGTGGAAATC

AAA

CDR1 (AA) (IMGT)
SEQ ID NO: 20
QSVSSSY

CDR1 (AA) (Kabat)
SEQ ID NO: 23
RASQSVSSSYLA

CDR2 (AA) (IMGT)
SEQ ID NO: 21
GAS

CDR2 (AA) (Kabat)
SEQ ID NO: 24
GASSRAT

-continued

CDR3 (AA) (IMGT)
SEQ ID NO: 34
*QQHNQYPNT*

CDR3 (AA) (Kabat)
SEQ ID NO: 34
*QQHNQYPNT*

Amino Acid and cDNA Sequences of Heavy Chain of FS28-256-023 mAb and its Variable Domain and Amino Acid Sequence of CDRs Heavy chain AA (without LALA)
SEQ ID NO: 123
*EVQLLESGGGLVQPGGSLRLSCAASGFTFTQTYMSWVRQAPGKGLEWVSNISPTYSTTNYADSVKG*

*RFTISRDNSKNTLYLQMNSLRAEDTAVYYCARYNAYQIGLDYWGQGTLVTVSS*ASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
SEQ ID NO: 124
GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA

-continued

Heavy chain AA (with LALA)
SEQ ID NO: 125
EVQLLESGGGLVQPGGSLRLSCAASGFTFTQTYMSWVRQAPGKGLEWVSN<u>ISPTYSTT</u>NYADSVKG RFTISRDNSKNTLYLQMNSLRAEDTAVYYCAR<u>YNAYQIGLDY</u>WGQGTLVTVSSASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPE<u>AA</u>GGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (with LALA)
SEQ ID NO: 126
GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCCAAGTCGTGCGACAAGACTCACACTTGCCCGCCTTGCCCAGCCCCCGGA

AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA

Variable domain AA
SEQ ID NO: 121
EVQLLESGGGLVQPGGSLRLSCAASGFTFTQTYMSWVRQAPGKGLEWVSN<u>ISPTYSTT</u>NYADSVKG RFTISRDNSKNTLYLQMNSLRAEDTAVYYCAR<u>YNAYQIGLDY</u>WGQGTLVTVSS Variable domain DNA
SEQ ID NO: 122
GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

-continued

```
AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGT
```

```
CDR1 (AA) (IMGT)
                                                           SEQ ID NO: 101
GFTFTQTY

CDR1 (AA) (Kabat)
                                                           SEQ ID NO: 102
QTYMS CDR2 (AA) (IMGT)
                                                           SEQ ID NO: 73
ISPTYSTT CDR2 (AA) Kabat)
                                                           SEQ ID NO: 74
NISPTYSTTNYADSVKG CDR3 (AA) (IMGT)
                                                           SEQ ID NO: 103
ARYNAYQIGLDY CDR3 (AA) (Kabat)
                                                           SEQ ID NO: 104
YNAYQIGLDY
```

Amino Acid and cDNA Sequences of Heavy Chain of FS28-256-026 mAb and its Variable Domain and Amino Acid Sequence of CDRs

```
Heavy chain AA (without LALA)
                                                           SEQ ID NO: 123
EVQLLESGGGLVQPGGSLRLSCAASGFTFTQTYMSWVRQAPGKGLEWVSNISPTYSTTNYADSVKG

RFTISRDNSKNTLYLQMNSLRAEDTAVYYCARYNAYQIGLDYWGQGTLVTVSSASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG
```

```
Heavy chain DNA (without LALA)
                                                           SEQ ID NO: 124
GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC
```

-continued

```
AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Heavy chain AA (with LALA)

SEQ ID NO: 125

*EVQLLESGGGLVQPGGSLRLSCAAS**GFTFTQTYMSWVRQAPGKGLEWVSNISPTYSTT**NYADSVKG*

*RFTISRDNSKNTLYLQMNSLRAEDTAVYYC**ARYNAYQIGLDY**WGQGTLVTVSS*ASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (with LALA)

SEQ ID NO: 126

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

-continued

Variable domain AA

SEQ ID NO: 121

EVQLLESGGGLVQPGGSLRLSCAASGFTFTQTYMSWVRQAPGKGLEWVSNISPTYSTTNYADSVKG

RFTISRDNSKNTLYLQMNSLRAEDTAVYYCARYNAYQIGLDYWGQGTLVTVSS

Variable domain DNA

SEQ ID NO: 122

GAAGTGCAACTGCTGGAGTCCGGTGGTGGTCTGGTACAGCCGGGTGGTTCTCTGCGTCTGAGT

TGCGCGGCCAGTGGCTTTACCTTCACTCAGACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAGCAAGAACACGCTGTACCTGCAGATGAACTCACT

GCGTGCCGAAGATACGGCCGTGTATTACTGTGCGAGATACAACGCTTATCAGATTGGGTTGGAC

TACTGGGGCCAGGGAACCCTGGTCACCGTCTCGAGT

CDR1 (AA) (IMGT)

SEQ ID NO: 101

GFTFTQTY

CDR1 (AA) (Kabat)

SEQ ID NO: 102

QTYMS

CDR2 (AA) (IMGT)

SEQ ID NO: 73

ISPTYSTT

CDR2 (AA) Kabat)

SEQ ID NO: 74

NISPTYSTTNYADSVKG

CDR3 (AA) (IMGT)

SEQ ID NO: 103

ARYNAYQIGLDY

CDR3 (AA) (Kabat)

SEQ ID NO: 104

YNAYQIGLDY

Amino Acid and cDNA Sequences of Light Chain of FS28-256-023 mAb and its Variable Domain and Amino Acid Sequence of CDRs Light chain AA

SEQ ID NO: 83

EIVLTQSPGTLSLSPGERATLSCRASQSVSSSYLAWYQQKPGQAPRLLIYGASSRATGIPDRFSGSG

SGTDFTLTISRLEPEDFAVYYCQQHNQYPNTFGQGTKVEIKRTVAAPSVFIFPPSDEQLKSGTASVVC

LLNN FYPREAKVQWKVDNALQSGNSQESVTEQDSKDSTYSLSSTLTLSKADYEKHKVYACEVTHQG

LSSPVTKSFNRGEC

Light chain DNA

SEQ ID NO: 92

GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAACATAATCAGTATCCGAATACGTTCGGCCAAGGGACCAAGGTGGAAATC

AAACGTACTGTAGCAGCTCCTTCCGTGTTCATCTTTCCGCCCAGTGATGAGCAGCTGAAGTCAG

GTACTGCTTCCGTGGTTTGCCTGCTCAACAACTTTTACCCCAGAGAAGCCAAAGTCCAGTGGAAA

```
-continued
GTGGACAATGCGTTGCAAAGCGGGAACTCTCAGGAATCCGTCACAGAGCAGGACTCTAAGGACT

CCACCTATAGCCTCTCTAGTACGCTGACACTGAGCAAAGCCGATTACGAGAAGCACAAGGTGTA

TGCCTGTGAGGTTACCCATCAAGGCCTTAGCTCACCAGTGACCAAGAGCTTCAATAGGGGAGAA

TGC

Variable domain AA
                                                    SEQ ID NO: 93
EIVLTQSPGTLSLSPGERATLSCRAS*QSVSSSY*LAWYQQKPGQAPRLLIY*GAS*SRATGIPDRFSGSG

SGTDFTLTISRLEPEDFAVYYC*QQHNQYPNT*FGQGTKVEIK

Variable domain DNA
                                                    SEQ ID NO: 94
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAACATAATCAGTATCCGAATACGTTCGGCCAAGGGACCAAGGTGGAAATC

AAA

CDR1 (AA) (IMGT)
                                                    SEQ ID NO: 20
*QSVSSSY*

CDR1 (AA) (Kabat)
                                                    SEQ ID NO: 23
*RASQSVSSSYLA*

CDR2 (AA) (IMGT)
                                                    SEQ ID NO: 21
*GAS*

CDR2 (AA) (Kabat)
                                                    SEQ ID NO: 24
*GASSRAT*

CDR3 (AA) (IMGT)
                                                    SEQ ID NO: 34
*QQHNQYPNT*

CDR3 (AA) (Kabat)
                                                    SEQ ID NO: 34
*QQHNQYPNT*
```

Amino Acid and cDNA Sequences of Heavy Chain of FS28-256-024 mAb and its Variable Domain and Amino Acid Sequence of CDRs

```
Heavy chain AA (without LALA)
                                                    SEQ ID NO: 105
EVQLLESGGGLVQPGGSLRLSCAAS*GFTFTQTYM*SWVRQAPGKGLEWVS*NISPTYSTT*NYADSVKG

RFTISRDNNKNTLYLQMNSLRAEDTAVYYC*ARYNAYHAALDY*WGQGTLVTVSSASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
                                                    SEQ ID NO: 106
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA
```

-continued

```
AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Heavy chain AA (with LALA)
SEQ ID NO: 107

*EVQLLESGGGLVQPGGSLRLSCAASGFTFTQTYMSWVRQAPGKGLEWVSNISPTYSTTNYADSVKG*
*RFTISRDNNKNTLYLQMNSLRAEDTAVYYCARYNAYHAALDYWGQGTLVTVSS*ASTKGPSVFPLAP
SSKSTSGGTAALGCLVKDYFPEPVTVSWNSGALTSGVHTFPAVLQSSGLYSLSSVVTVPSSSLGTQT
YICNVNH KPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Heavy chain DNA (with LALA)
SEQ ID NO: 108

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA
```

-continued
```
AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Variable domain AA

SEQ ID NO: 109

*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*

Variable domain DNA

SEQ ID NO: 110
```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGT
```

CDR1 (AA) (IMGT)

SEQ ID NO: 98

GFTFTHTY

CDR1 (AA) (Kabat)

SEQ ID NO: 97

<u>HTYMS</u>

CDR2 (AA) (IMGT)

SEQ ID NO: 73

*ISPTYSTT*

CDR2 (AA) Kabat)

SEQ ID NO: 74

<u>NISPTYSTTNYADSVKG</u>

CDR3 (AA) (IMGT)

SEQ ID NO: 99

ARYNAYHAALDY

CDR3 (AA) (Kabat)

SEQ ID NO: 100

<u>YNAYHAALDY</u>

Amino Acid and cDNA Sequences of Light Chain of FS28-256-024 mAb and its Variable Domain and Amino Acid Sequence of CDRs Light chain AA

SEQ ID NO: 90

*EIVLTQSPGTLSLSPGERATLSCRASQSVSSSYLAWYQQKPGQAPRLLIYGASSRATGIPDRFSGSG*

*SGTDFTLTISRLEPEDFAVYYCQQALGYPHTFGQGTKVEIKRTVAAPSVFIFPPSDEQLKSGTASVVC*

```
LLNNFYPREAKVQWKVDNALQSGNSQESVTEQDSKDSTYSLSSTLTLSKADYEKHKVYACEVTHQG

LSSPVTKSFNRGEC

Light chain DNA
                                                         SEQ ID NO: 91
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAGCTTTGGGTTATCCTCATACGTTCGGCCAAGGGACCAAGGTGGAAATC

AAACGTACTGTAGCAGCTCCTTCCGTGTTCATCTTTCCGCCCAGTGATGAGCAGCTGAAGTCAG

GTACTGCTTCCGTGGTTTGCCTGCTCAACAACTTTTACCCCAGAGAAGCCAAAGTCCAGTGGAAA

GTGGACAATGCGTTGCAAAGCGGGAACTCTCAGGAATCCGTCACAGAGCAGGACTCTAAGGACT

CCACCTATAGCCTCTCTAGTACGCTGACACTGAGCAAAGCCGATTACGAGAAGCACAAGGTGTA

TGCCTGTGAGGTTACCCATCAAGGCCTTAGCTCACCAGTGACCAAGAGCTTCAATAGGGGAGAA

TGC

Variable domain AA
                                                         SEQ ID NO: 53
EIVLTQSPGTLSLSPGERATLSCRASQSVSSSYLAWYQQKPGQAPRLLIYGASSRATGIPDRFSGSG

SGTDFTLTISRLEPEDFAVYYCQQALGYPHTFGQGTKVEIK

Variable domain DNA
                                                         SEQ ID NO: 54
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAGCTTTGGGTTATCCTCATACGTTCGGCCAAGGGACCAAGGTGGAAATC

AAA

CDR1 (AA) (IMGT)
                                                         SEQ ID NO: 20
QSVSSSY

CDR1 (AA) (Kabat)
                                                         SEQ ID NO: 23
RASQSVSSSYLA CDR2 (AA) (IMGT)
                                                         SEQ ID NO: 21
GAS

CDR2 (AA) (Kabat)
                                                         SEQ ID NO: 24
GASSRAT CDR3 (AA) (IMGT)
                                                         SEQ ID NO: 43
QQALGYPHT

CDR3 (AA) (Kabat)
                                                         SEQ ID NO: 43
QQALGYPHT
```

Amino Acid and cDNA Sequences of Light Chain of FS28-256-026 mAb and its Variable Domain and Amino Acid Sequence of CDRs Light chain AA
SEQ ID NO: 90
*EIVLTQSPGTLSLSPGERATLSCRAS<u>QSVSSSY</u>LAWYQQKPGQAPRLLIY<u>GAS</u>SRATGIPDRFSGSG*

*SGTDFTLTISRLEPEDFAVYYC<u>QQALGYPHT</u>FGQGTKVEIK*RTVAAPSVFIFPPSDEQLKSGTASVVC

LLNNFYPREAKVQWKVDNALQSGNSQESVTEQDSKDSTYSLSSTLTLSKADYEKHKVYACEVTHQG

LSSPVTKSFNRGEC

Light chain DNA
SEQ ID NO: 91
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAGCTTTGGGTTATCCTCATACGTTCGGCCAAGGGACCAAGGTGGAAATC

AAACGTACTGTAGCAGCTCCTTCCGTGTTCATCTTTCCGCCCAGTGATGAGCAGCTGAAGTCAG

GTACTGCTTCCGTGGTTTGCCTGCTCAACAACTTTTACCCCAGAGAAGCCAAAGTCCAGTGGAAA

GTGGACAATGCGTTGCAAAGCGGGAACTCTCAGGAATCCGTCACAGAGCAGGACTCTAAGGACT

CCACCTATAGCCTCTCTAGTACGCTGACACTGAGCAAAGCCGATTACGAGAAGCACAAGGTGTA

TGCCTGTGAGGTTACCCATCAAGGCCTTAGCTCACCAGTGACCAAGAGCTTCAATAGGGGAGAA

TGC

Variable domain AA
SEQ ID NO: 53
*EIVLTQSPGTLSLSPGERATLSCRAS<u>QSVSSSY</u>LAWYQQKPGQAPRLLIY<u>GAS</u>SRATGIPDRFSGSG*

*SGTDFTLTISRLEPEDFAVYYC<u>QQALGYPHT</u>FGQGTKVEIK*

Variable domain DNA
SEQ ID NO: 54
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAGCTTTGGGTTATCCTCATACGTTCGGCCAAGGGACCAAGGTGGAAATC

AAA

CDR1 (AA) (IMGT)
SEQ ID NO: 20
<u>QSVSSSY</u>

CDR1 (AA) (Kabat)
SEQ ID NO: 23
<u>RASQSVSSSYLA</u>

CDR2 (AA) (IMGT)
SEQ ID NO: 21
<u>GAS</u>

CDR2 (AA) (Kabat)
SEQ ID NO: 24
<u>GASSRAT</u>

-continued

CDR3 (AA) (IMGT)
SEQ ID NO: 43
*QQALGYPHT*

CDR3 (AA) (Kabat)
SEQ ID NO: 43
*QQALGYPHT*

Amino Acid and cDNA Sequences of Heavy Chain of FS28-256-027 mAb and its Variable Domain and Amino Acid Sequence of CDRs Heavy chain AA (without LALA)
SEQ ID NO: 105
*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Heavy chain DNA (without LALA)
SEQ ID NO: 106
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

ACTGCTGGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

-continued

```
AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Heavy chain AA (with LALA)                                    SEQ ID NO: 107

*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Heavy chain DNA (with LALA)                                   SEQ ID NO: 108

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGTGCTAGCACTAAGGGCCCGTCGGTGTTC

CCGCTGGCCCCATCGTCCAAGAGCACATCAGGGGGTACCGCCGCCCTGGGCTGCCTTGTGAAG

GATTACTTTCCCGAGCCCGTCACAGTGTCCTGGAACAGCGGAGCCCTGACCTCCGGAGTGCATA

CTTTCCCGGCTGTGCTTCAGTCCTCTGGCCTGTACTCATTGTCCTCCGTGGTCACCGTCCCTTCG

TCCTCCCTGGGCACCCAGACCTATATCTGTAATGTCAACCATAAGCCCTCGAACACCAAGGTCGA

CAAGAAGGTCGAGCCGAAGTCGTGCGACAAGACTCACACTTGCCCGCCTTGCCCAGCCCCGGA

AGCTGCCGGTGGTCCTTCGGTGTTCCTCTTCCCGCCCAAGCCGAAGGATACCCTGATGATCTCA

CGGACCCCCGAAGTGACCTGTGTGGTGGTGGACGTGTCCCACGAGGACCCGGAAGTGAAATTC

AATTGGTACGTGGATGGAGTGGAAGTGCACAACGCCAAGACCAAGCCACGGGAAGAACAGTAC

AACTCTACCTACCGCGTGGTGTCCGTGCTCACTGTGCTGCACCAAGACTGGCTGAACGGGAAGG

AGTACAAGTGCAAAGTGTCCAACAAGGCGCTGCCTGCCCCAATTGAGAAAACTATCTCGAAAGC

CAAGGGACAGCCTCGAGAGCCTCAAGTGTACACCCTGCCTCCCTCTCGGGACGAGCTGACCAA

GAACCAAGTCTCCCTGACCTGTCTGGTCAAGGGATTCTACCCATCGGATATCGCCGTGGAATGG

GAAAGCAACGGACAGCCCGAGAACAACTACAAGACGACTCCGCCCGTGCTGGATTCCGACGGG

AGCTTCTTCTTGTACTCCAAGCTGACCGTCGACAAGAGCAGATGGCAGCAGGGAAACGTGTTCT

CCTGCTCCGTGATGCATGAGGCGCTGCACAACCACTACACTCAGAAGAGCTTGTCCCTGTCGCC

CGGA
```

Variable domain AA                                            SEQ ID NO: 109

*EVQLLESGGGLVQPGGSLRLSCAASGFTFTHTYMSWVRQAPGKGLEWVSNISPTYSTTNYADSVKG*

*RFTISRDNNKNTLYLQMNSLRAEDTAVYYCARYNAYHAALDYWGQGTLVTVSS*

Variable domain DNA                                           SEQ ID NO: 110

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA
```

```
AAGGTCTGGAATGGGTTAGCAATATTTCTCCGACTTATAGCACTACCAACTATGCGGATAGCGTG

AAAGGCCGTTTTACCATTTCTCGCGACAACAACAAGAACACGCTGTACCTGCAGATGAACTCACT

GCGTGCCGAAGATACGGCCGTGTATTACTGTGCGAGATACAACGCGTATCATGCTGCTCTGGAC

TACTGGGGCCAGGGAACCCTGGTCACCGTCTCGAGT
```

CDR1 (AA) (IMGT)
SEQ ID NO: 98
GFTFTHTY

CDR1 (AA) (Kabat)
SEQ ID NO: 97
HTYMS

CDR2 (AA) (IMGT)
SEQ ID NO: 73
*ISPTYSTT*

CDR2 (AA) Kabat)
SEQ ID NO: 74
NIS*PTYSTT*NYADSVKG

CDR3 (AA) (IMGT)
SEQ ID NO: 99
ARYNAYHAALDY

CDR3 (AA) (Kabat)
SEQ ID NO: 100
YNAYHAALDY

Amino Acid and cDNA Sequences of Light Chain of FS28-256-027 mAb and its Variable Domain and Amino Acid Sequence of CDRs Light chain AA
SEQ ID NO: 95
*EIVLTQSPGTLSLSPGERATLSCARYNAYHAALDYWYQQKPGQAPRLLIYGASSRATGIPDRFSGSG*

*SGTDFTLTISRLEPEDFAVYYCQQTVPYPYTFGQGTKVEIK*RTVAAPSVFIFPPSDEQLKSGTASVVCL

LNNFYPREAKVQWKVDNALQSGNSQESVTEQDSKDSTYSLSSTLTLSKADYEKHKVYACEVTHQGL

SSPVTKSFNRGEC

Light chain DNA
SEQ ID NO: 96
```
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAACTGTGCCGTATCCGTATACGTTCGGCCAAGGGACCAAGGTGGAAAT

CAAACGTACTGTGGCCGCTCCTAGCGTGTTCATTTTTCCGCCATCCGACGAGCAGCTCAAGTCC

GGCACCGCCTCCGTGGTCTGCCTGCTCAACAACTTCTACCCTCGCGAAGCTAAGGTCCAGTGGA

AGGTCGACAATGCCCTGCAGTCCGGAAACTCGCAGGAAAGCGTGACTGAACAGGACTCCAAGG

ACTCCACCTATTCACTGTCCTCGACTCTGACCCTGAGCAAGGCGGATTACGAAAAGCACAAAGT

GTACGCATGCGAAGTGACCCACCAGGGTCTTTCGTCCCCCGTGACCAAGAGCTTCAACAGAGGA

GAGTGT
```

Variable domain AA
SEQ ID NO: 56
*EIVLTQSPGTLSLSPGERATLSCRASQSVSSSYLAWYQQKPGQAPRLLIYGASSRATGIPDRFSGSG*

*SGTDFTLTISRLEPEDFAVYYCQQTVPYPYTFGQGTKVEIK*

-continued

Variable domain DNA
SEQ ID NO: 57
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAACTGTGCCGTATCCGTATACGTTCGGCCAAGGGACCAAGGTGGAAAT

CAAA

CDR1 (AA) (IMGT)
SEQ ID NO: 20
QSVSSSY

CDR1 (AA) (Kabat)
SEQ ID NO: 23
<u>RASQSVSSSYLA</u>

CDR2 (AA) (IMGT)
SEQ ID NO: 21
GAS

CDR2 (AA) (Kabat)
SEQ ID NO: 24
<u>GASSRAT</u>

CDR3 (AA) (IMGT)
SEQ ID NO: 44
QQTVPYPYT

CDR3 (AA) (Kabat)
SEQ ID NO: 44
<u>QQTVPYPYT</u>

Human MSLN preprotein
SEQ ID NO: 175
cDNAAAGCTTGAATTCGCCGCCACCATGGCCCTGCCTACCGCTAGGCCTCTGCTCGGATCCTGC

GGCACACCTGCCCTGGGAAGCCTCCTGTTCCTGCTGTTCTCCCTGGGCTGGGTGCAGCCCTCC

AGAACACTGGCCGGCGAAACAGGACAAGAGGCTGCCCCTCTCGATGGCGTGCTCGCTAACCCC

CCCAACATCAGCTCCCTGTCCCCTAGGCAGCTCCTGGGCTTTCCCTGTGCCGAGGTCAGCGGC

CTCTCCACCGAGAGGGTGAGGGAGCTGGCTGTGGCCCTGGCTCAGAAGAACGTGAAACTGAGC

ACCGAGCAACTCAGGTGCCTGGCTCATAGGCTGTCCGAGCCCCCCGAGGATCTGGATGCCCTG

CCTCTCGACCTGCTGCTGTTCCTGAACCCCGACGCTTTTAGCGGCCCCCAGGCCTGCACAAGGT

TCTTCAGCAGAATCACCAAGGCCAACGTGGATCTGCTGCCCAGAGGCGCTCCCGAGAGGCAAA

GACTGCTGCCCGCCGCTCTCGCCTGTTGGGGCGTCAGAGGATCCCTGCTGAGCGAGGCCGAC

GTGAGAGCCCTGGGCGGCCTGGCTTGTGATCTGCCCGGCAGGTTTGTCGCTGAGAGCGCCGAA

GTGCTCCTGCCCAGACTGGTGAGCTGCCCTGGACCTCTGGACCAGGATCAACAGGAGGCCGCC

AGAGCTGCTCTGCAGGGAGGAGGACCCCCCTACGGACCTCCTAGCACCTGGTCCGTGAGCACA

ATGGACGCCCTGAGAGGCCTGCTGCCTGTGCTGGGACAGCCCATCATTAGGAGCATTCCCCAG

GGCATTGTGGCCGCCTGGAGACAGAGGAGCAGCAGGGACCCCTCCTGGAGGCAGCCTGAGAG

AACAATCCTGAGGCCCAGATTCAGAAGAGAGGTGGAGAAAACCGCCTGCCCTAGCGGCAAGAA

GGCCAGAGAGATTGACGAGAGCCTGATCTTCTATAAAAAGTGGGAGCTCGAAGCCTGCGTGGAT

GCTGCCCTGCTGGCCACACAGATGGACAGGGTGAACGCCATCCCCTTCACCTACGAGCAGCTG

GACGTCCTGAAGCACAAGCTCGATGAGCTGTACCCCCAGGGCTACCCCGAGTCCGTGATTCAG

CATCTCGGCTACCTGTTCCTGAAAATGAGCCCCGAAGACATCAGGAAGTGGAACGTGACAAGCC

TGGAGACCCTCAAGGCCCTGCTGGAAGTGAACAAGGGACACGAGATGAGCCCCCAGGTGGCCA

-continued

```
CCCTCATCGACAGATTTGTGAAGGGAAGGGGACAGCTGGATAAGGACACCCTCGACACCCTGAC

CGCCTTCTACCCTGGATACCTCTGCAGCCTGTCCCCCGAAGAGCTGTCCAGCGTGCCTCCCTCC

TCCATCTGGGCCGTCAGACCCCAGGATCTCGACACATGCGACCCCAGACAGCTGGATGTGCTGT

ACCCCAAGGCTAGGCTGGCCTTCCAGAACATGAACGGATCCGAATATTTCGTCAAAATCCAGAG

CTTTCTGGGCGGAGCCCCCACAGAGGACCTCAAAGCCCTGAGCCAGCAGAACGTCAGCATGGA

CCTGGCCACCTTTATGAAACTGAGAACCGACGCCGTCCTCCCTCTGACAGTGGCCGAAGTGCAG

AAGCTCCTGGGCCCCCATGTGGAAGGCCTGAAGGCCGAGGAGAGACACAGACCCGTGAGAGAC

TGGATTCTGAGGCAGAGGCAGGACGATCTGGATACCCTGGGCCTGGGACTGCAGGGCGGCATT

CCTAACGGATACCTGGTCCTCGACCTGAGCATGCAGGAAGCCCTGAGCGGCACACCTTGTCTGC

TGGGACCTGGCCCTGTCCTCACCGTGCTCGCTCTGCTGCTGGCTTCCACCCTCGCCTGATGAGC

GGCCGC
```

Amino Acid and cDNA Sequences of Heavy Chain of FS28-256-271 mAb and its Variable Domain and Amino Acid Sequence of CDRs Heavy chain AA (without LALA)
SEQ ID NO: 176

*EVQLLESGGGLVQPGGSLRLSCAAS**GFTFTHTYMSWVRQAPGKGLEWVSAISPTYSTTNYADSVKG RFTISRDNNKNTLYLQMNSLRAEDTAVYYCARYNAYHAALDY**WGQGTLVTVSS*ASTKGPSVFPLAP SSKSTSGGTAALGCLVKDYFPEPVTVSWNSGALTSGVHTFPAVLQSSGLYSLSSVVTVPSSSLGTQT YICNVNH KPSNTKVDKKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPG

Heavy chain DNA (without LALA)
SEQ ID NO: 177

```
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCGCGATTTCTCCGACTTATAGCACTACCAACTATGCGGATAGCGT

GAAAGGCCGTTTTACCATTTCTCGCGACAACAACAAGAACACGCTGTACCTGCAGATGAACTCAC

TGCGTGCCGAAGATACGGCCGTGTATTACTGTGCGAGATACAACGCGTATCATGCTGCTCTGGA

CTACTGGGGCCAGGGAACCCTGGTCACCGTCTCGAGTGCTAGCACTAAGGGCCCGTCGGTGTT

CCCGCTGGCCCCATCGTCCAAGAGCACATCAGGGGGTACCGCCGCCCTGGGCTGCCTTGTGAA

GGATTACTTTCCCGAGCCCGTCACAGTGTCCTGGAACAGCGGAGCCCTGACCTCCGGAGTGCAT

ACTTTCCCGGCTGTGCTTCAGTCCTCTGGCCTGTACTCATTGTCCTCCGTGGTCACCGTCCCTTC

GTCCTCCCTGGGCACCCAGACCTATATCTGTAATGTCAACCATAAGCCCTCGAACACCAAGGTC

GACAAGAAGGTCGAGCCGAAGTCGTGCGACAAGACTCACACTTGCCCGCCTTGCCCAGCCCCG

GAACTGCTGGGTGGTCCTTCGGTGTTCCTCTTCCCGCCCAAGCCGAAGGATACCCTGATGATCT

CACGGACCCCCGAAGTGACCTGTGTGGTGGTGGACGTGTCCCACGAGGACCCGGAAGTGAAAT

TCAATTGGTACGTGGATGGAGTGGAAGTGCACAACGCCAAGACCAAGCCACGGGAAGAACAGTA

CAACTCTACCTACCGCGTGGTGTCCGTGCTCACTGTGCTGCACCAAGACTGGCTGAACGGGAAG

GAGTACAAGTGCAAAGTGTCCAACAAGGCGCTGCCTGCCCCAATTGAGAAAACTATCTCGAAAG

CCAAGGGCCAGCCTCGAGAACCACAGGTGTACACCCTGCCCCCATCCCGGGATGAGCTGACCA
```

```
AGAACCAGGTCAGCCTGACCTGCCTGGTCAAAGGCTTCTATCCCAGCGACATCGCCGTGGAGTG
GGAGAGCAATGGGCAGCCGGAGAACAACTACAAGACCACGCCTCCCGTGCTGGACTCCGACGG
ATCCTTCTTCCTCTACAGCAAGCTCACCGTGGACAAGAGCAGGTGGCAGCAGGGGAACGTCTTC
TCCTGCAGCGTGATGCATGAGGCTCTGCACAACCACTACACACAGAAGAGCCTCTCCCTGTCTC
CGGGT
```

Heavy chain AA (with LALA)                                      SEQ ID NO: 178

*EVQLLESGGGLVQPGGSLRLSCAASGFTFTHTYMSWVRQAPGKGLEWVSAISPTYSTTNYADSVKG*

*RFTISRDNNKNTLYLQMNSLRAEDTAVYYCARYNAYHAALDYWGQGTLVTVSS*ASTKGPSVFPLAP

SSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Heavy chain DNA (with LALA)                                     SEQ ID NO: 179

```
GAAGTGCAACTGCTGGAGTCCGGTGGTGGTCTGGTACAGCCGGGTGGTTCTCTGCGTCTGAGT
TGCGCGGCCAGTGGCTTTACCTTCACTCATACTTATATGAGCTGGGTGCGTCAGGCTCCGGGCA
AAGGTCTGGAATGGGTTAGCGCGATTTCTCCGACTTATAGCACTACCAACTATGCGGATAGCGT
GAAAGGCCGTTTTACCATTTCTCGCGACAACAACAAGAACACGCTGTACCTGCAGATGAACTCAC
TGCGTGCCGAAGATACGGCCGTGTATTACTGTGCGAGATACAACGCGTATCATGCTGCTCTGGA
CTACTGGGGCCAGGGAACCCTGGTCACCGTCTCGAGTGCTAGCACTAAGGGCCCGTCGGTGTT
CCCGCTGGCCCCATCGTCCAAGAGCACATCGGGGGGTACCGCCGCCCTGGGCTGCCTTGTGAA
GGATTACTTTCCCGAGCCCGTCACAGTGTCCTGGAACAGCGGAGCCCTGACCTCCGGAGTGCAT
ACTTTCCCGGCTGTGCTTCAGTCCTCTGGCCTGTACTCATTGTCCTCCGTGGTCACCGTCCCTTC
GTCCTCCCTGGGCACCCAGACCTATATCTGTAATGTCAACCATAAGCCCTCGAACACCAAGGTC
GACAAGAAGGTCGAGCCGAAGTCGTGCGACAAGACTCACACTTGCCCGCCTTGCCCAGCCCCG
GAAGCTGCCGGTGGTCCTTCGGTGTTCCTCTTCCCGCCCAAGCCGAAGGATACCCTGATGATCT
CACGGACCCCCGAAGTGACCTGTGTGGTGGTGGACGTGTCCCACGAGGACCCGGAAGTGAAAT
TCAATTGGTACGTGGATGGAGTGGAAGTGCACAACGCCAAGACCAAGCCACGGGAAGAACAGTA
CAACTCTACCTACCGCGTGGTGTCCGTGCTCACTGTGCTGCACCAAGACTGGCTGAACGGGAAG
GAGTACAAGTGCAAAGTGTCCAACAAGGCGCTGCCTGCCCCAATTGAGAAAACTATCTCGAAAG
CCAAGGGCCAGCCTCGAGAACCACAGGTGTACACCCTGCCCCCATCCCGGGATGAGCTGACCA
AGAACCAGGTCAGCCTGACCTGCCTGGTCAAAGGCTTCTATCCCAGCGACATCGCCGTGGAGTG
GGAGAGCAATGGGCAGCCGGAGAACAACTACAAGACCACGCCTCCCGTGCTGGACTCCGACGG
ATCCTTCTTCCTCTACAGCAAGCTCACCGTGGACAAGAGCAGGTGGCAGCAGGGGAACGTCTTC
TCCTGCAGCGTGATGCATGAGGCTCTGCACAACCACTACACACAGAAGAGCCTCTCCCTGTCTC
CGGGT
```

Variable domain AA                                              SEQ ID NO: 180

*EVQLLESGGGLVQPGGSLRLSCAASGFTFTHTYMSWVRQAPGKGLEWVSAISPTYSTTNYADSVKG*

*RFTISRDNNKNTLYLQMNSLRAEDTAVYYCARYNAYHAALDYWGQGTLVTVSS*

-continued

```
Variable domain DNA
                                                      SEQ ID NO: 181
GAAGTGCAACTGCTGGAGTCCGGTGGTGGTCTGGTACAGCCGGGTGGTTCTCTGCGTCTGAGT

TGCGCGGCCAGTGGCTTTACCTTCACTCATACTTATATGAGCTGGGTGCGTCAGGCTCCGGGCA

AAGGTCTGGAATGGGTTAGCGCGATTTCTCCGACTTATAGCACTACCAACTATGCGGATAGCGT

GAAAGGCCGTTTTACCATTTCTCGCGACAACAACAAGAACACGCTGTACCTGCAGATGAACTCAC

TGCGTGCCGAAGATACGGCCGTGTATTACTGTGCGAGATACAACGCGTATCATGCTGCTCTGGA

CTACTGGGGCCAGGGAACCCTGGTCACCGTCTCGAGT

CDR1 (AA) (IMGT)
                                                       SEQ ID NO: 98
GFTFTHTY

CDR1 (AA) (Kabat)
                                                       SEQ ID NO: 97
HTYMS CDR2 (AA) (IMGT)
                                                       SEQ ID NO: 73
ISPTYSTT

CDR2 (AA) Kabat
                                                       SEQ ID NO: 182
AISPTYSTTNYADSVKG CDR3 (AA) (IMGT)
                                                       SEQ ID NO: 99
ARYNAYHAALDY

CDR3 (AA) (Kabat)
                                                       SEQ ID NO: 100
YNAYHAALDY
```

Amino Acid and cDNA Sequences of Light Chain of FS28-256-271 mAb and its Variable Domain and Amino Acid Sequence of CDRs

```
Light chain AA
                                                       SEQ ID NO: 95
EIVLTQSPGTLSLSPGERATLSCRASQSVSSSYLAWYQQKPGQAPRLLIYGASSRATGIPDRFSGSG

SGTDFTLTISRLEPEDFAVYYCQQTVPYPYTFGQGTKVEIKRTVAAPSVFIFPPSDEQLKSGTASVVCL

LNNFYPREAKVQWKVDNALQSGNSQESVTEQDSKDSTYSLSSTLTLSKADYEKHKVYACEVTHQGL

SSPVTKSFNRGEC

Light chain DNA
                                                       SEQ ID NO: 96
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAACTGTGCCGTATCCGTATACGTTCGGCCAAGGGACCAAGGTGGAAAT

CAAACGTACTGTGGCCGCTCCTAGCGTGTTCATTTTTCCGCCATCCGACGAGCAGCTCAAGTCC

GGCACCGCCTCCGTGGTCTGCCTGCTCAACAACTTCTACCCTCGCGAAGCTAAGGTCCAGTGGA

AGGTCGACAATGCCCTGCAGTCCGGAAACTCGCAGGAAAGCGTGACTGAACAGGACTCCAAGG

ACTCCACCTATTCACTGTCCTCGACTCTGACCCTGAGCAAGGCGGATTACGAAAAGCACAAAGT

GTACGCATGCGAAGTGACCCACCAGGGTCTTTCGTCCCCCGTGACCAAGAGCTTCAACAGAGGA

GAGTGT
```

-continued

```
Variable domain AA
                                                      SEQ ID NO: 56
EIVLTQSPGTLSLSPGERATLSCRASQSVSSSYLAWYQQKPGQAPRLLIYGASSRATGIPDRFSGSG

SGTDFTLTISRLEPEDFAVYYCQQTVPYPYTFGQGTKVEIK

Variable domain DNA
                                                      SEQ ID NO: 57
GAAATTGTGCTGACCCAGTCTCCGGGCACGTTATCTCTGAGCCCTGGTGAGCGCGCCACTCTGT

CATGCCGGGCTTCTCAAAGTGTTAGCAGTAGCTACCTGGCGTGGTATCAGCAAAAACCGGGCCA

GGCCCCGCGTCTGCTGATTTACGGTGCATCCAGCCGTGCCACCGGCATTCCAGATCGTTTTTCC

GGTAGTGGTTCTGGGACGGACTTCACTCTGACAATCTCACGCCTGGAACCGGAGGATTTTGCGG

TGTATTACTGCCAGCAAACTGTGCCGTATCCGTATACGTTCGGCCAAGGGACCAAGGTGGAAAT

CAAA

CDR1 (AA) (IMGT)
                                                      SEQ ID NO: 20
QSVSSSY

CDR1 (AA) (Kabat)
                                                      SEQ ID NO: 23
RASQSVSSSYLA CDR2 (AA) (IMGT)
                                                      SEQ ID NO: 21
GAS CDR2 (AA) (Kabat)
                                                      SEQ ID NO: 24
GASSRAT CDR3 (AA) (IMGT)
                                                      SEQ ID NO: 44
QQTVPYPYT CDR3 (AA) (Kabat)
                                                      SEQ ID NO: 44
QQTVPYPYT
```

Amino Acid Sequences of the Heavy and Light Chain of FS22-053-008/FS28-024 mab[2]

```
Heavy chain AA (without LALA)
                                                      SEQ ID NO: 143
EVQLLESGGGLVQPGGSLRLSCAASGFTLSYSSMSWVRQAPGKGLEWVSFITPSTGYTHYADSVKG

RFTISRDNSKNTLYLQMNSLRAEDTAVYYCARRALTFDYWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEK

TISKAKGQPREPQVYTLPPSRDELNPPYLFSNQVSLTCLVKGFYPSDIAVEWESNGQPENNYKTTPP

VLDSDGSFFLYSKLTVDYWRWLEGNVFSCSVMHEALHNHYTQKSLSLSPG

Heavy chain AA (with LALA)
                                                      SEQ ID NO: 144
EVQLLESGGGLVQPGGSLRLSCAASGFTLSYSSMSWVRQAPGKGLEWVSFITPSTGYTHYADSVKG

RFTISRDNSKNTLYLQMNSLRAEDTAVYYCARRALTFDYWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKDTLMISRTPEVTCVVVDVSH
```

-continued

```
EDPEVKFNWYVDGVEVHNAKTKPREEQYNSTYRVVSVLTVLHQDWLNGKEYKCKVSNKALPAPIEK

TISKAKGQPREPQVYTLPPSRDELNPPYLFSNQVSLTCLVKGFYPSDIAVEWESNGQPENNYKTTPP

VLDSDGSFFLYSKLTVDYWRWLEGNVFSCSVMHEALHNHYTQKSLSLSPG
```

Light chain AA

SEQ ID NO: 16

```
EIVLTQSPGTLSLSPGERATLSCRASQSVSSSYLAWYQQKPGQAPRLLIYGASSRATGIPDRFSGSGS

GTDFTLTISRLEPEDFAVYYCQQASSYPLTFGQGTKVEIKRTVAAPSVFIFPPSDEQLKSGTASVNICLL

NNFYPREAKVQWKVDNALQSGNSQESVTEQDSKDSTYSLSSTLTLSKADYEKHKVYACEVTHQGLS

SPVTKSFNRGEC
```

Amino Acid Sequence of the Heavy and Light Chain of FS22-053-008/FS28-024-051 mAb²

Heavy chain AA (without LALA)

SEQ ID NO: 145

```
EVQLLESGGGLVQPGGSLRLSCAASGFTLSYSSMSWVRQAPGKGLEWVSFITPSTGYTHYADSVKG

RFTISRDNSKNTLYLQMNSLRAEDTAVYYCARRALIFDYWGQGTLVTVSSASTKGPSVFPLAPSSKST

SGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTI

SKAKGQPREPQVYTLPPSRDELNPPYLFSNQVSLTCLVKGFYPSDIAVEWESNGQPENNYKTTPPVL

DSDGSFFLYSKLTVDYWRWLEGNVFSCSVMHEALHNHYTQKSLSLSPG
```

Heavy chain AA (with LALA)

SEQ ID NO: 146

```
EVQLLESGGGLVQPGGSLRLSCAASGFTLSYSSMSWVRQAPGKGLEWVSFITPSTGYTHYADSVKG

RFTISRDNSKNTLYLQMNSLRAEDTAVYYCARRALIFDYWGQGTLVTVSSASTKGPSVFPLAPSSKST

SGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTI

SKAKGQPREPQVYTLPPSRDELNPPYLFSNQVSLTCLVKGFYPSDIAVEWESNGQPENNYKTTPPVL

DSDGSFFLYSKLTVDYWRWLEGNVFSCSVMHEALHNHYTQKSLSLSPG
```

Light chain AA

SEQ ID NO: 16

```
EIVLTQSPGTLSLSPGERATLSCRASQSVSSSYLAWYQQKPGQAPRLLIYGASSRATGIPDRFSGSGS

GTDFTLTISRLEPEDFAVYYCQQASSYPLTFGQGTKVEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGLS

SPVTKSFNRGEC
```

Amino Acid Sequence of the Heavy and Light Chain of FS22-053-008/FS28-024-052 mAb²

Heavy chain AA (without LALA)
SEQ ID NO: 147
*EVQLLESGGGLVQPGGSLRLSCAASGFTLSYSSMSWVRQAPGKGLEWVSF*

*ITPSTGYTHYADSVKGRFTISRDNSKNTLYLQMNSLRAEDTAVYYCARRA*

*LLFDYWGQGTLVTVSSASTKGPSVFPLAPSSKSTSGGTAALGCLVKDYFP*

*EPVTVSWNSGALTSGVHTFPAVLQSSGLYSLSSVVTVPSSSLGTQTYICN*

*VNHKPSNTKVDKKVEPKSCDKTHTCPPCPAPELLGGPSVFLFPPKPKDTL*

*MISRTPEVTCVVVDVSHEDPEVKFNWYVDGVEVHNAKTKPREEQYNSTYR*

*VVSVLTVLHQDWLNGKEYKCKVSNKALPAPIEKTISKAKGQPREPQVYTL*

*PPSRDELNPPYLFSNQVSLTCLVKGFYPSDIAVEWESNGQPENNYKTTPP*

*VLDSDGSFFLYSKLTVDYWRWLEGNVFSCSVMHEALHNHYTQKSLSLSPG*

Heavy chain AA (with LALA)
SEQ ID NO: 148
*EVQLLESGGGLVQPGGSLRLSCAASGFTLSYSSMSWVRQAPGKGLEWVSF*

*ITPSTGYTHYADSVKGRFTISRDNSKNTLYLQMNSLRAEDTAVYYCARRA*

*LLFDYWGQGTLVTVSSASTKGPSVFPLAPSSKSTSGGTAALGCLVKDYFP*

*EPVTVSWNSGALTSGVHTFPAVLQSSGLYSLSSVVTVPSSSLGTQTYICN*

*VNHKPSNTKVDKKVEPKSCDKTHTCPPCPAPEAAGGPSVFLFPPKPKDTL*

*MISRTPEVTCVVVDVSHEDPEVKFNWYVDGVEVHNAKTKPREEQYNSTYR*

*VVSVLTVLHQDWLNGKEYKCKVSNKALPAPIEKTISKAKGQPREPQVYTL*

*PPSRDELNPPYLFSNQVSLTCLVKGFYPSDIAVEWESNGQPENNYKTTPP*

*VLDSDGSFFLYSKLTVDYWRWLEGNVFSCSVMHEALHNHYTQKSLSLSPG*

Light chain AA
SEQ ID NO: 16
*EIVLTQSPGTLSLSPGERATLSCRASQSVSSSYLAWYQQKPGQAPRLLIY*

*GASSRATGIPDRFSGSGSGTDFTLTISRLEPEDFAVYYCQQASSYPLTFG*

*QGTKVEIKRTVAAPSVFIFPPSDEQLKSGTASVVNICLLNNFYPREAKVQW*

*KVDNALQSGNSQESVTEQDSKDSTYSLSSTLTLSKADYEKHKVYACEVTH*

*QGLSSPVTKSFNRGEC*

Amino Acid Sequence of the Heavy and Light Chain of FS22-053-008/FS28-024-053 mAb²

Heavy chain AA (without LALA)
SEQ ID NO: 149
*EVQLLESGGGLVQPGGSLRLSCAASGFTLSYSSMSWVRQAPGKGLEWVSFITPSTGYTHYADSVKG*

*RFTISRDNSKNTLYLQMNSLRAEDTAVYYCARRALVFDYWGQGTLVTVSSASTKGPSVFPLAPSSKS*

*TSGGTAALGCLVKDYFPEPVTVSWNSGALTSGVHTFPAVLQSSGLYSLSSVVTVPSSSLGTQTYICN*

*VNHKPSNTKVDKKVEPKSCDKTHTCPPCPAPELLGGPSVFLFPPKPKDTLMISRTPEVTCVVVDVSH*

*EDPEVKFNWYVDGVEVHNAKTKPREEQYNSTYRVVSVLTVLHQDWLNGKEYKCKVSNKALPAPIEK*

*TISKAKGQPREPQVYTLPPSRDELNPPYLFSNQVSLTCLVKGFYPSDIAVEWESNGQPENNYKTTPP*

*VLDSDGSFFLYSKLTVDYWRWLEGNVFSCSVMHEALHNHYTQKSLSLSPG*

Heavy chain AA (with LALA)
SEQ ID BO: 150
*EVQLLESGGGLVQPGGSLRLSCAASGFTLSYSSMSWVRQAPGKGLEWVSFITPSTGYTHYADSVKG*

*RFTISRDNSKNTLYLQMNSLRAEDTAVYYCARRALVFDYWGQGTLVTVSSASTKGPSVFPLAPSSKS*

*TSGGTAALGCLVKDYFPEPVTVSWNSGALTSGVHTFPAVLQSSGLYSLSSVVTVPSSSLGTQTYICN*

*VNHKPSNTKVDKKVEPKSCDKTHTCPPCPAPEAAGGPSVFLFPPKPKDTLMISRTPEVTCVVVDVSH*

*EDPEVKFNWYVDGVEVHNAKTKPREEQYNSTYRVVSVLTVLHQDWLNGKEYKCKVSNKALPAPIEK*

*TISKAKGQPREPQVYTLPPSRDELNPPYLFSNQVSLTCLVKGFYPSDIAVEWESNGQPENNYKTTPP*

*VLDSDGSFFLYSKLTVDYWRWLEGNVFSCSVMHEALHNHYTQKSLSLSPG*

Light chain AA
SEQ ID NO: 16
*EIVLTQSPGTLSLSPGERATLSCRASQSVSSSYLAWYQQKPGQAPRLLIYGASSRATGIPDRFSGSGS*

*GTDFTLTISRLEPEDFAVYYCQQASSYPLTFGQGTKVEIKRTVAAPSVFIFPPSDEQLKSGTASVVQLL*

*NNFYPREAKVQWKVDNALQSGNSQESVTEQDSKDSTYSLSSTLTLSKADYEKHKVYACEVTHQGLS*

*SPVTKSFNRGEC*

Amino Acid Sequences of the Heavy and Light Chain of FS22-053-008-AA/FS28-024-060 mAb² (with LALA)

Heavy chain AA (with LALA)
SEQ ID NO: 151
EVQLLESGGGLVQPGGSLRLSCAASGFTLSYSSMSWVRQAPGKGLEWVSF

ITPSTGYTHYADSVKGRFTISRDNSKNTLYLQMNSLRAEDTAVYYCARRA

LWFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELNPPYLFSNQVSLTCLVKGFYPSDIAVEWESNGQPENNYKTTPP

VLDSDGSFFLYSKLTVDYWRWLEGNVFSCSVMHEALHNHYTQKSLSLSPG

Light chain AA
SEQ ID NO: 16
EIVLTQSPGTLSLSPGERATLSCRASQSVSSSYLAWYQQKPGQAPRLLIY

GASSRATGIPDRFSGSGSGTDFTLTISRLEPEDFAVYYCQQASSYPLTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid Sequences of the Heavy and Light Chain of FS22-053-008-AA/FS28-026 mAb² (with LALA)

Heavy chain AA (with LALA)
SEQ ID NO: 152
EVQLLESGGGLVQPGGSLRLSCAASGFTFSNYAMTWVRQAPGKGLEWVSS

ITPYYSKTDYADSVKGRFTISRDNSKNTLYLQMNSLRAEDTAVYYCARNW

YRFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELNPPYLFSNQVSLTCLVKGFYPSDIAVEWESNGQPENNYKTTPP

VLDSDGSFFLYSKLTVDYWRWLEGNVFSCSVMHEALHNHYTQKSLSLSPG

Light chain AA
SEQ ID NO: 59
EIVLTQSPGTLSLSPGERATLSCRASQSVSSSYLAWYQQKPGQAPRLLIY

GASSRATGIPDRFSGSGSGTDFTLTISRLEPEDFAVYYCQQYSSYPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino acid sequences of the heavy and light chain of FS22-053-008-AA/FS28-091 mAb² (with LALA)

Heavy chain AA (with LALA)
SEQ ID NO: 153
EVQLLESGGGLVQPGGSLRLSCAASGFTFTNYAMSWVRQAPGKGLEWVSS

IKPYDGNTYYADSVKGRFTISRDNSKNTLYLQMNSLRAEDTAVYYCARNR

WVFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELNPPYLFSNQVSLTCLVKGFYPSDIAVEWESNGQPENNYKTTPP

VLDSDGSFFLYSKLTVDYWRWLEGNVFSCSVMHEALHNHYTQKSLSLSPG

Light chain AA
SEQ ID NO: 61
EIVLTQSPGTLSLSPGERATLSCRASQSVSSSYLAWYQQKPGQAPRLLIY

GASSRATGIPDRFSGSGSGTDFTLTISRLEPEDFAVYYCQQYSSSPFTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid Sequences of the Heavy and Light Chain of FS22-053-008-AA/FS28-185 mAb² (with LALA)

Heavy chain AA (with LALA)
SEQ ID NO: 154
EVQLLESGGGLVQPGGSLRLSCAASGFTFTTSAMSWVRQAPGKGLEWVSR

INPYEGETNYADSVKGRFTISRDNSKNTLYLQMNSLRAEDTAVYYCARGW

SIATYYKSAMDYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPEAAGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSRDELNPPYLFSNQVSLTCLVKGFYPSDIAVEWESNGQPEN

NYKTTPPVLDSDGSFFLYSKLTVDYWRWLEGNVFSCSVMHEALHNHYTQK

SLSLSPG

Light chain AA
SEQ ID NO: 195
EIVLTQSPGTLSLSPGERATLSCRASQSVSSSYLAWYQQKPGQAPRLLIY

GASSRATGIPDRFSGSGSGTDFTLTISRLEPEDFAVYYCQQSSYSAPVTF

GQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTH

QGLSSPVTKSFNRGEC

Amino Acid Sequences of the Heavy and Light Chain of FS22-053-008/FS28-256 mAb²

Heavy chain AA (without LALA)
SEQ ID NO: 155
*EVQLLESGGGLVQPGGSLRLSCAASGFTFTNTYMSWVRQAPGKGLEWVSN*
*ISPTYSTTNYADSVKGRFTISRDNSKNTLYLQMNSLRAEDTAVYYCARYN*
*SYQGGLDYWGQGTLVTVSSASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPELLGGPSVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSRDELNPPYLFSNQVSLTCLVKGFYPSDIAVEWESNGQPENNYKT*
*TPPVLDSDGSFFLYSKLTVDYWRWLEGNVFSCSVMHEALHNHYTQKSLSL*
*SPG*

Heavy chain AA (with LALA)
SEQ ID NO: 156
*EVQLLESGGGLVQPGGSLRLSCAASGFTFTNTYMSWVRQAPGKGLEWVSN*
*ISPTYSTTNYADSVKGRFTISRDNSKNTLYLQMNSLRAEDTAVYYCARYN*
*SYQGGLDYWGQGTLVTVSSASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPEAAGGPSVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSRDELNPPYLFSNQVSLTCLVKGFYPSDIAVEWESNGQPENNYKT*
*TPPVLDSDGSFFLYSKLTVDYWRWLEGNVFSCSVMHEALHNHYTQKSLSL*
*SPG*

Light chain AA
SEQ ID NO: 77
*EIVLTQSPGTLSLSPGERATLSCRASQSVSSSYLAWYQQKPGQAPRLLIY*
*GASSRATGIPDRFSGSGSGTDFTLTISRLEPEDFAVYYCQQSYYYPITFG*
*QGTKVEIKRTVAAPSVFIFPPSDEQLKSGTASVVCLLNNFYPREAKVQWK*
*VDNALQSGNSQESVTEQDSKDSTYSLSSTLTLSKADYEKHKVYACEVTHQ*
*GLSSPVTKSFNRGEC*

Amino Acid and cDNA Sequences of Heavy and Light Chain of FS22-053-008/FS28-256-001 mAb²

Heavy chain AA (without LALA)
SEQ ID NO: 157
*EVQLLESGGGLVQPGGSLRLSCAASGFTFTETYMSWVRQAPGKGLEWVSN*
*ISPTYSTTNYADSVKGRFTISRDNSKNTLYLQMNSLRAEDTAVYYCARYN*
*SYQGGLDYWGQGTLVTVSSASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPELLGGPSVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSRDELNPPYLFSNQVSLTCLVKGFYPSDIAVEWESNGQPENNYKT*
*TPPVLDSDGSFFLYSKLTVDYWRWLEGNVFSCSVMHEALHNHYTQKSLSL*
*SPG*

Heavy chain AA (with LALA)
SEQ ID NO: 158
*EVQLLESGGGLVQPGGSLRLSCAASGFTFTETYMSWVRQAPGKGLEWVSN*
*ISPTYSTTNYADSVKGRFTISRDNSKNTLYLQMNSLRAEDTAVYYCARYN*
*SYQGGLDYWGQGTLVTVSSASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPEAAGGPSVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSRDELNPPYLFSNQVSLTCLVKGFYPSDIAVEWESNGQPENNYKT*
*TPPVLDSDGSFFLYSKLTVDYWRWLEGNVFSCSVMHEALHNHYTQKSLSL*
*SPG*

Light chain AA
SEQ ID NO: 83
*EIVLTQSPGTLSLSPGERATLSCRASQSVSSSYLAWYQQKPGQAPRLLIY*
*GASSRATGIPDRFSGSGSGTDFTLTISRLEPEDFAVYYCQQHNQYPNTFG*
*QGTKVEIKRTVAAPSVFIFPPSDEQLKSGTASVVCLLNNFYPREAKVQWK*
*VDNALQSGNSQESVTEQDSKDSTYSLSSTLTLSKADYEKHKVYACEVTHQ*
*GLSSPVTKSFNRGEC*

Amino Acid and cDNA Sequences of the Heavy and Light Chain of FS22-053-008/FS28-256-005 mAb²

Heavy chain AA (without LALA)
SEQ ID NO: 159
*EVQLLESGGGLVQPGGSLRLSCAASGFTFTETYMSWVRQAPGKGLEWVSN*
*ISPTYSTTNYADSVKGRFTISRDNSKNTLYLQMNSLRAEDTAVYYCARYN*
*SYQGGLDYWGQGTLVTVSSASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPELLGGPSVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSRDELNPPYLFSNQVSLTCLVKGFYPSDIAVEWESNGQPENNYKT*
*TPPVLDSDGSFFLYSKLTVDYWRWLEGNVFSCSVMHEALHNHYTQKSLSL*
*SPG*

Heavy chain AA (with LALA)
SEQ ID NO: 160
*EVQLLESGGGLVQPGGSLRLSCAASGFTFTETYMSWVRQAPGKGLEWVSN*
*ISPTYSTTNYADSVKGRFTISRDNSKNTLYLQMNSLRAEDTAVYYCARYN*
*SYQGGLDYWGQGTLVTVSSASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPEAAGGPSVFLFPPKPK*
*DTLMISRTPEVTCVVVDVSHEDPEVKFNWYVDGVEVHNAKTKPREEQYNS*

-continued
TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Light chain AA
SEQ ID NO: 90
EIVLTQSPGTLSLSPGERATLSCRASQSVSSSYLAWYQQKPGQAPRLLIY

GASSRATGIPDRFSGSGSGTDFTLTISRLEPEDFAVYYCQQALGYPHTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid and cDNA Sequences of the Heavy and Light Chain of FS22-053-008/FS28-256-012 mAb²

Heavy chain AA (without LALA)
SEQ ID NO: 127
EVQLLESGGGLVQPGGSLRLSCAASGFTFTHTYMSWVRQAPGKGLEWVSN

ISPTYSTTNYADSVKGRFTISRDNNKNTLYLQMNSLRAEDTAVYYCARYN

AYHAALDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Heavy chain AA (with LALA)
SEQ ID NO: 128
EVQLLESGGGLVQPGGSLRLSCAASGFTFTHTYMSWVRQAPGKGLEWVSN

ISPTYSTTNYADSVKGRFTISRDNNKNTLYLQMNSLRAEDTAVYYCARYN

AYHAALDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Light chain AA
SEQ ID NO: 77
EIVLTQSPGTLSLSPGERATLSCRASQSVSSSYLAWYQQKPGQAPRLLIY

GASSRATGIPDRFSGSGSGTDFTLTISRLEPEDFAVYYCQQSYYYPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid and cDNA Sequences of the Heavy and Light Chain of FS22-053-008/FS28-256-014 mAb²

Heavy chain AA (without LALA)
SEQ ID NO: 129
EVQLLESGGGLVQPGGSLRLSCAASGFTFTDTYMSWVRQAPGKGLEWVSN

ISPTYSTTNYADSVKGRFTISRDNSKNTLYLQMNSLRAEDTAVYYCARYN

AYAAGLDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Heavy chain AA (with LALA)
SEQ ID NO: 130
EVQLLESGGGLVQPGGSLRLSCAASGFTFTDTYMSWVRQAPGKGLEWVSN

ISPTYSTTNYADSVKGRFTISRDNSKNTLYLQMNSLRAEDTAVYYCARYN

AYAAGLDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Light chain AA
SEQ ID NO: 77
EIVLTQSPGTLSLSPGERATLSCRASQSVSSSYLAWYQQKPGQAPRLLIY

GASSRATGIPDRFSGSGSGTDFTLTISRLEPEDFAVYYCQQSYYYPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid and cDNA Sequences of the Heavy and Light Chain of FS22-053-008/FS28-256-018 mAb²

Heavy chain AA (without LALA)
SEQ ID NO: 131
EVQLLESGGGLVQPGGSLRLSCAASGFTFTQTYMSWVRQAPGKGLEWVSN

ISPTYSTTNYADSVKGRFTISRDNSKNTLYLQMNSLRAEDTAVYYCARYN

AYQIGLDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Heavy chain AA (with LALA)
SEQ ID NO: 132
*EVQLLESGGGLVQPGGSLRLSCAASGFTFTQTYMSWVRQAPGKGLEWVSN*

*ISPTYSTTNYADSVKGRFTISRDNSKNTLYLQMNSLRAEDTAVYYCARYN*

*AYQIGLDYWGQGTLVTVSS*ASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Light chain AA
SEQ ID NO: 77
*EIVLTQSPGTLSLSPGERATLSCRASQSVSSSYLAWYQQKPGQAPRLLIY*

*GASSRATGIPDRFSGSGSGTDFTLTISRLEPEDFAVYYCQQSYYYPITFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid and cDNA Sequences of the Heavy and Light Chain of FS22-053-008/FS28-256-021 mAb²

Heavy chain AA (without LALA)
SEQ ID NO: 133
*EVQLLESGGGLVQPGGSLRLSCAASGFTFTHTYMSWVRQAPGKGLEWVSN*

*ISPTYSTTNYADSVKGRFTISRDNNKNTLYLQMNSLRAEDTAVYYCARYN*

*AYHAALDYWGQGTLVTVSS*ASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Heavy chain AA (with LALA)
SEQ ID NO: 134
*EVQLLESGGGLVQPGGSLRLSCAASGFTFTHTYMSWVRQAPGKGLEWVSN*

*ISPTYSTTNYADSVKGRFTISRDNNKNTLYLQMNSLRAEDTAVYYCARYN*

*AYHAALDYWGQGTLVTVSS*ASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Light chain AA
SEQ ID NO: 83
*EIVLTQSPGTLSLSPGERATLSCRASQSVSSSYLAWYQQKPGQAPRLLIY*

*GASSRATGIPDRFSGSGSGTDFTLTISRLEPEDFAVYYCQQHNQYPNTFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid and cDNA Sequences of the Heavy and Light Chain of FS22-053-008/FS28-256-023 mAb²

Heavy chain AA (without LALA)
SEQ ID NO: 135
*EVQLLESGGGLVQPGGSLRLSCAASGFTFTQTYMSWVRQAPGKGLEWVSN*

*ISPTYSTTNYADSVKGRFTISRDNSKNTLYLQMNSLRAEDTAVYYCARYN*

*AYQIGLDYWGQGTLVTVSS*ASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Heavy chain AA (with LALA)
SEQ ID NO: 136
*EVQLLESGGGLVQPGGSLRLSCAASGFTFTQTYMSWVRQAPGKGLEWVSN*

*ISPTYSTTNYADSVKGRFTISRDNSKNTLYLQMNSLRAEDTAVYYCARYN*

*AYQIGLDYWGQGTLVTVSS*ASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Light chain AA
SEQ ID NO: 83
*EIVLTQSPGTLSLSPGERATLSCRASQSVSSSYLAWYQQKPGQAPRLLIY*

*GASSRATGIPDRFSGSGSGTDFTLTISRLEPEDFAVYYCQQHNQYPNTFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid and cDNA Sequences of the Heavy and Light Chain of FS22-053-008/FS28-256-024 mAb²

Heavy chain AA (without LALA)
SEQ ID NO: 137
EVQLLESGGGLVQPGGSLRLSCAASGFTFTHTYMSWVRQAPGKGLEWVSN
ISPTYSTTNYADSVKGRFTISRDNNKNTLYLQMNSLRAEDTAVYYCARYN
AYHAALDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELNPPYLFSNQVSLTCLVKGFYPSDIAVEWESNGQPENNYKT
TPPVLDSDGSFFLYSKLTVDYWRWLEGNVFSCSVMHEALHNHYTQKSLSL
SPG Heavy chain AA (with LALA)
SEQ ID NO: 138
EVQLLESGGGLVQPGGSLRLSCAASGFTFTHTYMSWVRQAPGKGLEWV
SNISPTYSTTNYADSVKGRFTISRDNNKNTLYLQMNSLRAEDTAVYYCAR
YNAYHAALDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSRDELNPPYLFSNQVSLTCLVKGFYPSDIAVEWESNGQPENNY
KTTPPVLDSDGSFFLYSKLTVDYWRWLEGNVFSCSVMHEALHNHYTQKSL
SLSPG Light chain AA
SEQ ID NO: 90
EIVLTQSPGTLSLSPGERATLSCRASQSVSSSYLAWYQQKPGQAPRLLIY
GASSRATGIPDRFSGSGSGTDFTLTISRLEPEDFAVYYCQQALGYPHTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Amino Acid Sequences of the Heavy and Light Chain of FS22-053-008/FS28-256-026

Heavy chain AA (without LALA)
SEQ ID NO: 139
EVQLLESGGGLVQPGGSLRLSCAASGFTFTQTYMSWVRQAPGKGLEWVSN
ISPTYSTTNYADSVKGRFTISRDNSKNTLYLQMNSLRAEDTAVYYCARYN
AYQIGLDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELNPPYLFSNQVSLTCLVKGFYPSDIAVEWESNGQPENNYKT
TPPVLDSDGSFFLYSKLTVDYWRWLEGNVFSCSVMHEALHNHYTQKSLSL
SPG Heavy chain AA (with LALA)
SEQ ID NO: 140
EVQLLESGGGLVQPGGSLRLSCAASGFTFTQTYMSWVRQAPGKGLEWVSN
ISPTYSTTNYADSVKGRFTISRDNSKNTLYLQMNSLRAEDTAVYYCARYN
AYQIGLDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPEAAGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELNPPYLFSNQVSLTCLVKGFYPSDIAVEWESNGQPENNYKT
TPPVLDSDGSFFLYSKLTVDYWRWLEGNVFSCSVMHEALHNHYTQKSLSL
SPG Light chain AA
SEQ ID NO: 90
EIVLTQSPGTLSLSPGERATLSCRASQSVSSSYLAWYQQKPGQAPRLLIY
GASSRATGIPDRFSGSGSGTDFTLTISRLEPEDFAVYYCQQALGYPHTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Amino Acid Sequences of the Heavy and Light Chain of FS22-053-008/FS28-256-027 mAb²

Heavy chain AA (without LALA)
SEQ ID NO: 141
EVQLLESGGGLVQPGGSLRLSCAASGFTFTHTYMSWVRQAPGKGLEWVSN
ISPTYSTTNYADSVKGRFTISRDNNKNTLYLQMNSLRAEDTAVYYCARYN
AYHAALDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELNPPYLFSNQVSLTCLVKGFYPSDIAVEWESNGQPENNYKT
TPPVLDSDGSFFLYSKLTVDYWRWLEGNVFSCSVMHEALHNHYTQKSLSL
SPG Heavy chain AA (with LALA)
SEQ ID NO: 142
EVQLLESGGGLVQPGGSLRLSCAASGFTFTHTYMSWVRQAPGKGLEWVSN
ISPTYSTTNYADSVKGRFTISRDNNKNTLYLQMNSLRAEDTAVYYCARYN
AYHAALDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPEAAGGPSVFLFPPKPK
DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELNPPYLFSNQVSLTCLVKGFYPSDIAVEWESNGQPENNYKT

TPPVLDSDGSFFLYSKLTVDYWRWLEGNVFSCSVMHEALHNHYTQKSLSL

SPG

Light chain AA
SEQ ID NO: 95
*EIVLTQSPGTLSLSPGERATLSCRASQSVSSSYLAWYQQKPGQAPRLLIY*

*GASSRATGIPDRFSGSGSGTDFTLTISRLEPEDFAVYYCQQTVPYPYTFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid Sequences of the Heavy and Light Chain Sequences of FS22-172-003-AA/FS28-256-271 mAb²

Heavy chain AA (with LALA)
SEQ ID NO: 187
EVQLLESGGGLVQPGGSLRLSCAASGFTFTHTYMSWVRQAPGKGLEWVSA

ISPTYSTTNYADSVKGRFTISRDNNKNTLYLQMNSLRAEDTAVYYCARYN

AYHAALDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELPYIIPPYNQVSLTCLVKGFYPSDIAVEWESNGQPENNYKT

TPPVLDSDGSFFLYSKLTVGADRWLEGNVFSCSVMHEALHNHYTQKSLSL

SPG

Light chain AA
SEQ ID NO: 188
EIVLTQSPGTLSLSPGERATLSCRASQSVSSSYLAWYQQKPGQAPRLLIY

GASSRATGIPDRFSGSGSGTDFTLTISRLEPEDFAVYYCQQTVPYPYTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid Sequences of the Heavy and Light Chain Sequences of OX40 (FS20-022-049)/FS28-256-271 mAb²

Heavy chain AA (with LALA)
SEQ ID NO: 189
EVQLLESGGGLVQPGGSLRLSCAASGFTFTHTYMSWVRQAPGKGLEWVSA

ISPTYSTTNYADSVKGRFTISRDNNKNTLYLQMNSLRAEDTAVYYCARYN

AYHAALDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDEYWDQEVSLTCLVKGFYPSDIAVEWESNGDEQFAYKTTPPVL

DSDGSFFLYSKLTVDQYRWNPADYFSCSVMHEALHNHYTQKSLSLSPG

Light chain AA
SEQ ID NO: 190
EIVLTQSPGTLSLSPGERATLSCRASQSVSSSYLAWYQQKPGQAPRLLIY

GASSRATGIPDRFSGSGSGTDFTLTISRLEPEDFAVYYCQQTVPYPYTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid Sequences of the Heavy and Light Chain of FS28m-228 mAb (with LALA)

Heavy chain AA (with LALA)
SEQ ID NO: 161
*EVQLLESGGGLVQPGGSLRLSCAASGFTFSTYFMVWVRQAPGKGLEWVSM*

*ISPKSSNTYYADSVKGRFTISRDNSKNTLYLQMNSLRAEDTAVYYCARWF*

*TPARFDYWGQGTLVTVSS*ASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

Light chain AA
SEQ ID NO: 162
*EIVLTQSPGTLSLSPGERATLSCRASQSVSSSYLAWYQQKPGQAPRLLIY*

*GASSRATGIPDRFSGSGSGTDFTLTISRLEPEDFAVYYCQQPFPFSFTFG*

*QGTKVEIK*RTVAAPSVFIFPPSDEQLKSGTASVNICLLNNFYPREAKVQW

KVDNALQSGNSQESVTEQDSKDSTYSLSSTLTLSKADYEKHKVYACEVTH

QGLSSPVTKSFNRGEC

Amino Acid Sequence of the Heavy and Light Chain of FS22-063-AA/FS28m-228 mAb² with LALA)

Heavy chain AA (with LALA)
SEQ ID NO: 163
*EVQLLESGGGLVQPGGSLRLSCAASGFTFSTYFMVWVRQAPGKGLEWVSM*

*ISPKSSNTYYADSVKGRFTISRDNSKNTLYLQMNSLRAEDTAVYYCARWF*

*TPARFDYWGQGTLVTVSS*ASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDEPYWSYVSLTCLVKGFYPSDIAVEWESNGQPENNYKTTPPVLD

SDGSFFLYSKLTVMNYRWELGNVFSCSVMHEALHNHYTQKSLSLSPG

-continued

Light chain AA

SEQ ID NO: 164

*EIVLTQSPGTLSLSPGERATLSCRASQSVSSSYLAWYQQKPGQAPRLLIY*

*GASSSRATGIPDRFSGSGSGTDFTLTISRLEPEDFAVYYCQQPFPFSFTFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid Sequence of the Heavy and Light Chain of FS22m-063-AA/FS28m-228-010 mAb2

Heavy chain AA (with LALA)

SEQ ID NO: 196

EVQLLESGGGLVQPGGSLRLSCAASGFTFSTYFMVWVRQAPGKGLEWVSM

ISPKSSNTYYADSVKGRFTISRDNSKNTLYLQMNSLRAEDTAVYYCARYH

ISPRFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDEPYWSYVSLTCLVKGFYPSDIAVEWESNGQPENNYKTTPPVLD

SDGSFFLYSKLTVMNYRWELGNVFSCSVMHEALHNHYTQKSLSLSPG

Light chain AA

SEQ ID NO: 197

EIVLTQSPGTLSLSPGERATLSCRASQSVSSSYLAWYQQKPGQAPRLLIY

GASSRATGIPDRFSGSGSGTDFTLTISRLEPEDFAVYYCQQPFPFSFTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino Acid Sequence of the Heavy and Light Chain of FS22m-063-AA/HelD1.3 mAb[2] (with LALA)

Heavy chain AA (with LALA)

SEQ ID NO: 191

*QVQLQESGPGLVRPSQTLSLTCTVSGSTFSGYGVNWVRQPPGRGLEWIGM*

*IWGDGNTDYNSALKSRVTMLVDTSKNQFSLRLSSVTAADTAVYYCARERD*

*YRLDYWGQGSLVTVSS*ASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDEPYWSYVSLTCLVKGFYPSDIAVEWESNGQPENNYKTTPPVLDSD

GSFFLYSKLTVMNYRWELGNVFSCSVMHEALHNHYTQKSLSLSPG

Light chain AA

SEQ ID NO: 192

DIQMTQSPASLSASVGETVTITCRASGNIHNYLAWYQQKQGKSPQLLVYN

AKTLADGVPSRFSGSGSGTQYSLKINSLQPEDFGSYYCQHFWSTPRTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Amino Acid Sequence of the Heavy and Light Chain of FS22m-063-AA/4420 mAb[2] (with LALA)

Heavy chain AA (with LALA)

SEQ ID NO: 193

EVKLDETGGGLVQPGRPMKLSCVASGFTFSDYWMNWVRQSPEKGLEWVAQ

IRNKPYNYETYYSDSVKGRFTISRDDSKSSVYLQMNNLRVEDMGIYYCTG

SYYGMDYWGQGTSVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDEPYWSYVSLTCLVKGFYPSDIAVEWESNGQPENNYKTTPPVLD

SDGSFFLYSKLTVMNYRWELGNVFSCSVMHEALHNHYTQKSLSLSPG

Light chain AA

SEQ ID NO: 194

DVVMTQTPLSLPVSLGDQASISCRSSQSLVHSNGNTYLRWYLQKPGQSPK

VLIYKVSNRFSGVPDRFSGSGSGTDFTLKISRVEAEDLGVYFCSQSTHVP

WTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Amino Acid Sequence of the Heavy and Light Chain of G1-AA/HelD1.3 mAb (with LALA)

Heavy chain AA (with LALA)

SEQ ID NO: 165

*QVQLQESGPGLVRPSQTLSLTCTVSGSTFSGYGVNWVRQPPGRGLEWIGM*

*IWGDGNTDYNSALKSRVTMLVDTSKNQFSLRLSSVTAADTAVYYCARERD*

*YRLDYWGQGSLVTVSS*ASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG

Light chain AA

SEQ ID NO: 166

*DIQMTQSPASLSASVGETVTITCRASGNIHNYLAWYQQKQGKSPQLLVYN*

*AKTLADGVPSRFSGSGSGTQYSLKINSLQPEDFGSYYCQHFWSTPRTFGG*

*GTKLEIK*RTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Amino Acid Sequence of the Heavy and Light Chain of the G1-AA/SS1 mAb (with LALA)

Heavy chain (with LALA)
SEQ ID NO: 167
QVQLQQSGPELEKPGASVKISCKASGYSFTGYTMNWVKQSHGKSLEWIGL
ITPYNGASSYNQKFRGKATLTVDKSSSTAYMDLLSLTSEDSAVYFCARGG
YDGRGFDYWGSGTPVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPEAAGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG Light chain
SEQ ID NO: 168
DIELTQSPAIMSASPGEKVTMTCSASSSVSYMHWYQQKSGTSPKRWIYDT
SKLASGVPGRFSGSGSGNSYSLTISSVEAEDDATYYCQQWSKHPLTFGSG
TKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC

MSLN-His-Avi
Mesothelin (without MPF and C Terminus) (Shown)
His and Avi Tags (not Shown)

Human
SEQ ID NO: 169
EVEKTACPSGKKAREIDESLIFYKKWELEACVDAALLATQMDRVNAIPFT
YEQLDVLKHKLDELYPQGYPESVIQHLGYLFLKMSPEDIRKWNVTSLETL
KALLEVNKGHEMSPQVATLIDRFVKGRGQLDKDTLDTLTAFYPGYLCSLS
PEELSSVPPSSIWAVRPQDLDTCDPRQLDVLYPKARLAFQNMNGSEYFVK
IQSFLGGAPTEDLKALSQQNVSMDLATFMKLRTDAVLPLTVAEVQKLLGP
HVEGLKAEERHRPVRDWILRQRQDDLDTLGLGLQGGIPNGYLVLDLSMQE
ALS Cyno
SEQ ID NO: 170
DVERTTCPPEKEVHEIDESLIFYKKRELEACVDAALLAAQMDRVDAIPFT
YEQLDVLKHKLDELYPQGYPESVIRHLGHLFLKMSPEDIRKWNVTSLETL
KALLKVSKGHEMSAQVATLIDRVVVGRGQLDKDTADTLTAFCPGCLCSLS
PERLSSVPPSIIGAVRPQDLDTCGPRQLDVLYPKARLAFQNMSGSEYFVK
IRPFLGGAPTEDLKALSQQNVSMDLATFMKLRREAVLPLSVAEVQKLLGP
HVEGLKVEEQHSPVRDWILKQRQDDLDTLGLGLQGGIPNGYLILDLSVRE
ALS Mouse
SEQ ID NO: 171
DAEQKACPPGKEPYKVDEDLIFYQNWELEACVDGTMLARQMDLVNEIPFT
YEQLSIFKHKLDKTYPQGYPESLIQQLGHFFRYVSPEDIHQWNVTSPDTV
KTLLKVSKGQKMNAQAIALVACYLRGGGQLDEDMVKALGDIPLSYLCDFS
PQDLHSVPSSVMWLVGPQDLDKCSQRHLGLLYQKACSAFQNVSGLEYFEK
IKTFLGGASVKDLRALSQHNVSMDIATFKRLQVDSLVGLSVAEVQKLLGP
NIVDLKTEEDKSPVRDWLFRQHQKDLDRLGLGLQGGIPNGYLVLDFNVRE
AFS

Amino Acid Sequence of Wild-Type CH3 Domain

SEQ ID NO: 172
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK

Amino Acid Sequence of CH2 Domain Containing LALA Mutation (LALA mutation in bold and underlined)
SEQ ID NO: 173
APEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAK

Amino Acid Sequence of CH2 Domain Containing LALA-PA Mutation (LALA-PA mutation in bold and underlined)
SEQ ID NO: 174
APEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALAA
PIEKTISKAK

Amino Acid Sequences of Fcab FS22-172-003 CH3 Domain Structural Loop Sequences FS22-172-003 First Sequence—PYIIPPY (SEQ ID NO: 198)
FS22-172-003 Second Sequence—GADRWLE (SEQ ID NO: 199)

Amino Acid and cDNA Sequences of Light Chain of FS22-172-003-AA/FS28-256-271

Light chain
SEQ ID NO: 200
AAEIVLTQSPGTLSLSPGERATLSCRASQSVSSSYLAWYQQKPGQAPRL
LIYGASSRATGIPDRFSGSGSGTDFTLTISRLEPEDFAVYYC
QQTVPYPYTFGQGTKVEIKRTVAAPSVFIFPPSDEQLKSGTASVVCLLNN
FYPREAKVQWKVDNALQSGNSQESVTEQDSKDSTYSLSSTLTLSKADYEK
HKVYACEVTHQGLSSPVTKSFNRGEC Heavy chain AA (with LALA)
SEQ ID NO: 201
EVQLLESGGGLVQPGGSLRLSCAAS GFTFTHTYMS WVRQAPGKGLEWVS
AISPTYSTTNYADSVKGRFTISRDNNKNTLYLQMNSLRAEDTAVYYC
ARYNAYHAALDYWGQGTLVTVSSASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLF -continued
PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELP<u>YIIPPYN</u>QVSLTCLVKGFYPSDIAVEWESNGQPE

NNYKTTPPVLDSDGSFFLYSKLTV<u>GADRWLE</u>GNVFSCSVMHEALHNHYTQ

KSLSLSPG

REFERENCES

All documents mentioned in this specification are incorporated herein by reference in their entirety.

Altschul S F, Gish W, Miller W, Myers E W, Lipman D J. Basic local alignment search tool. J. Mol. Biol. 215(3), 403-10 (1990).

Altschul S F, Madden T L, Schäffer A A, Zhang J, Zhang Z, Miller W, Lipman D J. Gapped BLAST and PSI-BLAST: a new generation of protein database search programs. Nucleic Acids Res. 25(17), 3389-402 (1997).

Andrade V C, Vettore A L, Felix R S, Almeida M S, Carvalho F, Oliveira J S, Chauffaille M L, Andriolo A, Caballero O L, Zago M A, Colleoni G W. Prognostic impact of cancer/testis antigen expression in advanced stage multiple myeloma patients. Cancer Immun. 8, 2 (2008).

Asgarov K, Balland J, Tirole C, Bouard A, Mougey V, Ramos D, Barroso A, Zangiacomi V, Jary M, Kim S, Gonzalez-Pajuelo M, Royer B, de Haard H, Clark A, Wijdenes J and Borg C (2017). A new anti-mesothelin antibody targets selectively the membrane-associated form. Mabs 9:567-577.

Bagshawe K D, Sharma S K, Springer C J, Antoniw P, Rogers G T, Burke P J, Melton R. Antibody-enzyme conjugates can generate cytotoxic drugs from inactive precursors at tumor sites. Antibody, Immunoconjugates and Radiopharmaceuticals 4, 915-922 (1991).

Bhome R, Bullock M D, A I Saihati H A, Goh R W, Primrose J N, Sayan A E, Mirnezami A H. A top-down view of the tumor microenvironment: structure, cells and signaling. Front. Cell. Dev. Biol. 3, 33 (2015).

Brinkmann U, Kontermann R E. The making of bispecific antibodies. MAbs (9)2, 182-212 (2017)

Bruhns P, Iannascoli B, England P, Mancardi D A, Fernandez N, Jorieux S, Daëron M. Specificity and affinity of human Fcγ receptors and their polymorphic variants for human IgG subclasses. Blood 113(16), 3716-25 (2009).

Carter P, Smith L, Ryan M. Identification and validation of cell surface antigens for antibody targeting in oncology. Endocr. Relat. Cancer 11(4), 659-87 (2004).

Cheever M A, Allison J P, Ferris A S, Finn O J, Hastings B M, Hecht T T, Mellman I, Prindiville S A, Viner J L, Weiner L M, Matrisian L M. Clin. Cancer Res. 15(17), 5323-37 (2009).

Chen S H, Hung W C, Wang P, Paul C, Konstantopoulos K (2013). Mesothelin binding to CA125/MUC16 promotes pancreatic cancer cell motility and invasion via MMP-7 activation. Sci Rep.3: 1870.

Chen D S, Mellman I. Oncology meets immunology: the cancer-immunity cycle. Immunity 39(1), 1-10 (2013).

Creaney J, Dick I M and Robinson B W (2015). Discovery of new biomarkers for malignant mesothelioma. Curr Pulmonol Rep. 4: 15-21.

Cui A, Jin X0G, Zhai K, Tong Z-H and Shi H-Z (2014). Diagnostic values of soluble mesothelin-related peptides for malignant pleural mesothelioma: updated meta-analysis. BMJ Open 4: e004145.

Grisshammer, R. and Nagai, K. (1995) Purification of overproduced proteins from *E. coli* cells In: DNA Cloning 2: Expression systems (Rickwood, D. and Hames, B. D., Eds.), The Practical Approach Series, pp. 59-92. IRL Press, Oxford University Press.

Gubin M M, Artyomov M N, Mardis E R, Schreiber R D. Tumor neoantigens: building a framework for personalized cancer immunotherapy. J. Clin. Invest. 125(9), 3413-21 (2015).

Gure A O, Chua R, Williamson B, Gonen M, Ferrera C A, Gnjatic S, Ritter G, Simpson A J, Chen Y T, Old L J, Altorki N K. Cancer-testis genes are coordinately expressed and are markers of poor outcome in non-small cell lung cancer. Clin. Cancer Res. 11(22), 8055-62 (2005).

Hassan R, Kindler H L, Jahan T, Bazhenova L, Reck M, Thomas A, Pastan I, Parno J, O'Shannessy D J, Fatato P, Maltzman J D and Wallin B A (2014). Phase II clinical trial of amatuximab, a chimeric antimesothelin antibody with pemetrexed and cisplatin in advanced unresectable pleural mesothelioma. Clin. Canc. Res. 20:5927-5936.

Hassan R, Kreitman R J, Pastan I and Willingham M C (2005). Localization of mesothelin in epithelial ovarian cancer. Appl Immunohistochem Mol Morphol AIMM Off Publ Soc Appl Immunohistochem13:243-47;

Hassan R, Lerner M R, Benbrook D, Lightfoot S A, Brackett D J, Wang Q C and Pastan I (2002). Clin. Cancer Res.: 8: 3520-3526.

Hassan R, Thomas, A, Alewine, C, Le, DT, Jaffee, E M and Pastan 1(2016). Mesothelin immunotherapy for cancer: ready for prime time?J. Clin. Onc. 34:4171-4180.

Hezareh M, Hessell A J, Jensen R C, van de Winkel J G and Parren P W. Effector function activities of a panel of mutants of a broadly neutralizing antibody against human immunodeficiency virus type 1. J. Virol. 75(24), 12161-8 (2001).

Hezareh M, Hessell A J, Jensen R C, van de Winkel J G, Parren P W. Effector function activities of a panel of mutants of a broadly neutralizing antibody against human immunodeficiency virus type 1. J. Virol. 75(24), 12161-8 (2001).

Hollevoet K, Reitsma J B, Creaney J, Grigoriu, B D, Robinson B W, Scherpereel A, Cristaudo A, Pass H I, Nackaerts K, Rodriques Portal J A, Schneider J, Muley, T, Di Serio F, Baas P, Tomasetti M, Rai A J and van Meerbeeck J P. Serum mesothelin for diagnosing malignant pleural mesothelioma: an individual patient data meta-analysis. J Clin. Oncol. 30 (13), 1541-1549 (2012).

Holliger P, Hudson P J. Engineered antibody fragments and the rise of single domains. Nat. Biotechnol. 23(9), 1126-36 (2005).

Idusogie E E, Presta L G, Gazzano-Santoro H, Totpal K, Wong P Y, Ultsch M, Meng Y G, Mulkerrin M G. Mapping of the C1q binding site on rituxan, a chimeric antibody with a human IgG1 Fc. J. Immunol. 164(8), 4178-84 (2000).

Kabat E A, Wu T T, Perry H M, Gottesman K S, Foeller C. Sequences of Proteins of Immunological Interest, 5th ed. NIH Publication No. 91-3242. Washington, D.C.: U.S. Department of Health and Human Services (1991).

Kaneko O, Gong, L, Zhang, J, Hansen, J K, Hassan, R, Lee B and Ho M (2009). A binding domain on mesothelin for CA125/MUC16. J. Biol. Chem. 284: 3739-3749.

Klein C, Schaefer W, Regula J T. The use of CrossMAb technology for the generation of bi- and multispecific antibodies. MAbs 8(6), 1010-20 (2016).

Kontermann (2012). Dual targeting strategies with bispecific antibodies. MAbs 4(2):182-97.

Ledermann J A, Begent R H, Massof C, Kelly A M, Adam T, Bagshawe K D. A phase-I study of repeated therapy with radiolabelled antibody to carcinoembryonic antigen using intermittent or continuous administration of cyclosporin A to supress the immune response. Int. J. Cancer 47(5), 659-64 (1991).

Lee J-H, Kim H, Yao Z, Szajek L, Grasso L, Kim I and Paik C. H (2018). Tumour-Shed Antigen Affects Antibody Tumour Targeting: Comparison of Two $^{89}$Zr-Labeled Antibodies Directed against Shed or Nonshed Antigens". Contrast Media and Molecular Imaging. ID: 2461257.

Lefranc M P, Giudicelli V, Duroux P, Jabado-Michaloud J, Folch G, Aouinti S, Carillon E, Duvergey H, Houles A, Paysan-Lafosse T, Hadi-Saljoqi S, Sasorith S, Lefranc G, Kossida S. IMGT®, the international ImMunoGeneTics information system@25 years on. Nucleic Acids Res. 43(Database issue), D413-22 (2015).

Ma J, Tang W K, Esser L, Pastan I, Xia D. (2012). Recognition of mesothelin by the therapeutic antibody MORAb-009: structural and mechanistic insights. J Biol. Chem. 287: 33123-31.

Malarkannan S, Horng T, Shih P P, Schwab S, Shastri N. Presentation of out-of-frame peptide/MHC class I complexes by a novel translation initiation mechanism. Immunity 10(6), 681-90 (1999).

Napoletano C, Bellati F, Tarquini E, Tomao F, Taurino F, Spagnoli G, Rughetti A, Muzii L, Nuti M, Benedetti Panici P. MAGE-A and NY-ESO-1 expression in cervical cancer: prognostic factors and effects of chemotherapy. Am. J. Obstet. Gynecol. 198(1), 99.e1-99.e7 (2008).

Pearson W R, Lipman D J. Improved tools for biological sequence comparison. Proc. Natl. Acad. Sci. U.S.A. 85(8), 2444-8 (1988).

Podojil J R, Miller S D. Potential targeting of B7-H4 for the treatment of cancer. Immunol. Rev. 276(1), 40-51 (2017).

Powers G A, Hudson P J, Wheatcroft M P. Design and production of multimeric antibody fragments, focused on diabodies with enhanced clinical efficacy. Methods Mol. Biol. 907, 699-712 (2012)

Rickert K W, Grinberg L, Woods R M, Wilson S, Bowen M A, Baca M. Combining phage display with de novo protein sequencing for reverse engineering of monoclonal antibodies. MAbs, 2016; 8(3):501-12

Rosenberg S. Development of Cancer Vaccines. ASCO Educational Book Spring: 60-62 (2000).

Sapede, C, Gauvrit A, Barbieux I, Padieu M, Cellerin L, Sagan C, Scherpereel A, Dabouis G, Gregoire M. Aberrant splicing and protease involvement in mesothelin release from epithelioid mesothelioma cells. Canc. Sci 99(3): 590-594 (2008)

Scott A M, Renner C. Tumour Antigens Recognized by Antibodies. eLS (2001). Simpson A J, Caballero O L, Jungbluth O L, Chen Y T, Old L J. Cancer/testis antigens, gametogenesis and cancer. Nat. Rev. Cancer 5(8), 615-25 (2005).

Smith T F, Waterman M S. Identification of common molecular subsequences. J. Mol. Biol. 147(1), 195-7 (1981).

Spiess, Zhai, Carter (2015). Alternative molecular formats and therapeutic applications for bispecific antibodies. Molecular Immunology. 67:95-106.

Tai Y T, Anderson K C. Targeting B-cell maturation antigen in multiple myeloma. Immunotherapy 7(11), 1187-99 (2015).

Tang Z, Feng, M, Gao, W, Chen W, Chaudhary, A, Croix, B S, Qian M, Dimitrov D S and Ho M, (2013). A human single-domain antibody elicits potent antitumor activity by targeting an epitope in mesothelin close to the cancer cell surface. Mol. Canc. Ther. 12:416-426.

Tinguely M, Jenni B, Knights A, Lopes B, Korol D, Rousson V, Curioni Fontecedro A, Cogliatti Bittermann A G, Schmid U, Dommann-Scherrer C, Maurer R, Renner C, Probst-Hensch N M, Moch H, Knuth A, Zippelius A. MAGE-C1/CT-7 expression in plasma cell myeloma: sub-cellular localization impacts on clinical outcome. Cancer Sci. 99(4), 720-5 (2008).

Tomasetti M, Rai A J and van Meerbeeck J P (2012). Serum mesothelin for diagnosing malignant pleural mesothelioma: an individual patient data meta-analysis. J Clin. Oncol. 30:1541-1549.

Velazquez E F, Jungbluth A A, Yancovitz M, Gnjatic S, Adams S, O'Neill D, Zavilevich K, Albukh T, Christos P, Mazumdar M, Pavlick A, Polsky D, Shapiro R, Berman R, Spira J, Busam K, Osman I, Bhardwaj N. Expression of the cancer/testis antigen NY-ESO-1 in primary and metastatic malignant melanoma (MM)—correlation with prognostic factors. Cancer Immun. 7, 11 (2007).

Wang X, Mathieu M, Brezski R J. IgG Fc engineering to modulate antibody effector functions. Protein Cell 9(1), 63-73 (2018).

Wozniak-Knopp G, Bartl S, Bauer A, Mostageer M, Woisetschläger M, Antes B, Ettl K, Kainer M, Weberhofer G, Wiederkum S, Himmler G, Mudde G C, Rüker F. Introducing antigen-binding sites in structural loops of immunoglobulin constant domains: Fc fragments with engineered HER2/neu-binding sites and antibody properties. Protein Eng. Des. Sel. 23(4), 289-97 (2010).

Zhang, Y, Chertov, O, Zhang, J, Hassan, R and Pastan I (2011). Cytotoxic activity of immunotoxin SS1P is modulated by TACE-dependent mesothelin shedding. Cancer Res. 71: 5915-5922.

Zhao X Y, Subramanyam B, Sarapa N, Golfier S and Dinter H (2016). Novel antibody therapeutics targeting mesothelin in solid tumours. Clin. Cancer Drugs 3:76-86.

The invention claimed is:

1. An antibody molecule that binds mesothelin (MSLN), wherein the antigen-binding site of the antibody molecule comprises the VH domain CDR1, CDR2 and CDR3 and the VL domain CDR1, CDR2 and CDR3 of antibody:
   (i) FS28-256-271 set forth in SEQ ID NO: 98, 73, 99, 20, 21, and 44, respectively;
   (ii) FS28-024-052 set forth in SEQ ID NO: 10, 11, 41, 20, 21 and 22, respectively;
   (iii) FS28-256-021 set forth in SEQ ID NO: 98, 73, 99, 20, 21 and 34, respectively;
   (iv) FS28-256-012 set forth in SEQ ID NO: 98, 73, 99, 20, 21 and 25, respectively;
   (v) FS28-256-023 set forth in SEQ ID NO: 101, 73, 103, 20, 21 and 34, respectively;
   (vi) FS28-256-024 set forth in SEQ ID NO: 98, 73, 99, 20, 21 and 43, respectively;

(vii) FS28-256-026 set forth in SEQ ID NO: 101, 73, 103, 20, 21 and 43, respectively;
(viii) FS28-256-027 set forth in SEQ ID NO: 98, 73, 99, 20, 21 and 44, respectively;
(ix) FS28-256-001 set forth in SEQ ID NO: 85, 73, 75, 20, 21 and 34, respectively;
(x) FS28-256-005 set forth in SEQ ID NO: 85, 73, 75, 20, 21 and 43, respectively;
(xi) FS28-256-014 set forth in SEQ ID NO: 111, 73, 113, 20, 21 and 25, respectively;
(xii) FS28-256-018 set forth in SEQ ID NO: 101, 73, 103, 20, 21 and 25, respectively;
(xiii) FS28-256 set forth in SEQ ID NO: 71, 73, 75, 20, 21 and 25, respectively;
(xiv) FS28-024-051 set forth in SEQ ID NO: 10, 11, 32, 20, 21 and 22, respectively;
(xv) FS28-024-053 set forth in SEQ ID NO: 10, 11, 51, 20, 21 and 22, respectively; or
(xvi) FS28-024 set forth in SEQ ID NO: 10, 11, 12, 20, 21 and 22, respectively; and wherein the CDR sequences are defined according to the ImMunoGeneTics (IMGT) numbering scheme; and/or wherein the antigen-binding site of the antibody molecule comprises the VH domain CDR1, CDR2 and CDR3 and the VL domain CDR1, CDR2 and CDR3 of antibody:

(i) FS28-256-271 set forth in SEQ ID NO: 97, 182, 100, 23, 24, and 44, respectively;
(ii) FS28-024-052 set forth in SEQ ID NO: 13, 14, 42, 23, 24 and 22, respectively;
(iii) FS28-256-021 set forth in SEQ ID NO: 97, 74, 100, 23, 24 and 34, respectively;
(iv) FS28-256-012 set forth in SEQ ID NO: 97, 74, 100, 23, 24 and 25, respectively;
(v) FS28-256-023 set forth in SEQ ID NO: 102, 74, 104, 23, 24 and 34, respectively;
(vi) FS28-256-024 set forth in SEQ ID NO: 97, 74, 100, 23, 24 and 43, respectively;
(vii) FS28-256-026 set forth in SEQ ID NO: 102, 74, 104, 23, 24 and 43, respectively;
(viii) FS28-256-027 set forth in SEQ ID NO: 97, 74, 100, 23, 24 and 44, respectively;
(ix) FS28-256-001 set forth in SEQ ID NO: 86, 74, 76, 23, 24 and 34, respectively;
(x) FS28-256-005 set forth in SEQ ID NO: 86, 74, 76, 23, 24 and 43, respectively;
(xi) FS28-256-014 set forth in SEQ ID NO: 112, 74, 114, 23, 24 and 25, respectively;
(xii) FS28-256-018 set forth in SEQ ID NO: 102, 74, 104, 23, 24 and 25, respectively;
(xiii) FS28-256 set forth in SEQ ID NO: 72, 74, 76, 23, 24 and 25, respectively;
(xiv) FS28-024-051 set forth in SEQ ID NO: 13, 14, 33, 23, 24 and 22, respectively;
(xiv) FS28-024-053 set forth in SEQ ID NO: 13, 14, 52, 23, 24 and 22, respectively; or
(xvi) FS28-024 set forth in SEQ ID NO: 13, 14, 15, 23, 24 and 22, respectively; and wherein the CDR sequences are defined according to the Kabat numbering scheme; and wherein the antibody molecule does not comprise a CD137 antigen-binding site located in a CH3 domain of the antibody molecule, said CD137 antigen-binding site comprising a first sequence as set forth in SEQ ID NO: 198 located in the AB structural loop of the CH3 domain and a second sequence as set forth in SEQ ID NO: 199 located in the EF structural loop of the CH3 domain.

2. The antibody molecule according to claim 1, comprising the VH domain and VL domain of antibody:
(i) FS28-256-271 set forth in SEQ ID NO: 180 and 56, respectively;
(ii) FS28-024-052 set forth in SEQ ID NO: 39 and 18, respectively;
(iii) FS28-256-021 set forth in SEQ ID NO: 109 and 93, respectively;
(iv) FS28-256-012 set forth in SEQ ID NO: 109 and 79, respectively;
(v) FS28-256-023 set forth in SEQ ID NO: 121 and 93, respectively;
(vi) FS28-256-024 set forth in SEQ ID NO: 109 and 53, respectively;
(vii) FS28-256-026 set forth in SEQ ID NO: 121 and 53, respectively;
(viii) FS28-256-027 set forth in SEQ ID NO: 109 and 56, respectively;
(ix) FS28-256-001 set forth in SEQ ID NO: 63 and 93, respectively;
(x) FS28-256-005 set forth in SEQ ID NO: 63 and 53, respectively;
(xi) FS28-256-014 set forth in SEQ ID NO: 115 and 79, respectively;
(xii) FS28-256-018 set forth in SEQ ID NO: 121 and 79, respectively;
(xiii) FS28-256 set forth in SEQ ID NO: 69 and 79, respectively;
(xiv) FS28-024-051 set forth in SEQ ID NO: 30 and 18, respectively;
(xv) FS28-024-053 set forth in SEQ ID NO: 49 and 18, respectively; or
(xvi) FS28-024 set forth in SEQ ID NO: 8 and 18, respectively.

3. The antibody molecule according to claim 1, wherein the antigen-binding site of the antibody molecule comprises the VH domain CDR1, CDR2 and CDR3 and the VL domain CDR1, CDR2 and CDR3 of antibody FS28-256-271 set forth in SEQ ID NO: 98, 73, 99, 20, 21, and 44, respectively, wherein the CDR sequences are defined according to the IMGT numbering scheme; the VH domain CDR1, CDR2 and CDR3 and the VL domain CDR1, CDR2 and CDR3 of antibody FS28-256-271 set forth in SEQ ID NO: 97, 182, 100, 23, 24, and 44, respectively, wherein the CDR sequences are defined according to the Kabat numbering scheme; and/or the VH and VL domain of antibody FS28-256-271 set forth in SEQ ID NO: 180 and 56, respectively.

4. The antibody molecule according to claim 1, wherein the antigen-binding site of the antibody molecule comprises the VH domain CDR1, CDR2 and CDR3 and the VL domain CDR1, CDR2 and CDR3 of antibody FS28-024-052 set forth in SEQ ID NO: 10, 11, 41, 20, 21 and 22, respectively, wherein the CDR sequences are defined according to the IMGT numbering scheme; the VH domain CDR1, CDR2 and CDR3 and the VL domain CDR1, CDR2 and CDR3 of antibody FS28-024-052 set forth in SEQ ID NO: 13, 14, 42, 23, 24 and 22, respectively, wherein the CDR sequences are defined according to the Kabat numbering scheme; and/or the VH and VL domain of antibody FS28-024-052 set forth in SEQ ID NO: 39 and 18, respectively.

5. The antibody molecule according to claim 1, wherein antibody molecule is a multispecific antibody molecule and comprises a second antigen-binding site that binds a second antigen.

6. The antibody molecule according to claim 5, wherein the second antigen-binding site is located in a constant domain of the antibody molecule.

7. The antibody molecule according to claim 6, wherein the constant domain is a CH3 domain.

8. The antibody molecule according to claim 5, wherein the second antigen-binding site binds an immune cell antigen.

9. The antibody molecule according to claim 8, wherein the immune cell antigen is a member of the tumour necrosis factor receptor superfamily (TNFRSF).

10. The antibody molecule according to claim 9, wherein the member of the TNFRSF is CD137.

11. The antibody molecule according to claim 6, wherein the second antigen-binding site comprises a first sequence, a second sequence, and/or a third sequence, wherein the first sequence, second sequence and third sequence are located in the AB structural loop, the CD structural loop and the EF structural loop of the constant domain, respectively.

12. The antibody molecule according to claim 8, wherein the antibody molecule is capable of activating an immune cell in the presence of MSLN.

13. The antibody molecule according to claim 12, wherein the immune cell is a T cell, B cell, natural killer (NK) cell, natural killer T (NKT) cell, or dendritic cell (DC).

14. The antibody molecule according to claim 1, wherein the antibody molecule has been modified to reduce or abrogate binding of the CH2 domain of the antibody molecule to one or more Fcγ receptors.

15. The antibody molecule according to claim 14, wherein the antibody molecule does not bind to one or more Fcγ receptors.

16. A nucleic acid molecule or molecules encoding the antibody molecule according claim 1.

17. A recombinant host cell comprising the nucleic acid molecules(s) according to claim 16.

18. A pharmaceutical composition comprising the antibody molecule according to claim 1 and a pharmaceutically acceptable excipient.

19. A method of detecting or diagnosing a cancer in an individual, the method comprising the use of the antibody molecule according to claim 1.

20. A method of treating cancer in an individual comprising administering to the individual a therapeutically effective amount of the antibody molecule according to claim 1.

* * * * *